(12) United States Patent
Vandyck et al.

(10) Patent No.: US 11,078,193 B2
(45) Date of Patent: Aug. 3, 2021

(54) SULPHAMOYLPYRROLAMIDE DERIVATIVES AND THE USE THEREOF AS MEDICAMENTS FOR THE TREATMENT OF HEPATITIS B

(71) Applicant: Janssen Sciences Ireland UC, Little Island, Co Cork (IE)

(72) Inventors: Koen Vandyck, Paal-Beringer (BE); Geerwin Yvonne Paul Haché, Kapellen (BE); Stefaan Julien Last, Lint (BE); Geert Rombouts, Borsbeek (BE); Wim Gaston Verschueren, Berchem (BE); Pierre Jean-Marie Bernard Raboisson, Rosieres (FR)

(73) Assignee: Janssen Sciences Ireland UC, Little Island (IE)

( * ) Notice: Subject to any disclaimer, the term of this patent is extended or adjusted under 35 U.S.C. 154(b) by 0 days.

(21) Appl. No.: 15/117,146

(22) PCT Filed: Feb. 5, 2015

(86) PCT No.: PCT/EP2015/052389
§ 371 (c)(1),
(2) Date: Aug. 5, 2016

(87) PCT Pub. No.: WO2015/118057
PCT Pub. Date: Aug. 13, 2015

(65) Prior Publication Data
US 2016/0347741 A1   Dec. 1, 2016

(30) Foreign Application Priority Data

Feb. 6, 2014  (EP) .................................. 14154167
May 22, 2014 (EP) .................................. 14169438
Jul. 17, 2014  (EP) .................................. 14177505
Nov. 19, 2014 (EP) .................................. 14193926

(51) Int. Cl.
| C07D 401/12 | (2006.01) |
|---|---|
| A61K 31/4439 | (2006.01) |
| C07D 405/14 | (2006.01) |
| A61K 31/4545 | (2006.01) |
| A61K 45/06 | (2006.01) |
| C07D 401/14 | (2006.01) |

(52) U.S. Cl.
CPC ........ *C07D 405/14* (2013.01); *A61K 31/4439* (2013.01); *A61K 31/4545* (2013.01); *A61K 45/06* (2013.01); *C07D 401/12* (2013.01); *C07D 401/14* (2013.01)

(58) Field of Classification Search
CPC .......................... C07D 401/12; A61K 31/4439
See application file for complete search history.

(56) References Cited

U.S. PATENT DOCUMENTS

| 3,843,662 A | 10/1974 | Holland |
|---|---|---|
| 4,569,940 A | 2/1986 | Watts |
| 4,962,101 A | 10/1990 | DiNinno et al. |
| 4,995,898 A | 2/1991 | Nasu et al. |
| 5,272,167 A | 12/1993 | Girijavallabhan et al. |
| 5,308,826 A | 5/1994 | Chin et al. |
| 5,314,880 A | 5/1994 | Whittaker et al. |
| 5,571,821 A | 11/1996 | Chan et al. |
| 5,585,327 A | 12/1996 | Chin et al. |
| 5,607,929 A | 3/1997 | Nicol et al. |
| 5,708,034 A | 1/1998 | Kleemann et al. |
| 5,723,411 A | 3/1998 | Stevenson |
| 5,756,524 A | 5/1998 | Riordan et al. |
| 5,795,907 A | 8/1998 | Kalindjian et al. |
| 5,912,260 A | 6/1999 | Kalindjian et al. |
| 5,919,970 A | 7/1999 | Song et al. |
| 5,939,423 A | 8/1999 | Karlin et al. |
| 6,025,367 A | 2/2000 | Forbes et al. |
| 6,265,408 B1 | 7/2001 | Forbes et al. |

(Continued)

FOREIGN PATENT DOCUMENTS

| CA | 2950807 A1 | 12/2013 |
|---|---|---|
| CN | 101039919 A | 9/2007 |

(Continued)

OTHER PUBLICATIONS

Database Registry [Online] Chemical Abstracts Service, Columbus, Ohio, US; Dec. 22, 2008 (Dec. 22, 2008), XP002720955, Database Accession No. 1088200-12-7 Abstract.
Database Registry [Online] Chemical Abstracts Service, Columbus, Ohio, US; Aug. 30, 2011 (Aug. 30, 2011), XP002720956, Database Accession No. 1325664-90-1 Abstract.
Weber et al., "Inhibition of Human Hepatitis B Virus (HBV) by a Novel Non-Nucleosidic Compound in a Transgenic Mouse Model", Antiviral Research 2002 vol. 43 pp. 69-78.
Extended European Search Report for Corresponding European Application EP1415416.7 dated Apr. 2, 2014 6 Pgs.

(Continued)

*Primary Examiner* — Jeffrey S Lundgren
*Assistant Examiner* — Chris E Simmons

(57) ABSTRACT

Inhibitors of HBV replication of Formula (A)

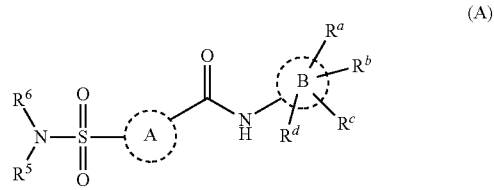

including stereochemically isomeric forms, and salts, hydrates, solvates thereof, wherein $R^a$ to $R^d$, and $R^5$ to $R^6$ have the meaning as defined herein.

The present invention also relates to processes for preparing said compounds, pharmaceutical compositions containing them and their use, alone or in combination with other HBV inhibitors, in HBV therapy.

20 Claims, No Drawings

(56) References Cited

U.S. PATENT DOCUMENTS

| | | |
|---|---|---|
| 6,476,025 B1 | 11/2002 | Gutterer |
| 6,650,463 B2 | 11/2003 | Obikawa et al. |
| 6,668,527 B2 | 12/2003 | Duplantier et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,368,457 B2 | 5/2008 | Josien |
| 7,384,967 B2 | 6/2008 | Polisetti et al. |
| 7,541,373 B2 | 6/2009 | Polisetti et al. |
| 7,544,700 B2 | 6/2009 | Halazy et al. |
| 7,576,688 B2 | 8/2009 | Lehtinen |
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | DuBois et al. |
| 7,790,726 B2 | 9/2010 | Zhang et al. |
| 7,838,525 B2 | 11/2010 | Jones et al. |
| 7,888,373 B2 | 2/2011 | Morgan et al. |
| 7,994,168 B2 | 8/2011 | Lennig et al. |
| 8,071,779 B2 | 12/2011 | Lampe et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,650 B2 | 4/2012 | Dubois et al. |
| 8,153,803 B2 | 4/2012 | Kazantsev |
| 8,207,195 B2 | 6/2012 | Navratil et al. |
| 8,227,489 B2 | 7/2012 | Dubois et al. |
| 8,273,754 B2 | 9/2012 | Ali et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,141 B2 | 4/2013 | Murata et al. |
| 8,410,147 B2 | 4/2013 | Peterson et al. |
| 8,536,168 B2 | 9/2013 | Dai et al. |
| 8,609,668 B2 | 12/2013 | Cuconati et al. |
| 8,629,274 B2 | 1/2014 | Hartman et al. |
| 8,722,742 B2 | 5/2014 | Reyes |
| 8,808,702 B2 | 8/2014 | Reddy et al. |
| 8,889,716 B2 | 11/2014 | Prime et al. |
| 8,993,771 B2 | 3/2015 | Hartman |
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil van Niel et al. |
| RE45,670 E | 9/2015 | Polisetti et al. |
| 9,156,839 B2 | 10/2015 | Vandyck |
| 9,169,212 B2 | 10/2015 | Hartman et al. |
| 9,181,288 B2 | 11/2015 | Hartman et al. |
| 9,205,079 B2 | 12/2015 | Hartman |
| 9,339,510 B2 | 5/2016 | Hartman et al. |
| 9,400,280 B2 | 7/2016 | Hartman |
| 9,458,176 B2 | 10/2016 | Takaishi et al. |
| 9,505,722 B2 | 11/2016 | Hartman et al. |
| 9,567,299 B2 | 2/2017 | Vandyck |
| 9,579,313 B2 | 2/2017 | Hartman |
| 9,676,747 B2 | 6/2017 | Hartman et al. |
| 10,071,961 B2 | 9/2018 | Vandyck et al. |
| 2002/0049236 A1 | 4/2002 | Duplantier et al. |
| 2003/0114443 A1 | 6/2003 | Imamura et al. |
| 2004/0039009 A1 | 2/2004 | Jagtap et al. |
| 2004/0110802 A1 | 6/2004 | Thorarensen et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0221272 A1 | 10/2005 | Housman et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0087415 A1 | 4/2010 | Whitten et al. |
| 2010/0113421 A1 | 5/2010 | Williams et al. |
| 2010/0204210 A1 | 8/2010 | Sorensen |
| 2011/0009622 A1 | 1/2011 | Makoto et al. |
| 2011/0064695 A1 | 3/2011 | Qiu et al. |
| 2011/0064696 A1 | 3/2011 | Or et al. |
| 2011/0065686 A1 | 3/2011 | Mazola Reyes et al. |
| 2011/0184019 A1 | 7/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Navratil et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 8/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Ku; Xiaodong ; et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0083383 A1 | 3/2016 | Guo et al. |
| 2016/0115125 A1 | 4/2016 | Vandyck et al. |
| 2016/0115149 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 | 12/2016 | Vandyck et al. |
| 2017/0002025 A1 | 1/2017 | Vendeville et al. |
| 2017/0015629 A1 | 1/2017 | Hartman et al. |
| 2017/0114018 A1 | 4/2017 | Hartman |
| 2017/0158634 A1 | 6/2017 | Vandyck et al. |
| 2017/0182021 A1 | 6/2017 | Hartman |
| 2017/0334882 A1 | 11/2017 | Hartman et al. |

FOREIGN PATENT DOCUMENTS

| | | |
|---|---|---|
| CN | 102093320 A | 6/2011 |
| CN | 102206172 A | 10/2011 |
| EP | 0232067 A2 | 8/1987 |
| EP | 0742200 A1 | 11/1996 |
| EP | 2280001 A4 | 1/2012 |
| JP | 62142164 | 6/1987 |
| JP | 2008179621 A | 7/2008 |
| JP | 2008525406 A | 7/2008 |
| JP | 2010535172 A | 11/2010 |
| JP | 2015531773 A | 11/2015 |
| JP | 2015533782 A1 | 11/2015 |
| NO | 2001051487 A1 | 7/2001 |
| WO | 198403281 A1 | 8/1984 |
| WO | 199207835 A1 | 5/1992 |

(56) References Cited

FOREIGN PATENT DOCUMENTS

| | | |
|---|---|---|
| WO | 1998023285 A1 | 6/1998 |
| WO | 199909022 A1 | 2/1999 |
| WO | 1999038845 A1 | 8/1999 |
| WO | 199948492 A1 | 9/1999 |
| WO | 199965906 A1 | 12/1999 |
| WO | 200105390 A2 | 1/2001 |
| WO | 200119788 A2 | 3/2001 |
| WO | 2001025200 A1 | 4/2001 |
| WO | 200155121 A1 | 8/2001 |
| WO | 200185694 A2 | 11/2001 |
| WO | 2002051410 | 7/2002 |
| WO | 2002064618 A2 | 8/2002 |
| WO | 2003002518 A1 | 1/2003 |
| WO | 2003007955 A2 | 1/2003 |
| WO | 2003044016 A1 | 5/2003 |
| WO | 2003101961 A1 | 12/2003 |
| WO | 2004010943 A2 | 2/2004 |
| WO | 2004011427 A2 | 2/2004 |
| WO | 2004022060 A2 | 3/2004 |
| WO | 2004058709 A2 | 7/2004 |
| WO | 2004086865 A1 | 10/2004 |
| WO | 2004099192 A2 | 11/2004 |
| WO | 2004100947 A2 | 11/2004 |
| WO | 2005016922 A1 | 2/2005 |
| WO | 2005000231 A3 | 5/2005 |
| WO | 2005044797 A1 | 5/2005 |
| WO | 2005087217 A1 | 9/2005 |
| WO | 2005105785 A2 | 11/2005 |
| WO | 2005115374 A1 | 12/2005 |
| WO | 2006002133 A1 | 1/2006 |
| WO | 2006012642 A2 | 2/2006 |
| WO | 2006024834 A1 | 3/2006 |
| WO | 2006053109 A1 | 5/2006 |
| WO | 2006067445 A2 | 6/2006 |
| WO | 2006067446 A1 | 6/2006 |
| WO | 2006123257 A2 | 11/2006 |
| WO | 2006128129 A2 | 11/2006 |
| WO | 2006128172 A2 | 11/2006 |
| WO | 2007031791 A1 | 3/2007 |
| WO | WO 2007/070556 A1 | 6/2007 |
| WO | 2008011476 A2 | 1/2008 |
| WO | 2008022171 A1 | 2/2008 |
| WO | 2008054605 A3 | 7/2008 |
| WO | 2008093614 A1 | 8/2008 |
| WO | 2008137794 A1 | 11/2008 |
| WO | 2008154819 A1 | 12/2008 |
| WO | 2009016088 A1 | 2/2009 |
| WO | 2009018219 A2 | 2/2009 |
| WO | 2009062402 A1 | 5/2009 |
| WO | 2009086303 A2 | 7/2009 |
| WO | 2009131065 A1 | 10/2009 |
| WO | 2009146013 A1 | 12/2009 |
| WO | 2010018113 A2 | 2/2010 |
| WO | 2010043592 A1 | 4/2010 |
| WO | 2010059658 A1 | 5/2010 |
| WO | 2010088000 A2 | 8/2010 |
| WO | 2010123139 A1 | 10/2010 |
| WO | 2010138758 A1 | 12/2010 |
| WO | 2011002635 A1 | 1/2011 |
| WO | 2011035143 A2 | 3/2011 |
| WO | 2011088015 A1 | 7/2011 |
| WO | 2011088561 A1 | 7/2011 |
| WO | 2011109237 A1 | 9/2011 |
| WO | 2011112191 A1 | 9/2011 |
| WO | 2011123609 A1 | 10/2011 |
| WO | 2011140324 A1 | 11/2011 |
| WO | 2011155898 A1 | 12/2011 |
| WO | 2012016133 A2 | 2/2012 |
| WO | 2012018635 A2 | 2/2012 |
| WO | 2012033956 A1 | 3/2012 |
| WO | 2012049277 A1 | 4/2012 |
| WO | 2012075235 A1 | 6/2012 |
| WO | 2012080050 A1 | 6/2012 |
| WO | 2012117216 A1 | 9/2012 |
| WO | 2012136834 A1 | 10/2012 |
| WO | WO 2013/006394 A1 | 1/2013 |
| WO | WO 2013/096744 A1 | 6/2013 |
| WO | 2013102655 A1 | 7/2013 |
| WO | 2013130703 A2 | 9/2013 |
| WO | 2013144129 A1 | 10/2013 |
| WO | 2013174962 | 11/2013 |
| WO | 2013181584 A2 | 12/2013 |
| WO | 2013184757 A1 | 12/2013 |
| WO | 2014033167 A1 | 3/2014 |
| WO | 2014033170 A1 | 3/2014 |
| WO | 2014033176 | 3/2014 |
| WO | 2014037480 A1 | 3/2014 |
| WO | 2014106019 A2 | 7/2014 |
| WO | 2014131847 A1 | 9/2014 |
| WO | 2014151958 A1 | 9/2014 |
| WO | 2014161888 A1 | 10/2014 |
| WO | 2014165128 A2 | 10/2014 |
| WO | 2014184328 A1 | 11/2014 |
| WO | 2014184350 A1 | 11/2014 |
| WO | 2014184365 A1 | 11/2014 |
| WO | WO 2014/184350 A1 | 11/2014 |
| WO | 2014191301 A1 | 12/2014 |
| WO | 2014191726 A1 | 12/2014 |
| WO | 2014198880 A1 | 12/2014 |
| WO | 2015011281 A1 | 1/2015 |
| WO | 2015055764 A1 | 4/2015 |
| WO | 2015057945 A1 | 4/2015 |
| WO | 2015059212 A1 | 4/2015 |
| WO | 2015073774 A1 | 5/2015 |
| WO | 2015109130 A1 | 7/2015 |
| WO | 2015116923 A1 | 8/2015 |
| WO | 2015118057 A1 | 8/2015 |
| WO | 2015132276 A1 | 9/2015 |
| WO | 2015138895 A1 | 9/2015 |
| WO | 2015144093 A1 | 10/2015 |
| WO | 2015180631 A1 | 12/2015 |
| WO | 2016089990 A1 | 6/2016 |
| WO | 2016109663 A2 | 7/2016 |
| WO | 2016109684 A2 | 7/2016 |
| WO | 2016109689 A1 | 7/2016 |
| WO | 2016149581 A1 | 9/2016 |
| WO | 2016113273 A1 | 10/2016 |
| WO | 2016161268 A1 | 10/2016 |
| WO | 2016168619 A1 | 10/2016 |
| WO | 2016183266 A1 | 11/2016 |
| WO | 2019011323 A1 | 1/2019 |

OTHER PUBLICATIONS

International Search Report and Written Opinion for Corresponding International Application PCT/EP2015/052389 dated Mar. 31, 2015 11 Pgs.
Online Registry Via STN, Mar. 2, 2007, RN 924514-21-6.
Online Registry Via STN, Sep. 2, 2003, RN 577752-12-6.
Bennes, et al., "Recognition-induced control and acceleration of a pyroole Diels-Alder reaction", Tetrahedron Letters, vol. 42 : pgs. 2377-2380 (2001).
Berke, et al., "Capsid Assembly Modulator JNJ-56136379 Prevents de Novo Infection of Primary Human Hepatocytes with Hepatitis B Virus", Hepatology, Oct. 2016, pp. 124A, 234.
Brahmania, et al., "New Therapeutic Agents for Chronic Hepatitis B", Lancet Infec Dis, vol. 16: pp. e10-21 (Feb. 2016).
Brezillon, et al., "Antiviral Activity of Bay 41-4109 on Hepatitis B Virus in Humanized Alb-uPA/SCID Mice", PLos ONE, vol. 6 (12): pp. e25096 (1-6) (Dec. 2011).
Cai, et al., "Identification of disubstituted sulfonamide compounds as specific inhibitors of hepatitis B virus covalently closed circular DNA formuation, Antimicrobial agents and chemotherapy", pp. vol. 56(8): pp. 4277-4288 (May 29, 2012).
Campagna et al., "Sulfamoylbenzamide Derivatives Inhibit the Assembly of Hepatitis B Virus Nucleocapsids", Journal of Virology, ),vol: 87 (12): pp. 6931-6942 (Jun. 2013).
Campagna, "Sulfamoylbenzamide Derivatives are a Novel Class of Hepatities B Virus Inhibitors Targeting PGRNA Encapsidation", 2011 International Meeting on Molecular Biology of Hepatitis B Viruses, Poster Presentation, (Oct. 9-12, 2011).

(56) References Cited

OTHER PUBLICATIONS

Chang, et al., "NMR-spectroscopy-based Metabonomic Approach to the Analysis of Bay41-4109, a novel anti-HBV Compound, induced Hepatotoxicity in Rats", Toxicology Letters, vol. 173: pp. 161-167 (2007).
Cho, et al, "2-Amino-N-(2,6-dichloropyridin-3-yl)acetamide derivatives as a novel class of HBV capsid assembly inhibitor", Journal of Viral Hepatitis, vol. 21: pp. 843-852 (2014).
Cowie, et al., "Mortality due to viral hepatitis in the Global Burden of Disease Study 2010: new evidence of an urgent global public health priority demanding action", Antiviral Therapy,vol. 18: pp. 953-54 (2013).
Delaney, et al., "Phenylpropenamide Derivatives AT-61 and AT-130 Inhibit Replication of Wild-Tpe and Lamivudine-Resistant Strains of Hepatitis B Virus in Vitro", Antimicrobial Agents and Chemotherapy, vol. 46(9): pp. 3057-3060 (Sep. 2002).
Deres, et al., "Inhibition of Hepatitis B Virus Replication by Drug-Induced Depletion of Nucleocpsids", Science, vol. 299: pp. 893-96 (Feb. 7, 2003).
Duan, et al., 2-Phenylquinazolin-4(3H)-one, a class of potent PDE5 Inhibitors with High Selectivity Versus PDE6, Bioorganic & Medicinal Chemistry Letter, vol. 19: pp. 2777-2779 (2009).
El-Sayed, et al, "A Comparative Study of the 1-9 Reactions of Thiophene-2-Carboxanilides and related compounds", Chemistry of Heterocyclic Compounds, vol. 34 (7): pp. 796-801 (Jan. 1, 1998). (XP000881506).
El-Sharief et al. "Synthesis of Different Types of Chlorinated Sulphonamides with Expected Insecticidal and Bactencidal Activities", Proceedings of the Indian National Science Academy, vol. 53(1): pp. 179-188 (1987).
Ermann, et al., "Arylsulfonamide CB2 Receptor Agonists: SAR and Optimization of CB2 Selectivity", Bioorganic & Medicinal Chemistry Letters, vol. 18: pp. 1725-1729 (2008).
Gane, et al., "Phase 1a Safety and Pharmacokinetics of NVR3-778, a Potential First-in-class HBV Core Inhibitor", The Abstract of the Liver Meeting 2014 (AASLD), Abstract LB-19, Boston, MA (2014).
Geies, et al., Synthesis of some Thiazolo[3,2-a]Pyrimidines, Phosphorus, Sulfur and Silicon, vol. 56: pp. 87-93 (1991).
Goodman, et al, "Discovery of potent, selective sulfonylfuran urea endothelial lipase inhibitors", Bioorganic & Medicinal Chemistry Letters, vol. 19:pp. 27-30 (2009).
Guo, et al., "HBc binds to the CpG island of HBV cccDNA and promotes an epigenetic permissive state", Epigenetics, vol. 6 (6): pp. 720-26 (Jun. 2011).
Hogan, et al., "Aqueous Process Chemistry: The Preparation of Aryl Sulfonyl Chlorides", Organic Process Research & Development, vol. 13: pp. 875-879 (2009).
Huang, et al., "Blockage of HBV Virus Replication and Inhibition of cccDNA Establishment by Core Protein Allosteric Modifiers (CpAMs)", Hepatology, vol. 64 (1 Suppl): pp. 937A-38A, ( Oct. 2016).
Jayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).
Katen, et al., "Assembly-Directed Antivirals Differentially Bind Quasiequivalend Pockets to Modify Hepatitis B Virus Capsid Tertiary and Quaternary Structure, Structure", vol. 21: pp. 1406-1416 (Aug. 6, 2013).
Kim, et al, "Discovery of novel HCV polymerase inhibitors using pharmacophore-based virtual screening", Bioorganic & Medicinal Chemistry Letters, vol. 21 (11): pp. 3329-3334 (Apr. 4, 2011). (XP028211474).
Klumpp, et al., "High Antiviral Activity of the HBV Core Inhibitor NVR 3-778 in the Humanized Upnscid Mouse Model", Journal of Hepatology, vol. 62:p. S235 (2015).
Klumpp, et al., "High-resolution crystal structure of a hepatitis B virus replication inhibitor bound to the viral core protein", PNAS, vol. 112(49): pp. 15196-15201 (Dec. 8, 2015).

Lam, et al., "HBV Corre Assembly Modulators Block Antigen Prouction When Present During Infection, but not during Persistent Infection", The Abstracts of the Liver Meeting 2016 (AASLD), vol. 64 (1 Suppl.), Boston, MA (Oct. 2016).
Lam et al., "Inhibition of Hepatitis B Virus Replication by the HBV Core Inhibitors NVR3-778", The Abstract of the Liver Meeting 2015 (AASLD), Abstract 33: p. 223A, San Francisco, CA (Oct. 2015).
Lam, et al., "Serum HBV RNA as a Pharmacodynamic (PD) Marker of HBV Treatment Response to Core Assembly Modulator NVR 3-778 and Pegylate-Interferon Alpha", Poster Presented in the AASLD/EASL—HBV Treatment Endpoints Workshop, Poster No. 3774, Alexandria, VA (Sep. 9, 2016).
Lambeng, et al, "Arylsulfonamides as a new class of cannabinoid CB1 receptor ligands:identification of a lead and Initial SAR studies", Bioorganic & Medicinal Chemistry Letters, vol. 17(1) pp. 272-277 (Dec. 22, 2006).
Lau, et al., "Peginterferon Alfa-2a, Lamivudine, and the Combination for HBeAg-Positive Chronic Hepatitis B", New England Journal of Medicine, vol. 352(26): pp. 2682-2695 (Jun. 30, 2005).
Li Bing, et al., Progress in anti Hepatitus B Virus non-nucleosidic drugs, J. Liaoning Medical University, vol. 30(1): pp. 88-91 (Dec. 31, 2009).
Liaw, et al., "Hepatitis B Virus Infection", Lancet, vol. 373: pp. 582-592 (Feb. 14, 2009).
Lucifora, et al., "Specific and Nonhepatotoxic Degradation of Nuclear Hepatitis B Virus cccDNA", Science, vol. 343: pp. 1221-1228 (Mar. 14, 2014).
Mabrouk, "Discovering best candidates for Hepatocellular Carcinoma (HCC) by in-silico techniques and tools", Int. J. Bioinformatics Research and Applications, vol. 8 (1/2): pp. 141-152 (Jan. 1, 2012).
Manzoor, et al., "Hepatitis B Virus Therapy: What's the future holding for us?", World Journal of Gastroenterology, vol. 21(44): pp. 12558-12575 (Nov. 28, 2015).
Marcellin, et al., "Peginterferon Alfa-2a Alone, Lamivudine Alone, and the Two in Combination in Patients with HBeAg-Negative Chronic Hepatitis B", The New England Journal of Medicine, vol. 351(12): pp. 1206-17 (Sep. 16, 2014).
Mohamed, et al, "Synthesis of Different Types of Chlorinated Sulphonamides with Expected Insecticidal and Antimicrobial Activities", Acta Pharmaceutica Jugoslavica, vol. 36 (3): pp. 301-310, (1986).
Online Registr Via STN, Dec. 28, 2008, RN 1090750-88-1.
Online Registry Via STN Aug. 6, 2012. RN 1386725-02-5.
Online Registry Via STN Jun. 7, 2012, RN 1375909-37-7.
Online Registry Via STN Oct. 10, 2001, RN 361373-90-2.
Online Registry Via STN Aug. 13, 2012, RN 1390500-09-0.
Online Registry Via STN Jan. 16, 2001, RN 314043-17-9.
Online Registry Via STN 2010, RN 1253220-91-5.
Online Registry Via STN, Jan. 24, 2008, RN 296790-26-6.
Online Registry Via STN, Feb. 2, 2007, RN 9019040-48-5.
Online Registry Via STN, May 6, 2011, RN 1291044-81-9.
Online Registry Via STN, Oct. 7, 2008, RN 1057788-44-9.
Online Registry Via STN, Oct. 7, 2008, RN 1057871-39-2.
Online Registry Via STN, Jan. 9, 2001, RN 313253-89-3.
Online Registry Via STN, Mar. 10, 2010, RN 1208400-27-4.
Online Registry Via STN, Feb. 15, 2007, RN 921179-95-5.
Online Registry Via STN, Aug. 15, 2011, RN 1317923-24-2.
Online Registry Via STN, Aug. 15, 2011, RN 1318022-74-0.
Online Registry Via STN, Mar. 17, 2003, RN 499189-09-2.
Online Registry Via STN, May 18, 2011, RN 1296380-95-4.
Online Registry Via STN, Oct. 18, 2000, RN 296894-70-7.
Online Registry Via STN, Sep. 20, 2013, RN 1452780-00-5.
Online Registry Via STN, Apr. 24, 2002, RN 406926-60-1.
Patani, et al., "Bioisoterism: a rational Approach in Drug Design", Chem. Rev., vol. 96: pp. 3147-3176 (1996).
Patel, et al., "Synthesis N-Ethylpiperazinyl Sulfonyl Group Incorporated Benzamides", Indian Journal of Heterocyclic Chemistry, vol. 15: pp. 201-02 (Oct.-Dec. 2005).

(56) References Cited

OTHER PUBLICATIONS

Qiu et al., "Design and Synthesis of Orally Bioavailable 4-Methyl Heteroaryldihydropyrimidine Based Hepatitis B Virus (HBV) Capsid Inhibitors", Journal of Medicinal Chemistry, vol. 59: pp. 7651-7666, (2016).
Schroder, et al., "Arzneimittelchemie Passage", Arzneimittelchemei Grundlagen Nerven Musklen and Gewebe Gewebe, vol. XX (XX): pp. 30-33 (Jan. 1, 1976).
Shi, et al., "NMR-spectroscopy-based metanonomic approach to the analysis of Bay41-4109, a novel anti-HBV compound, induced hepatotoxcity in rats", Toxicology Letters, vol. 173: pp. 161-167 (2007).
Stalder, et al, "Selective antagonists of mouse trace amine-associated receptor 1 (mTAAR1): Discovery of EPPTB (RO5212773)", Bioorganic & Medicinal Chemistry Letters, vol. 21: pp. 1227-1231 (Dec. 21, 2010).
Stray, et al., "A Heteroaryldihydropyrimidine Activates and Can Misdirect Hepatitis B Virus Capsid Assembly", PNAS, vol. 102(23): pp. 8138-8143 (Jun. 7, 2005).
Stray, et al., "Bay 41/4109 has multiple effects on Hepatitis B virus capsid assembly", Journal of Molecular Recognition,vol. 19: pp. 542-48 (2006).
Tan, et al., Genetically Altering the Thermodynamics and Kinetics of Hepatitis B Virus Capsid Assembly has Profound Effects on Virus Replication in Cell Culture, Journal of Virology, vol. 87(6): pp. 3208-3216 (Mar. 2013).
Taylor, et al., "A Brain-Permeable Small Molecule Reduces Neuronal Cholesterol by Inhibiting Activity of Sirtuin 2 Deacetylase", ASC Chemical Biology, vol. 6: pp. 540-546 (2011).
The Merk Index "Infliximab", An Encyclopedia of Chemicals, Drugs and Biologicals, 14th Ed., p. 924 (2013).
The Merk Index, "Zidovudine", An Encyclopedia of Chemicals, Drugs and Biologicals, 14th Ed., p. 1885 (2013).
Thompson et al., "Toll-like receptors, RIG-I-like RNA Helicases and the Antiviral Innate Immune Response", Immunology and Cell Biology, vol. 85: pp. 435-445 (2007).
Wang, et al "In vitro inhibition of HBV replication by a novel compound, GLS4, and its efficacy against adefovir-dipovoxil-resistant HBV mutations", Antiviral Therapy, vol. 17:pp. 793-803 (2012).
Wang, et al, "Serum hepatitis B virus RNS is encapsidated pregenome RNA that may be associated with persistence of viral infection and rebound", Journal of Hepatology, vol. 65: pp. 700-710(2016).
Wang, et al, "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Watanabe, et al, "Ortho lithiation of N,N-dimethylbenzenesulfunamide by n-butyllithium. Condensation with electrophilic compounds", Candian Journal of Chemistry, vol. 47: pp. 1543-1546 (Oct. 30, 1968).
West, "Chapter 10 Solid Solutions", Solid State Chemistry and Its Applications, John Wiley & Sons, pp. 33-36 (1984).
Wu, et al, "Preclinical Characterization of GLS4, an Inhibitor of Hepatitis B Virus Core Particle Assembly", Antimicrobial Agents and Chemotherapy, vol. 57(11): pp. 5344-5354 (Nov. 2013).
Yang, et al., "Effects of a Hepatitis B Virus Inhibitor, NZ-4, on Capsid Formation", Antiviral Research, vol. 125: pp. 25-33 (2016).
Yang, et al., "Isothiafludine, a novel non-nucleoside compound inhibits hepatitis B virus replication through blocking pregenomic RNA encapsidation", Acta Pharmacologica Sinica, vol. 35: pp. 410-418 (2014).
Yarmolchuk et al., "Synthesis of beta-fluoro-beta-proline", Tetrahedron Letters, vol. 52: pp. 1300-02, (2011).
Yogaratnam, et al., "Safety, Tolerability and Pharmacokentics of JNJ 56136379, a Novel HBV Capsid Assembly Modulator in Healthy Subjects", The Abstracts of the Liver Meeting 2016 (AASLD), Abstract 1881: pp. 930A-31A, Boston, MA (Oct. 2016).
Yuen, et al, "ARC-520 Produces Deep and Durable Knockdown of Viral Antigen and DNA in Phase II Study in Patients with Chronic Hepatitis B", The Abstracts of the Liver Meeting 2015, Abstract LB-10, pp. 1385A-1386A, San Francisco, CA (Oct. 2015).
Yuen, et al, "NVR 3-778, a first-in-class HBV core inhibitor, alone and in combination with PEG-Interferon (PEGIFN), In treatment-naive HBEAG-positive patients: early reductions in HBV DNA and HBEAG", The Abstracts of the International Liver Congress (EASL), Abstract LB-06: pp. S210-S211 (Oct. 2016).
Zhang, et al., "A Potent Small Molecule Inhibits Polyglutamine Aggregation in Huntington's Disease Neurons and Suppresses Neurodegeneration in Vivo", PNAS, vol. 102 (3): pp. 892-897 (2005).
Zhang, Xiaoqian, A potent small molecule inhibits polyglutamine aggregation in Hungtintores disease neurons and suppress neurodegeneration in vivo, Proceedings of the national academy of sciences, Jan. 18, 2005, pp. 892-897, vol. 102(3), PNAS.
Zlotnick, et al., "Core Protein: A pleiotropic Keystone in the HBV Lifecycle", Antiviral Research, vol. 121: pp. 82-93 (2015).
Zoulim, et al, "Current Treatments for Chronic Hepatitis B Virus Infections", Current Opinion in Virology, vol. 18: pp. 109-116 (2016).
Foley, "An Effecient Synthesis of 2-Chloro-3-carboethoxy or 2-Chloro-3-cyano- 4,5-disubstituted and 5-substituted Pyrroles", Tetrahedron Letters, vol. 35(33): pp. 5989-5992, (1994).
Gang Liu et al, discovery of Highly Potent and Selective Pan-Aurora Kinase Inhibitors with Enhanced in Vivo Antitumor Therapeutic Index, Journal of Medicinal chemistry, Mar. 1, 2012, pp. 3250-3260, vol. 55.
Geng et al, "Small-Molecule Inhibitors for the Treatment of Hepatitis B Virus Documented in Patents", Mini-Reviews in Medicinal Chemistry, Apr. 1, 2013, pp. 749-776 (XP055105561-XP009176654), vol. 13.
Hughes, et al., "Hepatitis Delta Virus", the Lancet, vol. 378: pp. 73-85, (Jul. 2, 2011).
Qidong You et al, Pharmaceutical Chemistry, Chemical Industry Press, Jan. 31, 2014, pp. 32-33.
Qiu, et al, "Antihepatitis B therapy: a review of current medications and novel small molecule inhibitors", Fudamental & Clinical Pharmacology, pp. 1-18 (XP055105340) (Nov. 1, 2013).
Weber, et al, "Inhibition of human hepatitis B virus (HBV) by a novel non-nucleosidic compound in a transgenic mouse model", Antiviral Research, vol. 54 (2): pp. 69-78 (Jan. 1, 2002).
Carver, et al, Polyfunctionalisation of Imidazole via Sequential Imidazolyl Anion Formation, Tetrahedron, 1997, pp. 14481-14496, vol. 53 Issue 42.
Online Registry Via STN, Aug. 13, 2012, RN 1390589-54-4.
Online Registry Via STN Feb. 2, 2007, RN 919040-39-4.
Online Registry Via STN Feb. 2, 2007, RN 919040-53-2.
Online Registry Via STN Feb. 2, 2007, RN 919040-55-4.
Online Registry Via STN Dec. 8, 2012, RN 1389720-57-3.
Online Registry Via STN Dec. 11, 2007, RN 957487-45-5.
Online Registry Via STN Dec. 11, 2007, RN 957487-49-9.
Online Registry Via STN Aug. 12, 2012, RN 1389686-79-6.
Online Registry Via STN Mar. 17, 2013, RN 1424462-66-7.
Online Registry Via STN Sep. 18, 2012, RN 1394742-82-5.
Online Registry Via STN, Feb. 2, 2007, RN 919040-37-2.
Online Registry Via STN, Sep. 6, 2011, RN 1328738-57-3.
Online Registry Via STN, Apr. 28, 2011, RN 1286906-97-5.
Online Registry Via STN. Apr. 19, 2008, RN 930914-71-9.
Horig, et al., from bemnch to Clinic and back : Perspective on the 1st IQPC translational Research conference, Journal of translational medicine, Dec. 20, 2004, pp. 1-8, vol. 2 Issue 44.
Mohebbi, et al., An Overview of Hepatitis B Virus Surface Antigen Secreation Inhibitors, Frontier in Microbiology, Apr. 5, 2018, pp. 1-9, vol. 9.
Schafer, et al, Failure Is option: learning from unsuccessful proof-ofconcepts trails, Drug Discovery Today, 2008, pp. 913-916, vol. 13 Issue 21/22.
Nijampatnam et al, "Recent advances in the development of HBV capsid assembly modulators", Current Opinion in Chemical Biology, vol. 50; pp. 73-79 (2019).
Online Registry Via STN Feb. 3, 2012, RN 1359583-56-4.
Online Registry Via STN Feb. 3, 2012, RN 1359596_55_6.

(56) References Cited

OTHER PUBLICATIONS

Basarab et al., Design of Helicobacter pylon glutamate racemase inhibitors as selective antibacterial agents : a novel pro-drug approach to increase exposure, Bioorg. Med. Chem. Lett., vol. 18; pp. 4716-4722 (Aug. 15, 2008).
Moranta et al., "Synthesis and properties of 1-alkyl-2-methyl-3-sulfonylpyrroles and 1-alkyl-2-methyl-3-sulfonylpyrrole-5-carboxylic acid derivates", J. Chem. Soc. Perkin Trans., vol. 19: pp. 3285-3292 (1998).
Online Registry Via STN Aug. 24, 2019, RN 1275589-30-4.
Online Registry Via STN Aug. 24, 2019, RN 311800-19-8.
Online Registry Via STN Aug. 24, 2019, RN 312756-74-4.
Online Registry Via STN Aug. 24, 2019, RN 312756-75-5.
Online Registry Via STN Aug. 24, 2019, RN 313225_30_8.
Online Registry Via STN Aug. 24, 2019, RN 313254-27-2.
Online Registry via STN Oct. 10, 1987, RN 110644-97-8.
Online Registry via STN Jul. 16, 1992, RN 142428-99-7.
Online Registry via STN Mar. 18, 2010 , RN 1211415-65-4.

SULPHAMOYLPYRROLAMIDE DERIVATIVES AND THE USE THEREOF AS MEDICAMENTS FOR THE TREATMENT OF HEPATITIS B

CROSS REFERENCE TO RELATED APPLICATIONS

This application is a 35 U.S.C. § 371 nationalization of PCT application PCT/EP2015/052389 filed Feb. 5, 2015, which claims priority to European patent application EP14154167.2 filed Feb. 6, 2014, European patent application EP14169438.0 filed May 22, 2014, European patent application EP14177505.6 filed Jul. 17, 2014, and European patent application EP14193926.4 filed Nov. 19, 2014, each of which are incorporated herein by reference in its entirety.

BACKGROUND ART

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

HBV has caused epidemics in parts of Asia and Africa, and it is endemic in China. HBV has infected approximately 2 billion people worldwide of which approximately 350 million people have developed chronic infections. The virus causes the disease hepatitis B and chronic infection is correlated with a strongly increased risk for the development cirrhosis and hepatocellular carcinoma.

Transmission of hepatitis B virus results from exposure to infectious blood or body fluids, while viral DNA has been detected in the saliva, tears, and urine of chronic carriers with high titer DNA in serum.

An effective and well-tolerated vaccine exists, but direct treatment options are currently limited to interferon and the following antivirals; tenofovir, lamivudine, adefovir, entecavir and telbivudine.

In addition, heteroaryldihydropyrimidines (HAPs) were identified as a class of HBV inhibitors in tissue culture and animal models (Weber et al., Antiviral Res. 54: 69-78).

WO2013/006394, published on Jan. 10, 2013, relates to a subclass of Sulphamoyl-arylamides active against HBV.

WO2013/096744, published on Jun. 26, 2013 relates to compounds active against HBV.

Amongst the problems which HBV direct antivirals may encounter are toxicity, mutagenicity, lack of selectivity, poor efficacy, poor bioavailability, low solubility and difficulty of synthesis.

There is a need for additional HBV inhibitors that may overcome at least one of these disadvantages or that have additional advantages such as increased potency or an increased safety window.

DESCRIPTION OF THE INVENTION

The present invention relates to a compound of Formula (A)

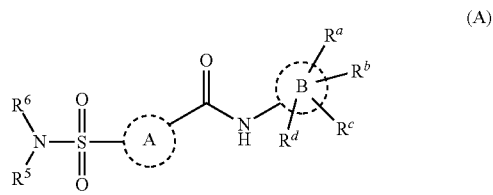

(A)

or a stereoisomer or tautomeric form thereof, wherein:

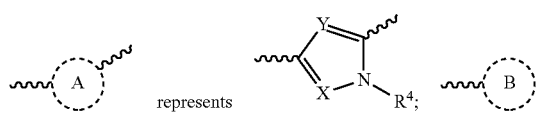

represents a 6 membered heteroaryl containing one nitrogen atom;
X represents $CR^7$;
Y represents $CR^8$;
$R^a$, $R^b$, $R^c$ and $R^d$ are independently selected from the group consisting of Hydrogen, Fluoro, Bromo, Chloro, —$CHF_2$, —$CF_2$-methyl, —$CH_2F$, —$CF_3$, —$OCF_3$, —CN, $C_3$-$C_4$cycloalkyl and —$C_1$-$C_4$alkyl;
$R^4$ is Hydrogen, —$C_1$-$C_3$alkyl or $C_3$-$C_4$cycloalkyl;
$R^5$ is Hydrogen;
$R^6$ is selected from the group consisting of $C_2$-$C_6$alkyl, a 3-7 membered saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, and $C_1$-$C_4$alkyl optionally substituted with one or more Fluoro and/or —OH;
$R^7$ and $R^8$ independently represent hydrogen, methyl, —CN, Fluoro, Bromo or Chloro;
or a pharmaceutically acceptable salt or a solvate thereof.

The invention further relates to a pharmaceutical composition comprising a compound of Formula (A), and a pharmaceutically acceptable carrier.

The invention also relates to the compounds of Formula (A) for use as a medicament, preferably for use in the prevention or treatment of an HBV infection in a mammal.

In a further aspect, the invention relates to a combination of a compound of Formula (A), and another HBV inhibitor.

Definitions

The term "heteroaryl" means a monocyclic- or polycyclic aromatic ring comprising carbon atoms, hydrogen atoms, and one or more heteroatoms, preferably, 1 to 3 heteroatoms, independently selected from nitrogen, oxygen, and sulfur, preferably nitrogen. As is well known to those skilled in the art, heteroaryl rings have less aromatic character than their all-carbon counter parts. Thus, for the purposes of the present invention, a heteroaryl group need only have some degree of aromatic character Illustrative examples of heteroaryl groups according to the invention include optionally substituted pyridinyl.

The terms "$C_{1-x}$alkyl" and $C_1$-$C_x$alkyl can be used interchangeably.

The term "$C_{1-3}$alkyl" as a group or part of a group refers to a hydrocarbyl radical of Formula $C_nH_{2n+1}$ wherein n is a number ranging from 1 to 3. In case $C_{1-3}$alkyl is coupled to a further radical, it refers to a Formula $C_nH_{2n}$. $C_{1-3}$alkyl groups comprise from 1 to 3 carbon atoms, more preferably 1 to 2 carbon atoms. $C_{1-3}$alkyl includes all linear, or branched alkyl groups with between 1 and 3 carbon atoms, and thus includes such as for example methyl, ethyl, n-propyl, and i-propyl.

$C_{1-4}$alkyl as a group or part of a group defines straight or branched chain saturated hydrocarbon radicals having from 1 to 4 carbon atoms such as the group defined for $C_{1-3}$alkyl and butyl and the like.

$C_{1-6}$alkyl and $C_{2-6}$alkyl as a group or part of a group defines straight or branched chain saturated hydrocarbon radicals having from 1 to 6 carbon atoms, or from 2 to 6 carbon atoms such as the groups defined for $C_{1-4}$alkyl and pentyl, hexyl, 2-methylbutyl and the like.

The term "$C_{1-3}$alkyloxy" as a group or part of a group refers to a radical having the Formula $-OR^c$ wherein $R^c$ is $C_{1-3}$alkyl. Non-limiting examples of suitable $C_{1-3}$alkyloxy include methyloxy (also methoxy), ethyloxy (also ethoxy), propyloxy and isopropyloxy.

As used herein, the term "3-7 membered saturated ring" means saturated cyclic hydrocarbon (cycloalkyl) with 3, 4, 5, 6 or 7 carbon atoms and is generic to cyclopropyl, cyclobutyl, cyclopentyl, cyclohexyl and cycloheptyl.

Such saturated ring optionally contains one or more heteroatoms, such that at least one carbon atom is replaced by a heteroatom selected from N, O and S, in particular from N and O. Examples include oxetane, tetrahydro-2H-pyranyl, piperidinyl, tetrahydrofuranyl, morpholinyl, thiolane 1,1-dioxide and pyrrolidinyl. Preferred are saturated cyclic hydrocarbon with 3 or 4 carbon atoms and 1 oxygen atom. Examples include oxetane, and tetrahydrofuranyl.

It should be noted that different isomers of the various heterocycles may exist within the definitions as used throughout the specification. For example, pyrrolyl may be 1H-pyrrolyl or 2H-pyrrolyl.

The term halo and halogen are generic to Fluoro, Chloro, Bromo or Iodo. Preferred halogens are Bromo, Fluoro and Chloro.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

The term

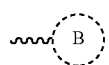

or heteroaryl B represents a 6 membered heteroaryl containing one nitrogen atom. Preferred are compounds wherein a carbon atom of such 6 membered heteroaryl B is connected with the nitrogen (*) atom depicted in Formula (A) below.

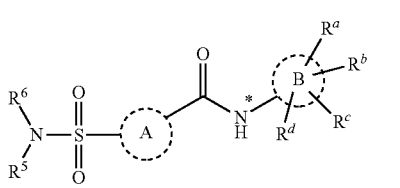

Positions indicated on heteroaryl B (e.g. ortho, meta and/or para) are indicated relative to the bond connecting heteroaryl B to the main structure. An example with regard to the position of meta $R^a$, location is indicated relative to the nitrogen (*) connected to the main structure as shown in Formula (IC).

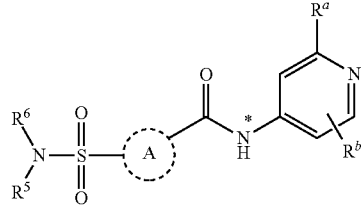

When any variable (e.g. halogen or $C_{1-4}$alkyl) occurs more than one time in any constituent, each definition is independent.

For therapeutic use, the salts of the compounds of Formula (A) are those wherein the counter ion is pharmaceutically or physiologically acceptable. However, salts having a pharmaceutically unacceptable counter ion may also find use, for example, in the preparation or purification of a pharmaceutically acceptable compound of Formula (A). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The term "salts" also comprises the hydrates and the solvent addition forms that the compounds of the present invention are able to form. Examples of such forms are e.g. hydrates, alcoholates and the like.

The present compounds may also exist in their tautomeric forms. For example, tautomeric forms of amide ($-C(=O)-NH-$) groups are iminoalcohols ($-C(OH)=N-$). Tautomeric forms, although not explicitly indicated in the structural formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The stereomeric forms of Formula (A) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of Hydrogen include tritium and deuterium. Isotopes of carbon include C-13 and C-14.

DETAILED DESCRIPTION OF THE INVENTION

Whenever used hereinafter, the term "compounds of Formula (A)",

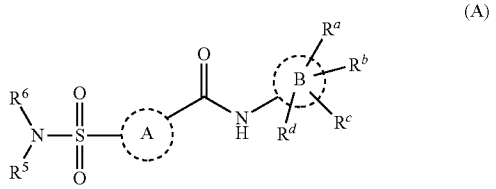

(A)

or "the present compounds" or similar term is meant to include the compounds of general Formula (A), Formula (I), Formula (IA), Formula (IB), Formula (IC), Formula (ID), Formula (IE), salts, stereoisomeric forms and racemic mixtures or any subgroups thereof

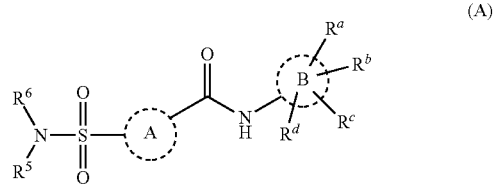

(A)

The present invention relates to compounds of Formula (A)
or a stereoisomer or tautomeric form thereof, wherein:

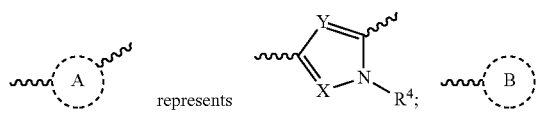

represents a 6 membered heteroaryl containing one nitrogen atom;
X represents $CR^7$;
Y represents $CR^8$;
$R^a$, $R^b$, $R^c$ and $R^d$ are independently selected from the group consisting of Hydrogen, Fluoro, Bromo, Chloro, —$CHF_2$, —$CF_2$-methyl, —$CH_2F$, —$CF_3$, —$OCF_3$, —CN, $C_3$-$C_4$cycloalkyl and —$C_1$-$C_4$alkyl;
$R^4$ is Hydrogen, —$C_1$-$C_3$alkyl or $C_3$-$C_4$cycloalkyl;
$R^5$ is Hydrogen;
$R^6$ is selected from the group consisting of $C_2$-$C_6$alkyl, a 3-7 membered saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, and $C_1$-$C_4$alkyl optionally substituted with one or more Fluoro and/or —OH;
$R^7$ and $R^8$ independently represent hydrogen, methyl, —CN, Fluoro, Bromo or Chloro;
or a pharmaceutically acceptable salt or a solvate thereof.

In one aspect, the present invention relates to a compound of Formula (I)

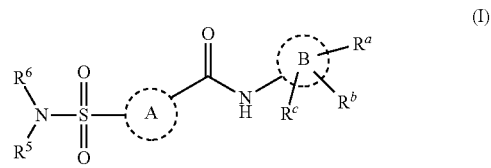

(I)

or a stereoisomer or tautomeric form thereof, wherein:

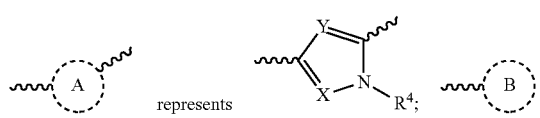

represents a 6 membered heteroaryl containing one nitrogen atom;

X represents $CR^7$;
Y represents $CR^8$;
$R^a$, $R^b$ and $R^c$ are independently selected from the group consisting of Hydrogen, Fluoro, Bromo, Chloro, —$CHF_2$, —$CF_2$-methyl, —$CH_2F$, —$CF_3$, —$OCF_3$, —CN, $C_3$-$C_4$cycloalkyl and —$C_1$-$C_4$alkyl;
$R^4$ is Hydrogen, —$C_1$-$C_3$alkyl or $C_3$-$C_4$cycloalkyl;
$R^5$ is Hydrogen;
$R^6$ is selected from the group consisting of $C_2$-$C_6$alkyl, a 3-7 membered saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, and $C_1$-$C_4$alkyl optionally substituted with one or more Fluoro and/or —OH;
$R^7$ and $R^8$ independently represent hydrogen, methyl, —CN, Fluoro, Bromo or Chloro;
or a pharmaceutically acceptable salt or a solvate thereof.

In another aspect, the present invention relates to a compound of Formula (ID)

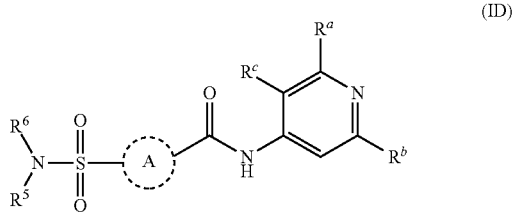

(ID)

or a stereoisomer or tautomeric form thereof, wherein:

X represents $CR^7$;
Y represents $CR^8$;
$R^a$ is selected from the group consisting of Fluoro, Bromo, Chloro, —$CHF_2$, —$CF_2$-methyl, —$CH_2F$, —$CF_3$, —$OCF_3$, —CN, $C_3$-$C_4$cycloalkyl and —$C_1$-$C_4$alkyl;
$R^b$ and $R^c$ are independently Hydrogen or Fluoro;
$R^4$ is Hydrogen, —$C_1$-$C_3$alkyl or $C_3$-$C_4$cycloalkyl;
$R^5$ is Hydrogen;
$R^6$ is selected from the group consisting of $C_2$-$C_6$alkyl, a 3-7 membered saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, and $C_1$-$C_4$alkyl optionally substituted with one or more Fluoro and/or —OH;
$R^7$ and $R^8$ independently represent hydrogen, methyl, —CN, Fluoro or Chloro;
or a pharmaceutically acceptable salt or a solvate thereof.

In another aspect, the present invention relates to a compound with Formula (IE)

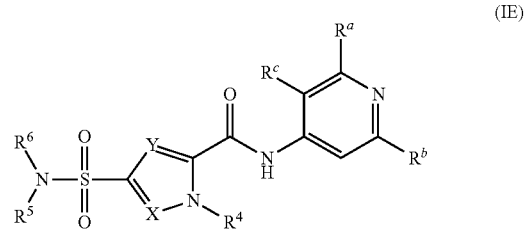

(IE)

or a stereoisomer or tautomeric form thereof, wherein:
X represents $CR^7$;
Y represents $CR^8$;
$R^a$ is selected from the group consisting of Fluoro, Bromo, Chloro, —$CHF_2$, —$CF_2$-methyl, —$CH_2F$, —$CF_3$, —$OCF_3$, —CN, $C_3$-$C_4$cycloalkyl and —$C_1$-$C_4$alkyl;
$R^b$ and $R^c$ are independently Hydrogen or Fluoro;
$R^4$ is Hydrogen, —$C_1$-$C_3$alkyl or $C_3$-$C_4$cycloalkyl;
$R^5$ is Hydrogen;
$R^6$ is selected from the group consisting of $C_2$-$C_6$alkyl, a 3-7 membered saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, and $C_1$-$C_4$alkyl optionally substituted with one or more Fluoro and/or —OH;
$R^7$ and $R^8$ independently represent hydrogen, methyl, —CN, Fluoro or Chloro;
or a pharmaceutically acceptable salt or a solvate thereof.

In a further aspect, the present invention relates to a compound of Formula (I)

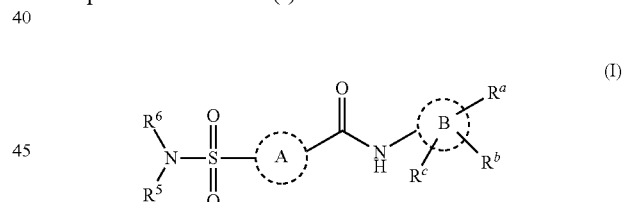

(I)

or a stereoisomer or tautomeric form thereof, wherein:

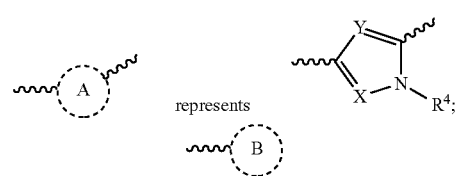

represents a 6 membered heteroaryl containing one nitrogen atom;
X represents $CR^7$;
Y represents $CR^8$;
$R^a$, $R^b$ and $R^c$ are independently selected from the group consisting of Hydrogen, Fluoro, Bromo, Chloro, —$CHF_2$, —$CF_2$-methyl, —$CH_2F$, —$CF_3$, —$OCF_3$, —CN, $C_3$-$C_4$cycloalkyl and —$C_1$-$C_4$alkyl;

$R^4$ is Hydrogen or —$C_1$-$C_3$alkyl, $C_3$-$C_4$cycloalkyl;
$R^5$ is Hydrogen;
$R^6$ is selected from the group consisting of $C_2$-$C_6$alkyl, a 3-7 membered saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, and $C_1$-$C_4$alkyl optionally substituted with one or more Fluoro;
$R^7$ and $R^8$ independently represent hydrogen, methyl, —CN, Fluoro or Chloro;
or a pharmaceutically acceptable salt or a solvate thereof.

In a further aspect, the present invention relates to a compound of Formula (IA),

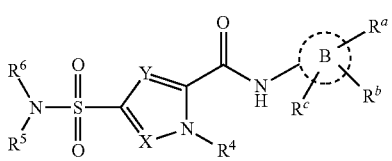

(IA)

or a stereoisomer or tautomeric form thereof, wherein:

represents a 6 membered heteroaryl containing one nitrogen atom;
X represents $CR^7$;
Y represents $CR^8$;
$R^a$, $R^b$ and $R^c$ are independently selected from the group consisting of Hydrogen, Fluoro, Bromo, Chloro, —$CHF_2$, —$CF_2$-methyl, —$CH_2F$, —$CF_3$, —$OCF_3$, —CN, $C_3$-$C_4$cycloalkyl and —$C_1$-$C_4$alkyl;
$R^4$ is Hydrogen or —$C_1$-$C_3$alkyl, $C_3$-$C_4$cycloalkyl;
$R^5$ is Hydrogen;
$R^6$ is selected from the group consisting of $C_2$-$C_6$alkyl, a 3-7 membered saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, and $C_1$-$C_4$alkyl optionally substituted with one or more Fluoro;
$R^7$ and $R^8$ independently represent hydrogen, methyl, —CN, Fluoro or Chloro;
or a pharmaceutically acceptable salt or a solvate thereof.

In another embodiment, the present invention relates to a compound of Formula (IB),

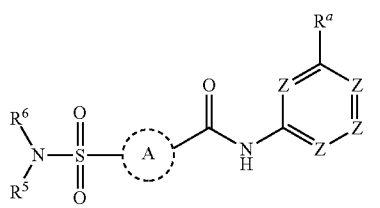

(IB)

or a stereoisomer or tautomeric form thereof, wherein:

 represents 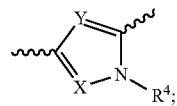

X represents $CR^7$;
Y represents $CR^8$;
Each Z represents $CR^9$ or N, wherein only one Z is N, and wherein $R^9$ is Fluoro or hydrogen;
$R^a$ is selected from the group consisting of Fluoro, Bromo, Chloro, —$CHF_2$, —$CF_2$-methyl, —$CH_2F$, —$CF_3$, —$OCF_3$, —CN and —$C_1$-$C_4$alkyl;
$R^4$ is Hydrogen or —$C_1$-$C_3$alkyl;
$R^5$ is Hydrogen;
$R^6$ is selected from the group consisting of $C_2$-$C_6$alkyl, a 3-7 membered saturated ring optionally containing one or more heteroatoms each independently selected from the group consisting of O, S and N, such 3-7 membered saturated ring or $C_2$-$C_6$alkyl optionally being substituted with one or more substituents each independently selected from the group consisting of Hydrogen, —OH, Fluoro, oxo, and $C_1$-$C_4$alkyl optionally substituted with one or more Fluoro;
$R^7$ and $R^8$ independently represent hydrogen, methyl, —CN, Fluoro or Chloro;
or a pharmaceutically acceptable salt or a solvate thereof.

In a further embodiment, the present invention relates to compounds of Formula (IC),

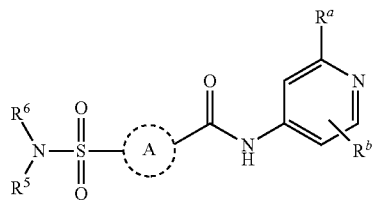

(IC)

or a stereoisomer or tautomeric form thereof:

 represents 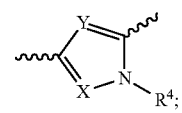

X represents $CR^7$;
Y represents $CR^8$;
$R^a$ and $R^b$ are independently selected from the group consisting of Hydrogen, Fluoro, Bromo, Chloro, —$CHF_2$, —$CF_2$-methyl, —$CH_2F$, —$CF_3$, —$OCF_3$, —CN, $C_3$-$C_4$cycloalkyl and —$C_1$-$C_4$alkyl;
$R^4$ is Hydrogen or —$C_1$-$C_3$alkyl, $C_3$-$C_4$cycloalkyl;
$R^5$ is Hydrogen;
$R^6$ is selected from the group consisting of $C_2$-$C_6$alkyl, a 3-7 membered saturated ring optionally containing one or more heteroatoms each independently selected from the group consisting of O, S and N, such 3-7 membered saturated ring or $C_2$-$C_6$alkyl optionally being substiselected from the group consisting of Hydrogen, —OH, Fluoro, oxo, and $C_1$-$C_4$alkyl optionally substituted with one or more Fluoro;

$R^7$ and $R^8$ independently represent hydrogen, methyl, —CN, Fluoro or Chloro;

or a pharmaceutically acceptable salt or a solvate thereof.

In one embodiment, each of $R^a$, $R^b$ and $R^c$ are independently selected from the group consisting of Hydrogen, Fluoro, Chloro —CN, —$CF_3$ and methyl. In one embodiment, $R^c$ is Hydrogen.

In one further embodiment, $R^6$ contains a 3-7 membered saturated ring optionally containing one oxygen, more specifically $R^6$ is a 4 membered saturated ring containing one oxygen, such 4 membered saturated ring optionally substituted with $C_1$-$C_4$alkyl.

In another embodiment, $R^6$ comprises a branched $C_3$-$C_6$alkyl optionally substituted with one or more Fluoro, or $R^6$ comprises a $C_3$-$C_6$cycloalkyl wherein such $C_3$-$C_6$cycloalkyl is substituted with one or more Fluoro or substituted with $C_1$-$C_4$ substituted with one or more Fluoro. More specifically, $R^6$ is a branched $C_3$-$C_6$alkyl substituted with one or more Fluoro.

In one embodiment, $R^8$ represents Fluoro or Chloro.

In yet another embodiment, compounds of the present invention are disclosed wherein $R^4$ is methyl or ethyl, preferably methyl.

Another embodiment of the present invention relates to those compounds of Formula (A), Formula (I), (IA), (IB), (IC), (ID), (IE) or any subgroup thereof as mentioned in any of the other embodiments wherein one or more of the following restrictions apply:
  (a) $R^4$ is $C_1$-$C_3$alkyl, preferably methyl; $R^6$ is selected from the group consisting of $C_2$-$C_6$alkyl optionally being substituted with one or more Fluoro.
  (b) $R^b$ is Hydrogen or Fluoro.
  (c) $R^b$ and $R^c$ are independently selected from Hydrogen or Fluoro and IV is selected from the group consisting of Fluoro, Chloro, —$CHF_2$, —$CF_3$, —CN and methyl.
  (d) $R^b$ and $R^c$ are independently selected from Hydrogen or Fluoro and IV is selected from the group consisting of Fluoro, Chloro, Bromo, —$CHF_2$, —$CF_3$, —CN and methyl.
  (e) $R^b$ and $R^c$ are both Hydrogen and IV is Chloro.
  (f) $R^8$ represent Fluoro or Chloro.
  (g) $R^6$ comprises a branched $C_3$-$C_6$alkyl optionally substituted with one or more Fluoro, or wherein $R^6$ comprises a $C_3$-$C_6$cycloalkyl wherein such $C_3$-$C_6$cycloalkyl is substituted with one or more Fluoro or substituted with $C_1$-$C_4$alkyl substituted with one or more Fluoro, or wherein $R^6$ comprises a $C_3$-$C_6$cycloalkyl optionally substituted with one or more Fluoro and/or substituted with $C_1$-$C_4$alkyl optionally substituted with one or more Fluoro.
  (h) $R^4$ is $C_1$-$C_3$alkyl, preferably methyl; $R^6$ is $C_2$-$C_6$alkyl optionally being substituted with one or more Fluoro or a $C_3$-$C_6$cycloalkyl wherein such $C_3$-$C_6$cycloalkyl is substituted with one or more Fluoro or substituted with $C_1$-$C_4$alkyl substituted with one or more Fluoro; and $R^7$ and $R^8$ independently represent hydrogen, Fluoro or Chloro.
  (i)

represents a 6 membered heteroaryl containing one nitrogen atom wherein a carbon atom of such 6 membered heteroaryl B is connected with the nitrogen (*) atom depicted in Formula (A) below

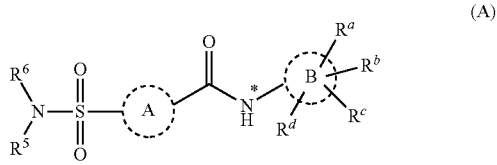

(A)

(j)

represents pyridyl.

Further combinations of any of the embodiments are also envisioned to be in the scope of the present invention.

Preferred compounds according to the invention are compound or a stereoisomer or tautomeric form thereof with a Formula as represented in the synthesis of compounds section and of which the activity is displayed in Table 1.

In a further aspect, the present invention concerns a pharmaceutical composition comprising a therapeutically or prophylactically effective amount of a compound of Formula (A) as specified herein, and a pharmaceutically acceptable carrier. A prophylactically effective amount in this context is an amount sufficient to prevent HBV infection in subjects being at risk of being infected. A therapeutically effective amount in this context is an amount sufficient to stabilize HBV infection, to reduce HBV infection, or to eradicate HBV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of Formula (A), as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of Formula (A) are active as inhibitors of the HBV replication cycle and can be used in the treatment and prophylaxis of HBV infection or diseases associated with HBV. The latter include progressive liver fibrosis, inflammation and necrosis leading to cirrhosis, end-stage liver disease, and hepatocellular carcinoma.

Due to their antiviral properties, particularly their anti-HBV properties, the compounds of Formula (A) or any subgroup thereof, are useful in the inhibition of the HBV replication cycle, in particular in the treatment of warm-blooded animals, in particular humans, infected with HBV, and for the prophylaxis of HBV infections. The present invention furthermore relates to a method of treating a warm-blooded animal, in particular human, infected by HBV, or being at risk of infection by HBV, said method comprising the administration of a therapeutically effective amount of a compound of Formula (A).

The compounds of Formula (A), as specified herein, may therefore be used as a medicine, in particular as medicine to treat or prevent HBV infection. Said use as a medicine or method of treatment comprises the systemic administration to HBV infected subjects or to subjects susceptible to HBV infection of an amount effective to combat the conditions associated with HBV infection or an amount effective to prevent HBV infection.

The present invention also relates to the use of the present compounds in the manufacture of a medicament for the treatment or the prevention of HBV infection.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of Formula (A) or any subgroup thereof, as specified herein with other anti-HBV agents. The term "combination" may relate to a product or kit containing (a) a compound of Formula (A), as specified above, and (b) at least one other compound capable of treating HBV infection (herein designated as anti-HBV agent), as a combined preparation for simultaneous, separate or sequential use in treatment of HBV infections. In an embodiment, the invention concerns combination of a compound of Formula (A) or any subgroup thereof with at least one anti-HBV agent. In a particular embodiment, the invention concerns combination of a compound of Formula (A) or any subgroup thereof with at least two anti-HBV agents. In a particular embodiment, the invention concerns combination of a compound of Formula (A) or any subgroup thereof with at least three anti-HBV agents. In a particular embodiment, the invention concerns combination of a compound of Formula (A) or any subgroup thereof with at least four anti-HBV agents.

The term anti-HBV agent also includes compounds that are therapeutic nucleic acids, antibodies or proteins either in their natural form or chemically modified and or stabilized. The term therapeutic nucleic acid includes but is not limited to nucleotides and nucleosides, oligonucleotides polynucleotides of which non limiting examples are antisense oligonucleotides, miRNA, siRNA, shRNA, therapeutic vectors and DNA/RNA editing components.

The term anti-HBV agent also includes compounds capable of treating HBV infection via immunomodulation. Examples of immunomodulators are interferon-α (IFN-α), pegylated interferon-α or stimulants of the innate immune system such as Toll-like receptor 7 and/or 8 agonists. One embodiment of the present invention relates to combinations of a compound of Formula (A), Formula (I), (IA), (IB), IC), (ID), (IE) or any subgroup thereof, as specified herein with an immunomodulating compound, more specifically a Toll-like receptor 7 and/or 8 agonist.

The combination of previously known anti-HBV agents, such as interferon-α (IFN-α), pegylated interferon-α, 3TC, adefovir or a combination thereof, and, a compound of Formula (A) or any subgroup thereof can be used as a medicine in a combination therapy.

Generic Synthesis:

The substituents represented by $R^{a,b,c,d}$ or $R^6$ in this general synthesis section are meant to include any substituent or reactive species that is suitable for transformation into any $R^{a,b,c,d}$ or $R^6$ substituent according to the present invention without undue burden for the person skilled in the art.

A possible synthesis of compound of general Formula (IA) is described in schemes 1, 2 and 3. Chlorosulfonation of a compound of general Formula (II), for example by treatment with chlorosulfonic acid at for example 0° C., if necessary, followed by quenching with water, results in compounds of general Formula (III). Compound (III) is reacted with an amine of general Formula (IV), for example in an organic solvent like $CH_2Cl_2$ in the presence of an organic base like triethylamine or DIPEA. The formed compound (V) is coupled with an amine of general Formula (VI) in the presence of an activating reagent like for example HATU and an organic base like triethylamine or DIPEA, resulting in a compound of general Formula (IA). Alternatively the acid of general formula (V) can be converted to the corresponding acid chloride, for example using oxalyl chloride in $CH_2Cl_2$, followed by reaction with and amine of general formula (VI) in the presence of a base, for example sodium hydride, resulting in a compound of general Formula (IA).

Scheme 1

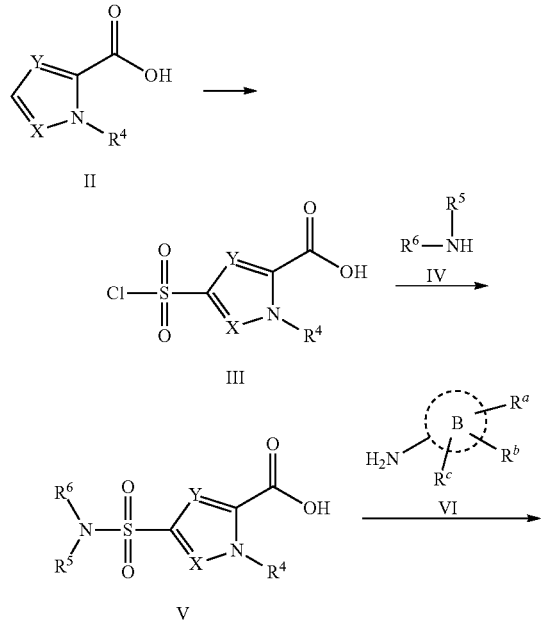

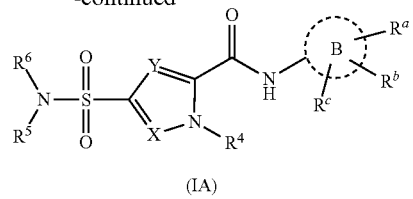

(IA)

Alternatively, as described in scheme 2, a compound of general Formula (VII), can be chlorosulfonated, resulting in compounds of general Formula (VIII), for example by treatment with chlorosulfonic acid, at for example 0° C. In case the corresponding sulfonic acid is isolated as an intermediate, this can be further converted towards the chlorosulfonic acid of general Formula (VIII), for example by treatment with thionyl chloride at for example 80° C. Coupling of a compound of general Formula (VIII), with amine of general Formula (IV), for example in an organic solvent like acetonitrile possibly in the presence of an organic base like for example triethylamine or DIPEA, or an inorganic base like for example sodium bicarbonate, resulting in a compound of general Formula (IX), followed by hydrolysis of the ester, for example with LiOH in THF/H$_2$O, followed by acidification, results in a compound of general Formula (V). The compound of general Formula (IX) can be coupled with and amine of general Formula (VI) in the presence of a base like for example lithium bis(trimethylsilyl)amide, in a solvent like for example THF, resulting in the formation of a compound of general Formula (IA).

Scheme 2

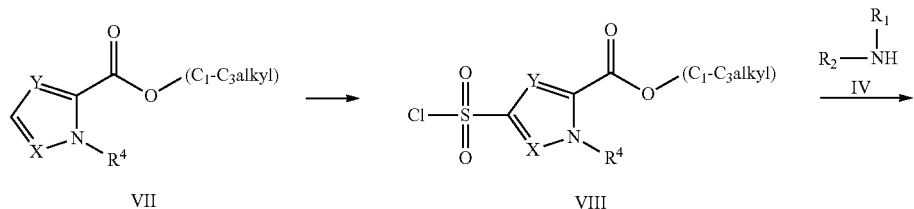

Alternatively, as described in scheme 3, a compound of general Formula (VII), can be coupled with and amine of general Formula (VI) in the presence of a base like for example lithium bis(trimethylsilyl)amide, in a solvent like for example THF, resulting in the formation of a compound of general Formula (X). A compound of general Formula (X), can be chlorosulfonated, resulting in compounds of general Formula (XI), for example by treatment with chlorosulfonic acid, at for example 0° C. Coupling of a compound of general Formula (XI), with amine of general Formula (IV), for example in an organic solvent like acetonitrile possibly in the presence of an organic base like for example triethylamine or DIPEA, or an inorganic base like for example sodium bicarbonate, results in a compound of general Formula (IA).

Scheme 3

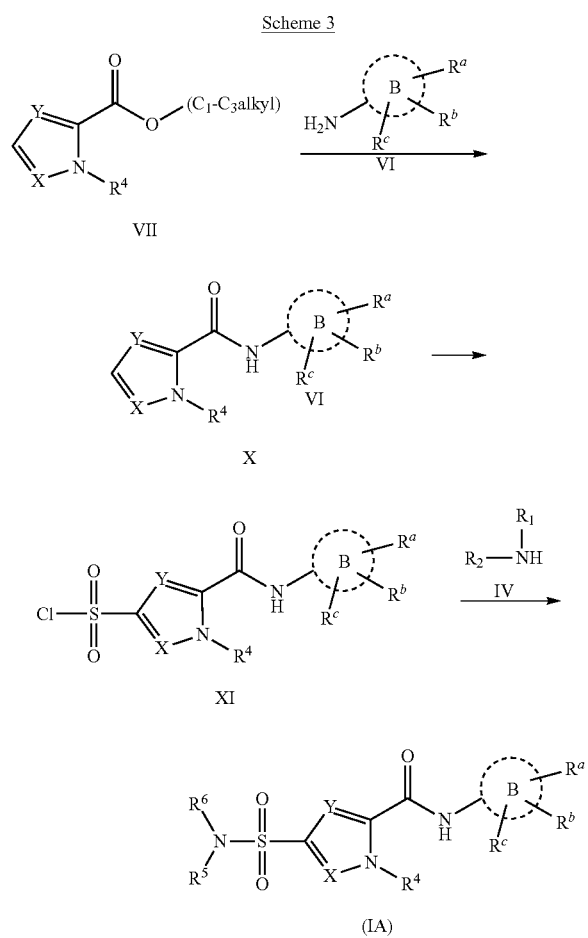

Similarly, compounds of general formula (A) can be prepared as described for compound of general formula (IA), using an amine of general formula (XII)

XII

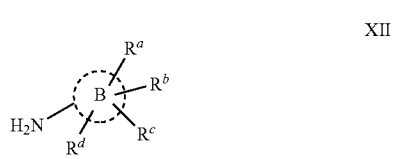

instead of an amine of general formula (VI). In case Ra, Rb, Rc and Rd are all different from hydrogen, the method shown in scheme 4, is preferred. An acid chloride of general formula XIII, formed from an acid of general formula (V), for example by treatment with oxalyl chloride in $CH_2Cl_2$, can be treated with a mixture of NaH and an amine of formula (XII), resulting in the formation of compounds of general formula (A).

Scheme 4

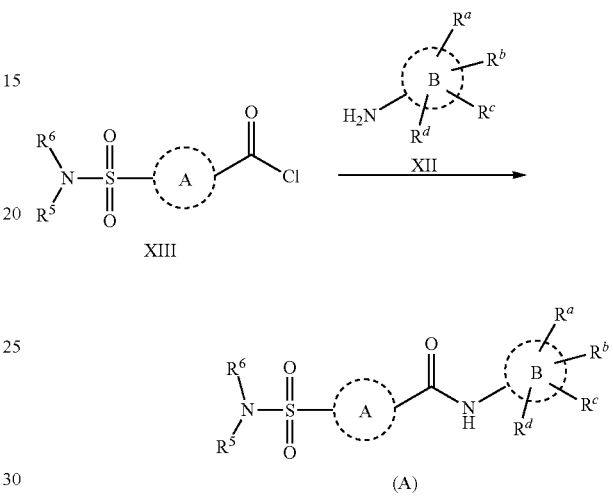

General Procedure LCMS Methods

The High Performance Liquid Chromatography (HPLC) measurement was performed using a LC pump, a diode-array (DAD) or a UV detector and a column as specified in the respective methods. If necessary, additional detectors were included (see table of methods below). Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica., "Q-Tof" Quadrupole Time-of-flight mass spectrometers, "CLND", ChemiLurninescent Nitrogen Detector, "ELSD" Evaporative Light Scanning Detector, LCMS Methods (Flow expressed in mL/min; column temperature (T) in ° C.; Run time in minutes).

| Method code | Instrument | Column | Mobile phase | Gradient | Flow / ColT | Run time |
|---|---|---|---|---|---|---|
| A | Waters: Acquity ® UPLC ® - DAD and SQD | Waters: HSS T3 (1.8 μm, 2.1*100 mm) | A: 10 mM CH₃COONH₄ in 95% H₂O + 5% CH₃CN B: CH₃CN | From 100% A to 5% A in 2.10 min, to 0% A in 0.90 min, to 5% A in 0.5 min | 0.8/55 | 3.5 |
| B | Waters: Acquity ® UPLC ® - DAD and SQD | Waters: BEH C18 (1.7 μm, 2.1*50 mm) | A: 10 mM CH₃COONH₄ in 95% H₂O + 5% CH₃CN B: CH₃CN | From 95% A to 5% A in 1.3 min, held for 0.7 min. | 0.8/55 | 2 |
| C | Waters: Acquity ® UPLC ® - DAD and SQD | Waters: HSS T3 (1.8 μm, 2.1*100 mm) | A: 10 mM CH₃COONH₄ in 95% H₂O + 5% CH₃CN B: CH₃CN | From 95% A to 0% A in 2.5 min, to 5% A in 0.5 min | 0.8/55 | 3 |
| D | Waters: Acquity ® UPLC ® - DAD and SQD | Waters: HSS T3 (1.8 μm, 2.1*100 mm) | A: 10 mM CH₃COONH₄ in 95% H₂O + 5% CH₃CN B: CH₃CN | From 100% A to 5% A in 2.10 min, to 0% A in 0.90 min, to 5% A in 0.5 min | 0.7/55 | 3.5 |

Synthesis of Compounds

Melting points (MP) reported in ° C. are referring to the maximum of the peak observed in differential scanning calorimetry (DSC): From 30 to 300° C. at 10° C./min.

Synthesis of 1-methyl-4-[(3-methyloxetan-3-yl)sulfamoyl]-1H-pyrrole-2-carboxylic acid

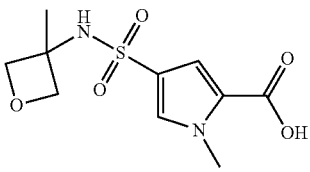 [SMILES: Cn1cc(S(=O)(=O)NC2(C)COC2)cc1C(=O)O]

Chlorosulfonic acid (80 mL) was cooled to 0° C. and methyl 1-methylpyrrole-2-carboxylate (20 g, 143.73 mmol) was added dropwise. After addition, the mixture was allowed to reach room temperature and stirred for another hour. The resulting mixture was added drop wise to a mechanically stirred, temperature controlled, ice-water mixture (1500 mL) keeping the temperature under 5° C. A white precipitation was formed. The obtained aqueous mixture was extracted using dichloromethane (3×500 mL). The combined extracts were dried on sodium sulphate, filtered and concentrated in vacuo yielding methyl 4-(chlorosulfonyl)-1-methyl-1H-pyrrole-2-carboxylate (29.4 g) as a white powder which was used as such. Methyl 4-(chlorosulfonyl)-1-methyl-1H-pyrrole-2-carboxylate (5 g, 1.04 mmol) was dissolved in acetonitrile (50 mL). diisopropylethylamine (9.06 mL, 52.6 mmol) was added, followed by 3-methyl-3-oxetanamine (1.92 g, 22.1 mmol) and the resulting mixture was refluxed for 2 hours. Then, the mixture was cooled to room temperature and concentrated in vacuo. The resulting residue was dissolved in dichloromethane (250 mL) and this was washed with HCl (2×150 mL). The organics were dried on sodium sulphate, filtered and concentrated in vacuo yielding methyl 1-methyl-4-[(3-methyloxetan-3-yl)sulfamoyl]-1H-pyrrole-2-carboxylate (6.07 g) as a beige powder which was used as such. Method B; Rt: 0.63 min. m/z: 287.1 (M−H)⁻ Exact mass: 288.1. Methyl 1-methyl-4-[(3-methyloxetan-3-yl)sulfamoyl]-1H-pyrrole-2-carboxylate (6.07 g, 21.05 mmol) was dissolved in tetrahydrofuran (60 mL). Lithium hydroxide (0.76 g, 31.58 mmol) in distilled water (8 mL) was added, followed by methanol (3 mL). The resulting mixture was stirred for 72 hours. Next, it was concentrated until only water remained and extra distilled water (15 mL) was added. After neutralization with hydrochloric acid (1M/aq/31.6 mL, 31.58 mmol). The resulting mixture was extracted using 2-methyltetrahydrofuran (3×20 mL). The combined extracts were dried on sodium sulphate, filtered and concentrated in vacuo yielding 1-methyl-4-[(3-methyloxetan-3-yl)sulfamoyl]-1H-pyrrole-2-carboxylic acid (5.77 g) as a bright white powder which was used as such. Method B; Rt: 0.26 min. m/z: 273.1 (M−H)⁻ Exact mass: 274.1

Compound 1: N-(2-Cyanopyridin-4-yl)-1-methyl-4-[(3-methyloxetan-3-yl)sulfamoyl]-1H-pyrrole-2-carboxamide

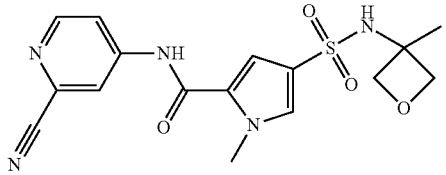 [SMILES: Cn1cc(S(=O)(=O)NC2(C)COC2)cc1C(=O)Nc1ccnc(C#N)c1]

1-methyl-4-[(3-methyloxetan-3-yl)sulfamoyl]-1H-pyrrole-2-carboxylic acid (200 mg, 0.729 mmol) was dissolved in DMF (1.7 mL) and triethylamine (0.41 mL, 2.9 mmol) and HATU (360 mg, 0.95 mmol) were added. After 10 minutes 4-aminopyridine-2-carbonitrile (174 mg, 1.46 mmol) was added. The reaction mixture was stirred at room temperature for 1 hour and heated at 65° C. for 42 hours. The mixture was poured into water (50 mL) and the organics were extracted with ethyl acetate (3×40 mL). The combined organic layers were dried (Na₂SO₄) and concentrated to dryness. The residue was purified using silica gel column chromatography (ethyl acetate in heptane from 0 to 100%) followed by prep. HPLC (Stationary phase: RP SunFire Prep C18 OBD-10 μm, 30×150 mm), Mobile phase: 0.5% NH₄OAc solution in water+10% CH₃CN, MeOH), resulting in compound 1 (4.6 mg). ¹H NMR (400 MHz, DMSO-d₆) δ ppm 1.54 (s, 3H), 3.94 (s, 3H), 4.14 (d, J=6.4 Hz, 2H), 4.60 (d, J=5.9 Hz, 2H), 7.43 (s, 1H), 7.66 (d, J=1.3 Hz, 1H), 7.86-8.12 (m, 2H), 8.26 (d, J=2.0 Hz, 1H), 8.60 (d, J=5.7 Hz, 1H), 10.68 (br. s., 1H). Method A; Rt: 1.22 min. m/z: 374.0 (M−H)⁻ Exact mass: 375.1.

Compound 2: 1-Methyl-4-[(3-methyloxetan-3-yl)sulfamoyl]-N-[5-(trifluoromethyl)pyridin-3-yl]-1H-pyrrole-2-carboxamide

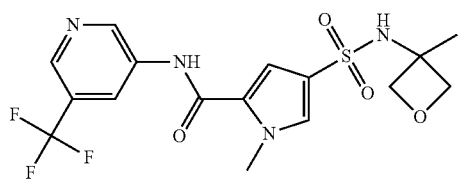 [SMILES: Cn1cc(S(=O)(=O)NC2(C)COC2)cc1C(=O)Nc1cncc(C(F)(F)F)c1]

Compound 2 was prepared similarly as described for compound 1, using 5-(trifluoromethyl)-3-aminopyridine instead of 4-aminopyridine-2-carbonitrile. The reaction mixture was stirred at room temperature for 1 hour and heated at 65° C. for 4 hours. The mixture was poured into water (50 mL), the formed precipitate was filtered and the solids were washed with water and recrystallised from methanol/ethyl acetate (10 mL, 1:1). The white solids were filtered, washed with methanol (2×3 mL) and dried overnight in vacuum oven resulting in compound 2 (74 mg) as a white solid. ¹H NMR (400 MHz, DMSO-d₆) δ ppm 1.55 (s, 3H), 3.94 (s, 3H), 4.14 (d, J=6.2 Hz, 2H), 4.60 (d, J=5.9 Hz, 2H), 7.41 (s, 1H), 7.63 (s, 1H), 8.01 (br. s., 1H), 8.56 (s, 1H), 8.66 (s, 1H), 9.13 (s, 1H), 10.55 (br. s., 1H). Method B; Rt: 0.84 min. m/z: 417.1 (M−H)⁻ Exact mass: 418.1.

Compound 3: N-(6-Fluoro-5-methylpyridin-3-yl)-1-methyl-4-[(3-methyloxetan-3-yl)sulfamoyl]-1H-pyrrole-2-carboxamide

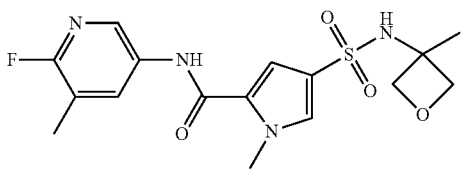 [SMILES: Cc1cc(NC(=O)c2cc(S(=O)(=O)NC3(C)COC3)cn2C)cnc1F]

A tube was charged with 1-methyl-4-[(3-methyloxetan-3-yl)sulfamoyl]-1H-pyrrole-2-carboxylic acid (0.2 g, 0.73 mmol) and HATU (0.29 g, 0.77 mmol). N,N-dimethylformamide (1 mL) and diisopropylethylamine (0.38 mL, 2.19 mmol) was added. The solution was stirred for 30 minutes and next 5-amino-2-fluoro-3-picoline (0.18 g, 1.46 mmol) was added at once. The resulting mixture was stirred at room temperature for 2 hours and added to distilled water (10 mL) under stirring. The resulting mixture was allowed to stir for 1 hour and then it was extracted using 2-methyl tetrahydrofuran (3×20 mL). The combined extracts were dried on sodium sulphate, filtered and concentrated in vacuo. The obtained crude was dissolved in dichloromethane (3 mL) and loaded directly on a silica plug. This was purified using column chromatography (gradient elution EtOAc/heptane 0:100 to 100:0). The desired fractions were concentrated in vacuo and further dried in vacuo at 55° C., resulting in compound 3 (230 mg) as a white powder. Method B; Rt: 0.75 min. m/z: 381.2 (M−H)⁻ Exact mass: 382.1. ¹H NMR (400 MHz, DMSO-d₆) δ ppm 1.54 (s, 3H), 2.25 (s, 3H), 3.92 (s, 3H), 4.14 (d, J=6.4 Hz, 2H), 4.60 (d, J=5.9 Hz, 2H), 7.36 (d, J=1.8 Hz, 1H), 7.60 (d, J=1.8 Hz, 1H), 7.84-8.09 (m, 1H), 8.13 (dd, J=9.0, 2.0 Hz, 1H), 8.23-8.38 (m, 1H), 9.90-10.61 (m, 1H).

Compound 4: 1-Methyl-4-[(3-methyloxetan-3-yl)sulfamoyl]-N-[4-(trifluoromethyl)pyridin-2-yl]-1H-pyrrole-2-carboxamide

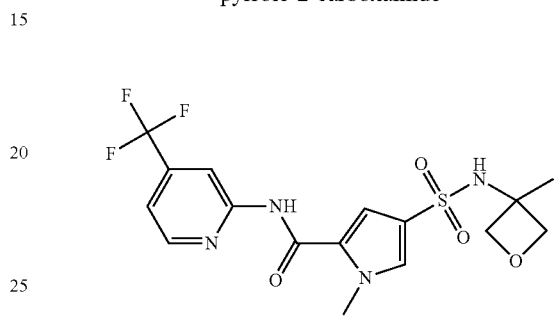

Compound 4 (79 mg) was prepared similarly as described for compound 3, using 2-amino-4-(trifluoromethyl)pyridine instead of 5-amino-2-fluoro-3-picoline and stirring for 24 hours instead of 2 hours. Method B; Rt: 0.91 min. m/z: 417.2 (M−H)⁻ Exact mass: 418.1. ¹H NMR (400 MHz, DMSO-d₆) δ ppm 1.57 (s, 3H), 3.94 (s, 3H), 4.13 (d, J=6.2 Hz, 2H), 4.61 (d, J=6.2 Hz, 2H), 7.34-7.53 (m, 1H), 7.59 (d, J=2.0 Hz, 1H), 7.63 (d, J=1.8 Hz, 1H), 7.96 (s, 1H), 8.35-8.49 (m, 1H), 8.59-8.73 (m, 1H), 11.17 (br. s, 1H).

Compound 5: 1-Methyl-4-[(3-methyloxetan-3-yl)sulfamoyl]-N-[6-(trifluoromethyl)pyridin-2-yl]-1H-pyrrole-2-carboxamide

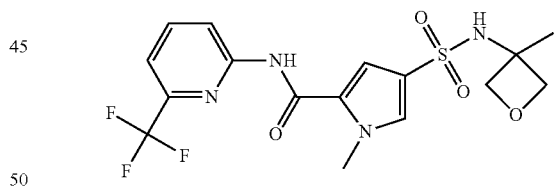

Compound 5 (27 mg) was prepared similarly as described for compound 3, using 2-amino-6-(trifluoromethyl)pyridine instead of 5-amino-2-fluoro-3-picoline and stirring for 24 hours instead of 2 hours. Method B; Rt: 0.90 min. m/z: 417.1 (M−H)⁻ Exact mass: 418.1. ¹H NMR (400 MHz, DMSO-d₆) δ ppm 1.56 (s, 3H), 3.93 (s, 3H), 4.13 (d, J=6.4 Hz, 2H), 4.61 (d, J=5.9 Hz, 2H), 7.55-7.65 (m, 3H), 7.95 (br. s., 1H), 8.08 (t, J=7.9 Hz, 1H), 8.34 (d, J=8.6 Hz, 1H), 11.07 (br. s., 1H).

Synthesis of methyl 4-(tert-butylsulfamoyl)-3-chloro-1-methyl-pyrrole-2-carboxylate Sodium hydride (3.46 g, 90.2 mmol, 60% dispersion in oil) was added portion wise, over a period of 10 minutes, to a solution of methyl 3-chloro-1H-pyrrole-2-carboxylate (12 g, 75.2 mmol), iodomethane (12.8 g, 90.2 mmol) and DMF (120 mL) at 0° C. under nitrogen in an ice bath. The ice bath was removed and the reaction mixture was stirred 3 hours at room temperature. The reaction mixture was acidified with aqueous hydrochloric acid (15.04 mL, 1 M) and concentrated. The residue was dissolved in water (100 mL)/ethyl acetate (300 mL). The organic layer was dried over $Na_2SO_4$, filtered and concentrated. The residue was dissolved in acetonitrile (150 mL), washed with heptane (100 mL) and concentrated at 70° C. yielding methyl 3-chloro-1-methyl-pyrrole-2-carboxylate (12.0 g) as yellow liquid which was used as such. $^1$H NMR (400 MHz, CHLOROFORM-d) δ ppm 3.87 (s, 3H), 3.88 (s, 3H), 6.13 (d, J=2.9 Hz, 1H), 6.69 (d, J=2.9 Hz, 1H) Methyl 3-chloro-1-methyl-pyrrole-2-carboxylate (5.0 g, 25.1 mmol) was added drop wise to chlorosulfonic acid (11 mL) at 0° C. under nitrogen atmosphere. The reaction mixture was warmed to room temperature and allowed to stir 2 hours. The resulting mixture was added drop wise to a stirred, temperature controlled ice-water mixture (200 mL) keeping the temperature under 5° C. A white precipitation was formed. The obtained aqueous suspension was extracted using dichloromethane (3×100 mL). The combined organic extracts were washed with brine and dried on sodium sulphate, filtered and concentrated in vacuo yielding methyl 3-chloro-4-chlorosulfonyl-1-methyl-pyrrole-2-carboxylate (5.56 g) as light green powder which was used as such. $^1$H NMR (400 MHz, CHLOROFORM-d) δ ppm 3.94 (s, 3H), 3.98 (s, 3H), 7.46 (s, 1H). Methyl 3-chloro-4-chlorosulfonyl-1-methyl-pyrrole-2-carboxylate (4 g, 14.7 mmol) was dispensed in acetonitrile (25 mL) and tert-butylamine (4388 mg, 58.8 mmol) was added. The reaction mixture was stirred for 30 minutes at room temperature. The solids were filtered off and the filtrate was evaporated to dryness. The residue was purified on silica using a heptane to EtOAc gradient yielding methyl 4-(tert-butylsulfamoyl)-3-chloro-1-methyl-pyrrole-2-carboxylate (3.57 g) as a white powder after trituration in $CH_2Cl_2$ and diisopropylether. $^1$H NMR (400 MHz, DMSO-$d_6$) δ ppm 1.14 (s, 9H), 3.82 (s, 3H), 3.86 (s, 3H), 7.35 (s, 1H), 7.69 (s, 1H).

Compound 6: 4-(tert-Butylsulfamoyl)-3-chloro-N-(2-cyanopyridin-4-yl)-1-methyl-1H-pyrrole-2-carboxamide

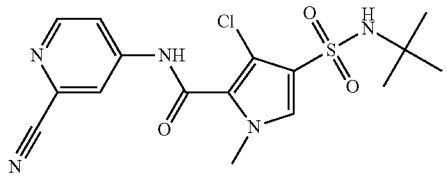 [SMILES: Cn1cc(S(=O)(=O)NC(C)(C)C)c(Cl)c1C(=O)Nc1ccnc(C#N)c1]

Methyl 4-(tert-butylsulfamoyl)-3-chloro-1-methyl-pyrrole-2-carboxylate (50 mg, 0.16 mmol) and 4-aminopyridine-2-carbonitrile (0.021 g, 0.18 mmol) were dissolved in THF (5 mL) and cooled in an ice bath. To this was added dropwise lithium bis(trimethylsilyl)amide in toluene (0.32 mL, 1 M, 0.32 mmol) over a period of 5 minutes. The resulting mixture was allowed to reach room temperature and was stirred for 3 hours. The resulting mixture was quenched using ammonium chloride (10 mL/aq. sat.). This was extracted using ethylacetate (3×20 mL). The combined extracts were washed with brine (20 mL), dried on $Na_2SO_4$, filtered and concentrated in vacuo. The obtained crude was purified by silica gel column chromatography using gradient elution from heptane to iPrOH. (100:0 to 70:30). The desired fractions were concentrated in vacuo and dried in a vacuum oven at 55° C. for 24 hours yielding compound 6 (10 mg) as a bright white powder. Method B; Rt: 0.91 min. m/z: 394.0 (M−H)$^-$ Exact mass: 395.1. $^1$H NMR (400 MHz, DMSO-$d_6$) δ ppm 1.18 (s, 9H), 3.79 (s, 3H), 7.38 (s, 1H), 7.65 (s, 1H), 7.90 (dd, J=5.6, 2.1 Hz, 1H), 8.20 (d, J=2.0 Hz, 1H), 8.63 (d, J=5.5 Hz, 1H), 10.97 (br. s., 1H).

Synthesis of methyl 3-chloro-1-methyl-4-[[(1R)-2,2,2-trifluoro-1-methyl-ethyl]-sulfamoyl]pyrrole-2-carboxylate Methyl 3-chloro-4-chlorosulfonyl-1-methyl-pyrrole-2-carboxylate (1 g, 3.68 mmol) was dissolved in hot acetonitrile (5 mL), molecular sieves (about 100 mg) were added and the reaction mixture was stirred. In a separate vessel (R)-1,1,1-trifluoro-2-propylamine (623 mg, 5.51 mmol) was dissolved in acetonitrile (5 mL), molecular sieves (about 100 mg) was added. This suspension was added to the reaction mixture and then $NaHCO_3$ (926 mg, 11.0 mmol) was added. The vessel was closed and it was stirred overnight at 80° C. The reaction mixture was filtered and the filtrate was concentrated under reduced pressure. The obtained residue was purified by silica gel chromatography, using a gradient from heptane to EtOAc, yielding methyl 3-chloro-1-methyl-4-[[(1R)-2,2,2-trifluoro-1-methyl-ethyl]sulfamoyl]pyrrole-2-carboxylate (1.04 g) as a white powder.

Compound 7: 3-Chloro-N-(5-fluoro-6-methylpyridin-2-yl)-1-methyl-4-{[(1R)-2,2,2-trifluoro-1-methylethyl]sulfamoyl}-1H-pyrrole-2-carboxamide

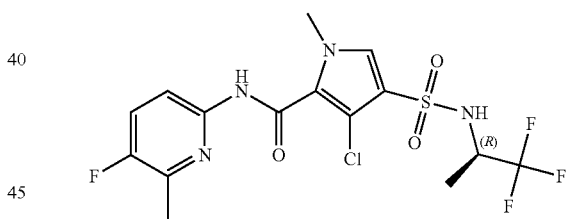

2-amino-5-fluoro-6-methylpyridine (0.559 mmol) and methyl 3-chloro-1-methyl-4-[[(1R)-2,2,2-trifluoro-1-methyl-ethyl]sulfamoyl]pyrrole-2-carboxylate (150 mg, 0.43 mmol) were dissolved in THF (10 mL). Lithium bis(trimethylsilyl)amide (1 M in THF) (1.29 mL, 1 M, 1.29 mmol) was added and the reaction mixture was stirred overnight. The reaction mixture was quenched with sat.$NH_4Cl$ (aq) (5 mL). The aqueous layer was extracted with $CH_2Cl_2$ (2×5 mL). The combined organic layers were evaporated to dryness and the residue was purified on silica using a heptane to EtOAc gradient. The obtained product was crystallized from $CH_2Cl_2$, triturated with diisopropylether and dried, resulting in compound 7 (83 mg) as a white powder.

Method D; Rt: 1.96 min. m/z: 441.0 (M−H)$^-$ Exact mass: 442.0. $^1$H NMR (400 MHz, DMSO-$d_6$) δ ppm 1.19 (d, J=7.0 Hz, 3H), 2.41 (d, J=2.9 Hz, 3H), 3.77 (s, 3H), 3.88-4.01 (m, 1H), 7.65 (s, 1H), 7.70 (t, J=9.0 Hz, 1H), 7.98 (dd, J=9.0, 3.1 Hz, 1H), 8.43 (br. s., 1H), 10.68 (s, 1H). MP: 173.1° C.

Compound 8: 3-Chloro-1-methyl-N-(2-methylpyridin-4-yl)-4-{[(1R)-2,2,2-trifluoro-1-methylethyl]sulfamoyl}-1H-pyrrole-2-carboxamide

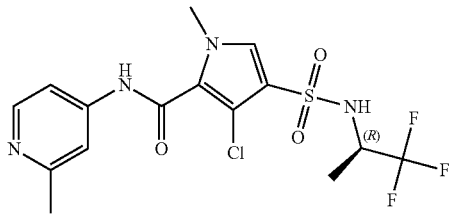

Compound 8 (148 mg) was prepared similarly as described for compound 7, using 4-amino-2-methylpyridine instead of 2-amino-5-fluoro-6-methylpyridine. Method D; Rt: 1.61 min. m/z: 423.0 (M–H)⁻ Exact mass: 424.1. ¹H NMR (400 MHz, DMSO-d$_6$) δ ppm 1.19 (d, J=7.0 Hz, 3H), 2.44 (s, 3H), 3.77 (s, 3H), 3.91-4.04 (m, 1H), 7.46 (dd, J=5.7, 1.8 Hz, 1H), 7.54 (d, J=2.0 Hz, 1H), 7.69 (s, 1H), 8.35 (d, J=5.5 Hz, 1H), 8.49 (br. s., 1H), 10.60 (s, 1H). MP: 203.5° C.

Compound 9: 3-Chloro-N-(2-cyanopyridin-4-yl)-1-methyl-4-{[(1R)-2,2,2-trifluoro-1-methylethyl]sulfamoyl}-1H-pyrrole-2-carboxamide

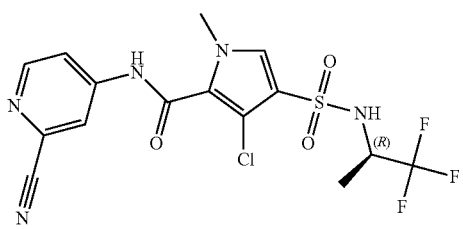

Compound 9 (132 mg) was prepared similarly as described for compound 7, using 4-amino-2-cyanopyridine instead of 2-amino-5-fluoro-6-methylpyridine. Method D; Rt: 1.72 min. m/z: 434.0 (M–H)⁻ Exact mass: 435.0. ¹H NMR (400 MHz, DMSO-d$_6$) δ ppm 1.19 (d, J=6.8 Hz, 3H), 3.80 (s, 3H), 3.91-4.06 (m, 1H), 7.73 (s, 1H), 7.91 (dd, J=5.6, 2.1 Hz, 1H), 8.20 (d, J=1.8 Hz, 1H), 8.55 (br. s., 1H), 8.66 (d, J=5.3 Hz, 1H), 11.03 (br. s., 1H). MP: 190.8° C.

Compound 10: 3-Chloro-1-methyl-4-{[(1R)-2,2,2-trifluoro-1-methylethyl]sulfamoyl}-N-[2-(trifluoromethyl)pyridin-4-yl]-1H-pyrrole-2-carboxamide

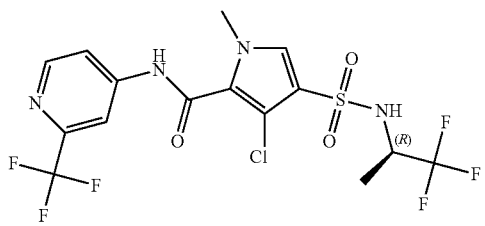

Compound 10 (109 mg) was prepared similarly as described for compound 7, using 4-amino-2-trifluoromethylpyridine instead of 2-amino-5-fluoro-6-methylpyridine. Method D; Rt: 1.89 min. m/z: 477.0 (M–H)⁻ Exact mass: 478.0. ¹H NMR (400 MHz, DMSO-d$_6$) δ ppm 1.19 (d, J=7.0 Hz, 3H), 3.80 (s, 3H), 3.93-4.06 (m, 1H), 7.73 (s, 1H), 7.90 (dd, J=5.5, 2.0 Hz, 1H), 8.19 (d, J=1.8 Hz, 1H), 8.54 (br. s., 1H), 8.68 (d, J=5.5 Hz, 1H), 11.03 (br. s., 1H).

Compound 11: 3-Chloro-N-(2-fluoropyridin-4-yl)-1-methyl-4-{[(1R)-2,2,2-trifluoro-1-methylethyl]sulfamoyl}-1H-pyrrole-2-carboxamide

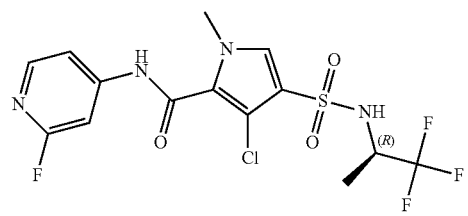

Compound 11 (143 mg) was prepared similarly as described for compound 7, using 4-amino-2-fluoropyridine instead of 2-amino-5-fluoro-6-methylpyridine. Method D: Rt: 1.74 min. m/z: 427.0 (M–H)⁻ Exact mass: 428.0. ¹H NMR (400 MHz, DMSO-d$_6$) δ ppm 1.19 (d, J=7.0 Hz, 3H), 3.79 (s, 3H), 3.92-4.05 (m, 1H), 7.42-7.49 (m, 1H), 7.49-7.55 (m, 1H), 7.72 (s, 1H), 8.17 (d, J=5.7 Hz, 1H), 8.53 (br. s., 1H), 10.96 (br. s., 1H). MP: 218.1° C.

Compound 12: 3-Chloro-N-(2-chloropyridin-4-yl)-1-methyl-4-{[(1R)-2,2,2-trifluoro-1-methylethyl]sulfamoyl}-1H-pyrrole-2-carboxamide

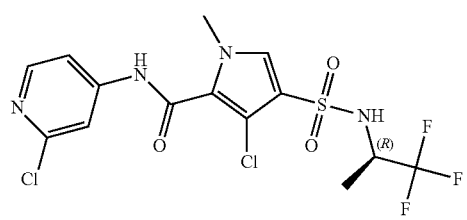

Compound 12 (122 mg) was prepared similarly as described for compound 7, using 4-amino-2-chloropyridine instead of 2-amino-5-fluoro-6-methylpyridine. Method D: Rt: 1.80 min. m/z: 443.0 (M–H)⁻ Exact mass: 444.0. ¹H NMR (400 MHz, DMSO-d$_6$) δ ppm 1.19 (d, J=7.0 Hz, 3H), 3.79 (s, 3H), 3.96-4.05 (m, 1H), 7.62 (dd, J=5.6, 1.9 Hz, 1H), 7.72 (s, 1H), 7.81 (d, J=1.5 Hz, 1H), 8.33 (d, J=5.7 Hz, 1H), 8.53 (br. s., 1H), 10.89 (br. s., 1H). MP: 214.8° C.

Compound 13: 3-Chloro-N-(6-fluoro-5-methylpyridin-3-yl)-1-methyl-4-{[(1R)-2,2,2-trifluoro-1-methylethyl]sulfamoyl}-1H-pyrrole-2-carboxamide

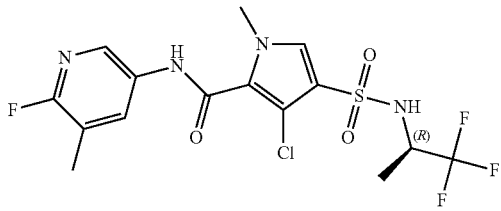

Compound 13 (152 mg) was prepared similarly as described for compound 7, using 6-fluoro-5-methyl-pyridin-3-amine instead of 2-amino-5-fluoro-6-methylpyridine Method D: Rt: 1.80 min. m/z: 441.0 (M−H)⁻ Exact mass: 442.0. ¹H NMR (400 MHz, DMSO-d$_6$) δ ppm 1.19 (d, J=7.0 Hz, 3H), 2.26 (s, 3H), 3.78 (s, 3H), 3.90-4.10 (m, 1H), 7.68 (s, 1H), 8.11 (dd, J=8.9, 1.9 Hz, 1H), 8.32 (s, 1H), 8.49 (s, 1H), 10.54 (s, 1H).

Compound 14: 3-chloro-N-(3-fluoro-2-methyl-4-pyridyl)-1-methyl-4-[[(1R)-2,2,2-trifluoro-1-methylethyl]sulfamoyl]pyrrole-2-carboxamide

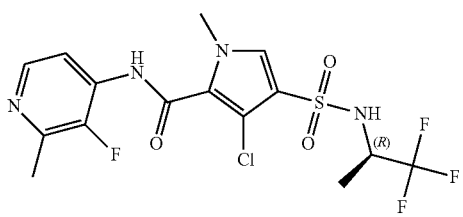

Compound 14 (63 mg) was prepared similarly as described for compound 7, using 3-fluoro-2-methylpyridin-4-amine instead of 2-amino-5-fluoro-6-methylpyridine.

Method B: Rt: 0.92 min. m/z: 441.1 (M−H)⁻ Exact mass: 442.0. ¹H NMR (400 MHz, DMSO-d$_6$) δ ppm 1.19 (d, J=7.0 Hz, 3H), 2.46 (d, J=3.3 Hz, 3H), 3.81 (s, 3H), 3.90-4.05 (m, 1H), 7.72 (s, 1H), 7.91 (t, J=5.5 Hz, 1H), 8.23 (d, J=5.3 Hz, 1H), 8.52 (d, J=7.3 Hz, 1H), 10.30 (br. s., 1H). MP: 197.8° C.

Compound 15: 3-chloro-1-methyl-N-(2-pyridyl)-4-[[(1R)-2,2,2-trifluoro-1-methyl-ethyl]sulfamoyl]pyrrole-2-carboxamide

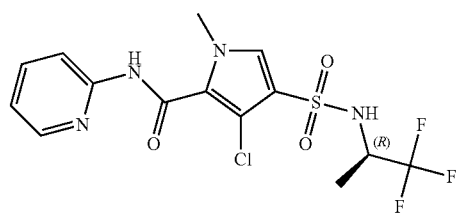

Compound 15 (94 mg) was prepared similarly as described for compound 7, using 2-aminopyridine instead of 2-amino-5-fluoro-6-methylpyridine. Method B: Rt: 0.92 min. m/z: 409.2 (M−H)⁻ Exact mass: 410.0. ¹H NMR (400 MHz, DMSO-d$_6$) δ ppm 1.19 (d, J=7.0 Hz, 3H), 3.80 (s, 3H), 3.89-4.00 (m, 1H), 7.18 (ddd, J=7.4, 4.8, 1.0 Hz, 1H), 7.67 (s, 1H), 7.81-7.88 (m, 1H), 8.11 (d, J=8.4 Hz, 1H), 8.34-8.41 (m, 1H), 8.45 (br. s., 1H), 10.56 (s, 1H). MP: 195.2° C.

Compound 16: 3-chloro-1-methyl-N-(4-pyridyl)-4-[[(1R)-2,2,2-trifluoro-1-methyl-ethyl]sulfamoyl]pyrrole-2-carboxamide

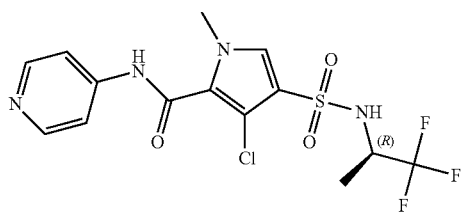

Compound 16 (63 mg) was prepared similarly as described for compound 7, using 4-aminopyridine instead of 2-amino-5-fluoro-6-methylpyridine. Method B: Rt: 0.82 min. m/z: 409.1 (M−H)⁻ Exact mass: 410.0. ¹H NMR (400 MHz, DMSO-d$_6$) δ ppm 1.19 (d, J=7.0 Hz, 3H), 3.78 (s, 3H), 3.90-4.10 (m, 1H), 7.62-7.72 (m, 3H), 8.49 (m, J=6.2 Hz, 3H), 10.70 (s, 1H). MP: 259.3° C.

Compound 17: 3-chloro-1-methyl-N-(3-pyridyl)-4-[[(1R)-2,2,2-trifluoro-1-methyl-ethyl]sulfamoyl]pyrrole-2-carboxamide

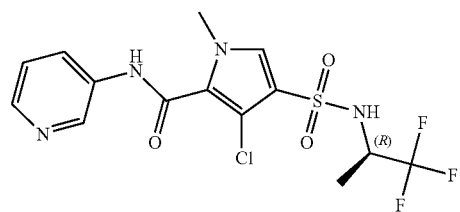

Compound 17 (76 mg) was prepared similarly as described for compound 7, using 3-aminopyridine instead of 2-amino-5-fluoro-6-methylpyridine. Method B: Rt: 0.81 min. m/z: 409.0 (M−H)⁻ Exact mass: 410.0. ¹H NMR (400 MHz, DMSO-d$_6$) δ ppm 1.19 (d, J=7.0 Hz, 3H), 3.78 (s, 3H), 3.91-4.06 (m, 1H), 7.40 (dd, J=8.3, 4.5 Hz, 1H), 7.68 (s, 1H), 8.06-8.16 (m, 1H), 8.34 (dd, J=4.7, 1.4 Hz, 1H), 8.48 (br. s., 1H), 8.85 (d, J=2.2 Hz, 1H), 10.54 (s, 1H). MP: 196.6° C.

Synthesis of ethyl 3-fluoro-1-methyl-4-[[(1R)-2,2,2-trifluoro-1-methyl-ethyl]sulfamoyl]pyrrole-2-carboxylate Sodium hydride (6.99 g, 183 mmol) was added portionwise to ethyl 3-fluoro-1H-pyrrole-2-carboxylate (CAS: 168102-05-4, commercial from aurum pharmatech; Q-4357, 23.9 g, 152 mmol), iodomethane (25.9 g, 183 mmol) in DMF (238 mL) under nitrogen in an icebath and stirred overnight at room temperature. The reaction mixture was acidified with 1M HCl and concentrated. The residue was dissolved in water/EtOAc. The organic layer was dried over Na$_2$SO$_4$, filtered and concentrated. The residue was dissolved in CH₃CN (150 mL), washed with heptane and concentrated at 60° C. and 40 mbar yielding a brown liquid which was submitted to silica gel column chromatography using a gradient from 10 till 25% EtOAc in heptane. The product fractions were concentrated resulting in ethyl 3-fluoro-1-methyl-pyrrole-2-carboxylate as a clear oil (14.0 g). Chlorosulfonic acid (9.97 g, 85.6 mmol) dissolved in dichloromethane (50 mL) was added to ethyl 3-fluoro-1-methyl-pyrrole-2-carboxylate (14.0 g, 81.5 mmol) dissolved in dichloromethane (250 mL) in an icebath and stirred 30 minutes. The formed light beige crystals were filtered off and dried overnight in vacuo at 50° C., resulting in 5-ethoxycarbonyl-4-fluoro-1-methyl-pyrrole-3-sulfonic acid (14.3 g). ¹H NMR (400 MHz, DMSO-d₆) δ ppm 1.26 (t, J=7.2 Hz, 3H), 3.72 (s, 3H), 4.23 (q, J=7.0 Hz, 2H), 7.02 (d, J=5.1 Hz, 1H). Method D: Rt: 0.88 min. m/z: 250.0 (M–H)⁻ Exact mass: 251.0. 5-ethoxycarbonyl-4-fluoro-1-methyl-pyrrole-3-sulfonic acid (20.3 g, 80.7 mmol), SOCl₂ (80 mL, 1.1 mol) was stirred 2 hours at 80° C. The reaction mixture was concentrated. The obtained dark green solid was subjected to silica gel column chromatography using a gradient from 10 till 50% EtOAc in heptane. The product fractions were concentrated yielding ethyl 4-chlorosulfonyl-3-fluoro-1-methyl-pyrrole-2-carboxylate (18.9 g) as light yellow crystals which was used as such.

Ethyl 4-chlorosulfonyl-3-fluoro-1-methyl-pyrrole-2-carboxylate (18.9 g, 70.1 mmol), (2R)-1,1,1-trifluoropropan-2-amine (11.89 g, 105.2 mmol) NaHCO₃ (17.7 g, 210 mmol), acetonitrile (150 mL, 2871 mmol) molecular sieves 4 Å (15.00 g) was refluxed overnight. The reaction mixture was filtered and concentrated. The residue was dissolved in EtOAc and washed with 1M HCl. The organic layer was dried over sodium sulphate, filtered and concentrated. The residue was purified via silica gel column chromatography (2×) using a gradient from 10 till 100% EtOAc in heptane, resulting in ethyl 3-fluoro-1-methyl-4-[[(1R)-2,2,2-trifluoro-1-methyl-ethyl]-sulfamoyl]pyrrole-2-carboxylate as a white powder which was dried overnight at 50° C. in vacuo (19.1 g in total). Method D: Rt: 1.77 min. m/z: 345.0 (M–H)⁻ Exact mass: 346.1. ¹H NMR (400 MHz, DMSO-d₆) δ ppm 1.15 (d, J=7.0 Hz, 3H), 1.28 (t, J=7.2 Hz, 3H), 3.83 (s, 3H), 3.90-4.03 (m, 1H), 4.28 (q, J=7.2 Hz, 2H), 7.60 (d, J=4.8 Hz, 1H), 8.60 (d, J=8.8 Hz, 1H).

Compound 18: N-(2-Cyanopyridin-4-yl)-3-fluoro-1-methyl-4-{[(1R)-2,2,2-trifluoro-1-methylethyl]sulfamoyl}-1H-pyrrole-2-carboxamide

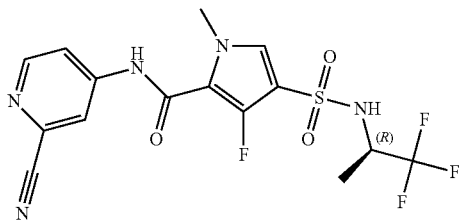

To ethyl 3-fluoro-1-methyl-4-[[(1R)-2,2,2-trifluoro-1-methyl-ethyl]sulfamoyl]pyrrole-2-carboxylate (128 mg, 0.37 mmol) and 4-aminopyridine-2-carbonitrile (57.2 mg, 0.48 mmol) dissolved in dry THF (20 mL) at 0° C. under nitrogen atmosphere, lithium bis(trimethylsilyl)amide in toluene (1.5 mL, 1 M, 1.478 mmol) was added. The mixture was stirred 1 hour at 0° C. and further overnight at room temperature. The reaction mixture was quenched with NH₄Cl solution (30 mL) and extracted with EtOAc (50 mL), diluted with brine (50 mL) and extracted again with EtOAc (50 mL). The combined organic layers were dried over sodium sulphate, filtered and concentrated. The residue (dissolved in 1 mL DMF) was purified by column chromatography on silica gel using a 120 g Reveleris cartridge with a gradient from 10 till 100% EtOAc in heptane. The product fractions were concentrated and the solid residue was crystallised from warm methanol (20 mL) upon addition of water. The light yellow crystals were filtered off and dried in vacuo at 50° C. overnight, resulting in compound 18 (47 mg). ¹H NMR (400 MHz, DMSO-d₆) δ ppm 1.18 (d, J=6.8 Hz, 3H), 3.82 (s, 3H), 3.93-4.04 (m, 1H), 7.62 (d, J=4.4 Hz, 1H), 7.91 (dd, J=5.7, 2.2 Hz, 1H), 8.21 (d, J=1.8 Hz, 1H), 8.60-8.69 (m, 2H), 10.72 (s, 1H). Method D: Rt: 1.70 min. m/z: 418.0 (M–H)⁻ Exact mass: 419.1.

Compound 19: N-(2-Cyanopyridin-4-yl)-3-fluoro-1-methyl-4-{[(1S)-2,2,2-trifluoro-1-methylethyl]sulfamoyl}-1H-pyrrole-2-carboxamide

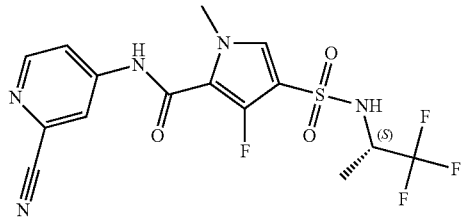

5-ethoxycarbonyl-4-fluoro-1-methyl-pyrrole-3-sulfonic acid (4.33 g, 17.2 mmol) and thionyl chloride (50 mL) were heated at 80° C. during 60 minutes. The reaction mixture was concentrated. The residue was dissolved in CH₃CN (50 mL), DIPEA (8.9 mL, 51.7 mmol) was added followed by (S)-1,1,1-trifluoro-2-propylamine (2.92 g, 25.9 mmol) and the reaction mixture was refluxed overnight. Next, the reaction mixture was filtered and concentrated. The residue was dissolved in EtOAc (200 mL), washed with water, dried over sodium sulphate, filtered and concentrated. The residue was purified by silica gel column chromatography using a gradient from 5 till 100% EtOAc in heptane, resulting in ethyl 3-fluoro-1-methyl-4-[[(1S)-2,2,2-trifluoro-1-methyl-ethyl]sulfamoyl]pyrrole-2-carboxylate (810 mg) as a light brown semisolid. Compound 19 (121 mg) was prepared similar as described for compound 18, using ethyl 3-fluoro-1-methyl-4-[[(1S)-2,2,2-trifluoro-1-methyl-ethyl]sulfamoyl]pyrrole-2-carboxylate instead of ethyl 3-fluoro-1-methyl-4-[[(1R)-2,2,2-trifluoro-1-methyl-ethyl]sulfamoyl]pyrrole-2-carboxylate. Method D: Rt: 1.70 min. m/z: 418.1 (M–H)⁻ Exact mass: 419.1. ¹H NMR (400 MHz, DMSO-d₆) δ ppm 1.18 (d, J=7.0 Hz, 3H), 3.83 (s, 3H), 3.93-4.04 (m, 1H), 7.62 (d, J=4.6 Hz, 1H), 7.91 (dd, J=5.7, 2.2 Hz, 1H), 8.21 (d, J=1.8 Hz, 1H), 8.60-8.69 (m, 2H), 10.71 (s, 1H).

Compound 20: N-(2-chloro-4-pyridyl)-3-fluoro-1-methyl-[[(1R)-2,2,2-trifluoro-1-methyl-ethyl]sulfamoyl]pyrrole-2-carboxamide

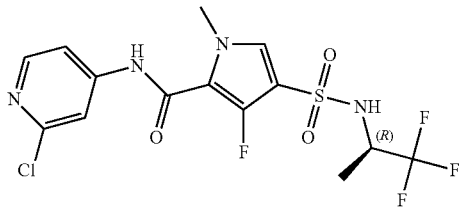

Compound 20 (131 mg) was prepared similarly as described for compound 18, using 4-amino-2-chloropyridine instead of 4-aminopyridine-2-carbonitrile. Method D: Rt: 1.76 min. m/z: 427.0 (M−H)⁻ Exact mass: 428.0. ¹H NMR (400 MHz, DMSO-d₆) δ ppm 1.18 (d, J=6.8 Hz, 3H), 3.81 (s, 3H), 3.92-4.04 (m, 1H), 7.58-7.63 (m, 2H), 7.82 (d, J=1.8 Hz, 1H), 8.30 (d, J=5.7 Hz, 1H), 8.64 (d, J=8.6 Hz, 1H), 10.58 (s, 1H).

Alternative Synthesis of Compound 20:

Ethyl 3-fluoropyrrole-2-carboxylate ([168102-05-4], 61.2 g, 389.45 mmol) was dissolved in THF (860 mL) and the mixture was mechanically stirred. Cesium carbonate (272.8 g, 837.3 mmol) was added while stirring, followed by iodomethane (118.9 g, 837.3 mmol). The reaction mixture was stirred overnight. Extra cesium carbonate (126.9 g, 389.45 mmol) and iodomethane (55.28 g, 389.5 mmol) were added and the mixture was stirred for another 5 hours. The mixture was filtered and the obtained filtrate was concentrated yielding ethyl 3-fluoro-1-methyl-pyrrole-2-carboxylate (66.3 g) as a brown oil which was used as such in the next step. Chlorosulfonic acid (4.95 mL, 1.75 g/mL, 74.53 mmol) dissolved in CH₂Cl₂ (100 mL) was added portion wise to a solution of ethyl 3-fluoro-1-methyl-pyrrole-2-carboxylate (12.15 g, 70.98 mmol) in CH₂Cl₂ (150 mL) at 0° C. After addition the mixture was stirred for 15 minutes while cooling was continued. The beige crystals were filtered off, washed with CH₂Cl₂ (400 mL) and dried overnight in vacuo at 55° C. yielding 5-ethoxycarbonyl-4-fluoro-1-methyl-pyrrole-3-sulfonic acid as a beige powder (14.2 g) which was used as such (this reaction was performed a second time under similar conditions). 5-ethoxycarbonyl-4-fluoro-1-methyl-pyrrole-3-sulfonic acid (24.2 g, 96.4 mmol) was dissolved in thionyl chloride (80 mL, 1103 mmol) and this was stirred 3 hours at 80° C. The mixture was concentrated and co-evaporated twice using toluene (2×150 mL). The dark green solid was dissolved in dichloromethane (150 mL) and 100 g of dicalite was added. This suspension was concentrated and the obtained white powder was purified by silica gel column chromatography using dry loading and gradient elution from heptane to EtOAc. (100:0 to 0:100). The desired fractions were concentrated in vacuo yielding ethyl 4-chlorosulfonyl-3-fluoro-1-methyl-pyrrole-2-carboxylate (25.5 g) as a pale yellow solid which was used as such in the next step. A pressure tube was loaded with acetonitrile (0.4 L), (R)-1,1,1-trifluoro-2-propylamine (7841 mg, 69.34 mmol) and molecular sieves 4 Å (10000 mg) The suspension was stirred for 10 minutes under nitrogen. Then ethyl 4-chlorosulfonyl-3-fluoro-1-methyl-pyrrole-2-carboxylate (17000 mg, 63.04 mmol) and sodium bicarbonate (15887 mg, 189.1 mmol) were added and the pressure tube was closed and stirred in an oilbath at 85° C. for 18 hours. The mixture was cooled to room temperature, filtered over a glass filter and concentrated in vacuo. The obtained crude was purified by silica gel column chromatography using gradient elution from heptane to EtOAc. (100:0 to 0:100) yielding ethyl 3-fluoro-1-methyl-4-[[(1R)-2,2,2-trifluoro-1-methyl-ethyl]sulfamoyl]pyrrole-2-carboxylate (19.4 g) which was used as such in the next step. Method D: Rt: 1.77 min. m/z: 345.1 (M−H)⁻ Exact mass: 346.06. A flask was loaded with ethyl 3-fluoro-1-methyl-4-[[(1R)-2,2,2-trifluoro-1-methyl-ethyl]sulfamoyl]pyrrole-2-carboxylate (19.4 g, 56.0 mmol) and 4-amino-2-chloropyridine (7922 mg, 61.6 mmol) and these were dissolved in tetrahydrofuran (500 mL). The flask was flushed with nitrogen, closed with a septum and stirred at room temperature. Lithium bis(trimethylsilyl)amide (140.1 mL, 1 M in THF, 140.1 mmol) was added over a period of two minutes. The resulting mixture was stirred for 2 hours and 30 minutes. The reaction mixture was quenched using ammonium chloride (aq./sat./500 mL). The layers were separated and the water layer was extracted with EtOAc (2×250 mL). The combined extracts were dried on sodium sulphate and filtered. To the filtrate dicalite (100 g) was added and this suspension was concentrated in vacuo. The obtained powder was purified by silica gel column chromatography using dry loading and a gradient elution from heptane to EtOAc. (100:0 to 0:100). The desired fractions were concentrated in vacuo. Just before the compound solidified on the rotary evaporator, diethylether (250 mL) was added and a white precipitation was formed. The obtained suspension was stirred for 18 hours and collected on a filter and dried in a vacuum oven at 55° C. for 6 hours. Then diisopropylether (250 mL) was added and the obtained suspension was stirred for 18 hours and collected on a filter. Next diethylether (250 mL) was added and the obtained suspension was stirred for 7 hours, filtered and rinsed with diethylether. The obtained bright white powder was dried in a vacuum oven at 55° C. for 18 hours resulting in compound 20 (15 g) as bright white powder. Method B: Rt: 0.93 min. m/z: 427.0 (M−H)⁻ Exact mass: 428.03. DSC: From 30 to 300° C. at 10° C./min, peak: 191.98° C. [α]₅₈₉=−29.8° (c 0.775 w/v %, DMF). ¹H NMR (600 MHz, DMSO-d₆) δ ppm 1.19 (d, J=6.9 Hz, 3H), 3.82 (s, 3H), 3.94-4.04 (m, 1H), 7.59 (d, J=4.2 Hz, 1H), 7.61 (dd, J=5.6, 1.9 Hz, 1H), 7.82 (d, J=1.8 Hz, 1H), 8.30 (d, J=5.6 Hz, 1H), 8.62 (d, J=8.8 Hz, 1H), 10.56 (s, 1H).

Compound 21: 3-fluoro-1-methyl-[[(1R)-2,2,2-trifluoro-1-methyl-ethyl]sulfamoyl]-N-[2-(trifluoromethyl)-4-pyridyl]pyrrole-2-carboxamide

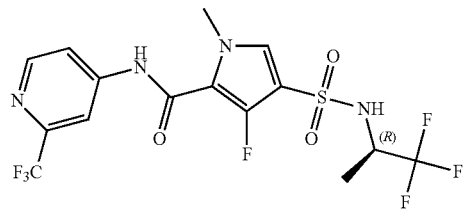

Compound 21 (125 mg) was prepared similarly as described for compound 18, using 4-amino-2-trifluoromethylpyridine instead of 4-aminopyridine-2-carbonitrile. Method D: Rt: 1.85 min. m/z: 461.0 (M−H)⁻ Exact mass: 462.1. ¹H NMR (400 MHz, DMSO-d₆) δ ppm 1.19 (d, J=7.0 Hz, 3H), 3.83 (s, 3H), 3.93-4.05 (m, 1H), 7.61 (d, J=4.4 Hz, 1H), 7.90 (dd, J=5.5, 1.8 Hz, 1H), 8.20 (d, J=1.8 Hz, 1H), 8.61-8.69 (m, 2H), 10.72 (s, 1H). DSC: From 30 to 300° C. at 10° C./min, peak: 208.1° C.

Compound 22: 3-chloro-N-(6-cyano-2-pyridyl)-1-methyl-[[(1R)-2,2,2-trifluoro-1-methyl-ethyl]sulfamoyl]pyrrole-2-carboxamide

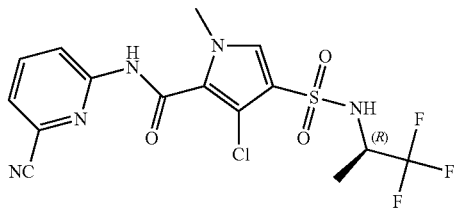

Compound 22 (85 mg) was prepared similarly as described for compound 7, using 6-aminopicolinonitrile instead of 2-amino-5-fluoro-6-methylpyridine. Method B: Rt: 0.97 min. m/z: 434.1 (M−H)⁻ Exact mass: 435.8. ¹H NMR (400 MHz, DMSO-d₆) δ ppm 1.20 (d, J=7.0 Hz, 3H), 3.79 (s, 3H), 3.95 (d, J=8.6 Hz, 1H), 7.69 (s, 1H), 7.82 (dd, J=7.5, 0.7 Hz, 1H), 8.10 (dd, J=8.6, 7.5 Hz, 1H), 8.39 (dd, J=8.6, 0.7 Hz, 1H), 8.48 (d, J=6.4 Hz, 1H), 11.16 (s, 1H). DSC: From 30 to 300° C. at 10° C./min, peak: 223.0° C.

Compound 23: N-(2-bromo-4-pyridyl)-3-fluoro-1-methyl-4-[[(1R)-2,2,2-trifluoro-1-methyl-ethyl]sulfamoyl]pyrrole-2-carboxamide

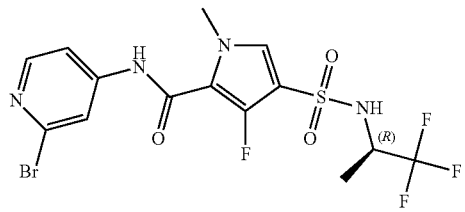

Compound 23 (152 mg) was prepared similarly as described for compound 18, using 2-bromopyridin-4-amine instead of 4-aminopyridine-2-carbonitrile. Method D: Rt: 1.80 min. m/z: 473.2 (M−H)⁻ Exact mass: 474.0. ¹H NMR (400 MHz, DMSO-d₆) δ ppm 1.18 (d, J=7.0 Hz, 3H), 3.81 (s, 3H), 3.92-4.04 (m, 1H), 7.60 (d, J=4.4 Hz, 1H), 7.64 (dd, J=5.6, 1.9 Hz, 1H), 7.97 (d, J=1.5 Hz, 1H), 8.28 (d, J=5.5 Hz, 1H), 8.64 (d, J=8.8 Hz, 1H), 10.56 (s, 1H). DSC: From 30 to 300° C. at 10° C./min, peak: 193.4° C.

Compound 24: 3-fluoro-N-(2-fluoro-4-pyridyl)-1-methyl-4-[[(1R)-2,2,2-trifluoro-1-methyl-ethyl]sulfamoyl]pyrrole-2-carboxamide

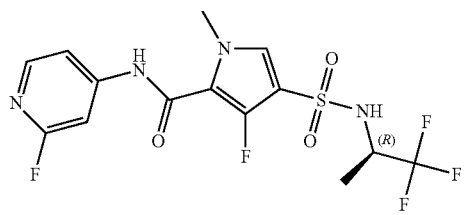

Compound 24 (95 mg) was prepared similarly as described for compound 18, using 2-fluoropyridin-4-amine instead of 4-aminopyridine-2-carbonitrile. Method D: Rt: 1.71 min. m/z: 411.3 (M−H)⁻ Exact mass: 412.1. ¹H NMR (400 MHz, DMSO-d₆) δ ppm 1.18 (d, J=7.0 Hz, 3H), 3.82 (s, 3H), 3.93-4.04 (m, 1H), 7.46 (d, J=1.5 Hz, 1H), 7.52 (dt, J=5.7, 1.5 Hz, 1H), 7.60 (d, J=4.4 Hz, 1H), 8.14 (d, J=5.5 Hz, 1H), 8.64 (d, J=8.8 Hz, 1H), 10.67 (s, 1H). DSC: From 30 to 300° C. at 10° C./min, peak: 204.4° C.

Compound 25: N-(6-cyano-2-pyridyl)-3-fluoro-1-methyl-4-[[(1R)-2,2,2-trifluoro-1-methyl-ethyl]sulfamoyl]pyrrole-2-carboxamide

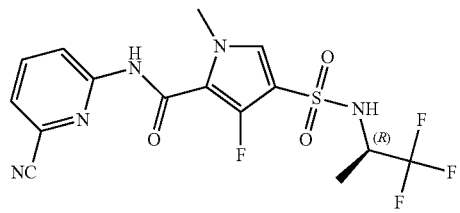

Compound 25 (24 mg) was prepared similarly as described for compound 18, using 6-aminopicolinonitrile instead of 4-aminopyridine-2-carbonitrile. Method D: Rt: 1.80 min. m/z: 418.3 (M−H)⁻ Exact mass: 419.1. ¹H NMR (400 MHz, DMSO-d₆) δ ppm 1.20 (d, J=7.0 Hz, 3H), 3.82 (s, 3H), 3.90-4.01 (m, 1H), 7.57 (d, J=4.6 Hz, 1H), 7.79 (dd, J=7.5, 0.7 Hz, 1H), 8.07 (dd, J=8.5, 7.6 Hz, 1H), 8.35 (dd, J=8.6, 0.7 Hz, 1H), 8.60 (d, J=8.6 Hz, 1H), 10.86 (s, 1H). DSC: From 30 to 300° C. at 10° C./min, peak: 197.6° C.

Compound 26: 3-fluoro-1-methyl-4-[[(1R)-2,2,2-trifluoro-1-methyl-ethyl]sulfamoyl]-N-[6-(trifluoromethyl)-2-pyridyl]pyrrole-2-carboxamide

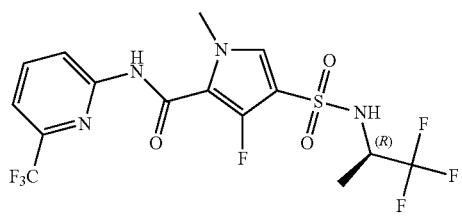

Compound 26 (153 mg) was prepared similarly as described for compound 18, using 2-amino-6-(trifluoromethyl)pyridine instead of 4-aminopyridine-2-carbonitrile. Method D: Rt: 2.01 min. m/z: 461.3 (M−H)⁻ Exact mass: 462.1. ¹H NMR (400 MHz, DMSO-d₆) δ ppm 1.20 (d, J=7.0 Hz, 3H), 3.82 (s, 3H), 3.89-4.01 (m, 1H), 7.56 (d, J=4.6 Hz, 1H), 7.65 (d, J=7.5 Hz, 1H), 8.12 (t, J=8.0 Hz, 1H), 8.34 (d, J=8.4 Hz, 1H), 8.58 (d, J=8.6 Hz, 1H), 10.84 (s, 1H). DSC: From 30 to 300° C. at 10° C./min, peak: 197.2° C.

Compound 27: N-(2-cyano-4-pyridyl)-3-fluoro-4-(isopropylsulfamoyl)-1-methyl-pyrrole-2-carboxamide

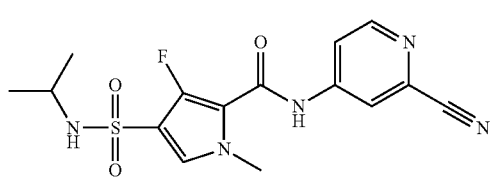 [SMILES: CC(C)NS(=O)(=O)c1cn(C)c(C(=O)Nc2ccnc(C#N)c2)c1F]

Ethyl 3-fluoro-4-(isopropylsulfamoyl)-1-methyl-pyrrole-2-carboxylate was prepared similarly as ethyl 3-fluoro-1-methyl-4-[[(1R)-2,2,2-tri fluoro-1-methyl-ethyl]sulfamoyl] pyrrole-2-carboxylate using isopropylamine instead of (2R)-1,1,1-trifluoropropan-2-amine.

Compound 27 (137 mg) was prepared similarly as described for compound 18, using ethyl 3-fluoro-4-(isopropylsulfamoyl)-1-methyl-pyrrole-2-carboxylate instead of ethyl 3-fluoro-1-methyl-4-[[(1R)-2,2,2-tri fluoro-1-methyl-ethyl]sulfamoyl]pyrrole-2-carboxylate. Method B: Rt: 0.81 min. m/z: 364 (M–H)⁻ Exact mass: 365.0. $^1$H NMR (400 MHz, DMSO-$d_6$) δ ppm 1.05 (d, J=6.4 Hz, 6H), 3.26-3.41 (m, 1H), 3.82 (s, 3H), 7.54 (d, J=4.6 Hz, 1H), 7.63 (d, J=7.3 Hz, 1H), 7.91 (dd, J=5.6, 2.1 Hz, 1H), 8.21 (d, J=1.5 Hz, 1H), 8.62 (d, J=5.7 Hz, 1H), 10.67 (s, 1H). DSC: From 30 to 300° C. at 10° C./min, peak: 207.7° C.

Compound 28: 3-fluoro-N-(5-fluoro-2-pyridyl)-1-methyl-4-[[(1R)-2,2,2-trifluoro-1-methyl-ethyl]sulfamoyl]pyrrole-2-carboxamide

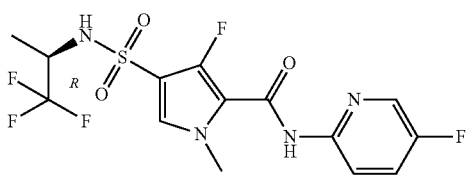

Compound 28 (126 mg) was prepared similarly as described for compound 18, using 2-amino-5-fluoropyridine instead of 4-aminopyridine-2-carbonitrile. Method D: Rt: 1.82 min. m/z: 413.4 (M+H)⁺ Exact mass: 412.0. $^1$H NMR (400 MHz, DMSO-$d_6$) δ ppm 1.19 (d, J=7.0 Hz, 3H), 3.82 (s, 3H), 3.89-4.02 (m, 1H), 7.55 (d, J=4.6 Hz, 1H), 7.79 (td, J=8.7, 3.2 Hz, 1H), 8.12 (dd, J=9.2, 4.2 Hz, 1H), 8.38 (d, J=3.1 Hz, 1H), 8.58 (d, J=8.6 Hz, 1H), 10.38 (s, 1H). DSC: From 30 to 300° C. at 10° C./min, peak: 160.9° C.

Compound 29: N-(5-bromo-6-fluoro-3-pyridyl)-3-fluoro-1-methyl-4-[[(1R)-2,2,2-trifluoro-1-methyl-ethyl]sulfamoyl]pyrrole-2-carboxamide

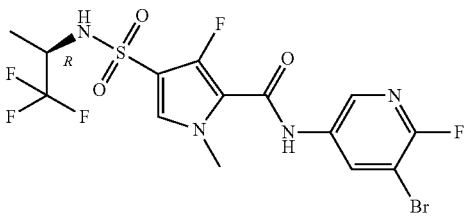

Compound 29 (143 mg) was prepared similarly as described for compound 18, using 5-amino-3-bromo-2-fluoropyridine instead of 4-aminopyridine-2-carbonitrile. Method D: Rt: 1.93 min. m/z: 488.9 (M–H)⁻ Exact mass: 490.0. $^1$H NMR (400 MHz, DMSO-$d_6$) δ ppm 1.18 (d, J=7.0 Hz, 3H), 3.82 (s, 3H), 3.92-4.04 (m, 1H), 7.58 (d, J=4.4 Hz, 1H), 8.46 (dd, J=2.3, 1.7 Hz, 1H), 8.56 (dd, J=8.0, 2.3 Hz, 1H), 8.63 (d, J=8.8 Hz, 1H), 10.37 (s, 1H). DSC: From 30 to 300° C. at 10° C./min, peak: 257.8° C.

Compound 30: N-(2,6-difluoro-4-pyridyl)-3-fluoro-1-methyl-4-[[(1R)-2,2,2-trifluoro-1-methyl-ethyl]sulfamoyl]pyrrole-2-carboxamide

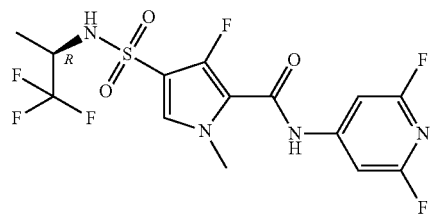

Compound 30 (128 mg) was prepared similarly as described for compound 18, using 2,6-difluoropyridin-4-amine instead of 4-aminopyridine-2-carbonitrile. Method D: Rt: 1.90 min. m/z: 429.3 (M–H)⁻ Exact mass: 430.0. $^1$H NMR (400 MHz, DMSO-$d_6$) δ ppm 1.18 (d, J=7.0 Hz, 3H), 3.82 (s, 3H), 3.93-4.05 (m, 1H), 7.34 (s, 2H), 7.63 (d, J=4.6 Hz, 1H), 8.66 (d, J=8.8 Hz, 1H), 10.87 (s, 1H). DSC: From 30 to 300° C. at 10° C./min, peak: 224.7° C.

Compound 31: N-(2-cyano-4-pyridyl)-3-fluoro-1-methyl-4-[[(1R)-1-(trifluoromethyl)propyl]-sulfamoyl]pyrrole-2-carboxamide

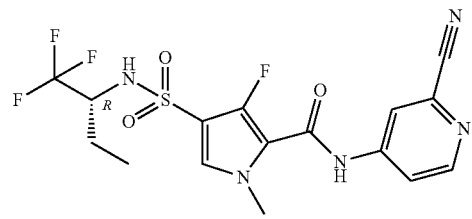

Ethyl 3-fluoro-1-methyl-4-[[(1R)-1-(trifluoromethyl)propyl]sulfamoyl]pyrrole-2-carboxylate was prepared similarly as ethyl 3-fluoro-1-methyl-4-[[(1R)-2,2,2-trifluoro-1-methyl-ethyl]-sulfamoyl]pyrrole-2-carboxylate using (R)-1,1,1-trifluoro-2-butylamine instead of (2R)-1,1,1-trifluoro-propan-2-amine.

Compound 31 (46 mg) was prepared similarly as described for compound 18, using ethyl 3-fluoro-1-methyl-4-[[(1R)-1-(trifluoromethyl)propyl]sulfamoyl]pyrrole-2-carboxylate instead of ethyl 3-fluoro-1-methyl-4-[[(1R)-2,2,2-trifluoro-1-methyl-ethyl]sulfamoyl]pyrrole-2-carboxylate. Method D: Rt: 1.79 min. m/z: 434.4 (M+H)$^+$ Exact mass: 433.0. $^1$H NMR (400 MHz, DMSO-d$_6$) δ ppm 0.80 (t, J=7.4 Hz, 3H), 1.43-1.56 (m, 1H), 1.63-1.74 (m, 1H), 3.71-3.80 (m, 1H), 3.82 (s, 3H), 7.60 (d, J=4.4 Hz, 1H), 7.92 (dd, J=5.6, 2.1 Hz, 1H), 8.22 (d, J=1.8 Hz, 1H), 8.59-8.65 (m, 2H), 10.70 (s, 1H). DSC: From 30 to 300° C. at 10° C./min, peak: 218.2° C.

Compound 32: 3-chloro-N-(2-cyano-4-pyridyl)-1,5-dimethyl-4-[[(1R)-2,2,2-trifluoro-1-methyl-ethyl]sulfamoyl]pyrrole-2-carboxamide

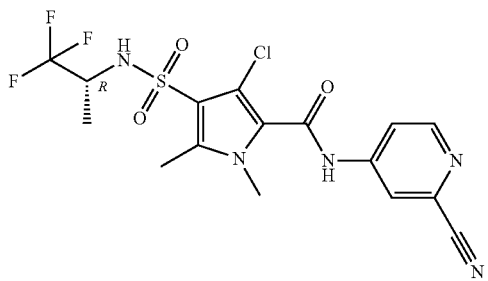

Ethyl 1,5-dimethyl-1H-pyrrole-2-carboxylate (2.5 g, 15 mmol) was added drop wise to chlorosulfonic acid (10 mL, 150 mmol) at 0° C. under nitrogen atmosphere. The reaction mixture was allowed to warm to room temperature and stirred overnight. The reaction mixture was slowly added to ice-water (200 mL), followed by extraction with DCM (3×100 mL). The combined organic extracts were dried (Na$_2$SO$_4$) and concentrated to give a light purple powder which decomposed over time to a dark sticky powder. This was dissolved in SOCl$_2$ (8 mL, 110 mmol) and stirred 1 hour at 80° C. The reaction mixture was concentrated and the residue was subjected to column chromatography on a Reveleris 120 g cartridge using a gradient from 10 till 50% EtOAc in heptane. The product fractions were concentrated to dryness yielding ethyl 4-chlorosulfonyl-1,5-dimethyl-pyrrole-2-carboxylate (600 mg) as white powder. Ethyl 4-chlorosulfonyl-1,5-dimethyl-pyrrole-2-carboxylate (600 mg, 2.26 mmol) was dissolved in ACN (4 mL) and dried on molecular sieves and NaHCO$_3$ (1.39 g, 16.5 mmol) was added. (R)-1,1,1-trifluoro-2-propylamine (766 mg, 6.77 mmol) was dissolved in ACN (1 mL) and dried on molecular sieves. The two suspensions were combined and heated at 80° C. for 4 hours. The reaction mixture was filtered and the filter cake was washed with acetonitrile. The combined filtrates were evaporated to dryness and the residue was purified using silica gel column chromatography to afford ethyl 1,5-dimethyl-4-[[(1R)-2,2,2-trifluoro-1-methyl-ethyl]sulfamoyl]pyrrole-2-carboxylate (600 mg) as colorless sticky powder.

Ethyl 1,5-dimethyl-4-[[(1R)-2,2,2-trifluoro-1-methyl-ethyl]sulfamoyl]pyrrole-2-carboxylate (400 mg, 1.17 mmol) was dissolved in HOAc (10 mL) and NCS (156 mg, 1.17 mmol) was added. The reaction mixture was heated at 40° C. over weekend. The reaction mixture was evaporated to dryness and the residue was purified using silica gel column chromatography (EtOAc in heptane from 0 to 100% to afford crude product which was purified again using silica gel column chromatography using methanol in DCM from 0.1 to 0.5% to afford ethyl 3-chloro-1,5-dimethyl-4-[[(1R)-2,2,2-trifluoro-1-methyl-ethyl]sulfamoyl]pyrrole-2-carboxylate (177 mg). Method D: Rt: 1.89 min. m/z: 375 (M–H)$^-$ Exact mass: 376.1. $^1$H NMR (400 MHz, DMSO-d$_6$) δ ppm 1.12 (d, J=7.0 Hz, 3H), 1.30 (t, J=7.2 Hz, 3H), 2.48 (s, 3H), 3.75 (s, 3H), 3.82-3.94 (m, 1H), 4.29 (q, J=7.0 Hz, 2H), 8.42 (br. s., 1H).

Ethyl 3-chloro-1,5-dimethyl-4-[[(1R)-2,2,2-trifluoro-1-methyl-ethyl]sulfamoyl]pyrrole-2-carboxylate (88 mg, 0.23 mmol) and 4-aminopyridine-2-carbonitrile (33.4 mg, 0.28 mmol) were dissolved in THF (10 mL). Lithium bis(trimethylsilyl)amide (0.7 mL, 1 M, 0.7 mmol) was added drop wise and the reaction mixture was stirred overnight at room temperature. The reaction mixture was quenched with sat. NH$_4$Cl (5 mL). The organic layer was removed and the aqueous layer extracted with DCM (2×5 mL). The combined organic layers were evaporated to dryness and the residue was purified on silica (EtOAc in heptane from 0 to 100%) to afford a white powder. A second purification was performed via Prep HPLC (Stationary phase: RP XBridge Prep C18 OBD-10 μm, 30×150 mm, Mobile phase: 0.25% NH$_4$HCO$_3$ solution in water, MeOH) yielding compound 32 (29 mg) as a white powder. Method B: Rt: 0.93 min. m/z: 448 (M–H)$^-$ Exact mass: 449.1. $^1$H NMR (400 MHz, DMSO-d$_6$) δ ppm 1.17 (d, J=6.8 Hz, 3H), 2.48-2.52 (m, 3H), 3.65 (s, 3H), 3.94 (spt, J=7.2 Hz, 1H), 7.91 (dd, J=5.6, 2.1 Hz, 1H), 8.21 (d, J=1.8 Hz, 1H), 8.45 (br. s., 1H), 8.65 (d, J=5.7 Hz, 1H), 11.05 (br. s., 1H).

Compound 33: 3-chloro-N-(2-chloro-3-fluoro-4-pyridyl)-1-methyl-4-[[(1R)-2,2,2-trifluoro-1-methyl-ethyl]sulfamoyl]pyrrole-2-carboxamide

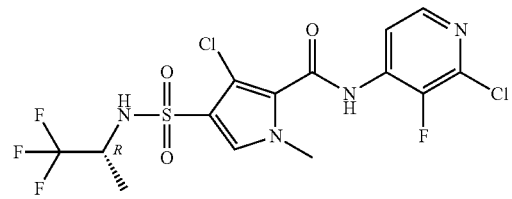

Compound 33 (95 mg) was prepared similarly as described for compound 7, using 2-chloro-3-fluoropyridin-4-amine instead of 2-amino-5-fluoro-6-methylpyridine. Method B: Rt: 1.04 min. m/z: 463 (M+H)$^+$ Exact mass: 462.0. $^1$H NMR (400 MHz, DMSO-d$_6$) δ ppm 1.19 (d, J=7.0 Hz, 3H), 3.81 (s, 3H), 3.92-4.05 (m, 1H), 7.74 (s, 1H), 8.08 (t, J=5.4 Hz, 1H), 8.23 (d, J=5.5 Hz, 1H), 8.54 (d, J=8.8 Hz, 1H), 10.64 (s, 1H). DSC: From 30 to 300° C. at 10° C./min, peak: 199.5° C.

Compound 34: N-(5-bromo-6-fluoro-3-pyridyl)-3-chloro-1-methyl-4-[[(1R)-2,2,2-trifluoro-1-methyl-ethyl]sulfamoyl]pyrrole-2-carboxamide

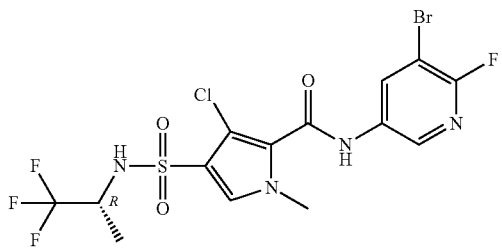

Compound 34 (121 mg) was prepared similarly as described for compound 7, using 5-amino-3-bromo-2-fluoropyridine instead of 2-amino-5-fluoro-6-methylpyridine. Method B: Rt: 1.07 min. m/z: 505 (M−H)⁻ Exact mass: 506.0. $^1$H NMR (400 MHz, DMSO-$d_6$) δ ppm 1.19 (d, J=7.0 Hz, 3H), 3.79 (s, 3H), 3.92-4.04 (m, 1H), 7.70 (s, 1H), 8.46-8.49 (m, 1H), 8.52 (d, J=8.8 Hz, 1H), 8.58 (dd, J=8.1, 2.4 Hz, 1H), 10.71 (s, 1H). DSC: From 30 to 300° C. at 10° C./min, peak: 213.3° C.

Compound 35: 3-chloro-N-(2,6-difluoro-4-pyridyl)-1-methyl-4-[[(1R)-2,2,2-trifluoro-1-methyl-ethyl]sulfamoyl]pyrrole-2-carboxamide

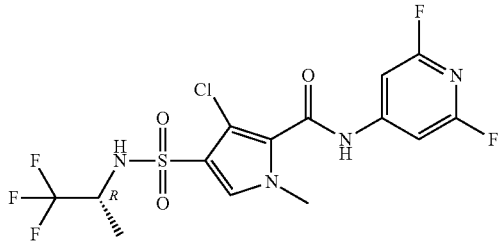

Compound 35 (79 mg) was prepared similarly as described for compound 7, using 4-amino-2,6-difluoropyridine instead of 2-amino-5-fluoro-6-methylpyridine. Method B: Rt: 1.05 min. m/z: 445 (M−H)⁻ Exact mass: 446.0. $^1$H NMR (400 MHz, DMSO-$d_6$) δ ppm 1.19 (d, J=6.8 Hz, 3H), 3.79 (s, 3H), 3.89-4.09 (m, 1H), 7.34 (s, 2H), 7.74 (s, 1H), 8.56 (d, J=8.1 Hz, 1H), 11.18 (br. s., 1H). DSC: From 30 to 300° C. at 10° C./min, peak: 219.5° C.

Synthesis of 4-amino-6-methyl-pyridine-2-carbonitrile 6-methyl-4-nitropyridine-2-carbonitrile (500 mg, 3.06 mmol) was dissolved in MeOH (50 mL), Pt/C 5% (0.61 mmol) was added and the reaction mixture was stirred overnight under a hydrogen atmosphere at 50° C. The solids were filtered off and the filtrate was evaporated to dryness. The residual brown solid was purified on silica using a heptane to EtOAc gradient yielding 4-amino-6-methyl-pyridine-2-carbonitrile as a yellow powder. (115 mg)

Compound 36: 3-chloro-N-(2-cyano-6-methyl-4-pyridyl)-1-methyl-4-[[(1R)-2,2,2-trifluoro-1-methyl-ethyl]sulfamoyl]pyrrole-2-carboxamide

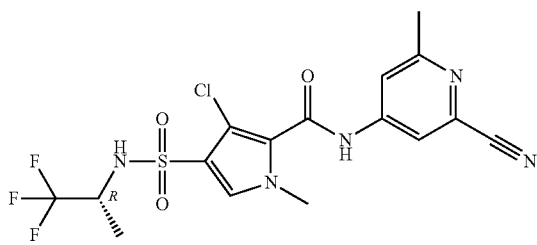

Compound 36 (133 mg) was prepared similarly as described for compound 7, using 4-amino-6-methyl-pyridine-2-carbonitrile instead of 2-amino-5-fluoro-6-methylpyridine. Method B: Rt: 0.99 min. m/z: 448 (M−H)⁻ Exact mass: 449.0. $^1$H NMR (400 MHz, DMSO-$d_6$) δ ppm 1.19 (d, J=7.0 Hz, 3H), 2.51 (s, 3H), 3.79 (s, 3H), 3.91-4.06 (m, 1H), 7.73 (s, 1H), 7.80 (d, J=1.8 Hz, 1H), 8.02 (d, J=1.8 Hz, 1H), 8.54 (br. s., 1H), 10.93 (br. s., 1H). DSC: From 30 to 300° C. at 10° C./min, peak: 210.6° C.

Compound 37: 3-chloro-N-(2-cyano-4-pyridyl)-1-methyl-4-[[(1S)-1-(trifluoromethyl)-propyl]sulfamoyl]pyrrole-2-carboxamide

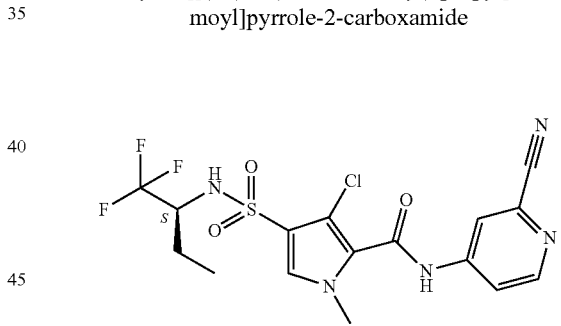

methyl 3-chloro-1-methyl-4-[[(1S)-1-(trifluoromethyl)propyl]sulfamoyl]pyrrole-2-carboxylate was prepared similarly as methyl 3-chloro-1-methyl-4-[[(1R)-2,2,2-trifluoro-1-methyl-ethyl]-sulfamoyl]pyrrole-2-carboxylate using (S)-1-trifluoromethyl-propylamine instead of (2R)-1,1,1-trifluoropropan-2-amine.

Compound 37 (16 mg) was prepared similarly as described for compound 9, using methyl 3-chloro-1-methyl-4-[[(1S)-1-(trifluoromethyl)propyl]sulfamoyl]pyrrole-2-carboxylate instead of methyl 3-chloro-1-methyl-4-[[(1R)-2,2,2-trifluoro-1-methyl-ethyl]sulfamoyl]pyrrole-2-carboxylate. Method D: Rt: 1.80 min. m/z: 450.4 (M+H)⁺ Exact mass: 449.0. $^1$H NMR (400 MHz, DMSO-$d_6$) δ ppm 0.81 (t, J=7.4 Hz, 3H), 1.45-1.59 (m, 1H), 1.60-1.73 (m, 1H), 3.73-3.82 (m, 4H), 7.71 (s, 1H), 7.92 (dd, J=5.6, 2.1 Hz, 1H), 8.21 (d, J=1.8 Hz, 1H), 8.53 (d, J=8.6 Hz, 1H), 8.65 (d, J=5.5 Hz, 1H), 11.00 (s, 1H).

Compound 38: 3-chloro-N-(2-cyano-4-pyridyl)-1-methyl-4-[[(1R)-1-(trifluoromethyl)propyl]-sulfamoyl]pyrrole-2-carboxamide

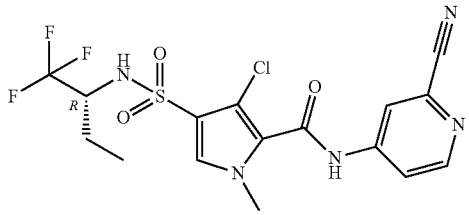

methyl 3-chloro-1-methyl-4-[[(1R)-1-(trifluoromethyl)propyl]sulfamoyl]pyrrole-2-carboxylate was prepared similarly as methyl 3-chloro-1-methyl-4-[[(1R)-2,2,2-trifluoro-1-methyl-ethyl]-sulfamoyl]pyrrole-2-carboxylate using (R)-1,1,1-trifluoro-2-butylamine instead of (2R)-1,1,1-trifluoropropan-2-amine.

Compound 38 (22.4 mg) was prepared similarly as described for compound 9, using methyl 3-chloro-1-methyl-4-[[(1R)-1-(trifluoromethyl)propyl]sulfamoyl]pyrrole-2-carboxylate instead of methyl 3-chloro-1-methyl-4-[[(1R)-2,2,2-trifluoro-1-methyl-ethyl]sulfamoyl]pyrrole-2-carboxylate. Method D: Rt: 1.80 min. m/z: 450.4 (M+H)+ Exact mass: 449.0. $^1$H NMR (400 MHz, DMSO-$d_6$) δ ppm 0.81 (t, J=7.4 Hz, 3H), 1.45-1.59 (m, 1H), 1.60-1.73 (m, 1H), 3.73-3.82 (m, 4H), 7.71 (s, 1H), 7.92 (dd, J=5.6, 2.1 Hz, 1H), 8.21 (d, J=1.8 Hz, 1H), 8.53 (d, J=8.6 Hz, 1H), 8.65 (d, J=5.5 Hz, 1H), 11.00 (s, 1H).

Compound 39: 3-chloro-N-(2-cyano-4-pyridyl)-1-methyl-4-[[1-(trifluoromethyl)cyclopropyl]-sulfamoyl]pyrrole-2-carboxamide

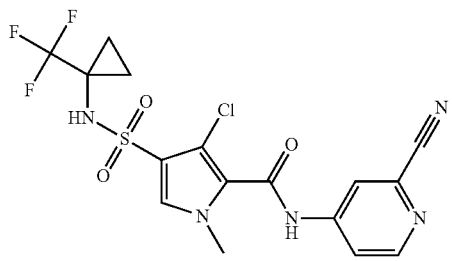 [SMILES: Cn1cc(S(=O)(=O)NC2(C(F)(F)F)CC2)c(Cl)c1C(=O)Nc1ccnc(C#N)c1]

Methyl 3-chloro-1-methyl-4-[[1-(trifluoromethyl)cyclopropyl]sulfamoyl]pyrrole-2-carboxylate was prepared similarly as methyl 3-chloro-1-methyl-4-[[(1R)-2,2,2-trifluoro-1-methyl-ethyl]-sulfamoyl]pyrrole-2-carboxylate using 1-(trifluoromethyl)cyclopropanamine instead of (2R)-1,1,1-trifluoropropan-2-amine.

Compound 39 (104 mg) was prepared similarly as described for compound 9, using methyl 3-chloro-1-methyl-4-[[1-(trifluoromethyl)cyclopropyl]sulfamoyl]pyrrole-2-carboxylate instead of methyl 3-chloro-1-methyl-4-[[(1R)-2,2,2-trifluoro-1-methyl-ethyl]sulfamoyl]pyrrole-2-carboxylate. Method B: Rt: 0.91 min. m/z: 448 (M+H)+ Exact mass: 447.0. $^1$H NMR (400 MHz, DMSO-$d_6$) δ ppm 1.06-1.30 (m, 4H), 3.79 (s, 3H), 7.72 (s, 1H), 7.91 (dd, J=5.9, 2.2 Hz, 1H), 8.20-8.21 (m, 1H), 8.64-8.67 (m, 1H), 9.09 (br. s., 1H), 11.05 (br. s., 1H).

Compound 40: 3-chloro-N-(2-cyano-4-pyridyl)-1-methyl-4-[[1-(trifluoromethyl)cyclobutyl]sulfamoyl]pyrrole-2-carboxamide

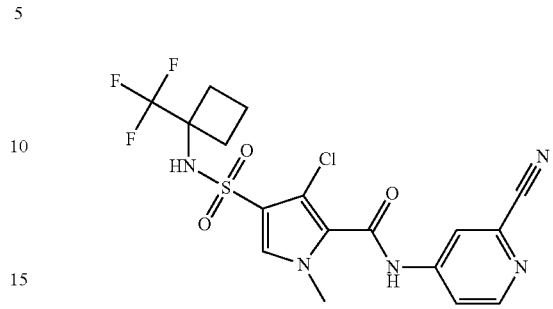

Methyl 3-chloro-1-methyl-4-[[1-(trifluoromethyl)cyclobutyl]sulfamoyl]pyrrole-2-carboxylate was prepared similarly as methyl 3-chloro-1-methyl-4-[[(1R)-2,2,2-trifluoro-1-methyl-ethyl]-sulfamoyl]pyrrole-2-carboxylate using 1-(trifluoromethyl)cyclobutan-1-amine instead of (2R)-1,1,1-trifluoropropan-2-amine.

Compound 40 (124 mg) was prepared similarly as described for compound 9, using methyl 3-chloro-1-methyl-4-[[1-(trifluoromethyl)cyclobutyl]sulfamoyl]pyrrole-2-carboxylate instead of methyl 3-chloro-1-methyl-4-[[(1R)-2,2,2-trifluoro-1-methyl-ethyl]sulfamoyl]pyrrole-2-carboxylate. Method B: Rt: 0.97 min. m/z: 462 (M+H)+ Exact mass: 461.0. $^1$H NMR (400 MHz, DMSO-$d_6$) δ ppm 1.82 (quin, J=8.1 Hz, 2H), 2.24-2.36 (m, 2H), 2.40-2.49 (m, 2H), 3.81 (s, 3H), 7.75 (s, 1H), 7.93 (dd, J=5.7, 2.0 Hz, 1H), 8.22 (dd, J=2.2, 0.7 Hz, 1H), 8.66 (d, J=5.1 Hz, 1H), 8.70 (br. s., 1H), 11.06 (br. s., 1H).

Compound 41: N-(2-cyano-4-pyridyl)-1-methyl-4-[[(1S)-1-(trifluoromethyl)propyl]-sulfamoyl]pyrrole-2-carboxamide

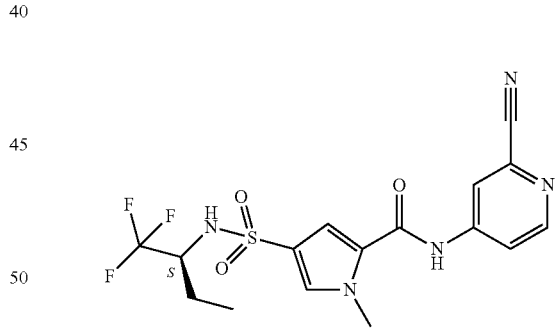

Methyl 4-(chlorosulfonyl)-1-methyl-1H-pyrrole-2-carboxylate (1500 mg, 6.31 mmol) was dissolved in ACN (18 mL) in a pressure tube and this was dried with powdered molecular sieves (4 Å) over a period of 30 minutes. Another tube was loaded with (S)-1-trifluoromethyl-propylamine (1.2 g, 9.5 mmol) and NaHCO$_3$ (1.59 g, 19 mmol) and this was dispersed in acetonitrile (2 mL) and dried with powdered molecular sieves (4 Å) over a period of 30 minutes. This was added to the pressure tube which was flushed with nitrogen, capped and stirred in a heating block at 80° C. for 48 hours. Due to leakage of the pressure tube, the solvent was evaporated completely. More (S)-1-trifluoromethyl-propylamine (1.00 g, 7.87 mmol) and ACN (20 mL) was added to the reaction mixture. The reaction mixture was capped and stirred in a heating block at 80° C. for 18 hours. The reaction mixture was filtered and the solids were washed with DCM (2×30 mL). The combined filtrates were evaporated to dryness and the residue was purified using silica gel column chromatography (EtOAc in heptane from 0 to 70%) to afford methyl 1-methyl-4-[[(1S)-1-(trifluoromethyl)propyl]sulfamoyl]pyrrole-2-carboxylate (1.35 g) as a white solid.

Compound 41 (155 mg) was prepared similarly as described for compound 9, using methyl 1-methyl-4-[[(1S)-1-(trifluoromethyl)propyl]sulfamoyl]pyrrole-2-carboxylate instead of methyl 3-chloro-1-methyl-4-[[(1R)-2,2,2-trifluoro-1-methyl-ethyl]sulfamoyl]pyrrole-2-carboxylate.
Method B: Rt: 0.93 min. m/z: 416 (M+H)$^+$ Exact mass: 415.0. $^1$H NMR (400 MHz, DMSO-$d_6$) δ ppm 0.68 (t, J=7.3 Hz, 3H), 1.34-1.51 (m, 1H), 1.55-1.71 (m, 1H), 3.68-3.84 (m, 1H), 3.93 (s, 3H), 7.47 (d, J=1.8 Hz, 1H), 7.72 (d, J=1.8 Hz, 1H), 7.98 (dd, J=5.9, 2.2 Hz, 1H), 8.23 (d, J=8.4 Hz, 1H), 8.28 (d, J=1.8 Hz, 1H), 8.62 (d, J=5.5 Hz, 1H), 10.70 (s, 1H).

Compound 42: N-(2-cyano-4-pyridyl)-1-methyl-4-[[1-(trifluoromethyl)cyclobutyl]-sulfamoyl]pyrrole-2-carboxamide

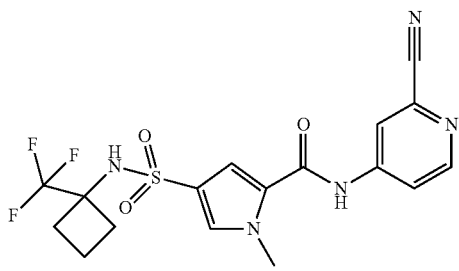 [SMILES: Cn1cc(S(=O)(=O)NC2(C(F)(F)F)CCC2)cc1C(=O)Nc1ccnc(C#N)c1]

Compound 42 (52 mg) was prepared similarly as described for compound 41, using 1-(trifluoromethyl)cyclobutan-1-amine instead of (S)-1-trifluoromethyl-propylamine. Method B: Rt: 0.94 min. m/z: 428 (M+H)$^+$ Exact mass: 427.0. $^1$H NMR (400 MHz, DMSO-$d_6$) δ ppm 1.67-1.89 (m, 2H), 2.23-2.36 (m, 2H), 2.37-2.47 (m, 2H), 3.95 (s, 3H), 7.48 (d, J=1.8 Hz, 1H), 7.71 (d, J=1.8 Hz, 1H), 7.98 (dd, J=5.9, 2.2 Hz, 1H), 8.28 (d, J=2.2 Hz, 1H), 8.44 (s, 1H), 8.62 (d, J=5.5 Hz, 1H), 10.73 (s, 1H).

Compound 43: 3-chloro-1-methyl-4-[[(1R)-2,2,2-trifluoro-1-methyl-ethyl]sulfamoyl]-N-(2,3,6-trifluoro-4-pyridyl)pyrrole-2-carboxamide

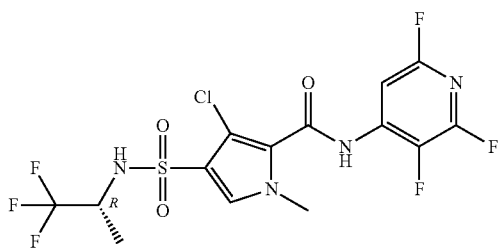

Methyl 3-chloro-1-methyl-4-[[(1R)-2,2,2-trifluoro-1-methyl-ethyl]sulfamoyl]pyrrole-2-carboxylate (2 g, 5.56 mmol) was dissolved in THF (5 mL). LiOH (666 mg, 27.8 mmol) dissolved in water (5 mL) was added and then MeOH (10 mL) to get a homogeneous reaction mixture. This was stirred 1 hour at 50° C. The volatiles were removed until water. HCl (25 mL, 1M aq.) was added and the precipitated compound was filtered off, triturated with DIPE (3×15 mL) and dried in a vacuum oven to yield 3-chloro-1-methyl-4-[[(1R)-2,2,2-trifluoro-1-methyl-ethyl]sulfamoyl]pyrrole-2-carboxylic acid (1.18 g) 3-chloro-1-methyl-4-[[(1R)-2,2,2-trifluoro-1-methyl-ethyl]sulfamoyl]pyrrole-2-carboxylic acid (100 mg, 0.3 mmol) was dissolved in DCM (5 mL), oxalyl chloride (87 μL, 0.9 mmol) was added and then DMF (2.3 μL, 0.03 mmol). The reaction mixture was stirred 1 hour at room temperature. The volatiles were removed under reduced pressure. The residue was coevaporated with toluene (2×20 mL) and then redissolved in THF (1 mL) and added to a solution containing 4-amino-2,3,6-trifluoropyridine (88.5 mg, 0.60 mmol) in THF (5 mL) treated with sodium hydride (13.7 mg, 0.60 mmol) and pre-stirred for 30 minutes. This reaction mixture was stirred overnight at room temperature. The reaction mixture was quenched with NH$_4$Cl (sat., 5 mL). The organic layer was removed and the aqueous layer extracted with DCM (2×5 mL). The combined organic layers were evaporated to dryness and the residue was purified on silica using a heptane to EtOAc gradient yielding compound 43 (88 mg) as a white powder after trituration with DIPE. Method B: Rt: 1.10 min. m/z: 463 (M−H)$^-$ Exact mass: 464.0. $^1$H NMR (400 MHz, DMSO-$d_6$) δ ppm 1.19 (d, J=7.0 Hz, 3H), 3.82 (s, 3H), 3.92-4.10 (m, 1H), 7.76 (s, 1H), 7.78 (d, J=3.5 Hz, 1H), 8.55 (d, J=8.8 Hz, 1H), 10.95 (s, 1H). DSC: From 30 to 300° C. at 10° C./min, peak: 216.5° C.

Compound 44: 3-chloro-1-methyl-4-[[(1R)-2,2,2-trifluoro-1-methyl-ethyl]sulfamoyl]-N-(2,3,5-trifluoro-4-pyridyl)pyrrole-2-carboxamide

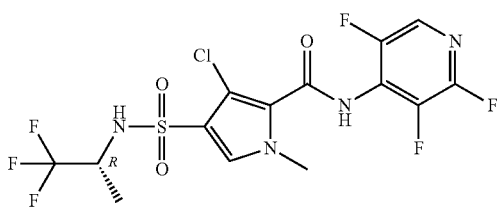

Compound 44 (58 mg) was prepared similarly as described for compound 43, using 2,3,5-trifluoro-4-pyridinamine instead of 4-amino-2,3,6-trifluoropyridine. Method B: Rt: 0.95 min. m/z: 463 (M−H)$^-$ Exact mass: 464.0. $^1$H NMR (400 MHz, DMSO-$d_6$) δ ppm 1.19 (d, J=7.0 Hz, 3H), 3.78 (s, 3H), 3.92-4.05 (m, 1H), 7.73 (s, 1H), 8.26 (s, 1H), 8.52 (d, J=8.8 Hz, 1H), 10.91 (s, 1H). DSC: From 30 to 300° C. at 10° C./min, peak: 177.9° C.

Compound 45: 3-chloro-N-(2-chloro-4-pyridyl)-1-methyl-4-[[1-(trifluoromethyl)cyclopropyl]-sulfamoyl]pyrrole-2-carboxamide

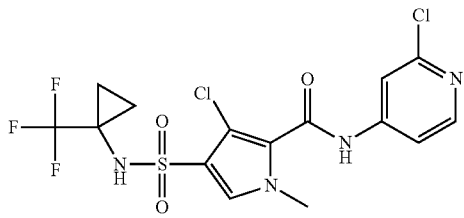 [SMILES: Cn1cc(S(=O)(=O)NC2(C(F)(F)F)CC2)c(Cl)c1C(=O)Nc1ccnc(Cl)c1]

Compound 45 (220 mg) was prepared similarly as described for compound 39, using 4-amino-2-chloropyridine instead of 4-aminopyridine-2-carbonitrile. Method B: Rt: 0.96 min. m/z: 457 (M+H)+ Exact mass: 456.0. ¹H NMR (400 MHz, DMSO-d₆) δ ppm 1.13-1.22 (m, 4H), 3.78 (s, 3H), 7.62 (dd, J=5.6, 1.9 Hz, 1H), 7.69 (s, 1H), 7.81 (d, J=1.5 Hz, 1H), 8.33 (d, J=5.5 Hz, 1H), 9.04 (s, 1H), 10.88 (s, 1H). DSC: From 30 to 300° C. at 10° C./min, peak: 208.8° C.

Compound 46: 3-chloro-N-(2-chloro-4-pyridyl)-1-methyl-4-[[1-(trifluoromethyl)cyclobutyl]-sulfamoyl]pyrrole-2-carboxamide

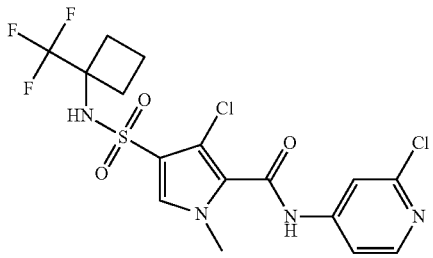 [SMILES: Cn1cc(S(=O)(=O)NC2(C(F)(F)F)CCC2)c(Cl)c1C(=O)Nc1ccnc(Cl)c1]

Compound 46 (391 mg) was prepared similarly as described for compound 40, using 4-amino-2-chloropyridine instead of 4-aminopyridine-2-carbonitrile. Method B: Rt: 1.02 min. m/z: 471 (M+H)+ Exact mass: 470.0. ¹H NMR (400 MHz, DMSO-d₆) δ ppm 1.75-1.89 (m, 2H), 2.25-2.35 (m, 2H), 2.40-2.49 (m, 2H), 3.80 (s, 3H), 7.63 (dd, J=5.6, 1.9 Hz, 1H), 7.72 (s, 1H), 7.82 (d, J=1.8 Hz, 1H), 8.33 (d, J=5.5 Hz, 1H), 8.65 (s, 1H), 10.90 (s, 1H). DSC: From 30 to 300° C. at 10° C./min, peak: 219.6° C.

Compound 47: N-(2-chloro-4-pyridyl)-1-methyl-4-[[(1S)-1-(trifluoromethyl)propyl]-sulfamoyl]pyrrole-2-carboxamide

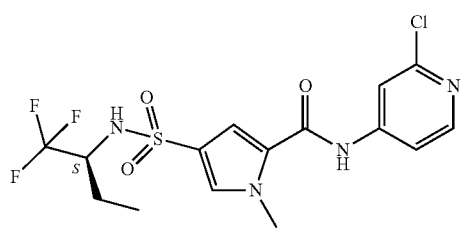

Compound 47 (52 mg) was prepared similarly as described for compound 41, using 4-amino-2-chloropyridine instead 4-amino-2-cyanopyridine. Compound 47 was crystallized from MeOH by slow addition of water. Method B: Rt: 0.97 min. m/z: 425 (M+H)+ Exact mass: 424.0. ¹H NMR (400 MHz, DMSO-d₆) δ ppm 0.69 (t, J=7.4 Hz, 3H), 1.36-1.50 (m, 1H), 1.58-1.72 (m, 1H), 3.66-3.83 (m, 1H), 3.92 (s, 3H), 7.45 (d, J=2.0 Hz, 1H), 7.67-7.71 (m, 2H), 7.90 (d, J=1.8 Hz, 1H), 8.19 (d, J=8.4 Hz, 1H), 8.29 (d, J=5.7 Hz, 1H), 10.53 (s, 1H). DSC: From 30 to 300° C. at 10° C./min, peak: 251.3° C.

Compound 48: N-(2-chloro-4-pyridyl)-1-methyl-4-[[1-(trifluoromethyl)cyclobutyl]-sulfamoyl]pyrrole-2-carboxamide

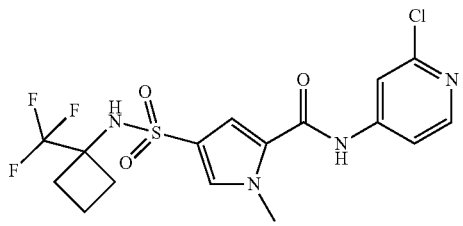 [SMILES: Cn1cc(S(=O)(=O)NC2(C(F)(F)F)CCC2)cc1C(=O)Nc1ccnc(Cl)c1]

Compound 48 (57 mg) was prepared similarly as described for compound 42, using 4-amino-2-chloropyridine instead of 4-amino-2-cyanopyridine. Compound 48 was crystallized from MeOH by slow addition of water. Method B: Rt: 0.99 min. m/z: 437 (M+H)+ Exact mass: 436.0. ¹H NMR (400 MHz, DMSO-d₆) δ ppm 1.70-1.87 (m, 2H), 2.22-2.37 (m, 2H), 2.39-2.47 (m, 2H), 3.94 (s, 3H), 7.46 (d, J=2.0 Hz, 1H), 7.67-7.71 (m, 2H), 7.90 (d, J=1.8 Hz, 1H), 8.29 (d, J=5.5 Hz, 1H), 8.39 (s, 1H), 10.56 (s, 1H). DSC: From 30 to 300° C. at 10° C./min, peak: 257.2° C.

Compound 49: N-(2-cyano-4-pyridyl)-1-methyl-4-[[1-(trifluoromethyl)cyclopropyl]-sulfamoyl]pyrrole-2-carboxamide

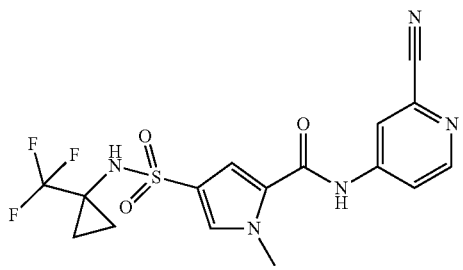 [SMILES: Cn1cc(S(=O)(=O)NC2(C(F)(F)F)CC2)cc1C(=O)Nc1ccnc(C#N)c1]

Compound 49 (125 mg) was prepared similarly as described for compound 41, using 1-(trifluoromethyl)cyclopropanamine instead of (S)-1-trifluoromethyl-propylamine. Method B: Rt: 0.88 min. m/z: 414 (M+H)+ Exact mass: 413.0. ¹H NMR (400 MHz, DMSO-d₆) δ ppm 1.11-1.21 (m, 4H), 3.93 (s, 3H), 7.41 (d, J=1.8 Hz, 1H), 7.64 (d, J=1.8 Hz, 1H), 7.97 (dd, J=5.5, 2.2 Hz, 1H), 8.27 (d, J=2.0 Hz, 1H), 8.62 (d, J=5.7 Hz, 1H), 8.78 (s, 1H), 10.68 (s, 1H). DSC: From 30 to 300° C. at 10° C./min, peak: 261.4° C.

Compound 50: 3-chloro-N-(6-fluoro-3-pyridyl)-1-methyl-4-[[(1R)-2,2,2-trifluoro-1-methyl-ethyl]sulfamoyl]pyrrole-2-carboxamide

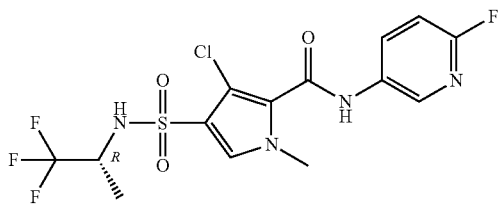

Compound 50 (87 mg) was prepared similarly as described for compound 43, using 5-amino-2-fluoropyridine instead of 4-amino-2,3,6-trifluoropyridine. Method B: Rt: 0.88 min. m/z: 427 (M−H)⁻ Exact mass: 428.0. $^1$H NMR (400 MHz, DMSO-d$_6$) δ ppm 1.19 (d, J=7.0 Hz, 3H), 3.78 (s, 3H), 3.91-4.05 (m, 1H), 7.22 (dd, J=8.8, 3.1 Hz, 1H), 7.68 (s, 1H), 8.18-8.29 (m, 1H), 8.44-8.58 (m, 2H), 10.62 (s, 1H). DSC: From 30 to 300° C. at 10° C./min, peak: 219.3° C.

Compound 51: 3-chloro-N-(5-fluoro-2-pyridyl)-1-methyl-4-[[(1R)-2,2,2-trifluoro-1-methyl-ethyl]sulfamoyl]pyrrole-2-carboxamide

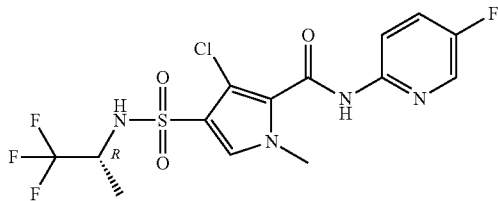

Compound 51 (4.8 mg) was prepared similarly as described for compound 43, using 2 amino-5-fluoropyridine instead of 4-amino-2,3,6-trifluoropyridine. Method B: Rt: 0.97 min. m/z: 427 (M−H)⁻ Exact mass: 428.0. $^1$H NMR (400 MHz, DMSO-d$_6$) δ ppm 1.19 (d, J=6.8 Hz, 3H), 3.79 (s, 3H), 3.88-4.04 (m, 1H), 7.67 (s, 1H), 7.81 (td, J=8.7, 3.1 Hz, 1H), 8.15 (dd, J=9.1, 4.1 Hz, 1H), 8.39 (d, J=3.1 Hz, 1H), 8.44 (d, J=31.5 Hz, 1H), 10.75 (s, 1H).

Compound 52: N-(2-chloro-4-pyridyl)-1-methyl-4-[[1-(trifluoromethyl)cyclopropyl]-sulfamoyl]pyrrole-2-carboxamide

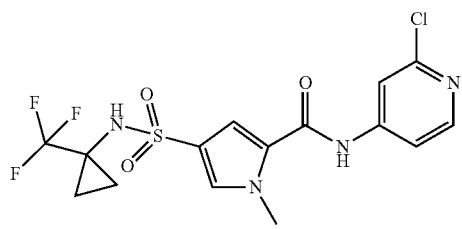 [SMILES: Cn1cc(S(=O)(=O)NC2(C(F)(F)F)CC2)cc1C(=O)Nc1ccnc(Cl)c1]

Compound 52 (111 mg) was prepared similarly as described for compound 49, using 4-amino-2-chloropyridine instead of 4-amino-2-cyanopyridine. Compound 52 was purified by prep. HPLC (Stationary phase: RP XBridge Prep C18 OBD-10 μm, 30×150 mm, mobile phase: 0.25% NH$_4$HCO$_3$ solution in water, ACN). Method B: Rt: 0.93 min. m/z: 423 (M+H)⁺ Exact mass: 422.0. $^1$H NMR (400 MHz, DMSO-d$_6$) δ ppm 1.05-1.24 (m, 4H), 3.92 (s, 3H), 7.39 (d, J=1.8 Hz, 1H), 7.61 (d, J=1.5 Hz, 1H), 7.68 (dd, J=5.7, 1.8 Hz, 1H), 7.89 (d, J=1.8 Hz, 1H), 8.28 (d, J=5.7 Hz, 1H), 8.77 (br. s., 1H), 10.51 (br. s., 1H).

Compound 53: N-(2-cyano-4-pyridyl)-4-[(3,3-difluoro-1-methyl-cyclobutyl)sulfamoyl]-3-fluoro-1-methyl-pyrrole-2-carboxamide

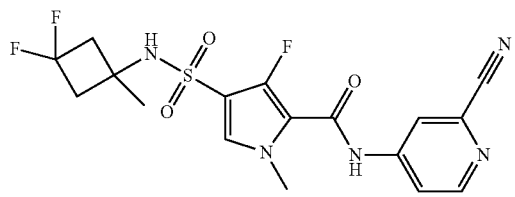 [SMILES: Cn1cc(S(=O)(=O)NC2(C)CC(F)(F)C2)c(F)c1C(=O)Nc1ccnc(C#N)c1]

Compound 53 (33 mg) was prepared similarly as described for compound 18, using ethyl 4-[(3,3-difluoro-1-methyl-cyclobutyl)sulfamoyl]-3-fluoro-1-methyl-pyrrole-2-carboxylate instead of ethyl 3-fluoro-1-methyl-4-[[(1R)-2,2,2-trifluoro-1-methyl-ethyl]sulfamoyl]pyrrole-2-carboxylate and using 3,3-difluoro-1-methylcyclobutanamine instead of (2R)-1,1,1-trifluoropropan-2-amine and refluxing for 2 hours instead of overnight during the synthesis of ethyl 4-[(3,3-difluoro-1-methyl-cyclobutyl)sulfamoyl]-3-fluoro-1-methyl-pyrrole-2-carboxylate. Method D: Rt: 1.74 min. m/z: 428 (M+H)⁺ Exact mass: 427.0. $^1$H NMR (400 MHz, DMSO-d$_6$) δ ppm 1.42 (s, 3H), 2.52-2.60 (m, 2H), 2.82-2.95 (m, 2H), 3.82 (s, 3H), 7.59 (d, J=4.6 Hz, 1H), 7.91 (dd, J=5.6, 2.1 Hz, 1H), 8.21 (d, J=1.8 Hz, 1H), 8.26 (s, 1H), 8.63 (d, J=5.7 Hz, 1H), 10.68 (s, 1H). DSC: From 30 to 300° C. at 10° C./min, peak: 153.2° C.

Compound 54: N-(2-chloro-4-pyridyl)-4-[(3,3-difluoro-1-methyl-cyclobutyl)sulfamoyl]-3-fluoro-1-methyl-pyrrole-2-carboxamide

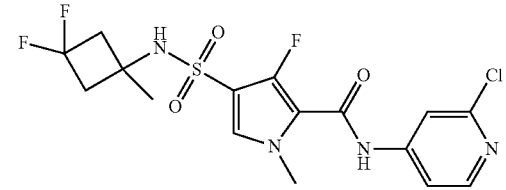 [SMILES: Cn1cc(S(=O)(=O)NC2(C)CC(F)(F)C2)c(F)c1C(=O)Nc1ccnc(Cl)c1]

Compound 54 (101 mg) was prepared similarly as described for compound 53, using 4-amino-2-chloropyridine instead of 4-amino-2-cyanopyridine. Method D: Rt: 1.78 min. m/z: 437 (M+H)⁺ Exact mass: 436.0. $^1$H NMR (400 MHz, DMSO-d$_6$) δ ppm 1.42 (s, 3H), 2.52-2.61 (m, 2H), 2.82-2.96 (m, 2H), 3.81 (s, 3H), 7.57 (d, J=4.6 Hz, 1H), 7.61 (dd, J=5.6, 1.9 Hz, 1H), 7.82 (d, J=1.8 Hz, 1H), 8.24 (s, 1H), 8.30 (d, J=5.5 Hz, 1H), 10.55 (s, 1H). DSC: From 30 to 300° C. at 10° C./min, peak: 183.7° C.

Compound 55: 4-[(3,3-difluoro-1-methyl-cyclobutyl)sulfamoyl]-3-fluoro-1-methyl-N-[2-(trifluoromethyl)-4-pyridyl]pyrrole-2-carboxamide

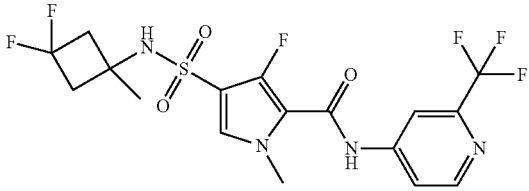 [SMILES: Cn1cc(S(=O)(=O)NC2(C)CC(F)(F)C2)c(F)c1C(=O)Nc1ccnc(C(F)(F)F)c1]

Compound 55 (79 mg) was prepared similarly as described for compound 53, using 4 amino-2-trifluoromethylpyridine instead of 4-amino-2-cyanopyridine. Method D: Rt: 1.89 min. m/z: 471 (M+H)$^+$ Exact mass: 470.0. $^1$H NMR (400 MHz, DMSO-d$_6$) δ ppm 1.42 (s, 3H), 2.52-2.61 (m, 2H), 2.82-2.96 (m, 2H), 3.83 (s, 3H), 7.58 (d, J=4.6 Hz, 1H), 7.90 (dd, J=5.5, 1.8 Hz, 1H), 8.20 (d, J=1.8 Hz, 1H), 8.25 (s, 1H), 8.65 (d, J=5.5 Hz, 1H), 10.69 (s, 1H).

Synthesis of 3-fluoro-2-(trifluoromethyl)pyridin-4-amine hydrochloride 3-fluoro-2-trifluoromethyl-isonicotinic acid (1.07 g, 5.11 mmol) was dissolved in tert. butyl alcohol (50 mL). Et$_3$N (0.78 mL, 5.62 mmol) and diphenylphosphoryl azide (1.12 mL, 5.21 mmol) were added and the reaction mixture was refluxed for 6 hours. The volatiles were removed under reduced pressure and the residue was purified on silica using a heptane to EtOAc gradient. The product fractions were concentrated in vacuo yielding tert-butyl N-[3-fluoro-2-(trifluoromethyl)-4-pyridyl]carbamate (1.20 g) as a clear oil. Method B: Rt: 1.11 min. m/z: 281 (M+H)$^+$ Exact mass: 280.1.

tert-Butyl N-[3-fluoro-2-(trifluoromethyl)-4-pyridyl]carbamate (1.20 g, 4.28 mmol) was dissolved in DCM (20 mL). HCl (6M in iPrOH) (20 mL, 120 mmol) was added and the reaction mixture was stirred overnight at room temperature. The volatiles were removed under reduced pressure and the residue was coevaporated with toluene (2×30 mL) to obtain 3-fluoro-2-(trifluoromethyl)pyridin-4-amine hydrochloride as a white powder. (812 mg)

Compound 56: 3-chloro-N-[3-fluoro-2-(trifluoromethyl)-4-pyridyl]-1-methyl-4-[[(1R)-2,2,2-trifluoro-1-methyl-ethyl]sulfamoyl]pyrrole-2-carboxamide

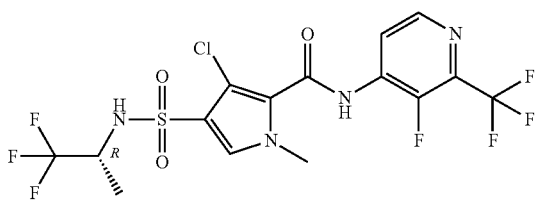

Compound 56 (118 mg) was prepared similarly as described for compound 7, using 3-fluoro-2-(trifluoromethyl)pyridin-4-amine instead of 2-amino-5-fluoro-6-methylpyridine. Method B: Rt: 1.07 min. m/z: 497 (M+H)$^+$ Exact mass: 496.0. $^1$H NMR (400 MHz, DMSO-d$_6$) δ 1.19 (d, J=6.8 Hz, 3H), 3.83 (s, 3H), 3.99 (dd, J=15.2, 7.7 Hz, 1H), 7.75 (s, 1H), 8.39 (t, J=5.5 Hz, 1H), 8.48-8.60 (m, 2H), 10.73 (s, 1H). DSC: From 30 to 300° C. at 10° C./min, peak: 202.6° C.

Synthesis of 5,6-difluoropyridin-3-amine 2,3-difluoro-5-nitropyridine (250 mg, 1.56 mmol) was dissolved in MeOH (20 mL), Pd/C (10%) (166 mg, 0.16 mmol) was added and the reaction mixture was stirred 2 hours under a hydrogen atmosphere. The solids were filtered off and the filtrate was evaporated to dryness yielding 5,6-difluoropyridin-3-amine as a brown oil.

Compound 57: 3-chloro-N-(5,6-difluoro-3-pyridyl)-1-methyl-4-[[(1R)-2,2,2-trifluoro-1-methyl-ethyl]sulfamoyl]pyrrole-2-carboxamide

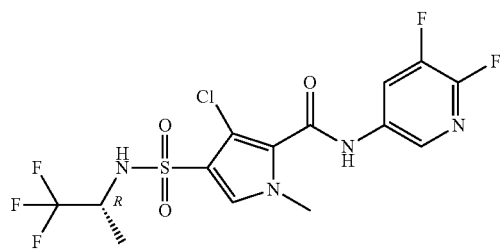

Compound 57 (145 mg) was prepared similarly as described for compound 7, using 5,6-difluoropyridin-3-amine instead of 2-amino-5-fluoro-6-methylpyridine. Method B: Rt: 0.98 min. m/z: 445 (M−H)$^-$ Exact mass: 446.0. $^1$H NMR (400 MHz, DMSO-d$_6$) δ ppm 1.19 (d, J=6.8 Hz, 3H), 3.79 (s, 3H), 3.97 (d, J=7.5 Hz, 1H), 7.70 (s, 1H), 8.25-8.38 (m, 2H), 8.51 (br. s., 1H), 10.78 (br. s., 1H). DSC: From 30 to 300° C. at 10° C./min, peak: 185.5° C.

Synthesis of (2S)-3,3-difluorobutan-2-amine hydrochloride (S)-2-((tert-butoxycarbonyl)amino)propanoic acid (39 g, 206 mmol), N,O-dimethyl-hydroxylamine hydrochloride (24 g, 246 mmol), HATU (117 g, 308 mmol) and N,N-diisopropylethylamine (66.3 g, 513 mmol) were dissolved in DMF (500 mL) and stirred at room temperature for 16 hours. The reaction mixture was poured into water (500 mL) and the formed precipitate was filtered off. The filter cake was washed with water (1 L) and dried to give tert-butyl N-[(1S)-2-[methoxy(methyl)amino]-1-methyl-2-oxo-ethyl]carbamate (36 g) as a white powder. tert-butyl N-[(1S)-2-[methoxy(methyl)amino]-1-methyl-2-oxo-ethyl]carbamate (35 g, 151 mmol) was dissolved in THF (500 mL) and cooled to 0° C. Methylmagnesium bromide (3.0 M in diethyl ether, 140 mL) was added and the reaction mixture was stirred 16 hours at room temperature. The reaction mixture was poured into water (100 mL) and evaporated to dryness. The residue was dissolved in EtOAc, washed with water, dried over Na$_2$SO$_4$, filtered and evaporated to dryness yielding tert-butyl N-[(1S)-1-methyl-2-oxo-propyl]carbamate (22 g) as a white powder. To a cooled (−78° C.) solution of tert-butyl N-[(1S)-1-methyl-2-oxo-propyl]carbamate (12 g, 64.1 mmol) in CH$_2$Cl$_2$ (200 mL) bis(2-methoxyethyl)-aminosulfur trifluoride (18.9 g, 117.5 mmol) was added. The reaction mixture was allowed to warm to room temperature and stirred overnight. The reaction mixture was poured into water and extracted with CH₂Cl₂. The organic layer was washed with water, dried over Na₂SO₄, filtered and evaporated to dryness. The obtained residue was purified by silica gel chromatography yielding tert-butyl N-[(1S)-2,2-difluoro-1-methyl-propyl]carbamate (5.8 g) as a pale yellow solid. Tert-butyl N-[(1S)-2,2-difluoro-1-methyl-propyl]carbamate (5.8 g, 27.7 mmol) was dissolved in EtOAc (100 mL). HCl (g) was bubbled through for 30 minutes and then the volatiles were removed under reduced pressure yielding (2S)-3,3-difluorobutan-2-amine hydrochloride (3.8 g) ¹H NMR (400 MHz, DMSO-d₆) δ ppm 8.69 (br. s., 3H), 3.76-3.63 (m, 1H), 1.72 (t, J=19.7 Hz, 3H), 1.28 (d, J=6.8 Hz, 3H).

Compound 58: N-(2-cyano-4-pyridyl)-4-[[(1S)-2,2-difluoro-1-methyl-propyl]sulfamoyl]-3-fluoro-1-methyl-pyrrole-2-carboxamide

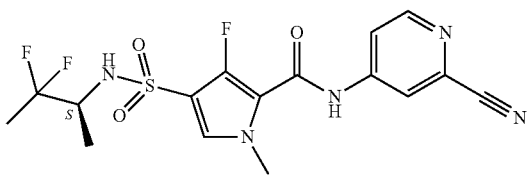

Ethyl 4-[[(1S)-2,2-difluoro-1-methyl-propyl]sulfamoyl]-3-fluoro-1-methyl-pyrrole-2-carboxylate was prepared similarly as ethyl 3-fluoro-1-methyl-4-[[(1R)-2,2,2-trifluoro-1-methyl-ethyl]-sulfamoyl]pyrrole-2-carboxylate using (2S)-3,3-difluorobutan-2-amine instead of (2R)-1,1,1-trifluoropropan-2-amine.

Compound 58 (48 mg) was prepared similarly as described for compound 18, using ethyl 4-[[(1S)-2,2-difluoro-1-methyl-propyl]sulfamoyl]-3-fluoro-1-methyl-pyrrole-2-carboxylate instead of ethyl 3-fluoro-1-methyl-4-[[(1R)-2,2,2-trifluoro-1-methyl-ethyl]sulfamoyl]pyrrole-2-carboxylate. Method B: Rt: 0.88 min. m/z: 414 (M−H)⁻ Exact mass: 415.0. ¹H NMR (400 MHz, DMSO-d₆) δ ppm 1.07 (d, J=7.0 Hz, 3H), 1.58 (t, J=19.1 Hz, 3H), 3.46-3.63 (m, 1H), 3.82 (s, 3H), 7.57 (d, J=4.6 Hz, 1H), 7.90 (dd, J=5.6, 2.1 Hz, 1H), 8.01-8.50 (m, 1H), 8.21 (d, J=2.0 Hz, 1H), 8.61 (d, J=5.7 Hz, 1H), 10.68 (br. s., 1H).

Compound 59: N-(2-chloro-4-pyridyl)-4-[[(1S)-2,2-difluoro-1-methyl-propyl]sulfamoyl]-3-fluoro-1-methyl-pyrrole-2-carboxamide

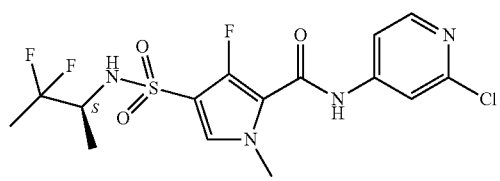

Compound 59 was prepared similarly as described for compound 58, using 4-amino-2-chloropyridine instead of 4-amino-2-cyanopyridine. Compound 59 (127 mg) was purified via prep. HPLC (Stationary phase: RP XBridge Prep C18 OBD-10 μm, 30×150 mm, Mobile phase: 0.25% NH₄HCO₃ solution in water, ACN). Method D: Rt: 1.76 min. m/z: 423 (M−H)⁻ Exact mass: 424.0. ¹H NMR (400 MHz, DMSO-d₆) δ ppm 1.07 (d, J=6.8 Hz, 3H), 1.58 (t, J=19.1 Hz, 3H), 3.55 (spt, J=7.2 Hz, 1H), 3.81 (s, 3H), 7.55 (d, J=4.4 Hz, 1H), 7.59-7.62 (m, 1H), 7.78-7.85 (m, 1H), 7.93-8.63 (m, 1H), 8.29 (d, J=5.5 Hz, 1H), 10.42 (br. s., 1H).

Synthesis of (2R)-3,3-difluorobutan-2-amine (R)-2-((tert-butoxycarbonyl)amino)propanoic acid (30 g, 159 mmol), N,O-dimethyl-hydroxylamine hydrochloride (17.5 g, 178 mmol), HATU (74 g, 195 mmol) and N,N-diisopropylethylamine (30 g, 232 mmol) were dissolved in DMF (300 mL) and stirred at room temperature for 15 hours. The reaction mixture was concentrated under vacuum and the residue was dissolved in CH₂Cl₂ (500 mL) and washed with brine (3×200 mL). The organic layer was dried over Na₂SO₄ and concentrated in vacuo. The residue was purified via silica gel chromatography using petroleum ether:EtOAc 2:1 as eluent yielding tert-butyl N-[(1R)-2-[methoxy(methyl)amino]-1-methyl-2-oxo-ethyl]carbamate (28.9 g). tert-butyl N-[(1R)-2-[methoxy(methyl)amino]-1-methyl-2-oxo-ethyl]carbamate was dissolved in THF (300 mL) and cooled to 0° C. Methylmagnesium bromide 3.0 m in diethyl ether (85 mL, 255 mmol) was added drop wise and the reaction mixture was stirred 15 hours at room temperature. The reaction mixture was quenched with sat. NH₄Cl and extracted with CH₂Cl₂ (3×100 mL). The combined organic layers were dried over Na₂SO₄, filtered and evaporated to dryness. The obtained residue was purified via silica gel chromatography yielding tert-butyl N-[(1R)-1-methyl-2-oxo-propyl]carbamate (18.9 g). To a cooled (−78° C.) solution of tert-butyl N-[(1R)-1-methyl-2-oxo-propyl]carbamate (10 g, 53.4 mmol) in CH₂Cl₂ (200 mL) bis(2-methoxyethyl)aminosulfur trifluoride (18.9 g, 117.5 mmol) was added drop wise and stirring was continued for 2 hours at −78° C. The reaction mixture was allowed to warm to room temperature and stirred overnight. The reaction mixture was quenched with sat. NaHCO₃ and extracted with EtOAc. The combined organic layers were washed with brine, dried over MgSO₄, filtered and evaporated to dryness. The residue was purified by silica gel chromatography using a gradient from petroleum ether to petroleum ether:EtOAc 1:1 yielding tert-butyl N-[(1R)-2,2-difluoro-1-methyl-propyl]carbamate (6.77 g). Tert-butyl N-[(1R)-2,2-difluoro-1-methyl-propyl]carbamate (6.77 g) was dissolved in EtOAc (50 mL). HCl in EtOAc was added at 0° C. and the reaction mixture was stirred for 4 hours at room temperature. The formed precipitate was filtered off and dried under high vacuum yielding (2R)-3,3-difluorobutan-2-amine hydrochloride (3.5 g).

Compound 60: 4-[[(1R)-2,2-difluoro-1-methyl-propyl]sulfamoyl]-3-fluoro-1-methyl-N-[2-(trifluoromethyl)-4-pyridyl]pyrrole-2-carboxamide

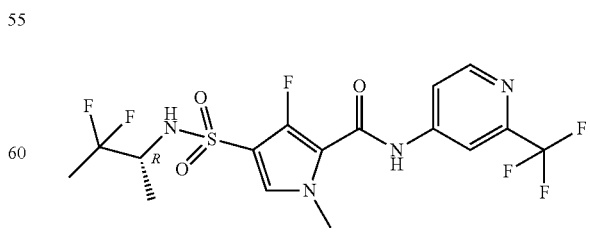

Compound 60 (93 mg) was prepared similarly as described for compound 63, using 4-amino-2-trifluoromethylpyridine instead of 4-amino-2-cyanopyridine. Method B:

Rt: 0.99 min. m/z: 457 (M−H)⁻ Exact mass: 458.1. ¹H NMR (400 MHz, DMSO-d₆) δ ppm 1.08 (d, J=6.8 Hz, 3H), 1.58 (t, J=19.1 Hz, 3H), 3.56 (spt, J=7.2 Hz, 1H), 3.83 (s, 3H), 7.58 (d, J=4.6 Hz, 1H), 7.90 (dd, J=5.5, 2.0 Hz, 1H), 8.00-8.48 (m, 1H), 8.21 (d, J=1.8 Hz, 1H), 8.65 (d, J=5.5 Hz, 1H), 10.69 (br. s., 1H).

Compound 61: N-(2-chloro-4-pyridyl)-4-[[(1R)-2,2-difluoro-1-methyl-propyl]sulfamoyl]-3-fluoro-1-methyl-pyrrole-2-carboxamide

Compound 61 (134 mg) was prepared similarly as described for compound 63, using 4-amino-2-chloropyridine instead of 4-amino-2-cyanopyridine. Method D: Rt: 1.76 min. m/z: 423 (M−H)⁻ Exact mass: 424.0. ¹H NMR (400 MHz, DMSO-d₆) δ ppm 1.07 (d, J=7.0 Hz, 3H), 1.58 (t, J=19.1 Hz, 3H), 3.55 (spt, J=7.2 Hz, 1H), 3.81 (s, 3H), 7.56 (d, J=4.6 Hz, 1H), 7.61 (dd, J=5.7, 1.8 Hz, 1H), 7.82 (d, J=1.7 Hz, 1H), 7.89-8.59 (m, 1H), 8.29 (d, J=5.7 Hz, 1H), 10.49 (br. s., 1H). DSC: From 30 to 300° C. at 10° C./min, peak: 193.1° C.

Compound 62: 4-[[(1S)-2,2-difluoro-1-methyl-propyl]sulfamoyl]-3-fluoro-1-methyl-N-[2-(trifluoromethyl)-4-pyridyl]pyrrole-2-carboxamide

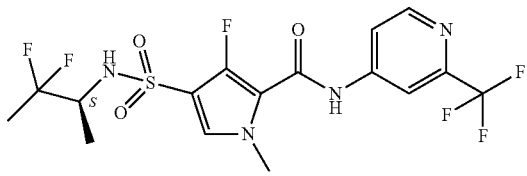

Compound 62 (178 mg) was prepared similarly as described for compound 58, using 4-amino-2-trifluoromethylpyridine instead of 4-amino-2-cyanopyridine. Method B: Rt: 0.99 min. m/z: 457 (M−H)⁻ Exact mass: 458.1. ¹H NMR (400 MHz, DMSO-d₆) δ ppm 1.07 (d, J=6.8 Hz, 3H), 1.58 (t, J=19.1 Hz, 3H), 3.44-3.64 (m, 1H), 3.83 (s, 3H), 7.58 (d, J=4.4 Hz, 1H), 7.90 (dd, J=5.6, 1.9 Hz, 1H), 8.10-8.28 (m, 2H), 8.65 (d, J=5.5 Hz, 1H), 10.69 (s, 1H).

Compound 63: N-(2-cyano-4-pyridyl)-4-[[(1R)-2,2-difluoro-1-methyl-propyl]sulfamoyl]-3-fluoro-1-methyl-pyrrole-2-carboxamide

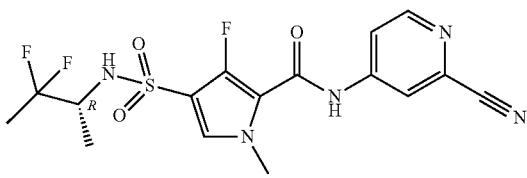

Ethyl 4-[[(1R)-2,2-difluoro-1-methyl-propyl]sulfamoyl]-3-fluoro-1-methyl-pyrrole-2-carboxylate was prepared similarly as ethyl 3-fluoro-1-methyl-4-[[(1R)-2,2,2-trifluoro-1-methyl-ethyl]sulfamoyl]pyrrole-2-carboxylate using (2R)-3,3-difluorobutan-2-amine instead of (2R)-1,1,1-trifluoropropan-2-amine.

Compound 63 (55 mg) was prepared similarly as described for compound 18, using ethyl 4-[[(1R)-2,2-difluoro-1-methyl-propyl]sulfamoyl]-3-fluoro-1-methyl-pyrrole-2-carboxylate instead of ethyl 3-fluoro-1-methyl-4-[[(1R)-2,2,2-trifluoro-1-methyl-ethyl]sulfamoyl]pyrrole-2-carboxylate. Method B: Rt: 0.89 min. m/z: 414 (M−H)⁻ Exact mass: 415.0. ¹H NMR (400 MHz, DMSO-d₆) δ ppm 1.07 (d, J=7.0 Hz, 3H), 1.58 (t, J=19.1 Hz, 3H), 3.49-3.63 (m, 1H), 3.82 (s, 3H), 7.59 (d, J=4.4 Hz, 1H), 7.91 (dd, J=5.6, 2.1 Hz, 1H), 8.10-8.33 (m, 2H), 8.63 (d, J=5.7 Hz, 1H), 10.69 (s, 1H). DSC: From 30 to 300° C. at 10° C./min, peak: 203.8° C.

Compound 64: 3-chloro-N-(2-cyano-4-pyridyl)-4-[(3,3-difluoro-1-methyl-cyclobutyl)-sulfamoyl]-1-methyl-pyrrole-2-carboxamide

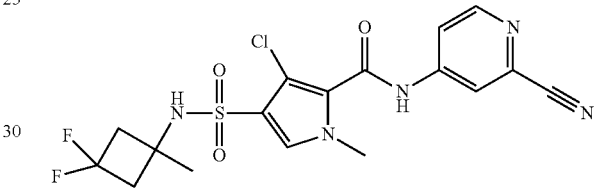

Methyl 3-chloro-4-[(3,3-difluoro-1-methyl-cyclobutyl)sulfamoyl]-1-methyl-pyrrole-2-carboxylate was prepared similarly as methyl 3-chloro-1-methyl-4-[[(1R)-2,2,2-trifluoro-1-methyl-ethyl]sulfamoyl]pyrrole-2-carboxylate using 3,3-difluoro-1-methylcyclobutanamine hydrochloride instead of (2R)-1,1,1-trifluoropropan-2-amine.

Compound 64 (131 mg) was prepared similarly as described for compound 9, using methyl 3-chloro-4-[(3,3-difluoro-1-methyl-cyclobutyl)sulfamoyl]-1-methyl-pyrrole-2-carboxylate instead of methyl 3-chloro-1-methyl-4-[[(1R)-2,2,2-trifluoro-1-methyl-ethyl]sulfamoyl]pyrrole-2-carboxylate. Method B: Rt: 0.99 min. m/z: 442 (M−H)⁻ Exact mass: 443.0. ¹H NMR (400 MHz, DMSO-d₆) δ ppm 1.40 (s, 3H), 2.46-2.60 (m, 2H), 2.81-3.00 (m, 2H), 3.80 (s, 3H), 7.72 (s, 1H), 7.92 (dd, J=5.5, 2.2 Hz, 1H), 8.17 (br. s, 1H), 8.21 (d, J=1.8 Hz, 1H), 8.65 (d, J=5.7 Hz, 1H), 11.00 (br. s., 1H). DSC: From 30 to 300° C. at 10° C./min, peak: 206.6° C.

Compound 65: 3-chloro-N-(2-chloro-4-pyridyl)-4-[(3,3-difluoro-1-methyl-cyclobutyl)-sulfamoyl]-1-methyl-pyrrole-2-carboxamide

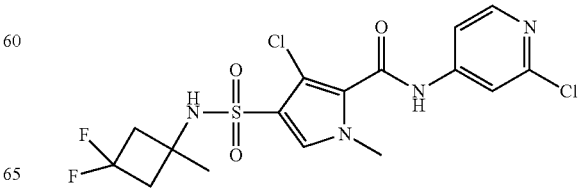

Compound 65 (184 mg) was prepared similarly as described for compound 64, using 4-amino-2-chloropyridine instead of 4-amino-2-cyanopyridine. Method B: Rt: 1.04 min. m/z: 451 (M−H)⁻ Exact mass: 452.0. ¹H NMR (400 MHz, DMSO-d₆) δ ppm 1.40 (s, 3H), 2.46-2.60 (m, 2H), 2.84-3.01 (m, 2H), 3.79 (s, 3H), 7.63 (dd, J=5.7, 1.8 Hz, 1H), 7.70 (s, 1H), 7.82 (d, J=1.8 Hz, 1H), 8.16 (br. s., 1H), 8.33 (d, J=5.5 Hz, 1H), 10.87 (br. s., 1H).

Compound 66: 3-chloro-4-[(3,3-difluoro-1-methyl-cyclobutyl)sulfamoyl]-1-methyl-N-[2-(trifluoromethyl)-4-pyridyl]pyrrole-2-carboxamide

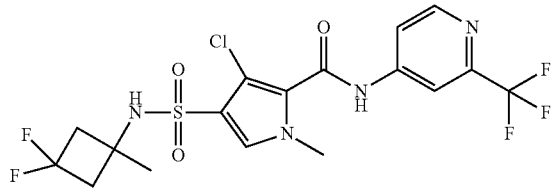 [SMILES: Cn1cc(S(=O)(=O)NC2(C)CC(F)(F)C2)c(Cl)c1C(=O)Nc1ccnc(C(F)(F)F)c1]

Compound 66 (149 mg) was prepared similarly as described for compound 64, using 4-amino-2-trifluoromethylpyridine instead of 4-amino-2-cyanopyridine with an extra purification via preparative HPLC (Stationary phase: RP XBridge Prep C18 OBD-10 μm, 30×150 mm, Mobile phase: 0.25% NH₄HCO₃ solution in water, ACN). Method B: Rt: 1.03 min. m/z: 485 (M−H)⁻ Exact mass: 486.0. ¹H NMR (400 MHz, DMSO-d₆) δ ppm 1.40 (s, 3H), 2.43-2.61 (m, 2H), 2.81-3.02 (m, 2H), 3.80 (s, 3H), 7.71 (s, 1H), 7.91 (dd, J=5.5, 2.0 Hz, 1H), 8.16 (br. s., 1H), 8.19 (d, J=1.8 Hz, 1H), 8.68 (d, J=5.5 Hz, 1H), 11.01 (br. s., 1H). DSC: From 30 to 300° C. at 10° C./min, peak: 200.9° C.

Compound 67: N-(2-chloro-4-pyridyl)-3-fluoro-1-methyl-4-[[(1R)-1-methylpropyl]-sulfamoyl]pyrrole-2-carboxamide

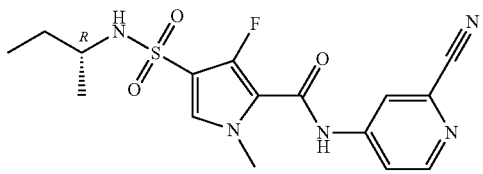

Ethyl 3-fluoro-1-methyl-4-[[(1R)-1-methylpropyl]sulfamoyl]pyrrole-2-carboxylate was prepared similarly as ethyl 3-fluoro-1-methyl-4-[[(1R)-2,2,2-trifluoro-1-methyl-ethyl]sulfamoyl]pyrrole-2-carboxylate using (R)-(−)-2-aminobutane instead of (2R)-1,1,1-trifluoropropan-2-amine and stirring overnight at room temperature instead of at reflux temperature.

Compound 67 (42 mg) was prepared similarly as described for compound 18, using ethyl 3-fluoro-1-methyl-4-[[(1R)-1-methylpropyl]sulfamoyl]pyrrole-2-carboxylate instead of ethyl 3-fluoro-1-methyl-4-[[(1R)-2,2,2-trifluoro-1-methyl-ethyl]sulfamoyl]pyrrole-2-carboxylate.

Method D: Rt: 1.71 min. m/z: 378.1 (M−H)⁻ Exact mass: 379.0. ¹H NMR (400 MHz, DMSO-d₆) δ ppm 0.78 (t, J=7.4 Hz, 3H), 1.01 (d, J=6.6 Hz, 3H), 1.32-1.44 (m, 2H), 3.08-3.19 (m, 1H), 3.82 (s, 3H), 7.54 (d, J=4.6 Hz, 1H), 7.59 (d, J=7.9 Hz, 1H), 7.91 (dd, J=5.7, 2.2 Hz, 1H), 8.21 (d, J=1.8 Hz, 1H), 8.62 (d, J=5.7 Hz, 1H), 10.66 (s, 1H). DSC: From 30 to 300° C. at 10° C./min, peak: 197.8° C.

Compound 68: 3-fluoro-1-methyl-4-[[(1R)-1-methylpropyl]sulfamoyl]-N-[2-(trifluoromethyl)-4-pyridyl]pyrrole-2-carboxamide

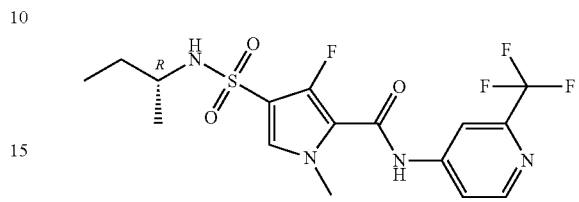

Compound 68 (178 mg) was prepared similarly as described for compound 67, using 4-amino-2-trifluoromethylpyridine instead of 4-amino-2-cyanopyridine. Method D: Rt: 1.90 min. m/z: 421.1 (M−H)⁻ Exact mass: 422.0. ¹H NMR (400 MHz, DMSO-d₆) δ ppm 0.78 (t, J=7.4 Hz, 3H), 1.01 (d, J=6.6 Hz, 3H), 1.32-1.44 (m, 2H), 3.08-3.19 (m, 1H), 3.82 (s, 3H), 7.53 (d, J=4.4 Hz, 1H), 7.58 (d, J=7.7 Hz, 1H), 7.90 (dd, J=5.5, 2.0 Hz, 1H), 8.21 (d, J=1.8 Hz, 1H), 8.65 (d, J=5.5 Hz, 1H), 10.67 (s, 1H). DSC: From 30 to 300° C. at 10° C./min, peak: 199.6° C.

Compound 69: N-(2-chloro-4-pyridyl)-3-fluoro-1-methyl-4-[[(1R)-1-methylpropyl]sulfamoyl]pyrrole-2-carboxamide

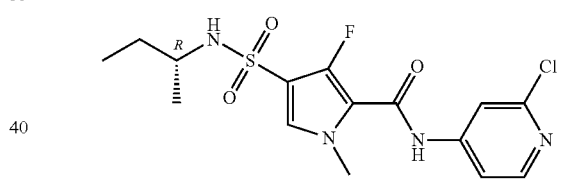

Compound 69 (111 mg) was prepared similarly as described for compound 67, using 4-amino-2-chloropyridine instead of 4-amino-2-cyanopyridine. Method D: Rt: 1.79 min. m/z: 387 (M−H)⁻ Exact mass: 388.0. ¹H NMR (400 MHz, DMSO-d₆) δ ppm 0.78 (t, J=7.4 Hz, 3H), 1.01 (d, J=6.6 Hz, 3H), 1.32-1.44 (m, 2H), 3.07-3.18 (m, 1H), 3.81 (s, 3H), 7.52 (d, J=4.6 Hz, 1H), 7.57 (d, J=7.9 Hz, 1H), 7.62 (dd, J=5.6, 1.9 Hz, 1H), 7.82 (d, J=1.8 Hz, 1H), 8.30 (d, J=5.5 Hz, 1H), 10.53 (s, 1H).

Compound 70: 3-chloro-1-methyl-4-[[(1R)-1-methylpropyl]sulfamoyl]-N-[2-(trifluoromethyl)-4-pyridyl]pyrrole-2-carboxamide

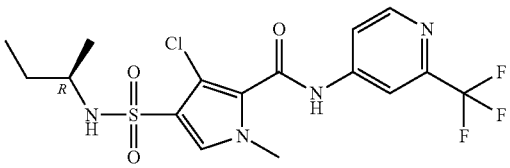

Compound 70 (178 mg) was prepared similarly as described for compound 72, using 4-amino-2-trifluoromethylpyridine instead of 4-amino-2-cyanopyridine. Method B: Rt: 1.02 min. m/z: 437 (M–H)⁻ Exact mass: 438.1. ¹H NMR (400 MHz, DMSO-d₆) δ ppm 0.79 (t, J=7.5 Hz, 3H), 1.00 (d, J=6.6 Hz, 3H), 1.38 (dq, J=14.6, 7.1 Hz, 2H), 3.05-3.16 (m, 1H), 3.79 (s, 3H), 7.47 (d, J=7.9 Hz, 1H), 7.66 (s, 1H), 7.90 (dd, J=5.5, 1.8 Hz, 1H), 8.19 (d, J=1.8 Hz, 1H), 8.67 (d, J=5.5 Hz, 1H), 10.99 (s, 1H).

Compound 71: N-(2-cyano-4-pyridyl)-3-fluoro-1,5-dimethyl-4-[[(1R)-2,2,2-trifluoro-1-methyl-ethyl]sulfamoyl]pyrrole-2-carboxamide

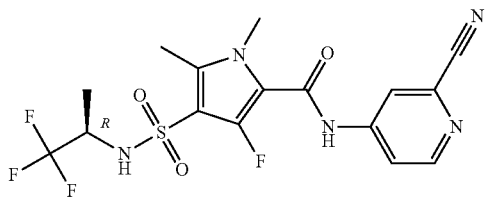

Br₂ (510 mg, 3.191 mmol) dissolved in HOAc (20 mL) was added to ethyl 3-fluoro-1-methyl-4-[[(1R)-2,2,2-trifluoro-1-methyl-ethyl]sulfamoyl]pyrrole-2-carboxylate (1050 mg, 3.03 mmol) and the solution was refluxed for 1 hour. More Br₂ (0.25 equiv) was added and the solution was refluxed for 1 hour more. More Br₂ (0.3 equiv) was added and the reaction mixture was allowed to reach room temperature overnight. The reaction mixture was concentrated and the obtained residue was dissolved in EtOAc (50 mL) washed with NaHCO₃ solution, dried over magnesium sulphate, filtered and concentrated, resulting in ethyl 5-bromo-3-fluoro-1-methyl-4-[[(1R)-2,2,2-trifluoro-1-methyl-ethyl]sulfamoyl]pyrrole-2-carboxylate (1.19 g) as a white powder. Method D: Rt: 1.92 min m/z: 423.2 (M-H)⁻ Exact mass: 424.0. ¹H NMR (400 MHz, DMSO-d₆) δ ppm 1.19 (d, J=7.0 Hz, 3H), 1.28 (t, J=7.2 Hz, 3H), 3.87 (s, 3H), 3.94-4.07 (m, 1H), 4.28 (q, J=7.0 Hz, 2H), 8.88 (d, J=8.8 Hz, 1H). A solution ethyl 5-bromo-3-fluoro-1-methyl-4-[[(1R)-2,2,2-trifluoro-1-methyl-ethyl]sulfamoyl]pyrrole-2-carboxylate (963 mg, 2.265 mmol), tetramethyltin (852.8 mg, 4.53 mmol) in DMF (7 mL), was flushed with nitrogen during 5 minutes. Tetrakis(triphenylphosphine)palladium(0) (261.7 mg, 0.226 mmol) was added and the reaction mixture was heated at 140° C. during 30 minutes by microwave irradiation. The reaction mixture was concentrated and the obtained residue was purified by silica gel column chromatography using a gradient from 10 to 100% EtOAc in heptane. The product fractions were concentrated yielding ethyl 3-fluoro-1,5-dimethyl-4-[[(1R)-2,2,2-trifluoro-1-methyl-ethyl]sulfamoyl]pyrrole-2-carboxylate (769 mg) as a white fluffy powder. Method D: Rt: 1.89 min m/z: 359.3 (M–H)⁻ Exact mass: 360.1. ¹H NMR (400 MHz, DMSO-d₆) δ ppm 1.14 (d, J=6.8 Hz, 3H), 1.27 (t, J=7.2 Hz, 3H), 2.42 (s, 3H), 3.76 (s, 3H), 3.86-3.98 (m, 1H), 4.26 (q, J=7.0 Hz, 2H), 8.54 (d, J=8.8 Hz, 1H).

Compound 71 (17 mg) was prepared similarly as described for compound 18, using ethyl 3-fluoro-1,5-dimethyl-4-[[(1R)-2,2,2-trifluoro-1-methyl-ethyl]sulfamoyl]pyrrole-2-carboxylate instead of ethyl 3-fluoro-1-methyl-4-[[(1R)-2,2,2-trifluoro-1-methyl-ethyl]sulfamoyl]pyrrole-2-carboxylate. Method D: Rt: 1.75 min. m/z: 432 (M-H)⁻ Exact mass: 433.0. ¹H NMR (400 MHz, DMSO-d₆) δ ppm 1.17 (d, J=6.8 Hz, 3H), 2.45 (s, 3H), 3.71 (s, 3H), 3.86-4.00 (m, 1H), 7.90 (dd, J=5.7, 2.2 Hz, 1H), 8.21 (d, J=1.8 Hz, 1H), 8.59 (d, J=8.8 Hz, 1H), 8.62 (d, J=5.5 Hz, 1H), 10.69 (s, 1H). DSC: From 30 to 300° C. at 10° C./min, peak: 211.8° C.

Compound 72: 3-chloro-N-(2-cyano-4-pyridyl)-1-methyl-4-[[(1R)-1-methylpropyl]-sulfamoyl]pyrrole-2-carboxamide

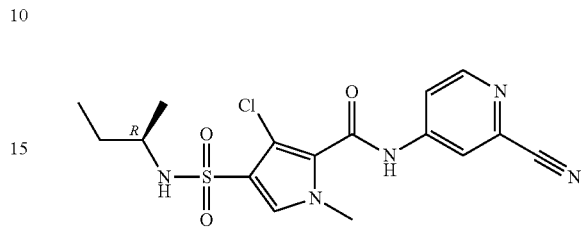

Methyl 3-chloro-1-methyl-4-[[(1R)-1-methylpropyl]sulfamoyl]pyrrole-2-carboxylate was prepared similarly as ethyl 3-fluoro-1-methyl-4-[[(1R)-2,2,2-trifluoro-1-methyl-ethyl]-sulfamoyl]pyrrole-2-carboxylate using (R)-(–)-2-aminobutane instead of (2R)-1,1,1-trifluoropropan-2-amine.

Compound 72 (33 mg) was prepared similarly as described for compound 9, using methyl 3-chloro-1-methyl-4-[[(1R)-1-methylpropyl]sulfamoyl]pyrrole-2-carboxylate instead of ethyl 3-fluoro-1-methyl-4-[[(1R)-2,2,2-trifluoro-1-methyl-ethyl]sulfamoyl]pyrrole-2-carboxylate. Method B: Rt: 0.90 min. m/z: 394 (M–H)⁻ Exact mass: 395.1. ¹H NMR (400 MHz, DMSO-d₆) δ ppm 0.79 (t, J=7.5 Hz, 3H), 1.00 (d, J=6.6 Hz, 3H), 1.38 (dq, J=14.6, 7.2 Hz, 2H), 3.05-3.16 (m, 1H), 3.79 (s, 3H), 7.48 (d, J=8.1 Hz, 1H), 7.66 (s, 1H), 7.92 (m, J=2.2 Hz, 1H), 8.21 (d, J=1.8 Hz, 1H), 8.65 (d, J=5.5 Hz, 1H), 10.98 (s, 1H).

Compound 73: 3-chloro-N-(2-chloro-4-pyridyl)-1-methyl-[[(1R)-1-methylpropyl]-sulfamoyl]pyrrole-2-carboxamide

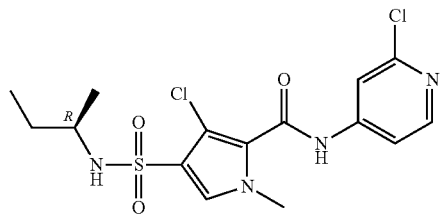

Compound 73 (178 mg) was prepared similarly as described for compound 72, using 4-amino-2-chloropyridine instead of 4-amino-2-cyanopyridine with an extra purification via preparative HPLC (Stationary phase: RP XBridge Prep C18 OBD-10 μm, 30×150 mm, Mobile phase: 0.25% NH₄HCO₃ solution in water, ACN). Method B: Rt: 0.95 min. m/z: 403 (M-H)⁻ Exact mass: 404.0. ¹H NMR (400 MHz, DMSO-d₆) δ ppm 0.79 (t, J=7.4 Hz, 3H), 1.01 (s, 2H), 1.38 (dq, J=14.8, 7.2 Hz, 2H), 3.03-3.19 (m, 1H), 3.78 (s, 3H), 7.46 (d, J=7.9 Hz, 1H), 7.58-7.70 (m, 2H), 7.81 (d, J=1.5 Hz, 1H), 8.32 (d, J=5.7 Hz, 1H), 10.75-10.79 (m, 1H), 10.85 (s, 1H).

Synthesis of 2-(difluoromethyl)pyridin-4-amine

A pressure vessel was charged with 4-bromo-2-(difluoromethyl)pyridine hydrobromide (5 g, 17.31 mmol), copper (I) oxide (383 mg, 2.6 mmol), NH$_3$ (28% in H$_2$O, 20 mL) and NMP (10 mL). The reaction mixture was heated at 110° C. overnight. The reaction mixture was partitioned between water (100 mL) and diethylether (100 mL). The organic layer was isolated and the aqueous layer was extracted with diethylether (4×50 mL). The combined organic layers were evaporated to dryness and the residue was purified on silica using a gradient from heptane to EtOAc yielding 2-(difluoromethyl)pyridin-4-amine (2.16 g) as a clear oil.

Compound 74: 3-chloro-N-[2-(difluoromethyl)-4-pyridyl]-1-methyl-4-[[(1R)-2,2,2-trifluoro-1-methyl-ethyl]sulfamoyl]pyrrole-2-carboxamide

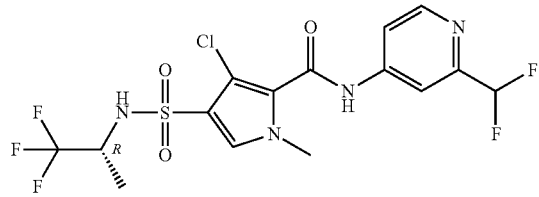

Methyl 3-chloro-1-methyl-4-[[(1R)-2,2,2-trifluoro-1-methyl-ethyl]sulfamoyl]pyrrole-2-carboxylate (1 g, 2.87 mmol) and 2-(difluoromethyl)pyridin-4-amine (455 mg, 3.15 mmol) were dissolved in dry THF (15 mL). Lithium bis(trimethylsilyl)amide (8.6 mL, 8.6 mmol) was added drop wise and the reaction mixture was stirred for 2 hours. The reaction mixture was quenched with sat. NH$_4$Cl (10 mL). The organic layer was removed and the aqueous layer extracted with DCM (2×5 mL). The combined organic layers were evaporated to dryness and the residue was purified on silica using a heptane to EtOAc gradient yielding the product as an off-white powder which was recrystallized from a MeOH:H$_2$O mixture to yield compound 74 (1.09 g) as a bright white powder. Method B: Rt: 0.88 min. m/z: 461 (M+H)$^+$ Exact mass: 460.0. $^1$H NMR (400 MHz, DMSO-d$_6$) δ ppm 1.19 (d, J=6.8 Hz, 3H), 3.79 (s, 3H), 3.93-4.04 (m, 1H), 6.94 (t, J=55.0 Hz, 1H), 7.71 (s, 1H), 7.79 (dd, J=5.5, 2.0 Hz, 1H), 8.03 (d, J=1.8 Hz, 1H), 8.52 (br. s., 1H), 8.59 (d, J=5.5 Hz, 1H), 10.93 (s, 1H). DSC: From 30 to 300° C. at 10° C./min, peak: 181.0° C.

Synthesis of 6-chloro-5-fluoro-pyridin-2-amine

A solution of 6-chloro-5-fluoropicolinic acid (1 g, 5.7 mmol), diphenylphosphoryl azide (1.93 g, 7 mmol) and triethylamine (1.73 g, 17 mmol) in tert.-butylaclohol (10 mL) was heated to 80° C. for 15 hours. The reaction mixture was washed with sat. NaHCO$_3$, and extracted with ethyl acetate. The organic phase was evaporated in vacuo to give the crude compound. This was purified by column chromatography over silica gel (eluent: petroleum ether/ether acetate 3/1) to give tert-butyl N-(6-chloro-5-fluoro-2-pyridyl)carbamate (300 mg).

Tert-butyl N-(6-chloro-5-fluoro-2-pyridyl)carbamate (2.1 g, 8.51 mmol) (synthesized similarly as described above) was dissolved in MeOH (10 mL). HCl in EtOAc (8 mL) was added drop wise and the solution was stirred for 2 hours at 20° C. The reaction mixture was concentrated and purified by preparative HPLC to give 6-chloro-5-fluoro-pyridin-2-amine (378 mg). $^1$H NMR (400 MHz, DMSO-d$_6$) δ ppm 7.49 (t, J=8.6 Hz, 1H), 6.40 (dd, J=2.4, 8.8 Hz, 1H), 6.31 (br. s., 2H).

Compound 75: 3-chloro-N-(6-chloro-5-fluoro-2-pyridyl)-1-methyl-4-[[(1R)-2,2,2-trifluoro-1-methyl-ethyl]sulfamoyl]pyrrole-2-carboxamide

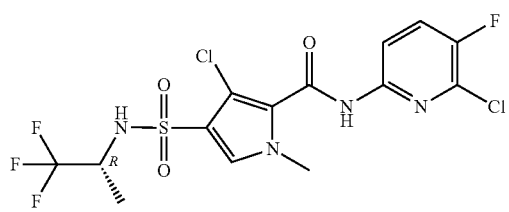

Compound 75 (121 mg) was prepared similarly as described for compound 7, using 6-chloro-5-fluoro-pyridin-2-amine instead of 2-amino-5-fluoro-6-methylpyridine. Method B: Rt: 1.08 min. m/z: 463 (M+H)$^+$ Exact mass: 462.0. $^1$H NMR (400 MHz, DMSO-d$_6$) δ ppm 1.19 (d, J=7.0 Hz, 3H), 3.78 (s, 3H), 3.87-4.03 (m, 1H), 7.67 (s, 1H), 7.96-8.05 (m, 1H), 8.14 (dd, J=8.9, 3.2 Hz, 1H), 8.46 (d, J=8.6 Hz, 1H), 11.11 (s, 1H). DSC: From 30 to 300° C. at 10° C./min, peak: 183.5° C.

Compound 76: N-(6-bromo-5-fluoro-2-pyridyl)-3-chloro-1-methyl-4-[[(1R)-2,2,2-trifluoro-1-methyl-ethyl]sulfamoyl]pyrrole-2-carboxamide

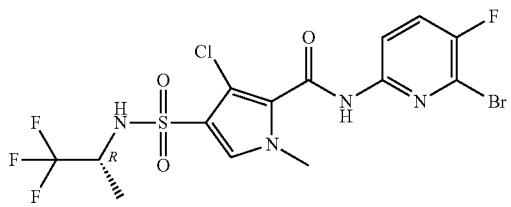

Compound 76 (118 mg) was prepared similarly as described for compound 7, using 6-bromo-5-fluoro-pyridin-2-amine instead of 2-amino-5-fluoro-6-methylpyridine. Method B: Rt: 1.09 min. m/z: 507 (M+H)$^+$ Exact mass: 506.0. $^1$H NMR (400 MHz, DMSO-d$_6$) δ ppm 1.19 (d, J=7.0 Hz, 3H), 3.77 (s, 3H), 3.88-4.01 (m, 1H), 7.67 (s, 1H), 7.94 (dd, J=8.9, 7.6 Hz, 1H), 8.15 (dd, J=8.8, 3.3 Hz, 1H), 8.45 (br. s., 1H), 11.14 (br. s., 1H). DSC: From 30 to 300° C. at 10° C./min, peak: 175.5° C.

Compound 77: 3-chloro-N-(2,6-difluoro-3-pyridyl)-1-methyl-4-[[(1R)-2,2,2-trifluoro-1-methyl-ethyl]sulfamoyl]pyrrole-2-carboxamide

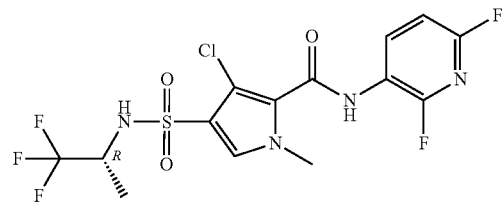

Compound 77 (1.9 mg) was prepared similarly as described for compound 7, using 2,6-difluoropyridin-3- amine instead of 2-amino-5-fluoro-6-methylpyridine. Method B: Rt: 0.96 min. m/z: 445 (M–H)⁻ Exact mass: 446.0. ¹H NMR (400 MHz, DMSO-d₆) δ ppm 1.19 (d, J=6.8 Hz, 3H), 3.79 (s, 3H), 3.97 (dq, J=15.4, 7.8 Hz, 1H), 7.23 (dd, J=8.4, 2.9 Hz, 1H), 7.69 (s, 1H), 8.36-8.46 (m, 1H), 8.50 (d, J=9.0 Hz, 1H), 10.27 (s, 1H).

Compound 78: 3-fluoro-4-(isopropylsulfamoyl)-1-methyl-N-[2-(trifluoromethyl)-4-pyridyl]pyrrole-2-carboxamide

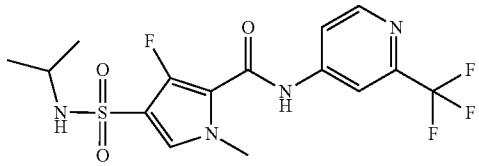 [SMILES: CC(C)NS(=O)(=O)c1cn(C)c(C(=O)Nc2ccnc(C(F)(F)F)c2)c1F]

To Ethyl 3-fluoro-4-(isopropylsulfamoyl)-1-methyl-pyrrole-2-carboxylate (200 mg, 0.68 mmol) and 2-(trifluoromethyl)pyridin-4-amine (133 mg, 0.82 mmol) dissolved in dry THF (5 mL) was added drop wise lithium bis(trimethylsilyl)amide in THF (1 mL, 1 M, 1 mmol). The reaction mixture was stirred 90 minutes at room temperature. The reaction mixture was quenched with sat.NH₄Cl (aq) (1 mL). The organic layer was separated and the aqueous layer was extracted with CH₂Cl₂ (5 mL). The combined organic layers were evaporated to dryness and the residue was purified on silica using a heptane to EtOAc gradient. The product fractions were concentrated and the solid residue was crystallized from MeOH to yield compound 78 (100 mg) as a white powder. Method B: Rt: 0.93 min. m/z: 409 (M+H)⁺ Exact mass: 408.0. ¹H NMR (400 MHz, DMSO-d₆) δ ppm 1.06 (d, J=6.4 Hz, 6H), 3.32-3.40 (m, 1H), 3.82 (s, 3H), 7.53 (d, J=4.6 Hz, 1H), 7.62 (d, J=7.5 Hz, 1H), 7.90 (dd, J=5.5, 2.0 Hz, 1H), 8.20 (d, J=1.8 Hz, 1H), 8.65 (d, J=5.5 Hz, 1H), 10.68 (s, 1H). DSC: From 30 to 300° C. at 10° C./min, peak: 240.9° C.

Compound 79: N-(2-chloro-4-pyridyl)-3-fluoro-4-(isopropylsulfamoyl)-1-methyl-pyrrole-2-carboxamide

Compound 79 (100 mg) was prepared similarly as described for compound 78, using 4-amino-2-chloropyridine instead of 2-(trifluoromethyl)pyridin-4-amine. Method B: Rt: 0.85 min. m/z: 375 (M+H)⁺ Exact mass: 374.0. ¹H NMR (400 MHz, DMSO-d₆) δ ppm 1.05 (d, J=6.6 Hz, 6H), 3.27-3.43 (m, 1H), 3.81 (s, 3H), 7.52 (d, J=4.6 Hz, 1H), 7.58-7.65 (m, 2H), 7.82 (d, J=1.8 Hz, 1H), 8.30 (d, J=5.5 Hz, 1H), 10.54 (s, 1H). DSC: From 30 to 300° C. at 10° C./min, peak: 201.7° C.

Compound 80: N-[2-(difluoromethyl)-4-pyridyl]-3-fluoro-1-methyl-4-[[(1R)-2,2,2-trifluoro-1-methyl-ethyl]sulfamoyl]pyrrole-2-carboxamide

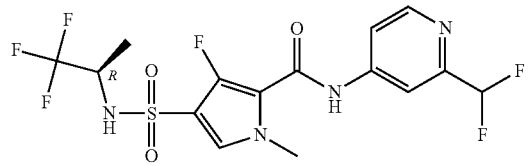

To ethyl 3-fluoro-1-methyl-4-[[(1R)-2,2,2-trifluoro-1-methyl-ethyl]sulfamoyl]pyrrole-2-carboxylate (150 mg, 0.43 mmol) and 2-(difluoromethyl)pyridin-4-amine (74.9 mg, 0.52 mmol) dissolved in dry THF (5 mL) was added drop wise lithium bis(trimethylsilyl)amide in THF (1 mL, 1 M, 1 mmol). The reaction mixture was stirred 90 minutes at room temperature. The reaction mixture was quenched with sat. NH₄Cl(aq) (1 mL). The organic layer was separated and the aqueous layer was extracted with CH₂Cl₂ (5 mL). The combined organic layers were evaporated to dryness and the residue was purified on silica using a heptane to EtOAc gradient. The product fractions were concentrated and the solid residue was crystallized from MeOH upon addition of water to yield compound 80 (66 mg) as a white powder. Method B: Rt: 0.89 min. m/z: 445 (M+H)⁺ Exact mass: 444.0. ¹H NMR (400 MHz, DMSO-d₆) δ ppm 1.18 (d, J=6.8 Hz, 3H), 3.82 (s, 3H), 3.92-4.05 (m, 1H), 6.92 (t, J=55.2 Hz, 1H), 7.59 (d, J=4.6 Hz, 1H), 7.77 (dd, J=5.6, 1.9 Hz, 1H), 8.03 (d, J=1.8 Hz, 1H), 8.57 (d, J=5.5 Hz, 1H), 8.64 (d, J=8.6 Hz, 1H), 10.63 (s, 1H). DSC: From 30 to 300° C. at 10° C./min, peak: 194.8° C.

Compound 81: N-(2-chloro-3-fluoro-4-pyridyl)-4-[(3,3-difluoro-1-methyl-cyclobutyl)sulfamoyl]-3-fluoro-1-methyl-pyrrole-2-carboxamide

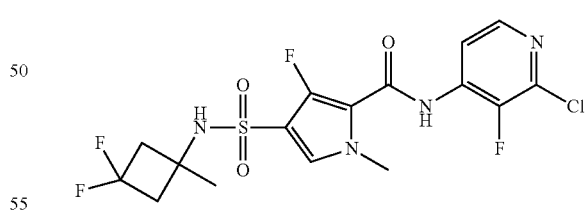

Compound 81 (62 mg) was prepared similarly as described for compound 53, using 2-chloro-3-fluoropyridin-4-amine instead of 4-amino-2-cyanopyridine. Method D: Rt: 1.91 min. m/z: 455 (M+H)⁺ Exact mass: 454.0. ¹H NMR (400 MHz, DMSO-d₆) δ ppm 1.42 (s, 3H), 2.52-2.61 (m, 2H), 2.81-2.96 (m, 2H), 3.84 (s, 3H), 7.60 (d, J=4.6 Hz, 1H), 8.04 (t, J=5.4 Hz, 1H), 8.21 (d, J=5.3 Hz, 1H), 8.27 (s, 1H), 10.22 (s, 1H). DSC: From 30 to 300° C. at 10° C./min, peak: 202.7° C.

Compound 82: N-[2-(difluoromethyl)-4-pyridyl]-3-fluoro-4-(isopropylsulfamoyl)-1-methyl-pyrrole-2-carboxamide

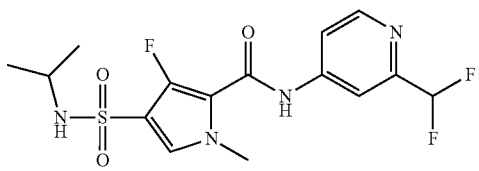 [SMILES: CC(C)NS(=O)(=O)c1cn(C)c(C(=O)Nc2ccnc(C(F)F)c2)c1F]

Compound 82 (100 mg) was prepared similarly as described for compound 78, using 2-(difluoromethyl)pyridin-4-amine instead of 2-(trifluoromethyl)pyridin-4-amine. Method D: Rt: 1.68 min. m/z: 391 (M+H)+ Exact mass: 390.0. $^1$H NMR (400 MHz, DMSO-d$_6$) δ ppm 1.06 (d, J=6.6 Hz, 6H), 3.27-3.42 (m, 1H), 3.82 (s, 3H), 6.92 (t, J=55.2 Hz, 1H), 7.51 (d, J=4.6 Hz, 1H), 7.61 (d, J=7.3 Hz, 1H), 7.77 (dd, J=5.5, 1.8 Hz, 1H), 8.03 (d, J=2.0 Hz, 1H), 8.56 (d, J=5.5 Hz, 1H), 10.58 (s, 1H). DSC: From 30 to 300° C. at 10° C./min, peak: 197.3° C.

Compound 83: 4-[(3,3-difluoro-1-methyl-cyclobutyl)sulfamoyl]-N-[2-(difluoromethyl)-4-pyridyl]-3-fluoro-1-methyl-pyrrole-2-carboxamide

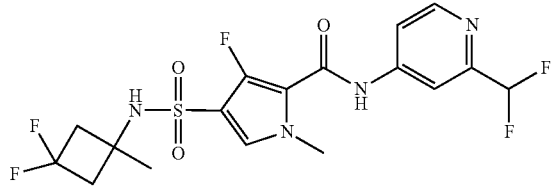 [SMILES: Cn1cc(S(=O)(=O)NC2(C)CC(F)(F)C2)c(F)c1C(=O)Nc1ccnc(C(F)F)c1]

Compound 83 (65 mg) was prepared similarly as described for compound 53, using 2-(difluoromethyl)pyridin-4-amine instead of 4-amino-2-cyanopyridine. Method D: Rt: 1.75 min. m/z: 453 (M+H)+ Exact mass: 452.0. $^1$H NMR (400 MHz, DMSO-d$_6$) δ ppm 1.43 (s, 3H), 2.52-2.60 (m, 2H), 2.81-2.97 (m, 2H), 3.82 (s, 3H), 6.92 (t, J=54.8 Hz, 1H), 7.57 (d, J=4.6 Hz, 1H), 7.78 (dd, J=5.5, 2.0 Hz, 1H), 8.03 (d, J=2.0 Hz, 1H), 8.24 (s, 1H), 8.57 (d, J=5.5 Hz, 1H), 10.60 (s, 1H). DSC: From 30 to 300° C. at 10° C./min, peak: 196.3° C.

Compound 84: 3-chloro-N-[2-(difluoromethyl)-4-pyridyl]-1-methyl-4-[[(1S)-1-(trifluoromethyl)propyl]sulfamoyl]pyrrole-2-carboxamide

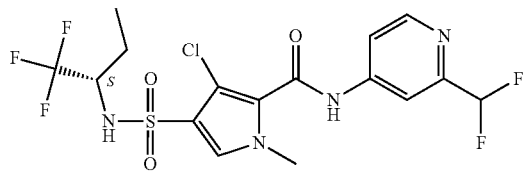

Compound 84 (116 mg) was prepared similarly as described for compound 37, using 2-(difluoromethyl)pyridin-4-amine instead of 4-amino-2-cyanopyridine. Method D: Rt: 1.81 min. m/z: 475 (M+H)+ Exact mass: 474.0. $^1$H NMR (400 MHz, DMSO-d$_6$) δ ppm 0.81 (t, J=7.4 Hz, 3H), 1.45-1.60 (m, 1H), 1.61-1.74 (m, 1H), 3.72-3.83 (m, 4H), 6.93 (t, J=54.8 Hz, 1H), 7.69 (s, 1H), 7.79 (dd, J=5.6, 1.9 Hz, 1H), 8.03 (d, J=1.8 Hz, 1H), 8.51 (d, J=8.6 Hz, 1H), 8.59 (d, J=5.5 Hz, 1H), 10.90 (s, 1H). DSC: From 30 to 300° C. at 10° C./min, peak: 182.8° C.

Compound 85: 3-chloro-N-[2-(difluoromethyl)-4-pyridyl]-1-methyl-4-[[(1R)-1-(trifluoromethyl)propyl]sulfamoyl]pyrrole-2-carboxamide

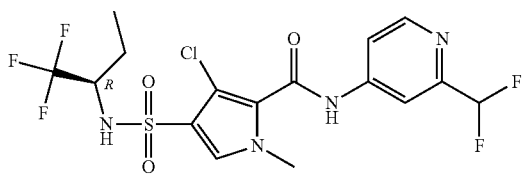

Compound 85 (116 mg) was prepared similarly as described for compound 38, using 2-(difluoromethyl)pyridin-4-amine instead of 4-amino-2-cyanopyridine. Method D: Rt: 1.85 min. m/z: 475 (M+H)+ Exact mass: 474.0. $^1$H NMR (400 MHz, DMSO-d$_6$) δ ppm 0.81 (t, J=7.4 Hz, 3H), 1.46-1.59 (m, 1H), 1.61-1.73 (m, 1H), 3.71-3.82 (m, 4H), 6.93 (t, J=55.2 Hz, 1H), 7.69 (s, 1H), 7.79 (dd, J=5.5, 2.0 Hz, 1H), 8.03 (d, J=2.0 Hz, 1H), 8.51 (d, J=8.6 Hz, 1H), 8.59 (d, J=5.5 Hz, 1H), 10.90 (s, 1H). DSC: From 30 to 300° C. at 10° C./min, peak: 183.0° C.

Compound 86: N-[2-(difluoromethyl)-4-pyridyl]-3-fluoro-1-methyl-4-[[(1R)-1-methylpropyl]sulfamoyl]pyrrole-2-carboxamide

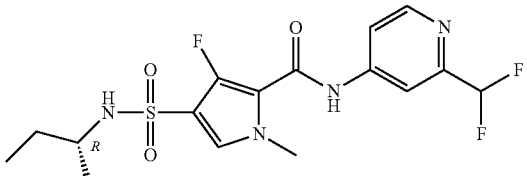

Compound 86 (111 mg) was prepared similarly as described for compound 67, using 2-(difluoromethyl)pyridin-4-amine instead of 4-amino-2-cyanopyridine. Method D: Rt: 1.77 min. m/z: 405 (M+H)+ Exact mass: 404.0. $^1$H NMR (400 MHz, DMSO-d$_6$) δ ppm 0.78 (t, J=7.4 Hz, 3H), 1.01 (d, J=6.6 Hz, 3H), 1.31-1.44 (m, 2H), 3.07-3.19 (m, 1H), 3.82 (s, 3H), 6.92 (t, J=55.7 Hz, 1H), 7.51 (d, J=4.6 Hz, 1H), 7.57 (d, J=7.7 Hz, 1H), 7.78 (dd, J=5.5, 1.8 Hz, 1H), 8.04 (d, J=1.8 Hz, 1H), 8.56 (d, J=5.5 Hz, 1H), 10.58 (s, 1H). DSC: From 30 to 300° C. at 10° C./min, peak: 175.6° C.

Compound 87: N-[2-(difluoromethyl)-4-pyridyl]-3-fluoro-1-methyl-4-[[(1R)-1-(trifluoromethyl)propyl]sulfamoyl]pyrrole-2-carboxamide

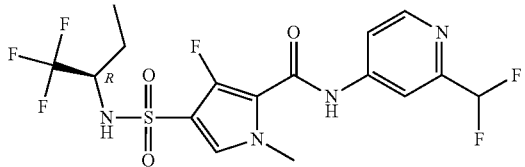

Compound 87 (77 mg) was prepared similarly as described for compound 31, using 2-(difluoromethyl)pyridin-4-amine instead of 4-amino-2-cyanopyridine. Method D: Rt: 1.83 min. m/z: 459 (M+H)⁺ Exact mass: 458.0. ¹H NMR (400 MHz, DMSO-d₆) δ ppm 0.79 (t, J=7.3 Hz, 3H), 1.43-1.57 (m, 1H), 1.62-1.75 (m, 1H), 3.71-3.86 (m, 4H), 6.92 (t, J=55.2 Hz, 1H), 7.58 (d, J=4.4 Hz, 1H), 7.78 (d, J=5.5 Hz, 1H), 8.04 (d, J=1.8 Hz, 1H), 8.57 (d, J=5.7 Hz, 1H), 8.60 (d, J=8.4 Hz, 1H), 10.61 (s, 1H).

Compound 88: 4-[[(1R)-2,2-difluoro-1-methyl-propyl]sulfamoyl]-N-[2-(difluoromethyl)-4-pyridyl]-3-fluoro-1-methyl-pyrrole-2-carboxamide

Compound 88 (50 mg) was prepared similarly as described for compound 63, using 2-(difluoromethyl)pyridin-4-amine instead of 4-amino-2-cyanopyridine. Method B: Rt: 0.88 min. m/z: 441 (M+H)⁺ Exact mass: 440.0. ¹H NMR (400 MHz, DMSO-d₆) δ ppm 1.07 (d, J=7.0 Hz, 3H), 1.58 (t, J=19.1 Hz, 3H), 3.46-3.64 (m, 1H), 3.82 (s, 3H), 6.92 (t, J=55.0 Hz, 1H), 7.57 (d, J=4.4 Hz, 1H), 7.78 (dd, J=5.2, 1.4 Hz, 1H), 8.04 (d, J=2.0 Hz, 1H), 8.21 (d, J=9.0 Hz, 1H), 8.57 (d, J=5.5 Hz, 1H), 10.61 (s, 1H).

Compound 89: 3-chloro-N-(2-chloro-4-pyridyl)-4-[[(1R)-2-hydroxy-1-methyl-ethyl]sulfamoyl]-1-methyl-pyrrole-2-carboxamide

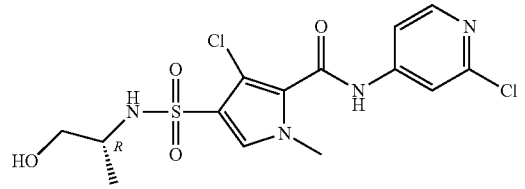

Methyl 3-chloro-1-methyl-pyrrole-2-carboxylate (5 g, 28.8 mmol) and 4-amino-2-chloropyridine (3.97 g, 30.24 mmol) were dissolved in THF (50 mL). Lithium bis(trimethylsilyl)amide (1M in THF) (43.2 mL, 1 M, 43.2 mmol) was added drop wise and the reaction mixture was stirred for 2 hours. Lithium bis(trimethylsilyl)amide (1M in THF) (4 mL, 1 M, 4 mmol) was added and the reaction mixture was stirred for 1 hour. Sat.NH₄Cl (aq) (20 mL) was added to the reaction mixture and the organic layer was removed and the aqueous layer was extracted with DCM (50 mL). The combined organic layers were evaporated to dryness and the residue was triturated in ACN and DIPE and dried under vacuum to give 3-chloro-N-(2-chloro-4-pyridyl)-1-methyl-pyrrole-2-carboxamide (4.3 g) as a pale pink solid. The filtrate was evaporated to dryness and purified on silica using a heptane to EtOAc gradient yielding a second crop of 3-chloro-N-(2-chloro-4-pyridyl)-1-methyl-pyrrole-2-carboxamide as a white powder (1.5 g) after trituration in DIPE. ¹H NMR (400 MHz, DMSO-d₆) δ ppm 3.75 (s, 3H), 6.23 (d, J=2.9 Hz, 1H), 7.10 (d, J=2.9 Hz, 1H), 7.60 (dd, J=5.6, 1.9 Hz, 1H), 7.80 (d, J=1.8 Hz, 1H), 8.29 (d, J=5.7 Hz, 1H), 10.51 (s, 1H).

3-chloro-N-(2-chloro-4-pyridyl)-1-methyl-pyrrole-2-carboxamide (5.8 g, 21.5 mmol) was dissolved in chlorosulfonic acid (25 g, 215 mmol) at 0° C. The reaction mixture was allowed to warm to room temperature and stirred for 2 hours. The reaction mixture was quenched in 200 mL ice water, filtered, triturated with DIPE to become a sticky solid. This was purified on silica using a heptane to EtOAc gradient yielding 4-chloro-5-[(2-chloro-4-pyridyl)carbamoyl]-1-methyl-pyrrole-3-sulfonyl chloride (5.93 g) as a white powder.

4-chloro-5-[(2-chloro-4-pyridyl)carbamoyl]-1-methyl-pyrrole-3-sulfonyl chloride (150 mg, 0.41 mmol), D-alaninol (45.9 mg, 0.61 mmol) and DIPEA (0.18 mL, 0.75 g/mL, 1.02 mmol) were dissolved in ACN (5 mL) and stirred for 1 hour. The volatiles were removed under reduced pressure and the residue was purified on silica using a heptane to EtOAc gradient yielding compound 89 (152 mg) as a white powder after trituration with DIPE. Method B: Rt: 0.70 min. m/z: 407 (M+H)⁺ Exact mass: 406.0. ¹H NMR (400 MHz, DMSO-d₆) δ ppm 1.02 (d, J=6.2 Hz, 3H), 3.09-3.22 (m, 2H), 3.33-3.40 (m, 1H), 3.78 (s, 3H), 4.69 (t, J=5.5 Hz, 1H), 7.40 (d, J=7.3 Hz, 1H), 7.62 (dd, J=5.6, 1.7 Hz, 1H), 7.66 (s, 1H), 7.81 (d, J=1.8 Hz, 1H), 8.32 (d, J=5.7 Hz, 1H), 10.87 (s, 1H). DSC: From 30 to 300° C. at 10° C./min, peak: 172.5° C.

Compound 90: (+/−)-3-chloro-N-(2-chloro-4-pyridyl)-4-[(2-hydroxy-1-methyl-propyl)sulfamoyl]-1-methyl-pyrrole-2-carboxamide

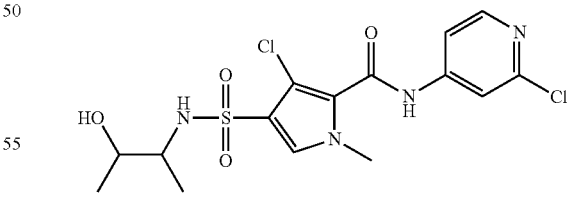

Compound 90 (157 mg) was prepared similarly as described for compound 89, using 3-amino-2-butanol instead of D-alaninol. Method B: Rt: 0.74 min. m/z: 421 (M+H)⁺ Exact mass: 420.0. ¹H NMR (400 MHz, DMSO-d₆) δ ppm 0.92-1.02 (m, 6H), 2.92-3.19 (m, 1H), 3.42-3.61 (m, 1H), 3.78 (s, 3H), 4.52-4.56 (m, 1H), 7.26-7.32 (m, 1H), 7.60-7.67 (m, 2H), 7.81 (d, J=1.8 Hz, 1H), 8.32 (d, J=5.7 Hz, 1H), 10.86 (s, 1H). DSC: From 30 to 300° C. at 10° C./min, peak: 187.8° C.

Compound 91: 3-chloro-N-(2-chloro-4-pyridyl)-1-methyl-4-[[(3S)-tetrahydrofuran-3-yl]sulfamoyl]pyrrole-2-carboxamide

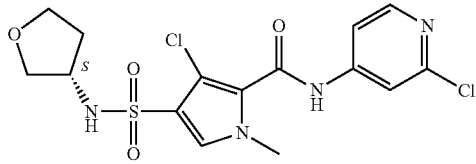

Compound 91 (112 mg) was prepared similarly as described for compound 89, using (S)-tetrahydrofuran-3-amine hydrochloride instead of D-alaninol. Method B: Rt: 0.75 min. m/z: 419 (M+H)⁺ Exact mass: 418.0. ¹H NMR (400 MHz, DMSO-d₆) δ ppm 1.77 (td, J=12.5, 5.8 Hz, 1H), 1.92-2.06 (m, 1H), 3.46 (dd, J=8.6, 4.4 Hz, 1H), 3.62 (td, J=8.0, 5.9 Hz, 1H), 3.67-3.77 (m, 3H), 3.79 (s, 3H), 7.62 (dd, J=5.6, 1.9 Hz, 1H), 7.68 (s, 1H), 7.81 (d, J=1.8 Hz, 1H), 7.92 (d, J=6.6 Hz, 1H), 8.33 (d, J=5.5 Hz, 1H), 10.88 (s, 1H). DSC: From 30 to 300° C. at 10° C./min, peak: 226.5° C.

Compound 92: 3-chloro-N-(2-chloro-4-pyridyl)-4-[[(3-(hydroxymethyl)oxetan-3-yl]sulfamoyl]-1-methyl-pyrrole-2-carboxamide

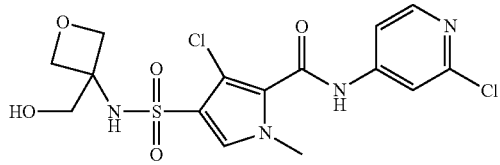 [SMILES: Cn1cc(S(=O)(=O)NC2(CO)COC2)c(Cl)c1C(=O)Nc1ccnc(Cl)c1]

Compound 92 (109 mg) was prepared similarly as described for compound 89, using (3-aminooxetan-3-yl)methanol instead of D-alaninol. Method B: Rt: 0.66 min. m/z: 435 (M+H)⁺ Exact mass: 434.0. ¹H NMR (400 MHz, DMSO-d₆) δ ppm 3.58 (d, J=5.7 Hz, 2H), 3.78 (s, 3H), 4.41 (d, J=6.4 Hz, 2H), 4.58 (d, J=6.4 Hz, 2H), 5.16 (t, J=5.7 Hz, 1H), 7.62 (dd, J=5.6, 1.9 Hz, 1H), 7.70 (s, 1H), 7.82 (d, J=1.8 Hz, 1H), 8.14 (s, 1H), 8.33 (d, J=5.5 Hz, 1H), 10.90 (s, 1H). DSC: From 30 to 300° C. at 10° C./min, peak: 202.7° C.

Compound 93: 3-chloro-N-(2-chloro-4-pyridyl)-4-[(3-hydroxycyclobutyl)sulfamoyl]-1-methyl-pyrrole-2-carboxamide

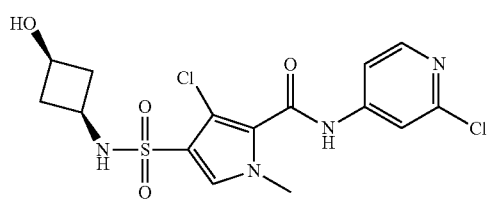 [SMILES: Cn1cc(S(=O)(=O)N[C@H]2C[C@@H](O)C2)c(Cl)c1C(=O)Nc1ccnc(Cl)c1]

Compound 93 (143 mg) was prepared similarly as described for compound 89, using cis-3-aminocyclobutanol hydrochloride instead of D-alaninol. Method B: Rt: 0.69 min. m/z: 419 (M+H)⁺ Exact mass: 418.0. ¹H NMR (400 MHz, DMSO-d₆) δ ppm 1.69-1.80 (m, 2H), 2.28-2.38 (m, 2H), 3.06-3.18 (m, 1H), 3.65-3.75 (m, 1H), 3.78 (s, 3H), 5.02 (d, J=5.7 Hz, 1H), 7.58-7.65 (m, 2H), 7.79-7.86 (m, 2H), 8.32 (d, J=5.5 Hz, 1H), 10.86 (s, 1H). DSC: From 30 to 300° C. at 10° C./min, peak: 230.5° C.

Compound 94: 3-chloro-N-(2-chloro-4-pyridyl)-4-[[(1R)-2,2-difluoro-1-methyl-propyl]sulfamoyl]-1-methyl-pyrrole-2-carboxamide

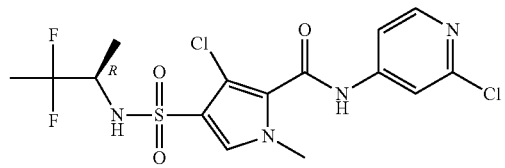

Methyl 3-chloro-4-chlorosulfonyl-1-methyl-pyrrole-2-carboxylate (1650 mg, 6.06 mmol), (2R)-3,3-difluorobutan-2-amine (680 mg, 6.23 mmol) and molecular sieves (1 g) were dispensed in ACN (10 mL). NaHCO₃ (1.57 g, 18.7 mmol) was added and the reaction mixture was stirred overnight at 80° C. The reaction mixture was filtered and the filtrate was evaporated to dryness.

The residue was purified on silica using a heptane to EtOAc gradient yielding methyl 3-chloro-4-[[(1R)-2,2-difluoro-1-methyl-propyl]sulfamoyl]-1-methyl-pyrrole-2-carboxylate (1.55 g) as a white powder. Method B: Rt: 0.86 min. m/z: 343 (M–H)⁻ Exact mass: 344.0. Methyl 3-chloro-4-[[(1R)-2,2-difluoro-1-methyl-propyl]sulfamoyl]-1-methyl-pyrrole-2-carboxylate (150 mg, 0.44 mmol) and 4-amino-2-chloropyridine (61.5 mg, 0.48 mmol) were dissolved in THF (5 mL). Lithium bis(trimethylsilyl)amide (1M in THF) (1.31 mL, 1 M, 1.31 mmol) was added drop wise and the reaction mixture was stirred for 1 hour. Sat.NH₄Cl (aq) (5 mL) was added to the reaction mixture and the organic layer was removed and the aqueous layer was extracted with DCM (2×5 mL). The combined organic layers were evaporated to dryness and the residue was purified on silica using a heptane to EtOAc gradient yielding compound 94 (171 mg) as a white powder after trituration in DIPE. Method B: Rt: 0.93 min. m/z: 441 (M+H)⁺ Exact mass: 440.0. ¹H NMR (400 MHz, DMSO-d₆) δ ppm 1.04-1.11 (m, 3H), 1.57 (t, J=19.1 Hz, 3H), 3.49-3.60 (m, 1H), 3.78 (s, 3H), 7.62 (dd, J=5.7, 1.8 Hz, 1H), 7.69 (s, 1H), 7.81 (d, J=1.8 Hz, 1H), 8.11 (d, J=9.2 Hz, 1H), 8.33 (d, J=5.5 Hz, 1H), 10.87 (s, 1H). DSC: From 30 to 300° C. at 10° C./min, peak: 199.5° C.

Compound 95: 3-chloro-4-[[(1R)-2,2-difluoro-1-methyl-propyl]sulfamoyl]-N-(2-fluoro-4-pyridyl)-1-methyl-pyrrole-2-carboxamide

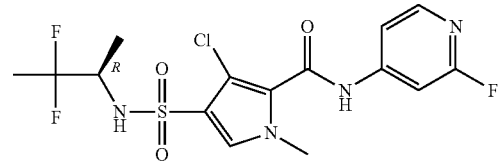

Compound 95 (136 mg) was prepared similarly as described for compound 94, using 4-amino-2-fluoropyridine instead of 4-amino-2-chloropyridine. Method B: Rt: 0.89 min. m/z: 425 (M+H)+ Exact mass: 424.0. $^1$H NMR (400 MHz, DMSO-$d_6$) δ ppm 1.08 (d, J=6.8 Hz, 3H), 1.58 (t, J=19.1 Hz, 3H), 3.49-3.61 (m, 1H), 3.79 (s, 3H), 7.46 (d, J=1.5 Hz, 1H), 7.52 (dd, J=5.7, 1.3 Hz, 1H), 7.69 (s, 1H), 8.11 (d, J=9.0 Hz, 1H), 8.16 (d, J=5.5 Hz, 1H), 10.94 (s, 1H). DSC: From 30 to 300° C. at 10° C./min, peak: 206.5° C.

Compound 96: 3-chloro-N-(2-cyano-4-pyridyl)-4-[[(1R)-2,2-difluoro-1-methyl-propyl]sulfamoyl]-1-methyl-pyrrole-2-carboxamide

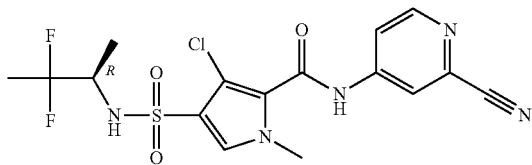

Compound 96 (84 mg) was prepared similarly as described for compound 94, using 4-aminopyridine-2-carbonitrile instead of 4-amino-2-chloropyridine. Method B: Rt: 0.88 min. m/z: 432 (M+H)+ Exact mass: 431.1. $^1$H NMR (400 MHz, DMSO-$d_6$) δ ppm 1.08 (d, J=6.8 Hz, 3H), 1.58 (t, J=19.3 Hz, 3H), 3.49-3.62 (m, 1H), 3.79 (s, 3H), 7.71 (s, 1H), 7.92 (dd, J=5.6, 2.1 Hz, 1H), 8.13 (d, J=9.0 Hz, 1H), 8.21 (d, J=2.0 Hz, 1H), 8.66 (d, J=5.7 Hz, 1H), 11.01 (s, 1H). DSC: From 30 to 300° C. at 10° C./min, peak: 211.9° C.

Compound 97: 3-chloro-4-[[(1R)-2,2-difluoro-1-methyl-propyl]sulfamoyl]-N-[2-(difluoromethyl)-4-pyridyl]-1-methyl-pyrrole-2-carboxamide

Compound 97 (137 mg) was prepared similarly as described for compound 94, using 2-(difluoromethyl)pyridin-4-amine instead of 4-amino-2-chloropyridine. Method B: Rt: 0.90 min. m/z: 457 (M+H)+ Exact mass: 456.1. $^1$H NMR (400 MHz, DMSO-$d_6$) δ ppm 1.08 (d, J=7.0 Hz, 3H), 1.58 (t, J=19.1 Hz, 3H), 3.48-3.63 (m, 1H), 3.79 (s, 3H), 6.94 (t, J=54.9 Hz, 1H), 7.69 (s, 1H), 7.76-7.82 (m, 1H), 8.03 (d, J=1.8 Hz, 1H), 8.11 (d, J=9.2 Hz, 1H), 8.59 (d, J=5.5 Hz, 1H), 10.91 (s, 1H). DSC: From 30 to 300° C. at 10° C./min, peak: 150.8° C.

Compound 98: 4-[[(1R)-2,2-difluoro-1-methyl-propyl]sulfamoyl]-3-fluoro-N-(2-fluoro-4-pyridyl)-1-methyl-pyrrole-2-carboxamide

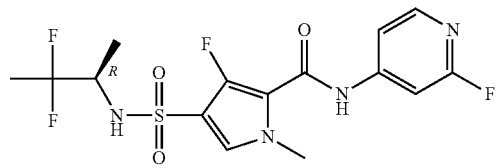

Compound 98 (70 mg) was prepared similarly as described for compound 63, using 4-amino-2-fluoropyridine instead of 4-amino-2-cyanopyridine. Method B: Rt: 0.87 min. m/z: 409 (M+H)+ Exact mass: 408.0. $^1$H NMR (400 MHz, DMSO-$d_6$) δ ppm 1.06 (d, J=6.8 Hz, 3H), 1.57 (t, J=19.1 Hz, 3H), 3.48-3.60 (m, 1H), 3.81 (s, 3H), 7.46 (d, J=1.5 Hz, 1H), 7.49-7.54 (m, 1H), 7.56 (d, J=4.4 Hz, 1H), 8.11 (br. s, 1H), 8.13 (d, J=5.7 Hz, 1H), 10.64 (br. s., 1H).

Compound 99: 3-chloro-4-[(3,3-difluoro-1-methyl-cyclobutyl)sulfamoyl]-N-[2-(difluoromethyl)-4-pyridyl]-1-methyl-pyrrole-2-carboxamide

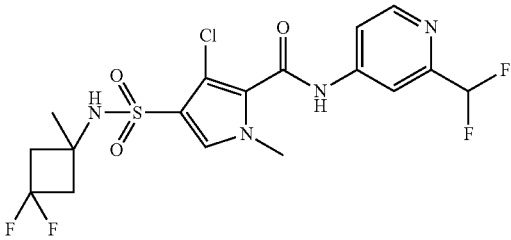 [SMILES: Cn1cc(S(=O)(=O)NC2(C)CC(F)(F)C2)c(Cl)c1C(=O)Nc1ccnc(C(F)F)c1]

Compound 99 (207 mg) was prepared similarly as described for compound 64, using 2-(difluoromethyl)pyridin-4-amine instead of 4-amino-2-cyanopyridine. Method B: Rt: 0.92 min. m/z: 469 (M+H)+ Exact mass: 468.0. $^1$H NMR (400 MHz, DMSO-$d_6$) δ ppm 1.40 (s, 3H), 2.46-2.59 (m, 2H), 2.83-2.92 (m, 2H), 3.80 (s, 3H), 6.94 (t, J=54.8 Hz, 1H), 7.70 (s, 1H), 7.79 (dd, J=5.5, 1.8 Hz, 1H), 8.03 (d, J=2.0 Hz, 1H), 8.16 (s, 1H), 8.59 (d, J=5.5 Hz, 1H), 10.91 (s, 1H). DSC: From 30 to 300° C. at 10° C./min, peak: 200.6° C.

Compound 100: 4-[[(1R)-2,2-difluoro-1-methyl-propyl]sulfamoyl]-N-[2-(difluoromethyl)-4-pyridyl]-1-methyl-pyrrole-2-carboxamide

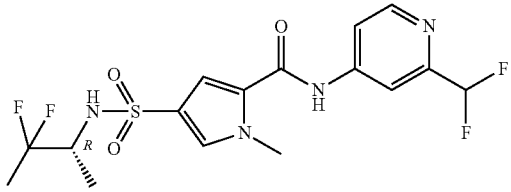

Methyl 4-(chlorosulfonyl)-1-methyl-1H-pyrrole-2-carboxylate (777 mg, 3.27 mmol), (2R)-3,3-difluorobutan-2- amine (500 mg, 3.43 mmol), NaHCO₃ (1.15 g, 13.7 mmol) and molecular sieves 4 Å (3 g) were dispensed in ACN (10 mL) and heated at 80° C. for 18 hours in a pressure tube. The reaction mixture was filtered and the solids on the filter were washed with ACN (2×10 mL). The filtrate was concentrated and the residue was subjected to silica gel column chromatography using a gradient from 0 till 60% EtOAc in heptane. The product fractions were concentrated and the residue was purified Prep HPLC (Stationary phase: Uptisphere C18 ODB—10 μm, 200 g, 5 cm, Mobile phase: 0.25% NH₄HCO₃ solution in water, ACN) yielding methyl 4-[[(1R)-2,2-difluoro-1-methyl-propyl]sulfamoyl]-1-methyl-pyrrole-2-carboxylate (660 mg) as a white powder. Method B: Rt: 0.81 min. m/z: 309 (M−H)⁻ Exact mass: 310.0.

Methyl 4-[[(1R)-2,2-difluoro-1-methyl-propyl]sulfamoyl]-1-methyl-pyrrole-2-carboxylate (100 mg, 0.32 mmol) and 2-(difluoromethyl)pyridin-4-amine (55.7 mg, 0.39 mmol) were dissolved in THF (5 mL). lithium bis(trimethylsilyl)amide (1.7 mL, 1 M, 1.7 mmol) was added drop wise and the reaction mixture was stirred at room temperature for 90 minutes. The reaction mixture was quenched with sat. NH₄Cl (0.4 mL) and the organic layer was separated. The aqueous layer was extracted with DCM (5 mL) and the combined organic layers were evaporated to dryness. The residue was dissolved in DMF (1 mL) and purified using silica gel column chromatography using ethyl acetate in heptane from 0 to 100%. The residual crude was crystallized from MeOH to afford compound 100 (40 mg) as a white powder. Method D: Rt: 1.66 min. m/z: 423 (M+H)⁺ Exact mass: 422.0. ¹H NMR (400 MHz, DMSO-d₆) δ ppm 0.97 (d, J=7.0 Hz, 3H), 1.57 (t, J=19.1 Hz, 3H), 3.40-3.66 (m, 1H), 3.94 (s, 3H), 6.91 (t, J=55.2 Hz, 1H), 7.47 (d, J=2.0 Hz, 1H), 7.67 (d, J=1.8 Hz, 1H), 7.80 (br. d, J=7.7 Hz, 1H), 7.87 (dd, J=5.5, 2.0 Hz, 1H), 8.10 (d, J=2.0 Hz, 1H), 8.55 (d, J=5.5 Hz, 1H), 10.56 (s, 1H). DSC: From 30 to 300° C. at 10° C./min, peak: 239.7° C.

Compound 101: N-(2-cyano-4-pyridyl)-4-[[(1R)-2,2-difluoro-1-methyl-propyl]sulfamoyl]-1-methyl-pyrrole-2-carboxamide

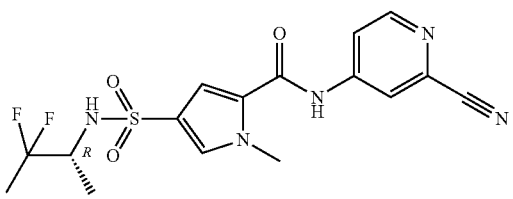

Compound 101 (63 mg) was prepared similarly as described for compound 100, using 4-amino-2-cyanopyridine instead of 2-(difluoromethyl)pyridin-4-amine. Method D: Rt: 1.63 min. m/z: 398 (M+H)⁺ Exact mass: 397.0. ¹H NMR (400 MHz, DMSO-d₆) δ ppm 0.97 (d, J=6.8 Hz, 3H), 1.57 (t, J=19.1 Hz, 3H), 3.41-3.59 (m, 1H), 3.94 (s, 3H), 7.46 (d, J=1.8 Hz, 1H), 7.69 (d, J=1.8 Hz, 1H), 7.82 (d, J=8.6 Hz, 1H), 7.97 (dd, J=5.6, 2.1 Hz, 1H), 8.28 (d, J=1.8 Hz, 1H), 8.62 (d, J=5.7 Hz, 1H), 10.68 (s, 1H). DSC: From 30 to 300° C. at 10° C./min, peak: 206.6° C.

Compound 102: 4-[[(1R)-2,2-difluoro-1-methyl-propyl]sulfamoyl]-N-(2-fluoro-4-pyridyl)-1-methyl-pyrrole-2-carboxamide

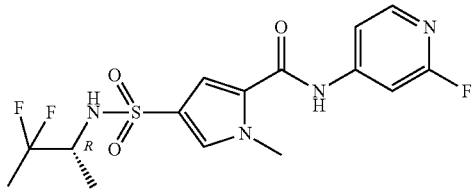

Compound 102 (13 mg) was prepared similarly as described for compound 100, using 4-amino-2-fluoropyridine instead of 2-(difluoromethyl)pyridin-4-amine. Method D: Rt: 1.64 min. m/z: 391 (M+H)⁺ Exact mass: 390.0. ¹H NMR (400 MHz, DMSO-d₆) δ ppm 0.97 (d, J=6.8 Hz, 3H), 1.57 (t, J=19.1 Hz, 3H), 3.42-3.57 (m, 1H), 3.93 (s, 3H), 7.44 (d, J=1.8 Hz, 1H), 7.53 (d, J=1.5 Hz, 1H), 7.57-7.62 (m, 1H), 7.67 (d, J=1.5 Hz, 1H), 7.80 (d, J=7.9 Hz, 1H), 8.12 (d, J=5.5 Hz, 1H), 10.60 (s, 1H). DSC: From 30 to 300° C. at 10° C./min, peak: 234.7° C.

Compound 103: N-(2-chloro-4-pyridyl)-4-[[(1R)-2,2-difluoro-1-methyl-propyl]sulfamoyl]-1-methyl-pyrrole-2-carboxamide

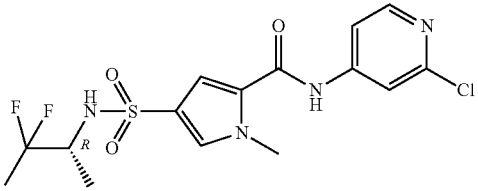

Compound 103 (61 mg) was prepared similarly as described for compound 100, using 4-amino-2-chloropyridine instead of 2-(difluoromethyl)pyridin-4-amine. Method B: Rt: 0.89 min. m/z: 407 (M+H)⁺ Exact mass: 406.0. ¹H NMR (400 MHz, DMSO-d₆) δ ppm 0.97 (d, J=6.8 Hz, 3H), 1.57 (t, J=19.1 Hz, 3H), 3.42-3.57 (m, 1H), 3.93 (s, 3H), 7.44 (d, J=2.0 Hz, 1H), 7.79 (br. s., 1H), 7.63-7.73 (m, 2H), 7.89 (d, J=1.8 Hz, 1H), 8.28 (d, J=5.7 Hz, 1H), 10.53 (br. s., 1H). DSC: From 30 to 300° C. at 10° C./min, peak: 244.8° C.

Compound 104: 3-chloro-4-[[(1R)-2,2-difluoro-1-methyl-propyl]sulfamoyl]-N-(2,6-difluoro-4-pyridyl)-1-methyl-pyrrole-2-carboxamide

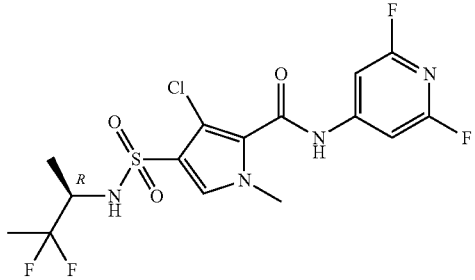

Lithium bis(trimethylsilyl)amide (1.7 mL, 1 M, 1.7 mmol) was added drop wise to a solution of methyl 3-chloro-4-[[(1R)-2,2-difluoro-1-methyl-propyl]sulfamoyl]-1-methyl-pyrrole-2-carboxylate (0.2 g, 0.58 mmol) and 2,6-difluoropyridin-4-amine (83 mg, 0.64 mmol) in THF (5 mL) at 0° C. under N$_2$. The reaction mixture was allowed to warm to room temperature and stirred overnight. The reaction mixture was quenched with NH$_4$Cl (sat., aq), extracted with ethyl acetate (3×10 mL). The combined organic layers were washed with brine (1×20 mL), dried over Na$_2$SO$_4$ and concentrated under reduced pressure. The residue was purified by flash chromatography using a heptane to EtOAc gradient. The collected fractions were evaporated to dryness and the residue was dissolved in methanol and water was added. The precipitate was filtered off and dried in the oven at 40° C. overnight to afford compound 104 (175 mg) as a white solid. Method B: Rt: 1.03 min. m/z: 443 (M+H)$^+$ Exact mass: 442.1. $^1$H NMR (400 MHz, DMSO-d$_6$) δ ppm 1.07 (d, J=6.8 Hz, 3H), 1.57 (t, J=19.1 Hz, 3H), 3.49-3.61 (m, 1H), 3.79 (s, 3H), 7.34 (s, 2H), 7.72 (s, 1H), 8.13 (d, J=9.0 Hz, 1H), 11.16 (s, 1H). DSC: From 30 to 300° C. at 10° C./min, peak: 190.2° C.

Compound 105: N-(2-bromo-4-pyridyl)-3-chloro-4-[[(1R)-2,2-difluoro-1-methyl-propyl]sulfamoyl]-1-methyl-pyrrole-2-carboxamide

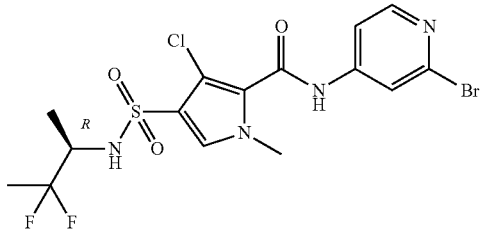

Compound 105 (143 mg) was prepared similarly as described for compound 104, using 4-amino-2-bromopyridine instead of 2,6-difluoropyridin-4-amine. After overnight stirring an extra aliquot lithium bis(trimethylsilyl)amide (0.8 eq) was added drop wise and the reaction mixture was stirred for an additional 2 hours. Method B: Rt: 0.97 min. m/z: 485 (M+H)$^+$ Exact mass: 484.0. $^1$H NMR (400 MHz, DMSO-d$_6$) δ ppm 1.08 (d, J=7.0 Hz, 3H), 1.57 (t, J=19.1 Hz, 3H), 3.48-3.63 (m, 1H), 3.78 (s, 3H), 7.65 (dd, J=5.6, 1.9 Hz, 1H), 7.69 (s, 1H), 7.96 (d, J=1.8 Hz, 1H), 8.11 (d, J=8.8 Hz, 1H), 8.30 (d, J=5.5 Hz, 1H), 10.84 (s, 1H). DSC: From 30 to 300° C. at 10° C./min, peak: 184.2° C.

Compound 106: N-(2-bromo-4-pyridyl)-3-chloro-1-methyl-4-[[(1R)-2,2,2-trifluoro-1-methyl-ethyl]sulfamoyl]pyrrole-2-carboxamide

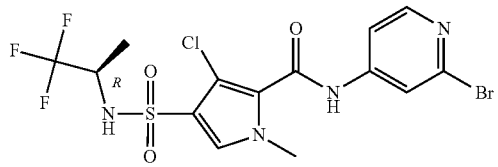

Compound 106 (286 mg) was prepared similarly as described for compound 105, using methyl 3-chloro-1-methyl-4-[[(1R)-2,2,2-trifluoro-1-methyl-ethyl]sulfamoyl]pyrrole-2-carboxylate instead of methyl 3-chloro-4-[[(1R)-2,2-difluoro-1-methyl-propyl]sulfamoyl]-1-methyl-pyrrole-2-carboxylate. Method B: Rt: 0.97 min. m/z: 489 (M+H)$^+$ Exact mass: 488.0. $^1$H NMR (400 MHz, DMSO-d$_6$) δ ppm 1.19 (d, J=7.0 Hz, 3H), 3.78 (s, 3H), 3.93-4.04 (m, 1H), 7.65 (dd, J=5.6, 1.9 Hz, 1H), 7.72 (s, 1H), 7.96 (d, J=1.8 Hz, 1H), 8.30 (d, J=5.5 Hz, 1H), 8.53 (d, J=7.3 Hz, 1H), 10.86 (s, 1H). DSC: From 30 to 300° C. at 10° C./min, peak: 208.4° C.

Compound 107: 3-chloro-N-(2-chloro-3-fluoro-4-pyridyl)-4-[[(1R)-2,2-difluoro-1-methyl-propyl]sulfamoyl]-1-methyl-pyrrole-2-carboxamide

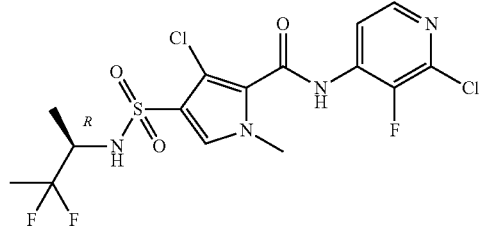

Compound 107 (149 mg) was prepared similarly as described for compound 104, using 4-amino-2-bromopyridine instead of 2,6-difluoropyridin-4-amine. After overnight stirring an extra aliquot lithium bis(trimethylsilyl)amide (0.9 eq) was added drop wise and the reaction mixture was stirred for an additional 2 hours. Method B: Rt: 1.02 min. m/z: 459 (M+H)$^+$ Exact mass: 458.0. $^1$H NMR (400 MHz, DMSO-d$_6$) δ ppm 1.08 (d, J=7.0 Hz, 3H), 1.58 (t, J=19.3 Hz, 3H), 3.47-3.62 (m, 1H), 3.82 (s, 3H), 7.72 (s, 1H), 8.06-8.15 (m, 2H), 8.23 (d, J=5.5 Hz, 1H), 10.60 (s, 1H). DSC: From 30 to 300° C. at 10° C./min, peak: 207.1° C.

Compound 108: 3-chloro-N-[2-(difluoromethyl)-4-pyridyl]-1-methyl-4-[[1-(trifluoromethyl)cyclobutyl]sulfamoyl]pyrrole-2-carboxamide

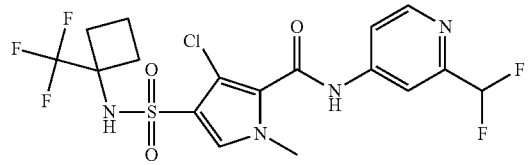 [SMILES: Cn1cc(S(=O)(=O)NC2(C(F)(F)F)CCC2)c(Cl)c1C(=O)Nc1ccnc(C(F)F)c1]

Methyl 3-chloro-4-chlorosulfonyl-1-methyl-pyrrole-2-carboxylate (3.00 g, 11.0 mmol) was dissolved in ACN (18 mL) in a pressure tube and this was dried with powdered molecular sieves (4 Å) over a period of 30 minutes. Another tube was loaded with 1-(trifluoromethyl)cyclobutan-1-amine (2.30 g, 16.5 mmol) and NaHCO$_3$ (2.78 g, 33.1 mmol) and this was dispersed in ACN (2 mL) and dried with powdered molecular sieves (4 Å) over a period of 30 minutes. This was added to the pressure tube which was flushed with nitrogen, capped and stirred in a heating block at 80° C. for 48 hours. The reaction mixture was filtered and the solids were washed with DCM. The filtrate was evaporated to dryness and the residue was purified using silica gel column chromatography (ethyl acetate in heptane from 0 to 100%) to afford methyl 3-chloro-1-methyl-4-[[1-(trifluoromethyl)cyclobutyl]sulfamoyl]pyrrole-2-carboxylate (2.03 g). Method B: Rt: 0.98 min. m/z: 373 (M−H)⁻ Exact mass: 374.0.

Methyl 3-chloro-1-methyl-4-[[1-(trifluoromethyl)cyclobutyl]sulfamoyl]pyrrole-2-carboxylate (200 mg, 0.53 mmol) and 2-(difluoromethyl)pyridin-4-amine (84.6 mg, 0.59 mmol) were dissolved in THF (5 mL). Lithium bis(trimethylsilyl)amide (1.7 mL, 1 M, 1.7 mmol) was added drop wise and the reaction mixture was stirred at room temperature for 30 minutes. Lithium bis(trimethylsilyl)amide (1 mL, 1 M, 1 mmol) was added and the reaction mixture was stirred for 30 minutes. The reaction mixture was quenched with sat. NH₄Cl (2 mL) and the organic layer was separated. The aqueous layer was extracted with DCM (5 mL) and the combined organic layers were evaporated to dryness. The residue was dissolved in DMF (1 mL) and purified using silica gel column chromatography using ethyl acetate in heptane from 0 to 100% to afford a white powders which was recrystallized from methanol/water to afford compound 108 (170 mg). Method B: Rt: 0.99 min. m/z: 487 (M+H)⁺ Exact mass: 486.0. ¹H NMR (400 MHz, DMSO-d₆) δ ppm 1.75-1.90 (m, 2H), 2.25-2.37 (m, 2H), 2.41-2.50 (m, 2H), 3.81 (s, 3H), 6.94 (t, J=55.0 Hz, 1H), 7.71 (s, 1H), 7.80 (dd, J=5.5, 2.0 Hz, 1H), 8.04 (d, J=1.8 Hz, 1H), 8.59 (d, J=5.5 Hz, 1H), 8.64 (s, 1H), 10.93 (s, 1H). DSC: From 30 to 300° C. at 10° C./min, peak: 230.2° C.

Compound 109: 3-chloro-N-(2,6-difluoro-4-pyridyl)-1-methyl-4-[[1-(trifluoromethyl)cyclobutyl]sulfamoyl]pyrrole-2-carboxamide

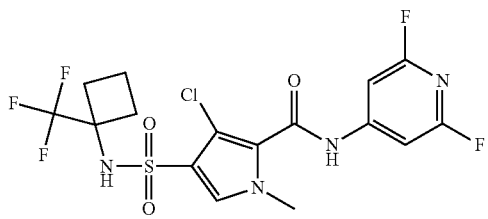 [SMILES: Cn1cc(S(=O)(=O)NC2(C(F)(F)F)CCC2)c(Cl)c1C(=O)Nc1cc(F)nc(F)c1]

Compound 109 (200 mg) was prepared similarly as described for compound 108, using 4-amino-2,6-difluoropyridine instead of 2-(difluoromethyl)pyridin-4-amine. Method B: Rt: 1.09 min. m/z: 473 (M+H)⁺ Exact mass: 472.0. ¹H NMR (400 MHz, DMSO-d₆) δ ppm 1.75-1.87 (m, 2H), 2.26-2.37 (m, 2H), 2.40-2.50 (m, 2H), 3.80 (s, 3H), 7.35 (s, 2H), 7.74 (s, 1H), 8.66 (s, 1H), 11.17 (s, 1H). DSC: From 30 to 300° C. at 10° C./min, peak: 193.1° C.

Compound 110: N-(2-bromo-4-pyridyl)-3-chloro-1-methyl-4-[[1-(trifluoromethyl)cyclobutyl]sulfamoyl]pyrrole-2-carboxamide

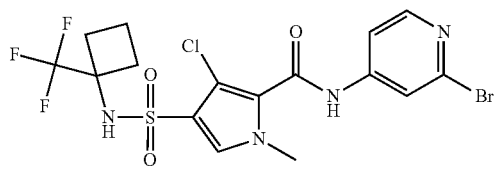 [SMILES: Cn1cc(S(=O)(=O)NC2(C(F)(F)F)CCC2)c(Cl)c1C(=O)Nc1ccnc(Br)c1]

Compound 110 (138 mg) was prepared similarly as described for compound 108, using 4-amino-2-bromopyridine instead of 2-(difluoromethyl)pyridin-4-amine. Method B: Rt: 1.04 min. m/z: 515 (M+H)⁺ Exact mass: 514.0. ¹H NMR (400 MHz, DMSO-d₆) δ ppm 1.72-1.89 (m, 2H), 2.25-2.35 (m, 2H), 2.40-2.50 (m, 2H), 3.79 (s, 3H), 7.66 (dd, J=5.6, 1.9 Hz, 1H), 7.71 (s, 1H), 7.97 (d, J=1.8 Hz, 1H), 8.30 (d, J=5.5 Hz, 1H), 8.64 (s, 1H), 10.86 (s, 1H). DSC: From 30 to 300° C. at 10° C./min, peak: 221.2° C.

Compound 111: 3-chloro-N-(2-fluoro-4-pyridyl)-1-methyl-4-[[1-(trifluoromethyl)cyclobutyl]sulfamoyl]pyrrole-2-carboxamide

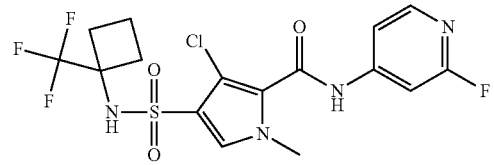 [SMILES: Cn1cc(S(=O)(=O)NC2(C(F)(F)F)CCC2)c(Cl)c1C(=O)Nc1ccnc(F)c1]

Compound 111 (190 mg) was prepared similarly as described for compound 108, using 4-amino-2-fluoropyridine instead of 2-(difluoromethyl)pyridin-4-amine. Method B: Rt: 0.98 min. m/z: 455 (M+H)⁺ Exact mass: 454.0. ¹H NMR (400 MHz, DMSO-d₆) δ ppm 1.77-1.88 (m, 2H), 2.26-2.36 (m, 2H), 2.42-2.50 (m, 2H), 3.80 (s, 3H), 7.47 (br. d, J=1.5 Hz, 1H), 7.53 (br. dt, J=5.7, 1.5, 1.5 Hz, 1H), 7.71 (s, 1H), 8.17 (d, J=5.7 Hz, 1H), 8.64 (s, 1H), 10.96 (s, 1H).

Compound 112: 3-chloro-N-(2-chloro-3-fluoro-4-pyridyl)-1-methyl-[[(1R)-1-(trifluoromethyl)propyl]sulfamoyl]pyrrole-2-carboxamide

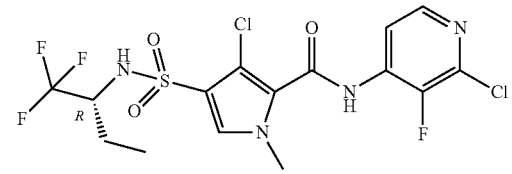

Compound 112 (116 mg) was prepared similarly as described for compound 38, using 2-chloro-3-fluoropyridin-4-amine instead of 4-amino-2-cyanopyridine. Method B: Rt: 1.08 min. m/z: 477 (M+H)⁺ Exact mass: 476.0. ¹H NMR (400 MHz, DMSO-d₆) δ ppm 0.80 (t, J=7.4 Hz, 3H), 1.46-1.58 (m, 1H), 1.60-1.73 (m, 1H), 3.70-3.86 (m, 1H), 3.81 (s, 3H), 7.72 (s, 1H), 8.08 (t, J=5.4 Hz, 1H), 8.23 (d, J=5.3 Hz, 1H), 8.53 (d, J=8.8 Hz, 1H), 10.58 (s, 1H). DSC: From 30 to 300° C. at 10° C./min, peak: 220.4° C.

Compound 113: N-(2-bromo-4-pyridyl)-3-chloro-4-[(3,3-difluoro-1-methyl-cyclobutyl)sulfamoyl]-1-methyl-pyrrole-2-carboxamide

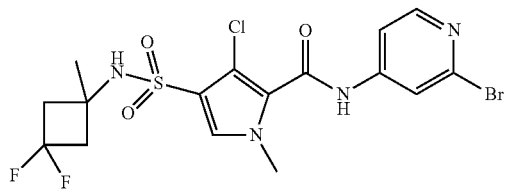 [SMILES: Cn1cc(S(=O)(=O)NC2(C)CC(F)(F)C2)c(Cl)c1C(=O)Nc1ccnc(Br)c1]

Compound 113 (243 mg) was prepared similarly as described for compound 64, using 4-amino-2-bromopyridine instead of 4-amino-2-cyanopyridine. Method B: Rt: 1.00 min. m/z: 497 (M+H)⁺ Exact mass: 496.0. ¹H NMR (400 MHz, DMSO-d$_6$) δ ppm 1.39 (s, 3H), 2.44-2.59 (m, 2H), 2.83-2.99 (m, 2H), 3.78 (s, 3H), 7.65 (dd, J=5.6, 1.9 Hz, 1H), 7.70 (s, 1H), 7.96 (d, J=1.8 Hz, 1H), 8.16 (s, 1H), 8.30 (d, J=5.5 Hz, 1H), 10.84 (s, 1H). DSC: From 30 to 300° C. at 10° C./min, peak: 205.2° C.

Compound 114: 3-chloro-N-(2-chloro-3-fluoro-4-pyridyl)-4-[(3,3-difluoro-1-methyl-cyclobutyl)sulfamoyl]-1-methyl-pyrrole-2-carboxamide

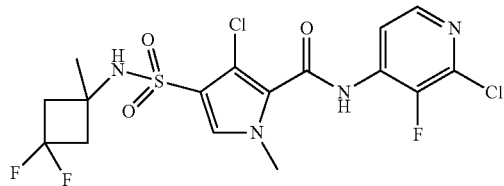 [SMILES: Cn1cc(S(=O)(=O)NC2(C)CC(F)(F)C2)c(Cl)c1C(=O)Nc1ccnc(Cl)c1F]

Compound 114 (63 mg) was prepared similarly as described for compound 64, using 2-chloro-3-fluoropyridin-4-amine instead of 4-amino-2-cyanopyridine. Method B: Rt: 1.05 min. m/z: 471 (M+H)⁺ Exact mass: 470.0. ¹H NMR (400 MHz, DMSO-d$_6$) δ ppm 1.39 (s, 3H), 2.43-2.59 (m, 2H), 2.84-3.02 (m, 2H), 3.82 (s, 3H), 7.73 (s, 1H), 8.09 (t, J=5.4 Hz, 1H), 8.17 (s, 1H), 8.23 (d, J=5.3 Hz, 1H), 10.62 (s, 1H). DSC: From 30 to 300° C. at 10° C./min, peak: 231.0° C.

Compound 115: 3-chloro-4-[(3,3-difluoro-1-methyl-cyclobutyl)sulfamoyl]-N-(2,6-difluoro-4-pyridyl)-1-methyl-pyrrole-2-carboxamide

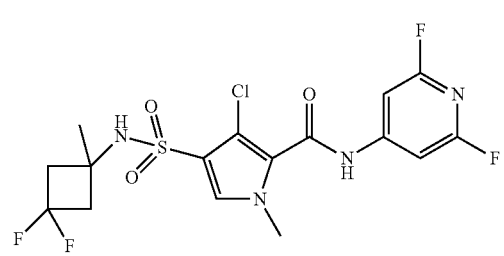 [SMILES: Cn1cc(S(=O)(=O)NC2(C)CC(F)(F)C2)c(Cl)c1C(=O)Nc1cc(F)nc(F)c1]

Compound 115 (185 mg) was prepared similarly as described for compound 64, using 4-amino-2,6-difluoropyridine instead of 4-amino-2-cyanopyridine. Method B: Rt: 1.06 min. m/z: 453 (M−H)⁻ Exact mass: 454.0. ¹H NMR (400 MHz, DMSO-d$_6$) δ ppm 1.39 (s, 3H), 2.46-2.59 (m, 2H), 2.83-3.00 (m, 2H), 3.79 (s, 3H), 7.34 (s, 2H), 7.73 (s, 1H), 8.18 (s, 1H), 11.15 (s, 1H). DSC: From 30 to 300° C. at 10° C./min, peak: 220.5° C.

Compound 116: 3-chloro-4-[(3,3-difluoro-1-methyl-cyclobutyl)sulfamoyl]-N-(2-fluoro-4-pyridyl)-1-methyl-pyrrole-2-carboxamide

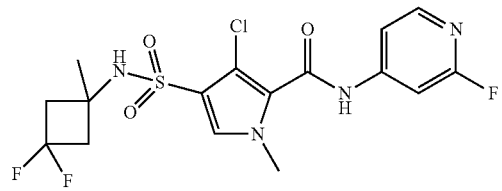 [SMILES: Cn1cc(S(=O)(=O)NC2(C)CC(F)(F)C2)c(Cl)c1C(=O)Nc1ccnc(F)c1]

Compound 116 (164 mg) was prepared similarly as described for compound 64, using 4-amino-2-fluoropyridine instead of 4-amino-2-cyanopyridine. Method B: Rt: 0.94 min. m/z: 437 (M+H)⁺ Exact mass: 436.0. ¹H NMR (400 MHz, DMSO-d$_6$) δ ppm 1.39 (s, 3H), 2.47-2.59 (m, 2H), 2.84-3.01 (m, 2H), 3.79 (s, 3H), 7.47 (d, J=1.5 Hz, 1H), 7.53 (dt, J=5.7, 1.5 Hz, 1H), 7.71 (s, 1H), 8.12-8.20 (m, 2H), 10.94 (s, 1H). DSC: From 30 to 300° C. at 10° C./min, peak: 217.1° C.

Compound 117: N-(2-bromo-4-pyridyl)-4-[(3,3-difluoro-1-methyl-cyclobutyl)sulfamoyl]-3-fluoro-1-methyl-pyrrole-2-carboxamide

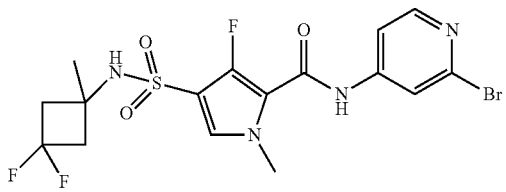

Compound 117 (114 mg) was prepared similarly as described for compound 53, using 2-bromopyridin-4-amine instead of 4-amino-2-cyanopyridine. Method D: Rt: 1.87 min. m/z: 481 (M+H)⁺ Exact mass: 480.0. ¹H NMR (400 MHz, DMSO-d$_6$) δ ppm 1.42 (s, 3H), 2.51-2.60 (m, 2H), 2.82-2.95 (m, 2H), 3.81 (s, 3H), 7.57 (d, J=4.4 Hz, 1H), 7.64 (dd, J=5.6, 1.9 Hz, 1H), 7.97 (d, J=1.8 Hz, 1H), 8.24 (s, 1H), 8.27 (d, J=5.7 Hz, 1H), 10.53 (s, 1H).

Compound 118: N-(2-chloro-3-fluoro-4-pyridyl)-3-fluoro-1-methyl-4-[[(1R)-2,2,2-trifluoro-1-methyl-ethyl]sulfamoyl]pyrrole-2-carboxamide

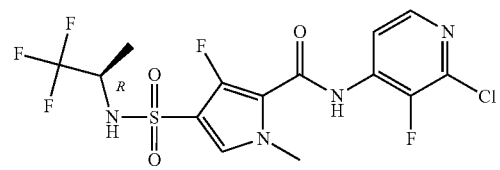

To a solution of ethyl 3-fluoro-1-methyl-4-{[(2R)-1,1,1-trifluoropropan-2-yl]sulfamoyl}-1H-pyrrole-2-carboxylate (150 mg, 0.41 mmol) in dry THF (5 mL) at 0° C. under inert atmosphere was added 2-chloro-3-fluoropyridin-4-amine (78 mg, 0.53 mmol) and lithium bis(trimethylsilyl)amide (1.6 mL, 1M, 1.6 mmol) dropwise. The solution was warmed up to ambient temperature and stirred for 4 hours. The solution was then quenched with sat. NH$_4$Cl (aq) and diluted with EtOAc (20 mL). The organic layer was separated and the aqueous layer was extracted again with EtOAc (20 mL). The combined organics were dried with anhydrous NaSO$_4$ and concentrated in vacuo. The crude was purified on HPLC (Stationary phase: RP XBridge Prep C18 OBD-10 µm, 30×150 mm, Mobile phase: 0.25% NH$_4$HCO$_3$ solution in water, MeOH) to give compound 118 (62 mg) as a solid. Method B: Rt: 1.00 min. m/z: 447 (M+H)$^+$ Exact mass: 446.0. $^1$H NMR (400 MHz, DMSO-d$_6$) δ ppm 1.18 (d, J=6.8 Hz, 3H), 3.84 (s, 3H), 3.93-4.04 (m, 1H), 7.61 (d, J=4.6 Hz, 1H), 8.03 (t, J=5.4 Hz, 1H), 8.20 (d, J=5.5 Hz, 1H), 8.66 (br. s, 1H), 10.26 (br. s, 1H). DSC: From 30 to 300° C. at 10° C./min, peak: 230.6° C.

Synthesis of ethyl 3-fluoro-1-methyl-4-[[1-(trifluoromethyl)cyclobutyl]sulfamoyl]pyrrole-2-carboxylate Ethyl 4-chlorosulfonyl-3-fluoro-1-methyl-pyrrole-2-carboxylate (3.16 g, 10.8 mmol), 1-(trifluoromethyl)cyclobutan-1-amine (6.03 g, 43.3 mmol), NaHCO$_3$ (2.73 g, 32.5 mmol) and powdered molecular sieves (4 Å) were dispensed in ACN (60 mL) and heated at reflux. After 1 day 1-(trifluoromethyl)cyclobutan-1-amine (1 eq) was added and again on day 2. On day 5 the reaction mixture was filtered while still hot. The filtrate was concentrated and the residue was purified by column chromatography using a gradient from 10 till 100% EtOAc in heptane. The product fractions were concentrated in vacuo yielding ethyl 3-fluoro-1-methyl-4-[[1-(trifluoromethyl)cyclobutyl]sulfamoyl]pyrrole-2-carboxylate (2.17 g). An impure fraction was repurified in the same manner yielding a second crop of pure product (492 mg). Method B: Rt: 1.88 min. m/z: 371 (M−H)$^-$ Exact mass: 372.1. $^1$H NMR (400 MHz, DMSO-d$_6$) δ ppm 1.29 (t, J=7.2 Hz, 3H), 1.76-1.88 (m, 2H), 2.25-2.36 (m, 2H), 2.38-2.48 (m, 2H), 3.84 (s, 3H), 4.28 (q, J=7.0 Hz, 2H), 7.58 (d, J=4.6 Hz, 1H), 8.70 (s, 1H).

Compound 119: N-[2-(difluoromethyl)-4-pyridyl]-3-fluoro-1-methyl-4-[[1-(trifluoromethyl)cyclobutyl]sulfamoyl]pyrrole-2-carboxamide

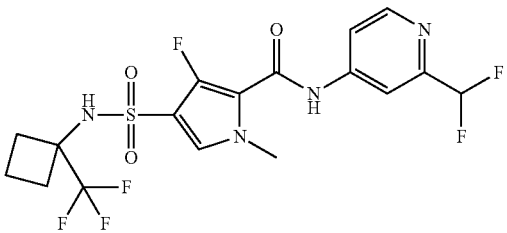 [SMILES: Cn1cc(S(=O)(=O)NC2(C(F)(F)F)CCC2)c(F)c1C(=O)Nc1ccnc(C(F)F)c1]

Lithium bis(trimethylsilyl)amide in THF (2 mL, 1 M, 2 mmol) was added to a solution of ethyl 3-fluoro-1-methyl-4-[[1-(trifluoromethyl)cyclobutyl]sulfamoyl]pyrrole-2-carboxylate (148 mg, 1.03 mmol) in THF (3 mL). The reaction mixture was stirred overnight, quenched with NH$_4$Cl solution, diluted with brine and extracted with EtOAc. The organic layer was dried over magnesium sulphate, filtered and concentrated. The residue was purified by column chromatography using a gradient from 10 till 100% EtOAc in heptane. The product fractions were concentrated and the residue was dissolved in methanol (20 mL). Water was added until crystallisation began. Compound 119 (244 mg) was filtered off as a pink powder. Method D: Rt: 1.85 min. m/z: 471 (M+H)$^+$ Exact mass: 470.0. $^1$H NMR (400 MHz, DMSO-d$_6$) δ ppm 1.79-1.91 (m, 2H), 2.27-2.39 (m, 2H), 2.41-2.50 (m, 2H), 3.83 (s, 3H), 6.92 (t, J=55.0 Hz, 1H), 7.58 (d, J=4.4 Hz, 1H), 7.78 (dd, J=5.5, 2.0 Hz, 1H), 8.04 (d, J=2.0 Hz, 1H), 8.57 (d, J=5.5 Hz, 1H), 8.74 (s, 1H), 10.63 (s, 1H). DSC: From 30 to 300° C. at 10° C./min, peak: 206.2° C.

Compound 120: N-(2-chloro-3-fluoro-4-pyridyl)-3-fluoro-1-methyl-4-[[1-(trifluoromethyl)cyclobutyl]sulfamoyl]pyrrole-2-carboxamide

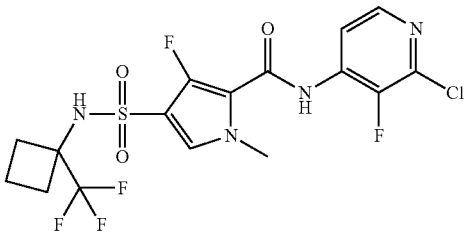 [SMILES: Cn1cc(S(=O)(=O)NC2(C(F)(F)F)CCC2)c(F)c1C(=O)Nc1ccnc(Cl)c1F]

Compound 120 (244 mg) was prepared similarly as described for compound 119, using 2-chloro-3-fluoropyridin-4-amine instead of 2-(difluoromethyl)pyridin-4-amine. Method D: Rt: 1.97 min. m/z: 473 (M+H)$^+$ Exact mass: 472.0. $^1$H NMR (400 MHz, DMSO-d$_6$) δ ppm 1.79-1.91 (m, 2H), 2.28-2.38 (m, 2H), 2.41-2.49 (m, 2H), 3.85 (s, 3H), 7.61 (d, J=4.6 Hz, 1H), 8.04 (t, J=5.4 Hz, 1H), 8.21 (d, J=5.5 Hz, 1H), 8.76 (s, 1H), 10.24 (s, 1H). DSC: From 30 to 300° C. at 10° C./min, peak: 218.0° C.

Compound 121: N-(2-chloro-6-cyano-4-pyridyl)-3-fluoro-1-methyl-4-[[1-(trifluoromethyl)cyclobutyl]sulfamoyl]pyrrole-2-carboxamide

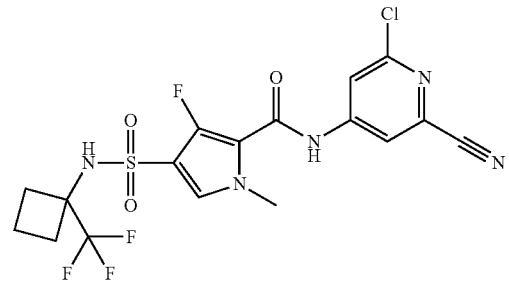 [SMILES: Cn1cc(S(=O)(=O)NC2(C(F)(F)F)CCC2)c(F)c1C(=O)Nc1cc(Cl)nc(C#N)c1]

Compound 121 (19 mg) was prepared similarly as described for compound 119, using 4-amino-6-chloropyridine-2-carbonitrile instead of 2-(difluoromethyl)pyridin-4-amine. Method D: Rt: 2.02 min. m/z: 480 (M+H)$^+$ Exact mass: 479.0. $^1$H NMR (400 MHz, DMSO-d$_6$) δ ppm 1.79-1.91 (m, 2H), 2.28-2.38 (m, 2H), 2.41-2.49 (m, 2H), 3.83 (s, 3H), 7.63 (d, J=4.6 Hz, 1H), 8.06 (d, J=1.8 Hz, 1H), 8.17 (d, J=1.8 Hz, 1H), 8.78 (s, 1H), 10.84 (s, 1H). DSC: From 30 to 300° C. at 10° C./min, peak: 189.0° C.

Compound 122: N-(2-chloro-4-pyridyl)-3-fluoro-1-methyl-4-[[1-(trifluoromethyl)cyclobutyl]sulfamoyl]pyrrole-2-carboxamide

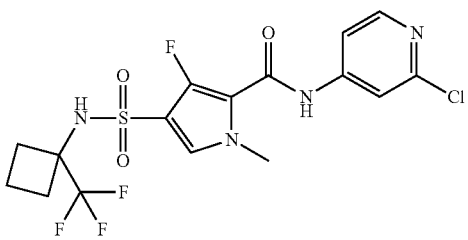 [SMILES: Cn1cc(S(=O)(=O)NC2(C(F)(F)F)CCC2)c(F)c1C(=O)Nc1ccnc(Cl)c1]

Compound 122 (155 mg) was prepared similarly as described for compound 119, using 4-amino-2-chloropyridine instead of 2-(difluoromethyl)pyridin-4-amine. Method B: Rt: 1.00 min. m/z: 455 (M+H)+ Exact mass: 454.1. $^1$H NMR (400 MHz, DMSO-d$_6$) δ ppm 1.74-1.92 (m, 2H), 2.26-2.39 (m, 2H), 2.41-2.48 (m, 2H), 3.82 (s, 3H), 7.58 (d, J=4.4 Hz, 1H), 7.62 (dd, J=5.7, 1.8 Hz, 1H), 7.82 (d, J=1.8 Hz, 1H), 8.30 (d, J=5.7 Hz, 1H), 8.74 (s, 1H), 10.59 (s, 1H). DSC: From 30 to 300° C. at 10° C./min, peak: 188.3° C.

Compound 123: N-(2-cyano-4-pyridyl)-3-fluoro-1-methyl-4-[[1-(trifluoromethyl)cyclobutyl]sulfamoyl]pyrrole-2-carboxamide

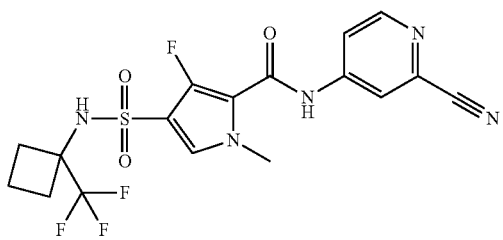 [SMILES: Cn1cc(S(=O)(=O)NC2(C(F)(F)F)CCC2)c(F)c1C(=O)Nc1ccnc(C#N)c1]

Compound 123 (71 mg) was prepared similarly as described for compound 119, using 4-aminopyridine-2-carbonitrile instead of 2-(difluoromethyl)pyridin-4-amine. Method B: Rt: 0.96 min. m/z: 446 (M+H)+ Exact mass: 445.1. $^1$H NMR (400 MHz, DMSO-d$_6$) δ ppm 1.78-1.91 (m, 2H), 2.28-2.38 (m, 2H), 2.41-2.48 (m, 2H), 3.83 (s, 3H), 7.60 (d, J=4.6 Hz, 1H), 7.92 (dd, J=5.6, 2.1 Hz, 1H), 8.22 (d, J=1.8 Hz, 1H), 8.63 (d, J=5.5 Hz, 1H), 8.75 (br. s., 1H), 10.72 (br. s., 1H). DSC: From 30 to 300° C. at 10° C./min, peak: 240.5° C.

Compound 124: N-(2-bromo-4-pyridyl)-4-[[(1R)-2,2-difluoro-1-methyl-propyl]sulfamoyl]-3-fluoro-1-methyl-pyrrole-2-carboxamide

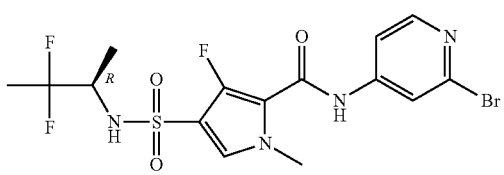

Compound 124 (218 mg) was prepared similarly as described for compound 63, using 4-amino-2-bromopyridine instead of 4-amino-2-cyanopyridine. Method D: Rt: 1.79 min. m/z: 469 (M+H)+ Exact mass: 468.0. $^1$H NMR (400 MHz, DMSO-d$_6$) δ ppm 1.07 (d, J=6.8 Hz, 3H), 1.58 (t, J=19.1 Hz, 3H), 3.47-3.63 (m, 1H), 3.81 (s, 3H), 7.57 (d, J=4.6 Hz, 1H), 7.64 (dd, J=5.7, 1.8 Hz, 1H), 7.97 (d, J=1.5 Hz, 1H), 8.21 (d, J=9.0 Hz, 1H), 8.27 (d, J=5.5 Hz, 1H), 10.53 (s, 1H). DSC: From 30 to 300° C. at 10° C./min, peak: 190.5° C.

Compound 125: N-(2-chloro-3-fluoro-4-pyridyl)-4-[[(1R)-2,2-difluoro-1-methyl-propyl]sulfamoyl]-3-fluoro-1-methyl-pyrrole-2-carboxamide

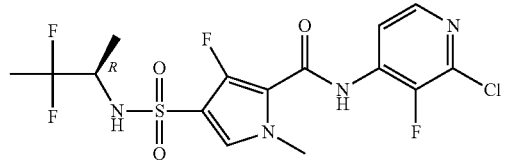

Compound 125 (195 mg) was prepared similarly as described for compound 63, using 2-chloro-3-fluoropyridin-4-amine instead of 4-amino-2-cyanopyridine. Method D: Rt: 1.87 min. m/z: 443 (M+H)+ Exact mass: 442.0. $^1$H NMR (400 MHz, DMSO-d$_6$) δ ppm 1.07 (d, J=6.8 Hz, 3H), 1.58 (t, J=19.3 Hz, 3H), 3.48-3.63 (m, 1H), 3.84 (s, 3H), 7.60 (d, J=4.6 Hz, 1H), 8.04 (t, J=5.4 Hz, 1H), 8.18-8.26 (m, 2H), 10.21 (s, 1H).

Compound 126: N-(2,6-dichloro-4-pyridyl)-3-fluoro-1-methyl-4-[[(1R)-2,2,2-trifluoro-1-methyl-ethyl]sulfamoyl]pyrrole-2-carboxamide

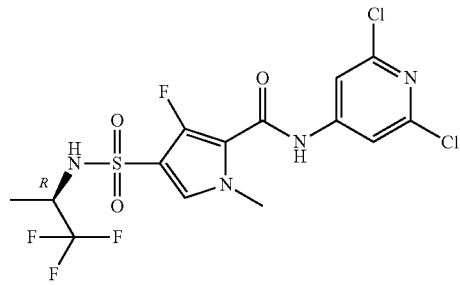

Compound 126 (136 mg) was prepared similarly as described for compound 18, using 2-chloro-3-fluoropyridin-4-amine instead of 4-amino-2-cyanopyridine. Method D: Rt: 2.02 min. m/z: 463 (M+H)+ Exact mass: 462.0. $^1$H NMR (400 MHz, DMSO-d$_6$) δ ppm 1.18 (d, J=7.0 Hz, 3H), 3.82 (s, 3H), 3.92-4.05 (m, 1H), 7.63 (d, J=4.4 Hz, 1H), 7.78 (s, 2H), 8.67 (d, J=8.6 Hz, 1H), 10.70 (s, 1H).

83

Compound 127: 4-[(2,2-difluorocyclobutyl)sulfamoyl]-N-[2-(difluoromethyl)-4-pyridyl]-3-fluoro-1-methyl-pyrrole-2-carboxamide

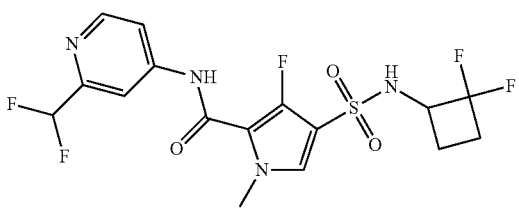 [SMILES: Cn1cc(S(=O)(=O)NC2CCC2(F)F)c(F)c1C(=O)Nc1ccnc(C(F)F)c1]

A mixture of ethyl 4-chlorosulfonyl-3-fluoro-1-methyl-pyrrole-2-carboxylate (360 mg, 1.34 mmol), 2,2-difluorocyclobutan-1-amine hydrochloride (Commercial from Enamine Building Blocks, EN300-89718, 201.2 mg, 1.401 mmol) NaHCO$_3$ (336 mg, 4.0 mmol), acetonitrile (20 mL), molecular sieves 4 Å (300 mg) was stirred and refluxed during 2 hours. The reaction mixture was filtered while still hot. The filtrate was concentrated and the obtained residue was purified by column chromatography on using a gradient from 10 till 100% EtOAc in heptane. The product fractions were concentrated in vacuo resulting in ethyl 4-[(2,2-difluorocyclobutyl)sulfamoyl]-3-fluoro-1-methyl-pyrrole-2-carboxylate as a light yellow oil (424 mg) which solidified on standing. Method D: Rt: 1.68 min. m/z: 339.0 (M−H)⁻ Exact mass: 340.1. Lithium bis(trimethylsilyl)amide (2.33 mL, 1 M in THF, 2.33 mmol) was added to ethyl 4-[(2,2-difluorocyclobutyl)sulfamoyl]-3-fluoro-1-methyl-pyrrole-2-carboxylate (198 mg, 0.582 mmol), 2-(difluoromethyl)pyridin-4-amine (109 mg, 0.756 mmol) in THF (3 mL) and the mixture was stirred for 30 minutes. The reaction mixture was quenched with NH$_4$Cl solution, diluted with brine and extracted with EtOAc. The organic layer was dried over magnesium sulphate, filtered and concentrated. The residue was purified by silica gel column chromatography using a gradient from 10 till 100% EtOAc in heptane. The product fractions were concentrated and dried in vacuo overnight at 50° C. resulting in compound 127 (208 mg) as a white powder. Method D: Rt: 1.72 min. m/z: 437.1 (M−H)⁻ Exact mass: 438.1. ¹H NMR (400 MHz, DMSO-d$_6$) δ ppm 1.57-1.71 (m, 1H), 2.00-2.12 (m, 1H), 2.18-2.32 (m, 2H), 3.81 (s, 3H), 4.06-4.20 (m, 1H), 6.92 (t, J=56.1 Hz, 1H), 7.54 (d, J=4.6 Hz, 1H), 7.76-7.79 (m, 1H), 8.03 (d, J=2.0 Hz, 1H), 8.56 (d, J=5.5 Hz, 1H), 8.60 (d, J=8.6 Hz, 1H), 10.61 (s, 1H). Compound 127 (183 mg) was separated in enantiomers via Preparative SFC (Stationary phase: Chiralpak Diacel AS 20×250 mm, Mobile phase: CO$_2$, EtOH with 0.4% iPrNH$_2$), resulting in 127a (first eluting, 68 mg) and 127b (second eluting, 68 mg), both were crystallized from MeOH/water. DSC: From 30 to 300° C. at 10° C./min, peak 127a: 189.4° C.; 127b: 189.5° C.

84

Compound 128: N-[2-(difluoromethyl)-4-pyridyl]-3-fluoro-4-[[1-(fluoromethyl)cyclobutyl]sulfamoyl]-1-methyl-pyrrole-2-carboxamide

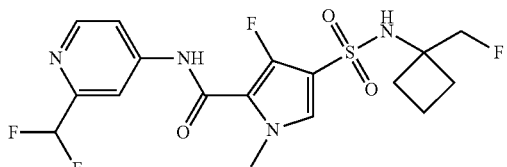

Compound 128 (89 mg) was prepared similarly as described for compound 127, using 1-(fluoromethyl)cyclobutanamine hydrochloride instead of 2,2-difluorocyclobutan-1-amine hydrochloride and stirring for 24 hours instead of 2 hours. Method D: Rt: 1.70 min. m/z: 433.1 (M−H)⁻ Exact mass: 434.1. DSC: From 30 to 300° C. at 10° C./min, peak 197.2° C. ¹H NMR (400 MHz, DMSO-d$_6$) δ ppm 1.69-1.80 (m, 2H), 1.90-1.99 (m, 2H), 2.16-2.27 (m, 2H), 3.82 (s, 3H), 4.51 (d, J=48.0 Hz, 2H), 6.92 (t, J=54.8 Hz, 1H), 7.53 (d, J=4.4 Hz, 1H), 7.78 (dd, J=5.2, 1.4 Hz, 1H), 8.04 (d, J=1.8 Hz, 1H), 8.11 (s, 1H), 8.56 (d, J=5.5 Hz, 1H), 10.59 (s, 1H)

Compound 129: N-[2-(1,1-difluoroethyl)-4-pyridyl]-3-fluoro-1-methyl-4-[[(1R)-2,2,2-trifluoro-1-methylethyl]sulfamoyl]pyrrole-2-carboxamide

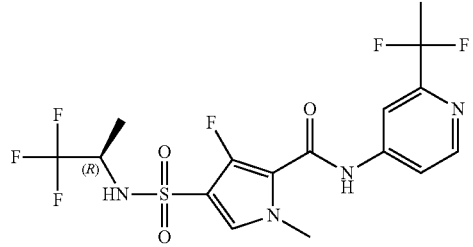

Compound 129 (162 mg) was prepared similarly as described for compound 80 using 2-(1,1-difluoroethyl)pyridin-4-amine instead of 2-(difluoromethyl)pyridin-4-amine. Method B: Rt: 0.96 min. m/z: 457.0 (M−H)⁻ Exact mass: 458.1. ¹H NMR (400 MHz, DMSO-d$_6$) δ ppm 1.18 (d, J=7.0 Hz, 3H), 1.99 (t, J=19.0 Hz, 3H), 3.82 (s, 3H), 3.92-4.06 (m, 1H), 7.59 (d, J=4.4 Hz, 1H), 7.76 (dd, J=5.6, 1.9 Hz, 1H), 8.04 (d, J=1.8 Hz, 1H), 8.55 (d, J=5.7 Hz, 1H), 8.63 (br. s., 1H), 10.60 (s, 1H).

Compound 130: N-(2-chloro-6-methyl-4-pyridyl)-4-[(3,3-difluoro-1-methyl-cyclobutyl)sulfamoyl]-3-fluoro-1-methyl-pyrrole-2-carboxamide

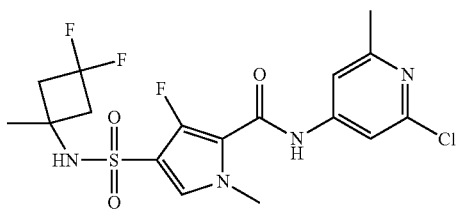 [SMILES: Cc1cc(NC(=O)c2c(F)c(S(=O)(=O)NC3(C)CC(F)(F)C3)cn2C)cc(Cl)n1]

Lithium bis(trimethylsilyl)amide in THF (4.23 mL, 1 M, 4.23 mmol) was added to a solution of ethyl 4-[(3,3-difluoro-1-methyl-cyclobutyl)sulfamoyl]-3-fluoro-1-methyl-pyrrole-2-carboxylate (500 mg, 1.41 mmol) and 2-chloro-6-methyl-pyridin-4-amine (316 mg, 1.76 mmol) in THF (7.6 mL) and the mixture was stirred for 2 hours at room temperature. The mixture was quenched with NH₄Cl solution, diluted with brine and extracted with EtOAc (25 mL). The combined extracts were dried on Na₂SO₄, filtered and concentrated in vacuo. The residue was purified by column chromatography using a gradient from 10 till 100% EtOAc in heptane. The product fractions were concentrated. The residue was crystallised out of isopropanol, the crystals were collected on a filter and dried overnight in vacuo at 50° C., resulting in compound 130 (378 mg) as a white powder. Method B: Rt: 1.08 min. m/z: 449.1 (M–H)⁻ Exact mass: 450.1. DSC: From 30 to 300° C. at 10° C./min, peak 217.7° C. ¹H NMR (400 MHz, DMSO-d₆) δ ppm 1.42 (s, 3H), 2.42 (s, 3H), 2.52-2.63 (m, 2H), 2.79-2.99 (m, 2H), 3.81 (s, 3H), 7.47-7.51 (m, 1H), 7.56 (d, J=4.6 Hz, 1H), 7.60-7.64 (m, 1H), 8.24 (s, 1H), 10.45 (s, 1H)

Synthesis of 2-bromo-3-fluoro-pyridin-4-amine 2-bromo-3-fluoroisonicotinic acid (5.33 g, 24.21 mmol) was dissolved in tert.-butyl alcohol (150 mL). Triethylamine (3.69 mL, 26.63 mmol) and diphenylphosphoryl azide (5.31 mL, 24.69 mmol) were added and the reaction mixture was refluxed overnight. The volatiles were removed under reduced pressure and the residue was purified on silica using a heptane to EtOAc gradient yielding the desired product as a clear oil which solidified on standing. tert-butyl N-(2-bromo-3-fluoro-4-pyridyl)carbamate (6.71 g, 23.05 mmol) was dissolved in CH₂Cl₂ (20 mL), HCl (6M in iPrOH, 75 mL, 450 mmol) was added and the reaction mixture was stirred for 2 days at room temperature. The volatiles were removed under reduced pressure and the residue was partitioned between water (100 mL) and CH₂Cl₂ (100 mL). The aqueous layer was basified and the organic layer was removed. The aqueous layer was extracted with CH₂Cl₂ (20 mL). The combined organic layers were dried over MgSO₄, filtered and evaporated to dryness yielding 2-bromo-3-fluoro-pyridin-4-amine (3.55 g) as a white powder.

Compound 131: N-(2-bromo-3-fluoro-4-pyridyl)-4-[(3,3-difluoro-1-methyl-cyclobutyl)sulfamoyl]-3-fluoro-1-methyl-pyrrole-2-carboxamide

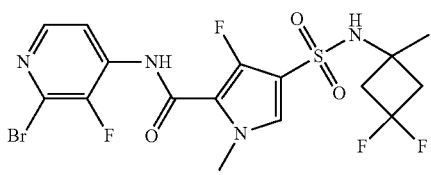 [SMILES: Cn1cc(S(=O)(=O)NC2(C)CC(F)(F)C2)c(F)c1C(=O)Nc1ccnc(Br)c1F]

Compound 131 (597 mg) was prepared similarly as described for compound 130, using 2-bromo-3-fluoro-pyridin-4-amine instead of 2-chloro-6-methyl-pyridin-4-amine. Method B: Rt: 1.11 min. m/z: 496.9 (M–H)⁻ Exact mass: 498.0. DSC: From 30 to 300° C. at 10° C./min, peak 194.1° C. ¹H NMR (400 MHz, DMSO-d₆) δ ppm 1.42 (s, 3H), 2.53-2.62 (m, 2H), 2.89 (q, J=14.7 Hz, 2H), 3.84 (s, 3H), 7.57 (d, J=4.4 Hz, 1H), 8.04 (t, J=5.4 Hz, 1H), 8.18 (d, J=5.3 Hz, 1H), 8.25 (br. s., 1H), 10.21 (br. s., 1H).

Compound 132: 4-[(3,3-difluoro-1-methyl-cyclobutyl)sulfamoyl]-N-(2,6-difluoro-4-pyridyl)-3-fluoro-1-methyl-pyrrole-2-carboxamide

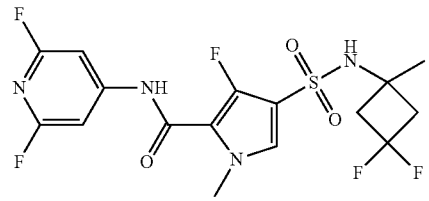 [SMILES: Cn1cc(S(=O)(=O)NC2(C)CC(F)(F)C2)c(F)c1C(=O)Nc1cc(F)nc(F)c1]

Compound 132 (135 mg) was prepared similarly as described for compound 130, using 4-amino-2,6-difluoropyridine instead of 2-chloro-6-methyl-pyridin-4-amine. Compound 132 was crystallized from MeOH/H₂O instead of iPrOH. Method D: Rt: 1.94 min. m/z: 437.1 (M–H)⁻ Exact mass: 438.1. DSC: From 30 to 300° C. at 10° C./min, peak 195.1° C. ¹H NMR (400 MHz, DMSO-d₆) δ ppm 1.42 (s, 3H), 2.51-2.61 (m, 2H), 2.81-2.95 (m, 2H), 3.82 (s, 3H), 7.34 (s, 2H), 7.60 (d, J=4.6 Hz, 1H), 8.26 (s, 1H), 10.84 (s, 1H).

Compound 133: 4-[(3,3-difluoro-1-methyl-cyclobutyl)sulfamoyl]-3-fluoro-N-(2-fluoro-4-pyridyl)-1-methyl-pyrrole-2-carboxamide

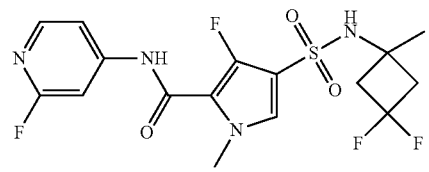 [SMILES: Cn1cc(S(=O)(=O)NC2(C)CC(F)(F)C2)c(F)c1C(=O)Nc1ccnc(F)c1]

Compound 133 (122 mg) was prepared similarly as described for compound 132, using 4-amino-2-fluoropyridine instead of 4-amino-2,6-difluoropyridine. Method D: Rt: 1.78 min. m/z: 419.1 (M–H)⁻ Exact mass: 420.1. DSC: From 30 to 300° C. at 10° C./min, peak 173.2° C. ¹H NMR (400 MHz, DMSO-d₆) δ ppm 1.42 (s, 3H), 2.51-2.61 (m, 2H), 2.82-2.95 (m, 2H), 3.82 (s, 3H), 7.46 (d, J=1.5 Hz, 1H), 7.51-7.54 (m, 1H), 7.57 (d, J=4.6 Hz, 1H), 8.14 (d, J=5.7 Hz, 1H), 8.24 (s, 1H), 10.63 (s, 1H).

Compound 134: 4-[(3,3-difluoro-1-methyl-cyclobutyl)sulfamoyl]-3-fluoro-N-(2-fluoro-6-methyl-4-pyridyl)-1-methyl-pyrrole-2-carboxamide

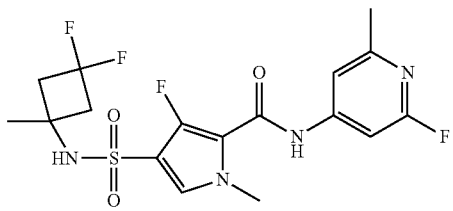 [SMILES: Cc1cc(NC(=O)c2c(F)c(S(=O)(=O)NC3(C)CC(F)(F)C3)cn2C)cc(F)n1]

Compound 134 (115 mg) was prepared similarly as described for compound 132, using 2-fluoro-6-methyl-pyridin-4-amine instead of 4-amino-2,6-difluoropyridine. Method D: Rt: 1.84 min. m/z: 433.1 (M−H)⁻; Exact mass: 434.1. DSC: From 30 to 300° C. at 10° C./min, peak 222.4° C. ¹H NMR (400 MHz, DMSO-d₆) δ ppm 1.42 (s, 3H), 2.38 (s, 3H), 2.51-2.61 (m, 2H), 2.81-2.96 (m, 2H), 3.81 (s, 3H), 7.25 (s, 1H), 7.40 (s, 1H), 7.56 (d, J=4.6 Hz, 1H), 8.24 (s, 1H), 10.53 (s, 1H)

Compound 135: N-(2,6-dibromo-4-pyridyl)-4-[(3,3-difluoro-1-methyl-cyclobutyl)sulfamoyl]-3-fluoro-1-methyl-pyrrole-2-carboxamide

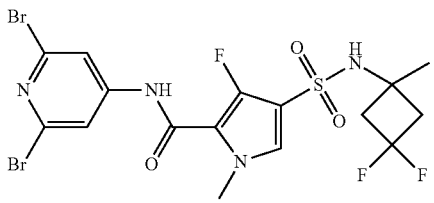 [SMILES: Cn1cc(S(=O)(=O)NC2(C)CC(F)(F)C2)c(F)c1C(=O)Nc1cc(Br)nc(Br)c1]

Compound 135 (569 mg) was prepared similarly as described for compound 132, using 4-amino-2,6-dibromopyridine instead of 4-amino-2,6-difluoropyridine, compound 135 was crystallized from MeOH instead of MeOH/H₂O. Method D: Rt: 2.11 min. m/z: 558.9 (M−H)⁻ Exact mass: 559.9. DSC: From 30 to 300° C. at 10° C./min, peak 233.2° C. ¹H NMR (400 MHz, DMSO-d₆) δ ppm 1.42 (s, 3H), 2.51-2.61 (m, 2H), 2.81-2.95 (m, 2H), 3.81 (s, 3H), 7.60 (d, J=4.6 Hz, 1H), 7.94 (s, 2H), 8.27 (s, 1H), 10.60 (s, 1H).

Compound 136: N-(2,6-dichloro-4-pyridyl)-4-[(3,3-difluoro-1-methyl-cyclobutyl)sulfamoyl]-3-fluoro-1-methyl-pyrrole-2-carboxamide

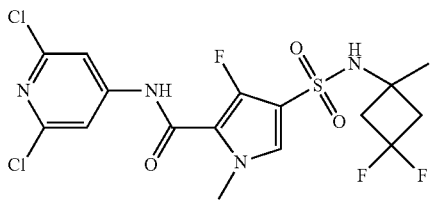 [SMILES: Cn1cc(S(=O)(=O)NC2(C)CC(F)(F)C2)c(F)c1C(=O)Nc1cc(Cl)nc(Cl)c1]

Compound 136 (132 mg) was prepared similarly as described for compound 132, using 4-amino-2,6-dichloropyridine instead of 4-amino-2,6-difluoropyridine. Method D: Rt: 2.07 min. m/z: 469.0 (M−H)⁻ Exact mass: 470.0. DSC: From 30 to 300° C. at 10° C./min, peak 237.1° C. ¹H NMR (400 MHz, DMSO-d₆) δ ppm 1.42 (s, 3H), 2.51-2.61 (m, 2H), 2.81-2.95 (m, 2H), 3.81 (s, 3H), 7.60 (d, J=4.6 Hz, 1H), 7.78 (s, 2H), 8.27 (s, 1H), 10.67 (s, 1H)

Compound 137: 3-chloro-N-(2-fluoro-6-methyl-4-pyridyl)-1-methyl-4-[[(1R)-2,2,2-trifluoro-1-methyl-ethyl]sulfamoyl]pyrrole-2-carboxamide

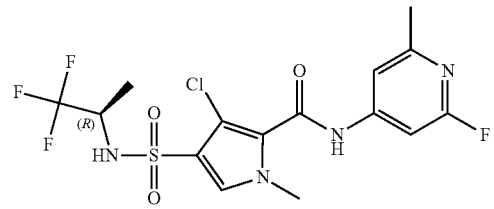

Methyl 3-chloro-1-methyl-4-[[(1R)-2,2,2-trifluoro-1-methyl-ethyl]sulfamoyl]pyrrole-2-carboxylate (250 mg, 0.72 mmol) and 2-fluoro-6-methyl-pyridin-4-amine (100.4 mg, 0.8 mmol) were dissolved in THF (5 mL). Lithium bis(trimethylsilyl)amide in THF (2.15 mL, 1 M, 2.15 mmol) was added drop wise and the reaction mixture was stirred at room temperature for 3 hours. The reaction mixture was quenched with sat. NH₄Cl (5 mL) and the organic layer was separated. The aqueous layer was extracted with CH₂Cl₂ (5 mL) and the combined organic layers were evaporated to dryness. The residue was dissolved in CH₂Cl₂ (5 mL) and purified using silica gel column chromatography using ethyl acetate in heptane from 0 to 100% resulting in compound 137 (238 mg) as a light yellow solid. Method B: Rt: 1.00 min. m/z: 442.0 (M−H)⁻ Exact mass: 441.0. DSC: From 30 to 300° C. at 10° C./min, peak 191.5° C. ¹H NMR (400 MHz, DMSO-d₆) δ ppm 1.20 (d, J=7.0 Hz, 3H), 2.40 (s, 3H), 3.79 (s, 3H), 3.93-4.05 (m, 1H), 7.27 (br. s, 1H), 7.38-7.41 (m, 1H), 7.72 (s, 1H), 8.54 (br. s., 1H), 10.86 (br. s., 1H).

Synthesis of 2,3-difluoropyridin-4-amine hydrochloride 2,3-difluoropyridine-4-carboxylic acid (923 mg, 5.8 mmol) was dissolved in tert.-butyl alcohol (50 mL). Triethylamine (0.88 mL, 6.38 mmol) and diphenylphosphoryl azide (1.27 mL, 5.92 mmol) were added and the reaction mixture was refluxed overnight. The volatiles were removed under reduced pressure and the residue was purified on silica using a heptane to EtOAc gradient yielding the desired product as a clear oil. Tert-butyl N-(2,3-difluoro-4-pyridyl) carbamate (1.2 g, 5.21 mmol) was dissolved in CH₂Cl₂ (10 mL), HCl (6M in iPrOH) (20 mL, 120 mmol) was added and the reaction mixture was stirred for 2 days at room temperature. The volatiles were removed under reduced pressure yielding 2,3-difluoropyridin-4-amine hydrochloride (620 mg) as a white powder.

Compound 138: 3-chloro-N-(2,3-difluoro-4-pyridyl)-1-methyl-4-[[(1R)-2,2,2-trifluoro-1-methyl-ethyl]sulfamoyl]pyrrole-2-carboxamide

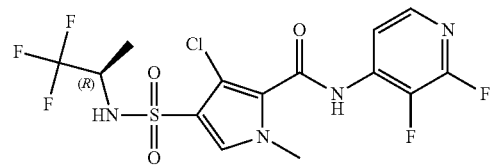

Compound 138 (163 mg) was prepared similarly as described for compound 137 using 2,3-difluoropyridin-4-amine hydrochloride instead of 2-fluoro-6-methyl-pyridin-4-amine, and stirring overnight instead of 3 hours. After silica gel column chromatography, compound 138 was triturated with diisopropylether. Method B: Rt: 1.00 min. m/z: 445.0 (M–H)⁻ Exact mass: 446.0. DSC: From 30 to 300° C. at 10° C./min, peak 215.1° C. ¹H NMR (400 MHz, DMSO-d₆) δ ppm 1.19 (d, J=6.8 Hz, 3H), 3.81 (s, 3H), 3.92-4.05 (m, 1H), 7.74 (s, 1H), 7.96 (t, J=5.2 Hz, 1H), 8.01 (d, J=5.7 Hz, 1H), 8.53 (d, J=8.8 Hz, 1H), 10.73 (s, 1H)

Compound 139: N-(2-bromo-3-fluoro-4-pyridyl)-3-chloro-1-methyl-4-[[(1R)-2,2,2-trifluoro-1-methyl-ethyl]sulfamoyl]pyrrole-2-carboxamide

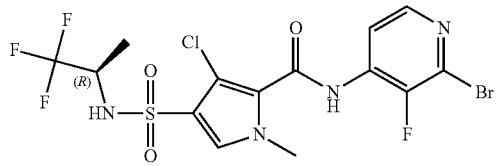

Compound 139 (88 mg) was prepared similarly as described for compound 137 using 2-bromo-3-fluoro-pyridin-4-amine instead of 2-fluoro-6-methyl-pyridin-4-amine, and stirring overnight instead of 3 hours. After silica gel column chromatography, compound 139 was triturated with diisopropylether. Method B: Rt: 1.04 min. m/z: 506.9 (M–H)⁻ Exact mass: 507.9. DSC: From 30 to 300° C. at 10° C./min, peak 203.8° C. ¹H NMR (400 MHz, DMSO-d₆) δ ppm 1.19 (d, J=7.0 Hz, 3H), 3.81 (s, 3H), 3.90-4.06 (m, 1H), 7.74 (s, 1H), 8.09 (t, J=5.5 Hz, 1H), 8.22 (d, J=5.3 Hz, 1H), 8.54 (d, J=8.8 Hz, 1H), 10.60 (s, 1H)

Synthesis of 2,5-difluoropyridin-4-amine 2,5-difluoropyridine-4-carboxylic acid (465 mg, 2.92 mmol) was dissolved in tert.-butyl alcohol (25 mL). Et₃N (445.7 μL, 3.22 mmol) and diphenylphosphoryl azide (641 μL, 2.98 mmol) were added and the reaction mixture was refluxed overnight. The volatiles were removed under reduced pressure and the residue was purified on silica using a heptane to EtOAc gradient. The product fractions were concentrated in vacuo yielding tert-butyl N-(2,5-difluoro-4-pyridyl)carbamate (537 mg) as a white solid. Tert-butyl N-(2,5-difluoro-4-pyridyl)carbamate (537 mg, 2.33 mmol) was dissolved in CH₂Cl₂ (25 mL), HCl (6M in iPrOH) (25 mL, 6 M, 150 mmol) was added and the reaction mixture was stirred for 2 days at room temperature. The volatiles were removed under reduced pressure yielding 2,5-difluoropyridin-4-amine hydrochloride (405 mg) as a white powder.

Compound 140: 3-chloro-N-(2,5-difluoro-4-pyridyl)-1-methyl-4-[[(1R)-2,2,2-trifluoro-1-methyl-ethyl]sulfamoyl]pyrrole-2-carboxamide

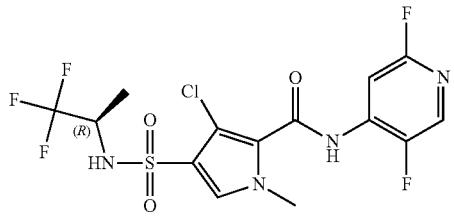

Compound 140 (161 mg) was prepared similarly as described for compound 137 using 2,5-difluoropyridin-4-amine hydrochloride instead of 2-fluoro-6-methyl-pyridin-4-amine, and stirring overnight instead of 3 hours. After silica gel column chromatography, compound 140 was triturated with diisopropylether. Method B: Rt: 1.01 min. m/z: 445.0 (M–H)⁻ Exact mass: 446.0. DSC: From 30 to 300° C. at 10° C./min, peak 197.4° C. ¹H NMR (400 MHz, DMSO-d₆) δ ppm 1.19 (d, J=7.0 Hz, 3H), 3.82 (s, 3H), 3.93-4.05 (m, 1H), 7.75 (s, 1H), 7.82-7.88 (m, 1H), 8.26-8.31 (m, 1H), 8.54 (d, J=8.8 Hz, 1H), 10.63 (s, 1H).

Compound 141: 3-chloro-N-(2-chloro-6-methyl-4-pyridyl)-1-methyl-4-[[(1R)-2,2,2-trifluoro-1-methyl-ethyl]sulfamoyl]pyrrole-2-carboxamide

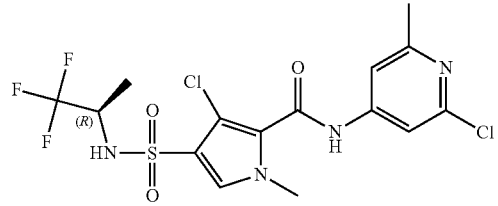

Compound 141 (68 mg) was prepared similarly as described for compound 137 using 2-chloro-6-methyl-pyridin-4-amine instead of 2-fluoro-6-methyl-pyridin-4-amine, and stirring overnight instead of 3 hours. After silica gel column chromatography, trituration with diisopropylether, compound 141 was purified via preparative HPLC (Stationary phase: RP XBridge Prep C18 OBD-10 μm, 30×150 mm, Mobile phase: 0.25% NH₄HCO₃ solution in water, MeOH). Method B: Rt: 1.03 min. m/z: 457.0 (M–H)⁻ Exact mass: 458.0. DSC: From 30 to 300° C. at 10° C./min, peak 208.7° C. ¹H NMR (400 MHz, DMSO-d₆) δ ppm 1.19 (d, J=6.8 Hz, 3H), 2.43 (s, 3H), 3.78 (s, 3H), 3.92-4.04 (m, 1H), 7.49 (d, J=1.1 Hz, 1H), 7.62 (d, J=1.1 Hz, 1H), 7.71 (s, 1H), 8.53 (br. s., 1H), 10.80 (s, 1H).

Synthesis of 2-(difluoromethyl)-3-fluoro-pyridin-4-amine

In a 500 mL one necked round bottom flask 2-chloro-3-fluoroisonicotinic acid (25.0 g, 142 mmol) was dissolved in thionyl chloride (300 mL). DMF (1 mL) was added to the solution and the mixture was heated to reflux for 2 hours. The solution was concentrated in vacuo resulting in a pale yellow oil. The oil was added to CH₂Cl₂ (130 mL) and cooled to 0° C. MeOH (18.3 g, 570 mmol) was added drop wise to the solution. After addition the solution was allowed to warm to room temperature and stirred for 16 hours. The solution was cooled to 0° C. and saturated NaHCO₃ was added. The pH went to about 7. The organic layer was washed with water (2×100 mL), brine, dried over Na₂SO₄ and filtered. The filtrate was concentrated in vacuo to give methyl 2-chloro-3-fluoro-pyridine-4-carboxylate (24.8 g) as a pale brown solid. In a 500 mL one necked round bottom flask, to a solution of methyl 2-chloro-3-fluoro-pyridine-4-carboxylate (24.8 g, 131 mmol) in DMF (250 mL) was added potassium vinyltrifluoroborate (26.3 g, 196 mmol), potassium carbonate (21.7 g, 157 mmol) and tetrakis(triphenylphosphine)palladium(0) (9.07 g, 7.85 mmol). The mixture was stirred at reflux for 16 hours. The reaction mixture was filtered and the filtrate was dissolved in CH₂Cl₂ (100 mL) and washed with water (3×200 mL), brine, dried over Na₂SO₄ and filtered. The filtrate was concentrated to give the crude product. This crude was combined with a second identical batch and purified on silica gel (EtOAc/petroleum ether 0%-20%) resulting in methyl 3-fluoro-2-vinyl-pyridine-4-carboxylate (16 g) as a brown oil. Methyl 3-fluoro-2-vinyl-pyridine-4-carboxylate (16 g, 88.3 mmol) was dissolved in CH₂Cl₂ (200 mL) and cooled to −78° C. Ozone was bubbled (15 PSI) through the solution at −78° C. until the blue color of excess ozone persisted. Nitrogen was bubbled through the solution for 1 minute to purge excess ozone then dimethyl sulfide (40 mL) was added. The solution was stirred at 0° C. for 1 hour. The solution was washed with water (2×150 mL) and brine (150 mL). The organic layer was dried over Na₂SO₄, filtered and concentrated in vacuo. The obtained crude was purified on silica (EtOAc/petroleum ether 20%-40%) resulting in methyl 3-fluoro-2-formyl-pyridine-4-carboxylate (7.8 g) as a yellow oil. In a 500 mL one necked round bottom flask, to a solution of methyl 3-fluoro-2-formyl-pyridine-4-carboxylate (7.8 g, 42.6 mmol) in CH₂Cl₂ (250 mL) and ethanol (0.2 mL) was added drop wise BAST (25 g, 113 mmol) at 0° C. After the addition, the solution was stirred at 0° C. for 1 hour. Water (150 mL) was added to the solution at 0° C. The mixture was extracted with CH₂Cl₂ (2×150 mL). The organic layer was washed with water (150 mL), brine, filtered and concentrated in vacuo resulting in methyl 2-(difluoromethyl)-3-fluoro-pyridine-4-carboxylate (3.5 g). In a 100 mL one necked round bottom flask, to a solution of methyl 2-(difluoromethyl)-3-fluoro-pyridine-4-carboxylate (3.5 g, 17.1 mmol) in THF (32 mL) a solution of LiOH (2.04 g, 85.3 mmol) in water (8 mL) was added. The mixture was stirred for 2 hours at room temperature. The reaction mixture was acidified by the addition of a solution of citric acid. The product was extracted with CH₂Cl₂ (3×20 mL). The combined extracts were dried over Na₂SO₄, filtered and concentrated resulting in 2-(difluoromethyl)-3-fluoro-pyridine-4-carboxylic acid (1.31 g) without further purification. In a 100 mL one necked round bottom flask, to a solution of 2-(difluoromethyl)-3-fluoro-pyridine-4-carboxylic acid (1.31 g, 6.85 mmol) in tert-butyl alcohol was added triethylamine (1.39 g, 13.7 mmol) and diphenylphosphoryl azide (2.26 g, 8.23 mmol). The solution was heated to reflux for 2 hours. To the solution NaOH (20 mL, 1M, aq.) was added and CH₂Cl₂ (50 mL). The aqueous layer was extracted with CH₂Cl₂ (2×20 mL). The combined organic layers were washed with brine, dried over Na₂SO₄ and concentrated in vacuo resulting in the crude product. This was purified by HPLC resulting in tert-butyl N-[2-(difluoromethyl)-3-fluoro-4-pyridyl]carbamate (400 mg). In a 100 mL one necked round bottom flask, HCl was added to tert-butyl N-[2-(difluoromethyl)-3-fluoro-4-pyridyl]carbamate (400 mg, 1.53 mmol). The solution was stirred at room temperature for 2 hours. The solution was concentrated in vacuo, redissolved in water and lyophilized resulting in 2-(difluoromethyl)-3-fluoro-pyridin-4-amine hydrochloride (140 mg). ¹H NMR (400 MHz, DMSO-d₆) δ ppm 8.06 (d, J=6.0 Hz, 1H), 7.25 (t, J=52.6 Hz, 1H), 7.05-6.98 (m, 1H)

Compound 142: 3-chloro-N-[2-(difluoromethyl)-3-fluoro-4-pyridyl]-1-methyl-4-[[(1R)-2,2,2-trifluoro-1-methyl-ethyl]sulfamoyl]pyrrole-2-carboxamide

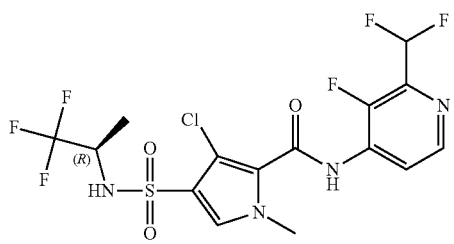

Compound 142 (77 mg) was prepared similarly as described for compound 137 using 2-(difluoromethyl)-3-fluoro-pyridin-4-amine hydrochloride instead of 2-fluoro-6-methyl-pyridin-4-amine. After silica gel column chromatography, compound 142 was crystallized from CH₂Cl₂/diisopropylether and triturated with diisopropylether. Method D: Rt: 1.83 min. m/z: 477.0 (M−H)⁻ Exact mass: 478.0. DSC: From 30 to 300° C. at 10° C./min, peak 182.8° C. ¹H NMR (400 MHz, DMSO-d₆) δ ppm 1.19 (d, J=7.0 Hz, 3H), 3.82 (s, 3H), 3.93-4.03 (m, 1H), 7.16 (t, J=53.0 Hz, 1H), 7.74 (s, 1H), 8.26 (t, J=5.6 Hz, 1H), 8.47 (d, J=5.3 Hz, 1H), 8.54 (d, J=8.8 Hz, 1H), 10.62 (s, 1H)

Compound 143: 3-chloro-N-(2-cyano-3-fluoro-4-pyridyl)-1-methyl-4-[[(1R)-2,2,2-trifluoro-1-methyl-ethyl]sulfamoyl]pyrrole-2-carboxamide

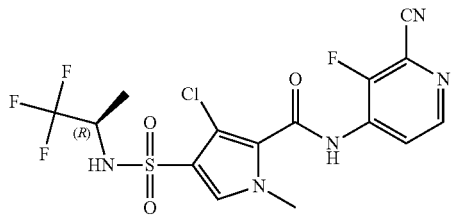

A 10 mL microwave vial was charged with compound 139 (prepared similarly as described above, 200 mg, 0.39 mmol), zinc cyanide (23 mg, 0.2 mmol), 1,1'-bis(diphenylphosphino)ferrocenedichloro palladium(II) (29 mg, 0.039 mmol) and DMF (5 mL). The reaction mixture was heated in the microwave for 30 minutes at 160° C. The reaction mixture was evaporated to dryness, loaded on a silica cartridge and a gradient form heptane to EtOAc was applied resulting in compound 143 (57 mg) as an off white powder after crystallization from a MeOH:water mixture. Method B: Rt: 1.07 min. m/z: 452.0 (M−H)⁻ Exact mass: 453.0. DSC: From 30 to 300° C. at 10° C./min, peak 192.6° C. ¹H NMR (400 MHz, DMSO-d₆) δ ppm 1.19 (d, J=7.0 Hz, 3H), 3.82 (s, 3H), 3.99 (dd, J=15.5, 7.6 Hz, 1H), 7.75 (s, 1H), 8.39 (dd, J=6.3, 5.4 Hz, 1H), 8.52-8.57 (m, 2H), 10.82 (s, 1H).

Compound 144: 3-chloro-N-(2,6-dimethyl-4-pyridyl)-1-methyl-4-[[(1R)-2,2,2-trifluoro-1-methyl-ethyl]sulfamoyl]pyrrole-2-carboxamide

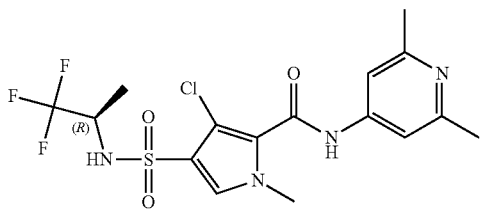

Compound 144 (188 mg) was prepared similarly as described for compound 137 using 2,6-dimethylpyridin-4-amine instead of 2-fluoro-6-methyl-pyridin-4-amine. After silica gel column chromatography, compound 144 was triturated with diisopropylether and crystallized from MeOH/H$_2$O. Method B: Rt: 0.96 min. m/z: 437.1 (M−H)$^-$ Exact mass: 438.1. DSC: From 30 to 300° C. at 10° C./min, peak 201.8° C. $^1$H NMR (400 MHz, DMSO-d$_6$) δ ppm 1.19 (d, J=7.0 Hz, 3H), 2.39 (s, 6H), 3.77 (s, 3H), 3.98 (dd, J=15.7, 7.6 Hz, 1H), 7.34 (s, 2H), 7.68 (s, 1H), 8.50 (d, J=8.8 Hz, 1H), 10.51 (br. s., 1H).

Compound 145: 3-chloro-N-[2-(fluoromethyl)-4-pyridyl]-1-methyl-4-[[(1R)-2,2,2-trifluoro-1-methyl-ethyl]sulfamoyl]pyrrole-2-carboxamide

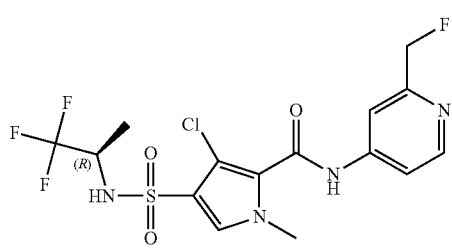

Methyl 3-chloro-1-methyl-4-[[(1R)-2,2,2-trifluoro-1-methyl-ethyl]sulfamoyl]pyrrole-2-carboxylate (400 mg, 0.57 mmol) and (4-aminopyridin-2-yl)methanol (157 mg, 1.26 mmol) were dissolved in dry THF (5 mL). Lithium bis(trimethylsilyl)amide (1M in THF) (3.4 mL, 1 M, 3.4 mmol) was added drop wise and the reaction mixture was stirred overnight at room temperature. The reaction mixture was next quenched with sat. NH$_4$Cl (10 mL). The organic layer was removed and the aqueous layer extracted with CH$_2$Cl$_2$ (2×5 mL). The combined organic layers were evaporated to dryness and the residue was purified on silica using a heptane to EtOAc gradient yielding 3-chloro-N-[2-(hydroxymethyl)-4-pyridyl]-1-methyl-4-[[(1R)-2,2,2-trifluoro-1-methyl-ethyl]sulfamoyl]pyrrole-2-carboxamide (249 mg) as an off-white powder after trituration with diisopropylether. Method B: Rt: 0.81 min. m/z: 439 (M−H)$^-$ Exact mass: 440.1. $^1$H NMR (400 MHz, DMSO-d$_6$) δ ppm 1.19 (d, J=7.0 Hz, 3H), 3.78 (s, 3H), 3.92-4.05 (m, 1H), 4.53 (d, J=5.7 Hz, 2H), 5.42 (t, J=5.8 Hz, 1H), 7.55 (dd, J=5.5, 2.0 Hz, 1H), 7.68 (s, 1H), 7.79 (d, J=1.5 Hz, 1H), 8.38 (d, J=5.5 Hz, 1H), 8.50 (br. s., 1H), 10.69 (s, 1H). DSC: From 30 to 300° C. at 10° C./min, peak 233.9° C. 3-chloro-N-[2-(hydroxymethyl)-4-pyridyl]-1-methyl-4-[[(1R)-2,2,2-trifluoro-1-methyl-ethyl]sulfamoyl]pyrrole-2-carboxamide (181 mg, 0.41 mmol) was dissolved in THF (5 mL). (Diethylamino)sulfur trifluoride (108.5 μL, 0.82 mmol) was added and the reaction mixture was stirred overnight at room temperature. The volatiles were removed under reduced pressure and the residue was purified via prep. HPLC (Stationary phase: RP XBridge Prep C18 OBD-10 μm, 30×150 mm, Mobile phase: 0.25% NH$_4$HCO$_3$ solution in water, MeOH) yielding 3-chloro-N-[2-(fluoromethyl)-4-pyridyl]-1-methyl-4-[[(1R)-2,2,2-trifluoro-1-methyl-ethyl]sulfamoyl]pyrrole-2-carboxamide (11.2 mg). Method B: Rt: 0.97 min. m/z: 441.1 (M−H)$^-$ Exact mass: 442.0. $^1$H NMR (400 MHz, CHLOROFORM-d) δ ppm 1.39 (d, J=6.8 Hz, 3H), 3.93-3.99 (m, 1H), 4.00 (s, 3H), 5.49 (d, J=46.9 Hz, 2H), 7.37 (s, 1H), 7.58-7.64 (m, 2H), 8.52 (d, J=5.3 Hz, 1H).

Compound 156: 3-chloro-N-(6-cyano-5-fluoro-2-pyridyl)-1-methyl-4-[[(1R)-2,2,2-trifluoro-1-methyl-ethyl]sulfamoyl]pyrrole-2-carboxamide

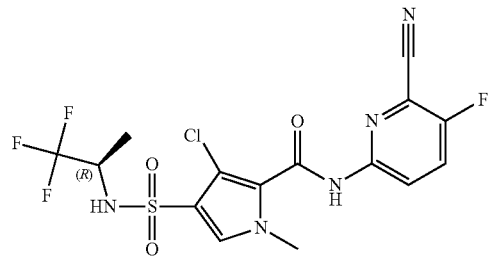

Compound 76 (100 mg, 0.2 mmol, zinc cyanide (11.56 mg, 0.098 mmol) and 1,1'-bis(diphenylphosphino)ferrocenedichloro palladium(II) (14.5 mg, 0.02 mmol) were dispensed in DMF (4 mL) and heated under microwave irradiation for 15 minutes at 160° C. The reaction mixture was filtered and purified via prep. HPLC (Stationary phase: RP XBridge Prep C18 OBD-10 μm, 30×150 mm, Mobile phase: 0.25% NH$_4$HCO$_3$ solution in water, MeOH) yielding compound 156 (39 mg). Method B: Rt: 1.03 min. m/z: 452.0 (M−H)$^-$ Exact mass: 453.0. $^1$H NMR (400 MHz, DMSO-d$_6$) δ ppm 1.19 (d, J=6.8 Hz, 3H), 3.78 (s, 3H), 3.95 (dt, J=14.5, 7.2 Hz, 1H), 7.69 (s, 1H), 8.14 (dd, J=9.1, 8.5 Hz, 1H), 8.45 (dd, J=9.5, 4.0 Hz, 1H), 11.28 (br. s., 1H)

Compound 177: 3-chloro-N-[2-(difluoromethyl)-6-methyl-4-pyridyl]-1-methyl-[[(1R)-2,2,2-trifluoro-1-methyl-ethyl]sulfamoyl]pyrrole-2-carboxamide

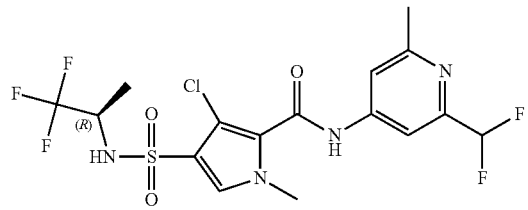

Compound 177 (72 mg) was prepared similarly as described for compound 137 using 2-(difluoromethyl)-6- methyl-pyridin-4-amine instead of 2-fluoro-6-methyl-pyridin-4-amine and stirring overnight instead of 3 hours. After silica gel column chromatography, compound 177 was crystallized from 1/1 MeOH/H$_2$O. Method B: Rt: 0.97 min. m/z: 473.0 (M−H)$^-$ Exact mass: 474.1. DSC: From 30 to 300° C. at 10° C./min, peak 201.2° C. $^1$H NMR (400 MHz, DMSO-d$_6$) δ ppm 1.20 (d, J=6.8 Hz, 3H), 2.50 (m, 3H, under DMSO signal), 3.79 (s, 3H), 3.93-4.04 (m, 1H), 6.88 (t, J=55.0 Hz, 1H), 7.67 (s, 1H), 7.71 (s, 1H), 7.83 (s, 1H), 8.52 (br. s., 1H), 10.83 (s, 1H).

Synthesis of 2-fluoro-6-methyl-pyridin-4-amine

To an oven-dried pressured tube was added 4-bromo-2-methyl-pyridine (6 g, 32.79 mmol) and MeCN (300 mL). While the solution was stirred rapidly, silver(II) fluoride (14.6 g, 98.4 mmol) was added at once. The tube was sealed with a teflon-lined cap and stirred at 60° C. for 2 hours. The reaction mixture was allowed to reach room temperature and poured into an erlenmeyer containing of saturated aqueous NaHCO$_3$ (300 mL). The suspension was stirred at room temperature and filtered over decalite. The solids were washed with diethyl ether. The layers were separated and the water layer was extracted with Et$_2$O (2×200 mL). The combined organic layers were washed once with brine (50 mL), dried over MgSO$_4$, and concentrated to afford a brown oil (6 g). The oil was purified using silica gel column chromatography (ethyl acetate in heptane from 0 to 40%) to afford 4-bromo-2-fluoro-6-methyl-pyridine (3450 mg) as a colorless oil. 1H NMR (400 MHz, DMSO-d$_6$) δ ppm 2.42 (s, 3H), 7.36-7.40 (m, 1H), 7.52-7.55 (m, 1H) A pressure tube was loaded with 4-bromo-2-fluoro-6-methyl-pyridine (2970 mg, 15.63 mmol), benzophenone imine (8.25 mL, 46.9 mmol), Cs$_2$CO$_3$ (15.3 g, 46.89 mmol) and toluene (80 mL). The resulting mixture was purged with nitrogen for 5 minutes. Pd(OAc)$_2$ (421.1 mg, 1.88 mmol) and BINAP (3.50 g, 5.63 mmol) were added under nitrogen to the mixture which was capped with a teflon-lined cap. The reaction mixture was stirred at 80° C. for 2 hours and allowed to reach room temperature. The reaction mixture was stirred at 80° C. for 2 more hours. The reaction mixture was poured into a separating funnel containing saturated aqueous sodium bicarbonate (100 mL). The organic layer was separated and the aqueous layer was extracted with toluene (100 mL). The combined organic layers were dried (MgSO$_4$) and concentrated to afford a brown oil (15 g). The oil was purified using silica gel column chromatography. The desired fractions were combined and evaporated to afford N-(2-fluoro-6-methyl-4-pyridyl)-1,1-diphenyl-methanimine (3.6 g). N-(2-fluoro-6-methyl-4-pyridyl)-1,1-diphenyl-methanimine (3.6 g, 10.5 mmol) was dissolved in THF (100 mL) and hydrochloric acid (50 mL, 1M, aq.). The reaction mixture was stirred at room temperature for 1 hour. The reaction is partitioned between ethyl acetate (100 mL) and brine (100 mL). The aqueous layer is separated and washed with ethyl acetate (2×100 mL). After basifying to pH 10 with solid potassium carbonate in order to liberate the free base, the aqueous layer is extracted with 2-MeTHF (5×100 mL). The combined organic layers were dried over sodium sulfate, filtered and the filtrate concentrated under reduced pressure. The resulting residue (1.5 g) is then purified by column chromatography (ethyl acetate in heptane from 0 to 100%) to afford 2-fluoro-6-methyl-pyridin-4-amine (1.36 g) as a white solid. $^1$H NMR (400 MHz, DMSO-d$_6$) δ ppm 2.17 (s, 3H), 5.86 (d, J=1.5 Hz, 1H), 6.23-6.26 (m, 1H), 6.26-6.32 (m, 2H).

Compound 146: 3-chloro-4-[[(1R)-2,2-difluoro-1-methyl-propyl]sulfamoyl]-N-(2-fluoro-6-methyl-4-pyridyl)-1-methyl-pyrrole-2-carboxamide

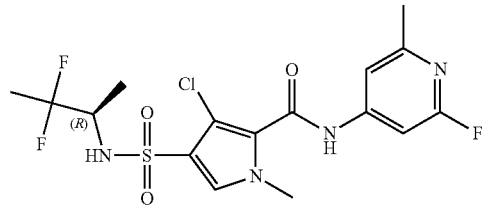

Compound 146 (227 mg) was prepared similarly as described for compound 94 using 2-fluoro-6-methyl-pyridin-4-amine instead of 4-amino-2-chloropyridine and stirring for 3 hours instead of 1 hour. Compound 146 was crystallized from CH$_2$Cl$_2$ and triturated with diisopropyl-ether. Method D: Rt: 1.78 min. m/z: 437.0 (M−H)$^-$ Exact mass: 438.1. $^1$H NMR (400 MHz, DMSO-d$_6$) δ ppm 1.08 (d, J=7.0 Hz, 3H), 1.57 (t, J=19.1 Hz, 3H), 2.39 (s, 3H), 3.48-3.56 (m, 1H), 3.78 (s, 3H), 7.26 (s, 1H), 7.39 (s, 1H), 7.68 (s, 1H), 8.10 (d, J=8.1 Hz, 1H), 10.84 (s, 1H).

Compound 147: 3-chloro-N-[2-(difluoromethyl)-3-fluoro-4-pyridyl]-4-[[(1R)-2,2-difluoro-1-methyl-propyl]sulfamoyl]-1-methyl-pyrrole-2-carboxamide

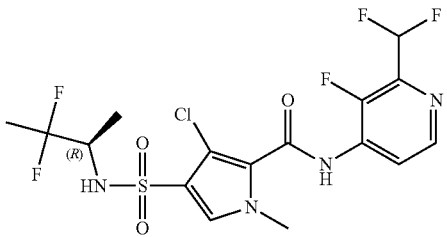

Compound 147 (90 mg) was prepared similarly as described for compound 94 using 2-(difluoromethyl)-3-fluoro-pyridin-4-amine hydrochloride instead of 4-amino-2-chloropyridine and stirring for 3 hours instead of 1 hour. Compound 147 was crystallized from CH$_2$Cl$_2$/diisopropyl-ether and triturated with diisopropylether. Method D: Rt: 1.82 min. m/z: 473.1 (M−H)$^-$ Exact mass: 474.1.

DSC: From 30 to 300° C. at 10° C./min, peak 174.3° C. $^1$H NMR (400 MHz, DMSO-d$_6$) δ ppm 1.08 (d, J=7.0 Hz, 3H), 1.58 (t, J=19.1 Hz, 3H), 3.49-3.61 (m, 1H), 3.82 (s, 3H), 7.16 (t, J=53.0 Hz, 1H), 7.72 (s, 1H), 8.12 (d, J=9.2 Hz, 1H), 8.26 (t, J=5.6 Hz, 1H), 8.47 (d, J=5.3 Hz, 1H), 10.59 (s, 1H)

Compound 148: N-(2-bromo-3-fluoro-4-pyridyl)-3-chloro-4-[[(1R)-2,2-difluoro-1-methyl-propyl]sulfamoyl]-1-methyl-pyrrole-2-carboxamide

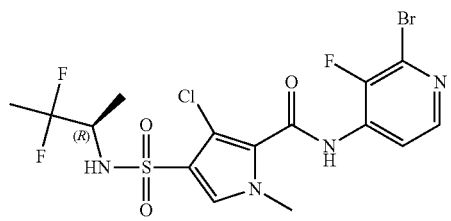

Compound 148 (438 mg) was prepared similarly as described for compound 94 using 2-bromo-3-fluoro-pyridin-4-amine instead of 4-amino-2-chloropyridine and stirring overnight instead of 1 hour. Compound 148 was crystallized from MeOH/H$_2$O. Method B: Rt: 1.12 min. m/z: 502.9 (M–H)$^-$ Exact mass: 504.0. DSC: From 30 to 300° C. at 10° C./min, peak 206.3° C. $^1$H NMR (400 MHz, DMSO-d$_6$) δ ppm 1.07 (d, J=7.0 Hz, 3H), 1.58 (t, J=19.1 Hz, 3H), 3.48-3.60 (m, 1H), 3.81 (s, 3H), 7.71 (s, 1H), 8.09 (t, J=5.5 Hz, 1H), 8.12 (d, J=9.2 Hz, 1H), 8.22 (d, J=5.5 Hz, 1H), 10.57 (s, 1H).

Compound 149: 3-chloro-N-(2-chloro-6-methyl-4-pyridyl)-4-[[(1R)-2,2-difluoro-1-methyl-propyl]sulfamoyl]-1-methyl-pyrrole-2-carboxamide

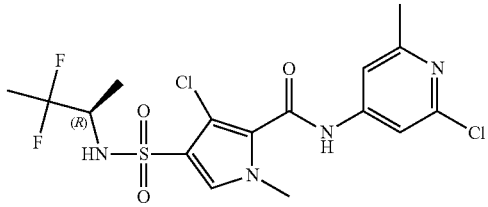

Compound 149 (58 mg) was prepared similarly as described for compound 94 using 2-chloro-6-methyl-pyridin-4-amine instead of 4-amino-2-chloropyridine and stirring overnight instead of 1 hour. Compound 149 was crystallized from MeOH/H$_2$O. Method B: Rt: 1.08 min. m/z: 453.0 (M–H)$^-$ Exact mass: 454.0. DSC: From 30 to 300° C. at 10° C./min, peak 156.3° C. $^1$H NMR (400 MHz, DMSO-d$_6$) δ ppm 1.07 (d, J=7.0 Hz, 3H), 1.57 (t, J=19.3 Hz, 3H), 2.43 (s, 3H), 3.48-3.62 (m, 1H), 3.78 (s, 3H), 7.49 (d, J=1.3 Hz, 1H), 7.62 (d, J=1.3 Hz, 1H), 7.68 (s, 1H), 8.11 (d, J=9.0 Hz, 1H), 10.77 (s, 1H).

Compound 150: 3-chloro-4-[[(1R)-2,2-difluoro-1-methyl-propyl]sulfamoyl]-1-methyl-N-[2-(trifluoromethyl)-4-pyridyl]pyrrole-2-carboxamide

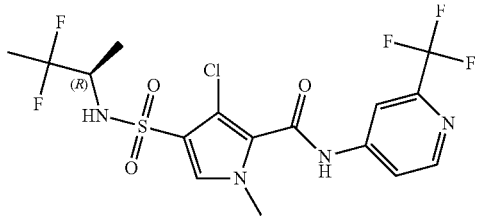

Compound 150 (221 mg) was prepared similarly as described for compound 94 using 2-(trifluoromethyl)pyridin-4-amine instead of 4-amino-2-chloropyridine and stirring overnight instead of 1 hour. Compound 150 was crystallized from MeOH/H$_2$O. Method B: Rt: 1.08 min. m/z: 473.0 (M–H)$^-$ Exact mass: 474.1. DSC: From 30 to 300° C. at 10° C./min, peak 198.7° C. $^1$H NMR (400 MHz, DMSO-d$_6$) δ ppm 1.08 (d, J=6.8 Hz, 3H), 1.58 (t, J=19.1 Hz, 3H), 3.49-3.63 (m, 1H), 3.80 (s, 3H), 7.70 (s, 1H), 7.91 (dd, J=5.6, 1.9 Hz, 1H), 8.12 (d, J=9.0 Hz, 1H), 8.19 (d, J=1.8 Hz, 1H), 8.68 (d, J=5.5 Hz, 1H), 11.01 (s, 1H).

Compound 151: 3-chloro-N-(2-cyano-3-fluoro-4-pyridyl)-4-[[(1R)-2,2-difluoro-1-methyl-propyl]sulfamoyl]-1-methyl-pyrrole-2-carboxamide

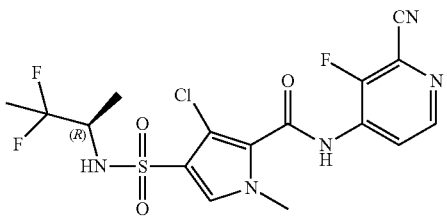

A 10 mL microwave vial was charged with compound 148 (397 mg, 0.79 mmol), zinc cyanide (46.21 mg, 0.39 mmol), 1,1'-bis(diphenylphosphino)ferrocenedichloro palladium(II) (58 mg, 0.079 mmol) and DMF (5 mL). The reaction mixture was heated in the microwave for 30 minutes at 160° C. The reaction mixture was evaporated to dryness, loaded on a silica cartridge and a gradient from heptane to EtOAc was applied yielding compound 151 (224 mg) as an off white powder after crystallization from a MeOH:water mixture. Method B: Rt: 1.04 min. m/z: 448.0 (M–H)$^-$ Exact mass: 449.1. DSC: From 30 to 300° C. at 10° C./min, peak 184.3° C. $^1$H NMR (400 MHz, DMSO-d$_6$) δ ppm 1.08 (d, J=6.8 Hz, 3H), 1.58 (t, J=19.1 Hz, 3H), 3.48-3.63 (m, 1H), 3.82 (s, 3H), 7.73 (s, 1H), 8.13 (d, J=9.2 Hz, 1H), 8.35-8.42 (m, 1H), 8.53 (d, J=5.3 Hz, 1H), 10.80 (s, 1H).

Compound 152: 3-fluoro-N-(2-fluoro-6-methyl-4-pyridyl)-1-methyl-4-[[(1R)-2,2,2-trifluoro-1-methyl-ethyl]sulfamoyl]pyrrole-2-carboxamide

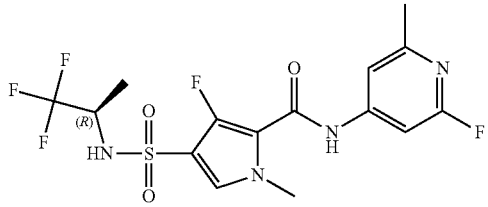

Ethyl 3-fluoro-1-methyl-4-[[(1R)-2,2,2-trifluoro-1-methyl-ethyl]sulfamoyl]pyrrole-2-carboxylate (250 mg, 0.72 mmol) and 2-fluoro-6-methyl-pyridin-4-amine (113.8 mg, 0.87 mmol) in THF (3.9 mL, 47.8 mmol) was stirred at room temperature and then lithium bis(trimethylsilyl)amide in THF (2.2 mL, 1 M, 2.2 mmol) was added at once. This was stirred for 1 hour and then quenched with NH$_4$Cl and extracted with EtOAc. The combined extracts were concentrated and the obtained crude was purified by silica gel column chromatography using gradient elution from heptane to EtOAc. (100:0 to 0:100). The desired fractions were concentrated in vacuo and the obtained oil was crystallised out of iPrOH. The crystals were collected and dried in a vacuum oven at 55° C. yielding compound 152 (238 mg) as a white powder. $^1$H NMR (400 MHz, DMSO-d$_6$) δ ppm 1.17 (d, J=6.8 Hz, 3H), 2.38 (s, 3H), 3.80 (s, 3H), 3.88-4.03 (m, 1H), 7.25 (s, 1H), 7.39 (s, 1H), 7.55 (d, J=4.2 Hz, 1H), 8.28-9.21 (m, 1H), 10.21-10.73 (m, 1H). Method B: Rt: 1.05 min. m/z: 425.1 (M−H)$^-$ Exact mass: 426.1. DSC: From 30 to 300° C. at 10° C./min, peak 199.4° C.

Compound 153: N-(2-bromo-3-fluoro-4-pyridyl)-3-fluoro-1-methyl-4-[[(1R)-2,2,2-trifluoro-1-methyl-ethyl]sulfamoyl]pyrrole-2-carboxamide

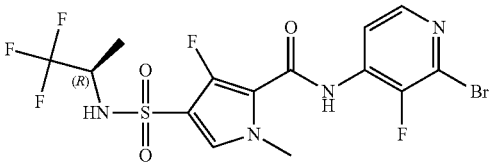

Compound 153 (523 mg) was prepared similarly as described for compound 152, using 2-bromo-3-fluoro-pyridin-4-amine instead of 2-fluoro-6-methyl-pyridin-4-amine. $^1$H NMR (400 MHz, DMSO-d$_6$) δ ppm 1.18 (d, J=7.0 Hz, 3H), 3.84 (s, 3H), 3.98 (dt, J=14.5, 7.3 Hz, 1H), 7.58 (d, J=4.6 Hz, 1H), 8.04 (t, J=5.5 Hz, 1H), 8.16 (d, J=5.3 Hz, 1H), 8.65 (br. s, 1H), 10.26 (br. s, 1H)). Method B: Rt: 1.12 min. m/z: 490.9 (M−H)$^-$ Exact mass: 492.0. DSC: From 30 to 300° C. at 10° C./min, peak 240.5° C.

Compound 154: N-(2-bromo-6-methyl-4-pyridyl)-3-fluoro-1-methyl-4-[[(1R)-2,2,2-trifluoro-1-methyl-ethyl]sulfamoyl]pyrrole-2-carboxamide

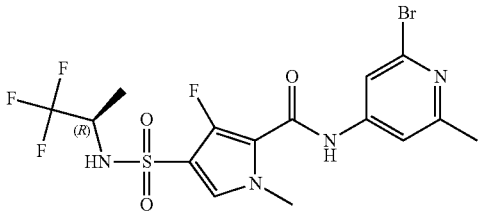

Compound 154 (168 mg) was prepared similarly as described for compound 152, using 2-bromo-6-methyl-pyridin-4-amine instead of 2-fluoro-6-methyl-pyridin-4-amine. Method D: Rt: 1.89 min. m/z: 487.0 (M−H)$^-$ Exact mass: 488.0. DSC: From 30 to 300° C. at 10° C./min, peak 201.5° C. $^1$H NMR (400 MHz, DMSO-d6) δ ppm 1.16 (d, J=6.8 Hz, 3H), 2.41 (s, 3H), 3.80 (s, 3H), 3.86-4.06 (m, 1H), 7.43-7.61 (m, 2H), 7.77 (d, J=1.3 Hz, 1H), 8.53 (br. s, 1H), 10.40 (br. s., 1H).

Compound 214: 3-fluoro-N-(5-fluoro-6-methyl-2-pyridyl)-1-methyl-4-[[(1R)-2,2,2-trifluoro-1-methyl-ethyl]sulfamoyl]pyrrole-2-carboxamide

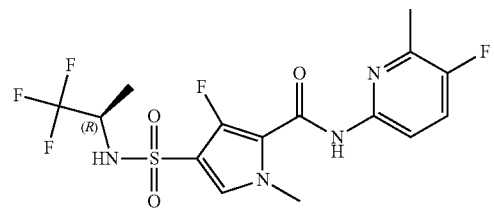

Compound 214 (173 mg) was prepared similarly as described for compound 152, using 2-amino-5-fluoro-6-methylpyridine instead of 2-fluoro-6-methyl-pyridin-4-amine.
$^1$H NMR (400 MHz, DMSO-d$_6$) δ ppm 1.19 (d, J=7.0 Hz, 3H) 2.41 (d, J=2.9 Hz, 3H) 3.81 (s, 3H) 3.86-4.02 (m, 1H) 7.53 (d, J=4.6 Hz, 1H) 7.68 (t, J=9.0 Hz, 1H) 7.95 (dd, J=8.8, 3.3 Hz, 1H) 8.57 (br d, J=7.9 Hz, 1H) 10.29 (s, 1H). Method B: Rt: 1.18 min. m/z: 425.2 (M−H)$^-$ Exact mass: 426.08.

Compound 155: N-(2-cyano-3-fluoro-4-pyridyl)-3-fluoro-1-methyl-4-[[(1R)-2,2,2-trifluoro-1-methyl-ethyl]sulfamoyl]pyrrole-2-carboxamide

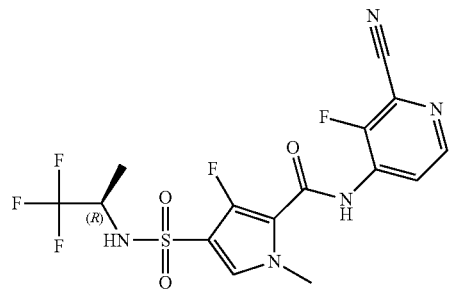

A microwave tube was loaded with compound 153 (400 mg, 0.81 mmol), zinc cyanide (66.9 mg, 0.57 mmol), 1,1'-bis(diphenylphosphino)ferrocenedichloro palladium(II) (59.8 mg, 0.081 mmol) and DMF (5 mL). This solution was purged with nitrogen for 10 minutes. The tube was closed and stirred and heated under MW-irradiation to 160° C. for 30 minutes. Then it was cooled to room temperature and filtered over a path of dicalite, rinsed with acetonitrile (10 mL) and concentrated in vacuo. The obtained crude was purified by silica gel column chromatography using gradient elution from heptane to EtOAc (100:0 to 0:100) and then repurified by Prep HPLC (RP SunFire Prep C18 OBD-10 μm, 30×150 mm). Mobile phase (0.25% NH$_4$HCO$_3$ solution in water, MeOH). The desired fractions were concentrated under reduced pressure and co-evaporated twice with methanol (2×20 mL) and dried in a vacuum oven at 55° C. resulting in compound 155 (387 mg) as a white powder. $^1$H NMR (400 MHz, DMSO-d$_6$) δ ppm 1.18 (d, J=7.0 Hz, 3H), 3.84 (s, 3H), 3.92-4.06 (m, 1H), 7.61 (d, J=4.4 Hz, 1H), 8.33 (t, J=5.8 Hz, 1H), 8.49 (d, J=5.7 Hz, 1H), 8.64 (br. s., 1H), 10.47 (br. s., 1H). Method B: Rt: 0.95 min. m/z: 436.0 (M−H)$^-$ Exact mass: 437.1. DSC: From 30 to 300° C. at 10° C./min, peak 179.4° C.

Compound 157: N-(2-bromo-6-methyl-4-pyridyl)-4-[[(1R)-2,2-difluoro-1-methyl-propyl]sulfamoyl]-3-fluoro-1-methyl-pyrrole-2-carboxamide

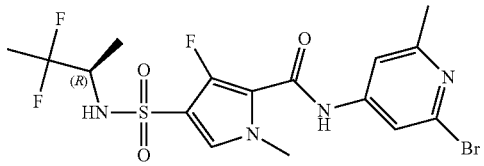

Ethyl 4-[[(1R)-2,2-difluoro-1-methyl-propyl]sulfamoyl]-3-fluoro-1-methyl-pyrrole-2-carboxylate (250 mg, 0.73 mmol) and 2-bromo-6-methylpyridin-4-amine (163.91 mg, 0.88 mmol) in THF (3.91 mL, 0.89 g/mL, 48.32 mmol) was stirred at room temperature and then lithium bis(trimethylsilyl)amide in THF (2.19 mL, 1 M, 2.19 mmol) was added at once. The mixture was stirred for 1 hour and then quenched with NH$_4$Cl and extracted with EtOAc. The combined extracts were concentrated and the obtained crude was purified by silica gel column chromatography using gradient elution from heptane to EtOAc. (100:0 to 0:100). The desired fractions were concentrated in vacuo and the obtained oil was crystallised out of iPrOH. The crystals were collected and dried in a vacuum oven at 55° C. yielding compound 157 (252 mg) of compound 157 as a white powder. $^1$H NMR (400 MHz, DMSO-d$_6$) δ ppm 1.07 (d, J=7.0 Hz, 3H), 1.57 (t, J=19.1 Hz, 3H), 2.41 (s, 3H), 3.47-3.64 (m, 1H), 3.80 (s, 3H), 7.49-7.53 (m, 1H), 7.55 (d, J=4.4 Hz, 1H), 7.77 (br. s, 1H), 8.22 (br. s., 1H), 10.44 (br. s., 1H). Method B: Rt: 1.00 min. m/z: 483.0 (M−H)$^-$ Exact mass: 484.0.

Compound 158: N-(2-chloro-6-methyl-4-pyridyl)-4-[[(1R)-2,2-difluoro-1-methyl-propyl]sulfamoyl]-3-fluoro-1-methyl-pyrrole-2-carboxamide

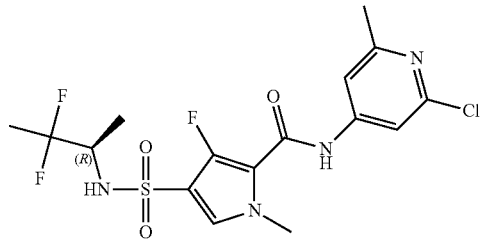

Compound 158 (205 mg) was prepared similarly as described for compound 157, using 2-chloro-6-methyl-pyridin-4-amine instead of 2-bromo-6-methylpyridin-4-amine. Method B: Rt: 0.97 min. m/z: 437.1 (M−H)$^-$ Exact mass: 438.1. $^1$H NMR (400 MHz, DMSO-d$_6$) δ ppm 1.07 (d, J=7.0 Hz, 3H), 1.58 (t, J=19.1 Hz, 3H), 2.42 (s, 3H), 3.48-3.58 (m, 1H), 3.81 (s, 3H), 7.49 (d, J=1.3 Hz, 1H), 7.56 (d, J=4.4 Hz, 1H), 7.62 (d, J=1.3 Hz, 1H), 8.21 (d, J=8.8 Hz, 1H), 10.46 (s, 1H).

Compound 159: 4-[[(1R)-2,2-difluoro-1-methyl-propyl]sulfamoyl]-N-(2,6-difluoro-4-pyridyl)-3-fluoro-1-methyl-pyrrole-2-carboxamide

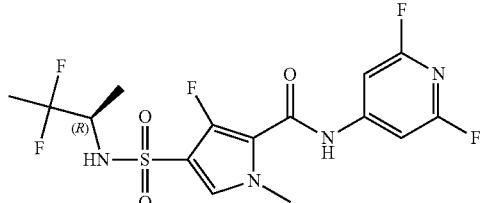

Compound 159 (130 mg) was prepared similarly as described for compound 157, using 4-amino-2,6-difluoro-pyridine instead of 2-bromo-6-methylpyridin-4-amine. Compound 159 was crystallized from MeOH/H$_2$O. Method D: Rt: 1.86 min. m/z: 425.0 (M−H)$^-$ Exact mass: 426.1. DSC: From 30 to 300° C. at 10° C./min, peak 194.0° C. $^1$H NMR (400 MHz, DMSO-d$_6$) δ ppm 1.07 (d, J=6.8 Hz, 3H), 1.58 (t, J=19.1 Hz, 3H), 3.48-3.63 (m, 1H), 3.82 (s, 3H), 7.34 (s, 2H), 7.60 (d, J=4.6 Hz, 1H), 8.23 (d, J=9.0 Hz, 1H), 10.84 (s, 1H).

Compound 160: 4-[[(1R)-2,2-difluoro-1-methyl-propyl]sulfamoyl]-3-fluoro-N-(2-fluoro-6-methyl-4-pyridyl)-1-methyl-pyrrole-2-carboxamide

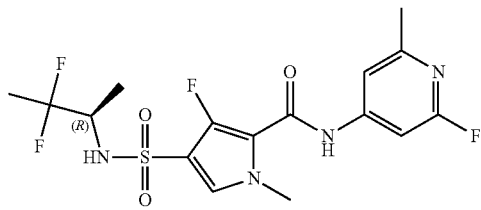

Compound 160 (82 mg) was prepared similarly as described for compound 157, using 2-fluoro-6-methyl-pyridin-4-amine instead of 2-bromo-6-methylpyridin-4-amine. Compound 160 was crystallized from MeOH/H$_2$O. Method D: Rt: 1.76 min. m/z: 421.1 (M−H)$^-$ Exact mass: 422.1. DSC: From 30 to 300° C. at 10° C./min, peak 190.5° C. $^1$H NMR (360 MHz, DMSO-d$_6$) δ ppm 1.06 (d, J=6.6 Hz, 3H), 1.58 (t, J=19.2 Hz, 3H), 2.38 (s, 3H), 3.46-3.62 (m, 1H), 3.81 (s, 3H), 7.25 (s, 1H), 7.40 (s, 1H), 7.57 (d, J=4.4 Hz, 1H), 8.24 (d, J=8.8 Hz, 1H), 10.57 (s, 1H)

Compound 176: N-(2-bromo-3-fluoro-4-pyridyl)-4-[[(1R)-2,2-difluoro-1-methyl-propyl]sulfamoyl]-3-fluoro-1-methyl-pyrrole-2-carboxamide

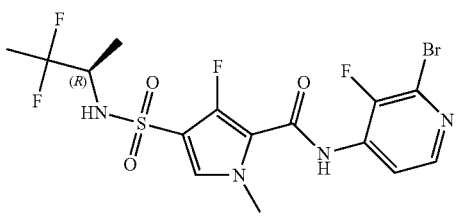

Compound 176 (383 mg) was prepared similarly as described for compound 157, using 2-bromo-3-fluoro-pyridin-4-amine instead of 2-bromo-6-methylpyridin-4-amine. Method B: Rt: 1.01 min. m/z: 486.9 (M−H)$^-$ Exact mass: 488.0. $^1$H NMR (400 MHz, DMSO-d$_6$) δ ppm 0.97-1.14 (m, 3H), 1.47-1.68 (m, 3H), 3.44-3.64 (m, 1H), 3.78-3.89 (m, 3H), 7.59 (d, J=4.6 Hz, 1H), 8.04 (t, J=5.4 Hz, 1H), 8.14-8.30 (m, 2H), 10.18 (br. s., 1H).

Compound 161: N-(2-bromo-3-fluoro-4-pyridyl)-3-chloro-4-[(3,3-difluoro-1-methyl-cyclobutyl)sulfamoyl]-1-methyl-pyrrole-2-carboxamide

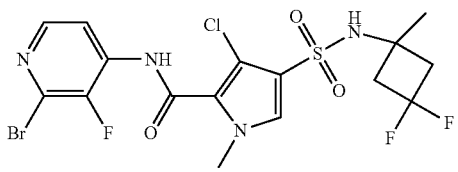 [SMILES: Cn1cc(S(=O)(=O)NC2(C)CC(F)(F)C2)c(Cl)c1C(=O)Nc1ccnc(Br)c1F]

Methyl 3-chloro-4-[(3,3-difluoro-1-methyl-cyclobutyl)sulfamoyl]-1-methyl-pyrrole-2-carboxylate (200 mg, 0.56 mmol) and 2-bromo-3-fluoro-pyridin-4-amine (117.8 mg, 0.62 mmol) were dissolved in dry THF (5 mL). Lithium bis(trimethylsilyl)amide (1M in THF) (1.68 mL, 1 M, 1.68 mmol) was added drop wise and the reaction mixture was stirred overnight at room temperature. The reaction mixture was quenched with sat. NH$_4$Cl (10 mL). The organic layer was removed and the aqueous layer extracted with CH$_2$Cl$_2$ (2×5 mL). The combined organic layers were evaporated to dryness and the residue was purified on silica using a heptane to EtOAc gradient yielding compound 161 (198 mg) after crystallization from MeOH:water. Method B: Rt: 1.14 min. m/z: 514.9 (M−H)$^-$ Exact mass: 516.0. DSC: From 30 to 300° C. at 10° C./min, peak 224.2° C. $^1$H NMR (400 MHz, DMSO-d$_6$) δ ppm 1.39 (s, 3H), 2.52-2.57 (m, 2H), 2.84-2.99 (m, 2H), 3.81 (s, 3H), 7.72 (s, 1H), 8.09 (t, J=5.5 Hz, 1H), 8.16 (s, 1H), 8.22 (d, J=5.3 Hz, 1H), 10.58 (s, 1H).

Compound 162: 3-chloro-N-(2-cyano-3-fluoro-4-pyridyl)-4-[(3,3-difluoro-1-methyl-cyclobutyl)sulfamoyl]-1-methyl-pyrrole-2-carboxamide

Compound 162 (40 mg) was prepared from compound 161 similarly as described for the formation of compound 151 from compound 148. Method B: Rt: 1.09 min. m/z: 460.0 (M−H)$^-$ Exact mass: 461.1. $^1$H NMR (400 MHz, DMSO-d$_6$) δ ppm 1.40 (s, 3H), 2.53-2.60 (m, 2H), 2.82-3.03 (m, 2H), 3.32 (s, 3H), 7.74 (s, 1H), 8.18 (s, 1H), 8.39 (t, J=5.9 Hz, 1H), 8.54 (d, J=5.3 Hz, 1H), 10.80 (br. s., 1H).

Compound 163: 3-chloro-4-[(3,3-difluoro-1-methyl-cyclobutyl)sulfamoyl]-N-(2-fluoro-6-methyl-4-pyridyl)-1-methyl-pyrrole-2-carboxamide

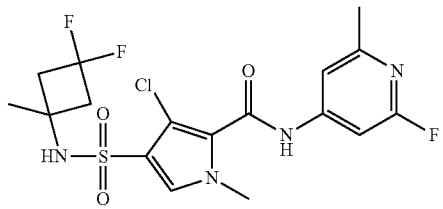 [SMILES: Cc1cc(NC(=O)c2c(Cl)c(S(=O)(=O)NC3(C)CC(F)(F)C3)cn2C)cc(F)n1]

Compound 163 (163 mg) was prepared similarly as described for compound 161, using 2-fluoro-6-methyl-pyridin-4-amine instead of 2-bromo-3-fluoro-pyridin-4-amine. Compound 163 was crystallised from MeOH/H$_2$O.

Method B: Rt: 1.06 min. m/z: 449.1 (M−H)$^-$ Exact mass: 450.1. DSC: From 30 to 300° C. at 10° C./min, peak 230.7° C. $^1$H NMR (400 MHz, DMSO-d$_6$) δ ppm 1.39 (s, 3H), 2.39 (s, 3H), 2.52-2.59 (m, 2H), 2.83-3.00 (m, 2H), 3.78 (s, 3H), 7.26 (s, 1H), 7.39 (s, 1H), 7.69 (s, 1H), 8.15 (s, 1H), 10.83 (s, 1H)

Compound 164: N-(2-bromo-6-methyl-4-pyridyl)-3-fluoro-1-methyl-4-[[1-(trifluoromethyl)cyclobutyl]sulfamoyl]pyrrole-2-carboxamide

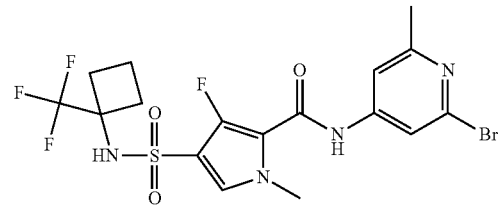 [SMILES: Cc1cc(NC(=O)c2c(F)c(S(=O)(=O)NC3(C(F)(F)F)CCC3)cn2C)cc(Br)n1]

Lithium bis(trimethylsilyl)amide in THF (4.63 mL, 1 M, 4.63 mmol) was added to ethyl 3-fluoro-1-methyl-4-[[1-(trifluoromethyl)cyclobutyl]sulfamoyl]pyrrole-2-carboxylate (492.4 mg, 1.322 mmol) and 2-bromo-6-methylpyridin-4-amine (371.0 mg, 1.98 mmol) in THF (4 mL) and the mixture was stirred for 1 hour. The reaction mixture was quenched with a saturated aqueous NH$_4$Cl solution, diluted with brine and extracted with EtOAc. The organic layer was dried over magnesium sulphate, filtered and concentrated. The residue was purified by column chromatography using a gradient from 10 till 100% EtOAc in heptane. The obtained solid was dissolved in methanol (40 mL) and water was added until crystallisation began. The product was filtered off and dried overnight in vacuo at 50° C. resulting in compound 164 (534 mg) as a white powder. Method D: Rt: 1.98 min. m/z: 511.1 (M−H)⁻ Exact mass: 512.0. DSC: From 30 to 300° C. at 10° C./min, peak 202.4° C. $^1$H NMR (400 MHz, ACETONITRILE-d$_3$) δ ppm 1.85-1.93 (m, 2H), 2.36-2.46 (m, 5H), 2.47-2.57 (m, 2H), 3.86 (s, 3H), 6.48 (br. s, 1H), 7.25 (d, J=4.8 Hz, 1H), 7.42 (d, J=1.5 Hz, 1H), 7.73 (d, J=1.5 Hz, 1H), 8.47 (br. s, 1H). $^1$H NMR (400 MHz, DMSO-d$_6$) δ ppm 1.79-1.91 (m, 2H), 2.27-2.38 (m, 2H), 2.39-2.49 (m, 5H), 3.82 (s, 3H), 7.52 (d, J=1.3 Hz, 1H), 7.57 (d, J=4.4 Hz, 1H), 7.77 (d, J=1.1 Hz, 1H), 8.73 (s, 1H), 10.46 (s, 1H).

Compound 165: N-[2-(difluoromethyl)-3-fluoro-4-pyridyl]-3-fluoro-1-methyl-4-[[1-(trifluoromethyl)cyclobutyl]sulfamoyl]pyrrole-2-carboxamide

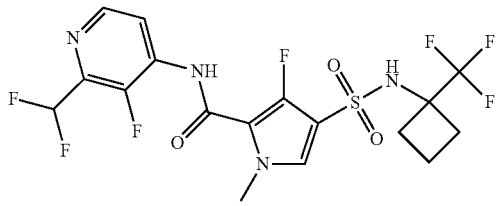 [SMILES: Cn1cc(S(=O)(=O)NC2(C(F)(F)F)CCC2)c(F)c1C(=O)Nc1ccnc(C(F)F)c1F]

Compound 165 (59 mg) was prepared similarly as described for compound 164, using 2-(difluoromethyl)-3-fluoro-pyridin-4-amine hydrochloride instead of 2-bromo-6-methylpyridin-4-amine. Compound 165 was crystallised from MeOH/H$_2$O. Method D: Rt: 1.90 min. m/z: 487.1 (M−H)⁻ Exact mass: 488.1. DSC: From 30 to 300° C. at 10° C./min, peak 203.8° C. $^1$H NMR (400 MHz, DMSO-d$_6$) δ ppm 1.77-1.92 (m, 2H) 2.26-2.39 (m, 2H) 2.41-2.48 (m, 2H) 3.85 (s, 3H) 7.15 (t, J=53.2 Hz, 1H) 7.61 (d, J=4.6 Hz, 1H) 8.21 (t, J=5.6 Hz, 1H) 8.45 (d, J=5.3 Hz, 1H) 8.76 (s, 1H) 10.22 (s, 1H).

Compound 166: N-(2-bromo-3-fluoro-4-pyridyl)-3-fluoro-1-methyl-4-[[1-(trifluoromethyl)cyclobutyl]sulfamoyl]pyrrole-2-carboxamide

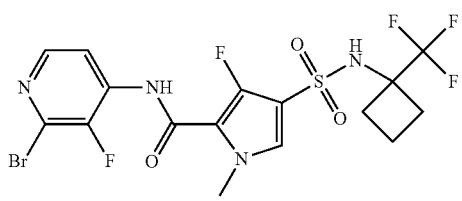 [SMILES: Cn1cc(S(=O)(=O)NC2(C(F)(F)F)CCC2)c(F)c1C(=O)Nc1ccnc(Br)c1F]

Compound 166 (283 mg) was prepared similarly as described for compound 164, using 2-bromo-3-fluoro-pyridin-4-amine instead of 2-bromo-6-methylpyridin-4-amine. Compound 166 was crystallised from MeOH/H$_2$O. Method D: Rt: 2.03 min. m/z: 517.0 (M−H)⁻ Exact mass: 518.0. DSC: From 30 to 300° C. at 10° C./min, peak 235.3° C. $^1$H NMR (360 MHz, DMSO-d$_6$) δ ppm 1.78-1.91 (m, 2H), 2.27-2.38 (m, 2H), 2.40-2.49 (m, 2H), 3.85 (s, 3H), 7.62 (d, J=4.8 Hz, 1H), 8.04 (t, J=5.5 Hz, 1H), 8.20 (d, J=5.5 Hz, 1H), 8.79 (s, 1H) 10.25 (s, 1H).

Compound 167: N-(2-cyano-3-fluoro-4-pyridyl)-3-fluoro-1-methyl-4-[[1-(trifluoromethyl)cyclobutyl]sulfamoyl]pyrrole-2-carboxamide

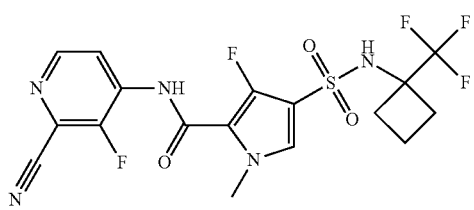 [SMILES: Cn1cc(S(=O)(=O)NC2(C(F)(F)F)CCC2)c(F)c1C(=O)Nc1ccnc(C#N)c1F]

A mixture of compound 166 (197 mg, 0.381 mmol), copper(I) cyanide (170.5 mg, 1.90 mmol) and propionitrile (3 mL) under a nitrogen atmosphere was heated for 3 hours at 160° C. by microwave irradiation. The reaction mixture was filtered and the precipitate rinsed with plenty of methanol. The filtrate was concentrated. The residue was subjected to silica gel column chromatography using a gradient from 10 to 100% EtOAc in heptane. The product fractions were concentrated. The obtained residue was dissolved in methanol (15 mL). The product crystallised upon addition of water. The white powder was filtered off and dried in vacuo at 50° C., resulting in compound 167 (43 mg). Method D: Rt: 1.92 min. m/z: 462.1 (M−H) Exact mass: 463.1. DSC: From 30 to 300° C. at 10° C./min, peak 182.6° C. $^1$H NMR (400 MHz, DMSO-d$_6$) δ ppm 1.79-1.91 (m, 2H), 2.28-2.38 (m, 2H), 2.41-2.49 (m, 2H), 3.85 (s, 3H), 7.62 (d, J=4.6 Hz, 1H), 8.33 (dd, J=6.4, 5.5 Hz, 1H), 8.52 (d, J=5.5 Hz, 1H), 8.77 (s, 1H), 10.44 (s, 1H).

Compound 168: N-(2,6-difluoro-4-pyridyl)-3-fluoro-1-methyl-4-[[1-(trifluoromethyl)cyclobutyl]sulfamoyl]pyrrole-2-carboxamide

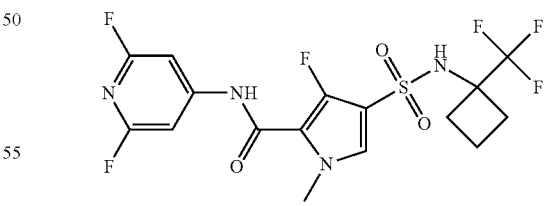

Compound 168 (99 mg) was prepared similarly as described for compound 164, using 2,6-difluoropyridin-4-amine instead of 2-bromo-6-methylpyridin-4-amine. Method D: Rt: 2.00 min. m/z: 455.1 (M−H)⁻ Exact mass: 456.1. DSC: From 30 to 300° C. at 10° C./min, peak 211.2° C. $^1$H NMR (400 MHz, DMSO-d$_6$) δ ppm 1.79-1.90 (m, 2H), 2.28-2.38 (m, 2H), 2.41-2.49 (m, 2H), 3.83 (s, 3H), 7.35 (s, 2H), 7.61 (d, J=4.4 Hz, 1H), 8.76 (s, 1H), 10.87 (s, 1H)

Compound 169: 3-fluoro-N-(2-fluoro-4-pyridyl)-1-methyl-4-[[1-(trifluoromethyl)cyclobutyl]sulfamoyl]pyrrole-2-carboxamide

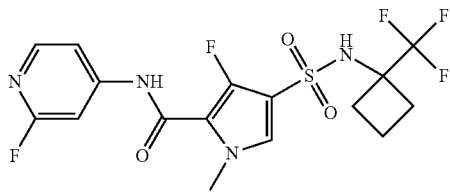 [SMILES: Cn1cc(S(=O)(=O)NC2(C(F)(F)F)CCC2)c(F)c1C(=O)Nc1ccnc(F)c1]

Compound 169 (128 mg) was prepared similarly as described for compound 164, using 2-fluoropyridin-4-amine instead of 2-bromo-6-methylpyridin-4-amine. Method D: Rt: 1.83 min. m/z: 437.1 (M−H)⁻ Exact mass: 438.1. DSC: From 30 to 300° C. at 10° C./min, peak 211.1° C. $^1$H NMR (400 MHz, DMSO-$d_6$) δ ppm 1.79-1.91 (m, 2H), 2.28-2.38 (m, 2H), 2.41-2.49 (m, 2H), 3.83 (s, 3H), 7.46 (d, J=1.8 Hz, 1H), 7.53 (dt, J=5.7, 1.5 Hz, 1H), 7.58 (d, J=4.6 Hz, 1H), 8.14 (d, J=5.5 Hz, 1H), 8.74 (s, 1H), 10.67 (s, 1H).

Compound 170: N-(2,3-difluoro-4-pyridyl)-3-fluoro-1-methyl-4-[[1-(trifluoromethyl)cyclobutyl]sulfamoyl]pyrrole-2-carboxamide

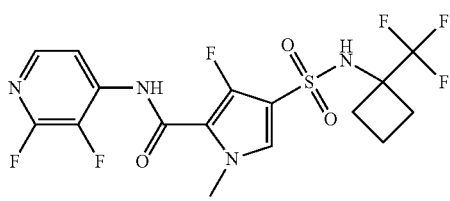 [SMILES: Cn1cc(S(=O)(=O)NC2(C(F)(F)F)CCC2)c(F)c1C(=O)Nc1ccnc(F)c1F]

Compound 170 (42 mg) was prepared similarly as described for compound 164, using 2,3-difluoropyridin-4-amine hydrochloride instead of 2-bromo-6-methylpyridin-4-amine. Method D: Rt: 1.94 min. m/z: 455.1 (M−H)⁻ Exact mass: 456.1. DSC: From 30 to 300° C. at 10° C./min, peak 219.2° C. $^1$H NMR (400 MHz, DMSO-$d_6$) δ ppm 1.79-1.91 (m, 2H), 2.28-2.38 (m, 2H), 2.42-2.49 (m, 2H), 3.85 (s, 3H), 7.61 (d, J=4.6 Hz, 1H), 7.90-8.01 (m, 2H), 8.76 (s, 1H), 10.34 (s, 1H)

Compound 171: N-(2-cyano-6-methyl-4-pyridyl)-3-fluoro-1-methyl-4-[[1-(trifluoromethyl)cyclobutyl]sulfamoyl]pyrrole-2-carboxamide

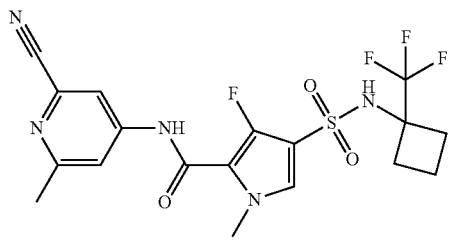 [SMILES: Cc1cc(NC(=O)c2c(F)c(S(=O)(=O)NC3(C(F)(F)F)CCC3)cn2C)cc(C#N)n1]

A mixture of compound 164 (146 mg, 0.284 mmol) and copper(I) cyanide (101.9 mg, 1.14 mmol) in DMF (2 mL) was heated for 3 hours at 160° C. under microwave irradiation. The reaction mixture was filtered and the solution was purified by silica gel column chromatography using a gradient from 10 till 100% EtOAc in heptane. The product fractions were concentrated. The obtained residue was dissolved in methanol and water was added until crystallisation began. The product was filtered and dried overnight in vacuo at 50° C. resulting in compound 171 (17 mg) as a white powder. Method D: Rt: 1.90 min. m/z: 458.1 (M−H)⁻ Exact mass: 459.1. DSC: From 30 to 300° C. at 10° C./min, peak 179.0° C. $^1$H NMR (400 MHz, DMSO-$d_6$) δ ppm 1.79-1.90 (m, 2H), 2.27-2.38 (m, 2H), 2.41-2.48 (m, 2H), 2.50 (s, 3H, signal under DMSO signal), 3.83 (s, 3H), 7.59 (d, J=4.4 Hz, 1H), 7.80 (d, J=1.8 Hz, 1H), 8.03 (d, J=1.8 Hz, 1H), 8.75 (s, 1H), 10.61 (s, 1H).

Compound 172: 3-fluoro-N-(2-fluoro-6-methyl-4-pyridyl)-1-methyl-4-[[1-(trifluoromethyl)cyclobutyl]sulfamoyl]pyrrole-2-carboxamide

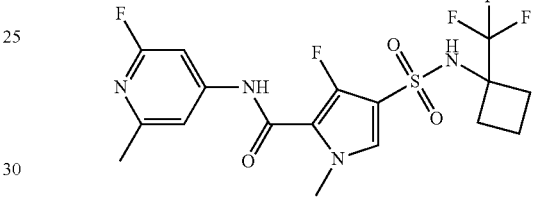

Compound 172 (77 mg) was prepared similarly as described for compound 164, using 2-fluoro-6-methyl-pyridin-4-amine instead of 2-bromo-6-methylpyridin-4-amine. Method D: Rt: 1.91 min. m/z: 451.1 (M−H)⁻ Exact mass: 452.1. DSC: From 30 to 300° C. at 10° C./min, peak 217.0° C. $^1$H NMR (360 MHz, DMSO-$d_6$) δ ppm 1.78-1.90 (m, 2H), 2.26-2.37 (m, 2H), 2.39 (s, 3H), 2.40-2.48 (m, 2H), 3.82 (s, 3H), 7.26 (s, 1H), 7.40 (s, 1H), 7.59 (d, J=4.8 Hz, 1H), 8.77 (s, 1H), 10.60 (s, 1H).

Synthesis 2-(difluoromethyl)-6-methyl-pyridin-4-amine 6-methylpyridine-2-carboxaldehyde (2000 mg, 16.51 mmol) was dissolved in dichloromethane (75 mL). Diethylaminosulfur trifluoride (6.65 g, 41.275 mmol) was added drop wise at 0° C. The solution was stirred for 2 hours allowing to reach room temperature. The reaction mixture was quenched with a saturated sodium bicarbonate solution and washed twice with brine (10 mL) dried over sodium sulphate, filtered and concentrated resulting in an oil (2.29 g) of 2-(difluoromethyl)-6-methyl-pyridine. 2-(difluoromethyl)-6-methyl-pyridine (2.29 g, 16 mmol) was dissolved in dichloromethane (100 mL). Hydrogen peroxide 30% (27.2 g, 240 mmol) and trifluoroacetic anhydride (50.41 g, 240 mmol) were added and the reaction mixture was stirred 12 hours at room temperature. The reaction mixture was neutralized with NaOH 1M (500 mL). The aqueous layer was extracted with dichloromethane (3×100 mL). The combined organic layers were washed with water twice (80 mL) dried over sodium sulphate, filtered and concentrated. The residue was purified by column chromatography on silica using a gradient from pentane to ethylacetate/pentane 50/50. The compound fractions were concentrated resulting 2-(difluoromethyl)-6-methyl-1-oxido-pyridin-1-ium as a yellow oil (1.09 g). ¹H NMR (400 MHz, DMSO-d₆) δ=7.65 (d, J=7.6 Hz, 1H), 7.63-7.56 (m, 1H), 7.39 (t, J=7.8 Hz, 1H), 7.36-7.08 (m, 1H), 2.38 (s, 3H). 2-(difluoromethyl)-6-methyl-1-oxido-pyridin-1-ium (1.09 g, 6.85 mmol) was dissolved in sulfuric acid (10 mL) and added drop wise to nitric acid (4 mL) at 0° C. The mixture was heated at 90° C. during 3 hours. The mixture was cooled to 0° C. and neutralized with NaOH 10 M (500 mL) The mixture was extracted with ethyl acetate (3×100 mL). The organic layer was washed with water (2×80 mL), brine (50 mL), dried over sodium sulphate, filtered and concentrated. The residue was purified by column chromatography on silica using a gradient from pentane/EtOAc 4/1 till 2/1. The compound fractions were concentrated resulting in 2-(difluoromethyl)-6-methyl-4-nitro-1-oxido-pyridin-1-ium as a white solid (0.9 g). ¹H NMR (400 MHz, DMSO-d₆) δ ppm 8.63 (d, J=2.8 Hz, 1H), 8.25 (d, J=3.2 Hz, 1H), 7.24 (t, J=52.6 Hz 1H), 2.48 (s, 3H). 2-(difluoromethyl)-6-methyl-4-nitro-1-oxido-pyridin-1-ium (0.9 g, 4.41 mmol) was dissolved in methanol (50 mL), Pd on carbon (10%, 300 mg) was added and the mixture was degassed under vacuum and pressurized with hydrogen several times. The mixture was hydrogenated during 18 hours under 50 psi hydrogen. The suspension was filtered over celite and the filtrate concentrated. The residue was purified by HPLC (condition: Base-CAN; eluent: CH₃CN in H₂O (0.05% NH₃.H₂O) from 12% to 32%, v/v; column: Gemini 150*25 5 u). The pure fractions were collected and the volatiles were removed under vacuum. The aqueous layer was adjusted to pH=9 by sodium bicarbonate solution (50 mL). The aqueous layer was extracted with ethyl acetate (3×100 mL). The combined organic layers were washed with water (2×80 mL), brine (50 mL) and dried over Na₂SO₄, The mixture was filtered and the filtrate concentrated. The residue was dried resulting in 2-(difluoromethyl)-6-methyl-pyridin-4-amine as a white solid (184 mg). ¹H NMR (400 MHz, DMSO-d₆) δ=6.61 (t, J=55.6 Hz, 1H), 6.58 (d, J=1.6 Hz, 1H), 6.41 (s, 1H), 6.25 (br.s., 2H), 2.26 (s, 3H)

Compound 173: N-[2-(difluoromethyl)-6-methyl-4-pyridyl]-3-fluoro-1-methyl-4-[[1-(trifluoromethyl)cyclobutyl]sulfamoyl]pyrrole-2-carboxamide

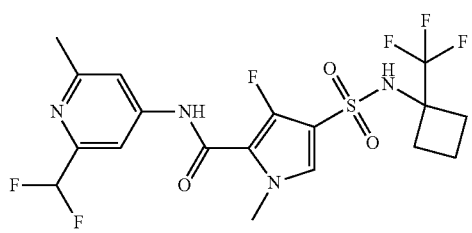 [SMILES: Cc1cc(NC(=O)c2c(F)c(S(=O)(=O)NC3(C(F)(F)F)CCC3)cn2C)cc(C(F)F)n1]

Compound 173 (69 mg) was prepared similarly as described for compound 164, using 2-(difluoromethyl)-6-methyl-pyridin-4-amine instead of 2-bromo-6-methylpyridin-4-amine. Method D: Rt: 1.91 min. m/z: 483.1 (M−H)⁻ Exact mass: 484.1. DSC: From 30 to 300° C. at 10° C./min, peak 186.5° C. ¹H NMR (400 MHz, DMSO-d₆) δ ppm 1.78-1.92 (m, 2H), 2.28-2.38 (m, 2H), 2.41-2.49 (m, 5H), 3.83 (s, 3H), 6.86 (t, J=55.0 Hz, 1H), 7.57 (d, J=4.4 Hz, 1H), 7.67 (s, 1H), 7.84 (d, J=1.5 Hz, 1H), 8.73 (s, 1H), 10.53 (s, 1H).

Compound 174: N-(2-chloro-4-pyridyl)-4-[(2,2-difluorocyclobutyl)sulfamoyl]-3-fluoro-1-methyl-pyrrole-2-carboxamide

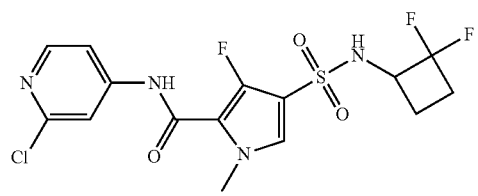 [SMILES: Cn1cc(S(=O)(=O)NC2CCC2(F)F)c(F)c1C(=O)Nc1ccnc(Cl)c1]

A mixture of ethyl 4-chlorosulfonyl-3-fluoro-1-methyl-pyrrole-2-carboxylate (360 mg, 1.34 mmol,) 2,2-difluoro-cyclobutan-1-amine hydrochloride (201 mg, 1.40 mmol, commercial from enamine EN300-89718), NaHCO₃ (336.4 mg, 4.00 mmol), acetonitrile (20 mL, 382.9 mmol) and molecular sieves 4 Å (300 mg) were stirred and refluxed during 2 hours. The reaction mixture was filtered while still hot. The filtrate was concentrated. The residue was purified by silica gel column chromatography using a gradient from 10 till 100% EtOAc in heptane. The product fractions were concentrated in vacuo yielding ethyl 4-[(2,2-difluorocyclobutyl)sulfamoyl]-3-fluoro-1-methyl-pyrrole-2-carboxylate (424 mg) as a light yellow oil which solidified on standing. Lithium bis(trimethylsilyl)amide (2.27 mL, 1 M, 2.27 mmol) was added to ethyl 4-[(2,2-difluorocyclobutyl)sulfamoyl]-3-fluoro-1-methyl-pyrrole-2-carboxylate (193 mg, 0.567 mmol) and 4-amino-2-chloropyridine (96.7 mg, 0.74 mmol) in THF (3 mL) and the mixture was stirred for 30 minutes. The reaction mixture was quenched with NH₄Cl solution and extracted with EtOAc. The organic layer was dried over magnesium sulphate, filtered and concentrated. The residue was subjected to silica gel column chromatography using a gradient from 10 to 100% EtOAc in heptane. The product fractions were concentrated and after drying overnight in vacuo at 50° C., compound 174 (199 mg) was obtained as a white powder. Method D: Rt: 1.76 min. m/z: 421.1 (M−H)⁻ Exact mass: 422.0. ¹H NMR (400 MHz, DMSO-d₆) δ ppm 1.57-1.70 (m, 1H), 1.99-2.12 (m, 1H), 2.18-2.31 (m, 2H), 3.80 (s, 3H), 4.06-4.19 (m, 1H), 7.54 (d, J=4.6 Hz, 1H), 7.61 (dd, J=5.6, 1.9 Hz, 1H), 7.82 (d, J=1.8 Hz, 1H), 8.30 (d, J=5.5 Hz, 1H), 8.61 (d, J=8.6 Hz, 1H), 10.58 (s, 1H). Compound 174 (183 mg) was separated in enantiomers 174a and 174b via Preparative SFC (Stationary phase: Chiralpak Diacel AD 20×250 mm, Mobile phase: CO₂, iPrOH with 0.2% iPrNH₂). 174a is the first eluting and 174b the second eluting on Chiralpak Diacel ADH 4.6×250 mm, Mobile phase: CO₂, 30% iPrOH with 0.2% iPrNH₂ hold 4 min towards 50% iPrOH with 0.2% iPrNH₂ in minutes and hold 2 min at 50%). 174a: DSC: From 30 to 300° C. at 10° C./min, peak 205.7° C. 174b: DSC: From 30 to 300° C. at 10° C./min, peak 205.5° C.

Compound 175: N-(2-chloro-4-pyridyl)-3-fluoro-1-methyl-4-[[1-(trifluoromethyl)cyclopropyl]sulfamoyl]pyrrole-2-carboxamide

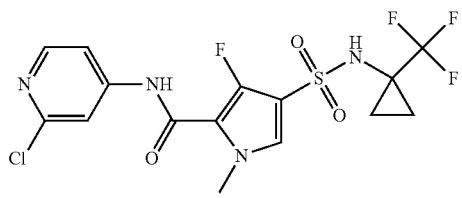 [SMILES: Cn1cc(S(=O)(=O)NC2(C(F)(F)F)CC2)c(F)c1C(=O)Nc1ccnc(Cl)c1]

1-(trifluoromethyl)cyclopropan-1-amine (2041 mg, 16.3 mmol) was dissolved in acetonitrile (93 mL) in a pressure tube under nitrogen. Molecular sieves (4 Å/1100 mg) were added and the suspension was stirred for 10 minutes under nitrogen. Then, ethyl 4-chlorosulfonyl-3-fluoro-1-methyl-pyrrole-2-carboxylate (4 g, 14.83 mmol) and sodium bicarbonate (3738 mg, 44.5 mmol) were added and the pressure tube was closed and stirred in an oil bath at 85° C. for 24 hours. The mixture was cooled to room temperature, filtered over a glass filter and concentrated in vacuo. The obtained crude was purified by silica gel column chromatography using gradient elution from heptane to EtOAc (100:0 to 0:100) yielding ethyl 3-fluoro-1-methyl-4-[[1-(trifluoromethyl)cyclopropyl]sulfamoyl]pyrrole-2-carboxylate (570 mg) which was used as such. Ethyl 3-fluoro-1-methyl-4-[[1-(trifluoromethyl)cyclopropyl]sulfamoyl]pyrrole-2-carboxylate (570 mg, 1.59 mmol) and 4-amino-2-chloropyridine (245.4 mg, 1.91 mmol) in THF (5 mL) was treated with lithium bis(trimethylsilyl)amide in THF (4.77 mL, 1 M, 4.77 mmol) and this was stirred for 30 minutes. Then ammonium chloride (aq./sat./10 mL) was added and the layers were separated. The water layer was extracted once using EtOAc (20 mL). The combined layers were concentrated in vacuo and the obtained crude was was purified by silica gel column chromatography using gradient elution from heptane to EtOAc. (100:0 to 0:100). The desired fractions were concentrated in vacuo and dried in a vacuum oven at 55° C. for 18 hours resulting in compound 175 (332 mg). $^1$H NMR (400 MHz, DMSO-$d_6$) δ ppm 1.20 (m, 4H), 3.81 (s, 3H), 7.55 (d, J=4.4 Hz, 1H), 7.61 (dd, J=5.6, 1.9 Hz, 1H), 7.81 (d, J=1.5 Hz, 1H), 8.30 (d, J=5.7 Hz, 1H), 9.12 (br. s., 1H), 10.57 (br. s., 1H). Method B: Rt: 0.94 min. m/z: 439.0 (M–H)– Exact mass: 440.0.

Compound 178: N-[2-(difluoromethyl)-6-methyl-4-pyridyl]-4-[[(1R)-2,2-difluoro-1-methyl-propyl]sulfamoyl]-3-fluoro-1-methyl-pyrrole-2-carboxamide

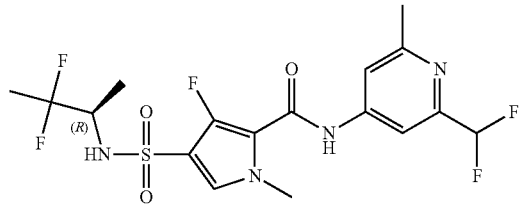

2-(difluoromethyl)-6-methyl-pyridin-4-amine (48.5 mg, 0.31 mmol) and ethyl 4-[[(1R)-2,2-difluoro-1-methyl-propyl]sulfamoyl]-3-fluoro-1-methyl-pyrrole-2-carboxylate (0.31 mmol) were dissolved in THF (5 mL). Lithium bis(trimethylsilyl)amide (1M in THF) (0.92 mL, 1 M, 0.92 mmol) was added and the reaction mixture was stirred overnight at room temperature. The reaction mixtures were quenched with NH$_4$Cl (aq., sat., 10 mL). The organic layer was removed and the aqueous layer extracted with CH$_2$Cl$_2$ (2×5 mL). The combined organic layers were evaporated to dryness and the residue purified on silica using a heptane to EtOAc gradient. The obtained products were crystallized from a MeOH:water 1:1 mixture yielding compound 178 (53 mg) as a white powder. Method B: Rt: 0.95 min. m/z: 453.1 (M–H)– Exact mass: 454.1. DSC: From 30 to 300° C. at 10° C./min, peak 187.5° C. $^1$H NMR (400 MHz, DMSO-$d_6$) δ ppm 1.08 (d, J=7.0 Hz, 3H), 1.58 (t, J=19.3 Hz, 3H), 2.49 (m, 3H), 3.56 (br. s., 1H), 3.82 (s, 3H), 6.87 (t, J=55.2 Hz, 1H), 7.56 (d, J=4.2 Hz, 1H), 7.66 (s, 1H), 7.83 (s, 1H), 8.20 (br. s., 1H), 10.50 (s, 1H).

Compound 179: N-[2-(difluoromethyl)-6-methyl-4-pyridyl]-3-fluoro-1-methyl-[[(1R)-2,2,2-trifluoro-1-methyl-ethyl]sulfamoyl]pyrrole-2-carboxamide

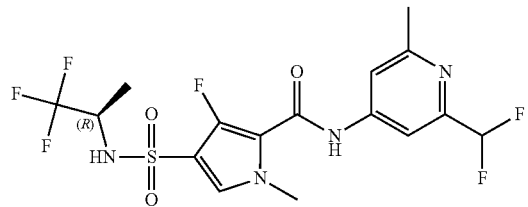

Compound 179 (53 mg) was prepared similarly as described for compound 178, using ethyl 3-fluoro-1-methyl-4-[[(1R)-2,2,2-trifluoro-1-methyl-ethyl]sulfamoyl]pyrrole-2-carboxylate instead ethyl 4-[[(1R)-2,2-difluoro-1-methyl-propyl]sulfamoyl]-3-fluoro-1-methyl-pyrrole-2-carboxylate. Method B: Rt: 0.96 min. m/z: 457.0 (M–H)– Exact mass: 458.1. DSC: From 30 to 300° C. at 10° C./min, peak 200.6° C. $^1$H NMR (400 MHz, DMSO-$d_6$) δ ppm 1.19 (d, J=7.0 Hz, 3H), 2.49 (m, 3H), 3.82 (s, 3H), 3.91-4.07 (m, 1H), 6.87 (t, J=55.1 Hz, 1H), 7.59 (d, J=4.4 Hz, 1H), 7.66 (s, 1H), 7.83 (s, 1H), 8.63 (br. s., 1H), 10.53 (s, 1H).

Compound 180: 3-chloro-N-(2-chloro-4-pyridyl)-1-methyl-4-[[4-(trifluoromethyl)tetrahydropyran-4-yl]sulfamoyl]pyrrole-2-carboxamide

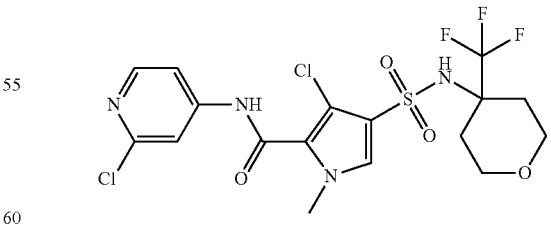

4-chloro-5-[(2-chloro-4-pyridyl)carbamoyl]-1-methyl-pyrrole-3-sulfonyl chloride (150 mg, 0.41 mmol), 4-(trifluoromethyl)tetrahydropyran-4-amine hydrochloride (0.61 mmol), NaHCO$_3$ (102.55 mg, 1.22 mmol) and molecular sieves (4 Å, 1 g) were dispensed in acetonitrile (5 mL) and heated overnight at 100° C. The reaction mixture was filtered and purified via prep. HPLC (Stationary phase: RP XBridge Prep C18 OBD-10 μm, 30×150 mm, Mobile phase: 0.25% NH₄HCO₃ solution in water, MeOH) yielding compound 178 (11 mg) as an oil. Method B: Rt: 0.92 min. m/z: 499.0 (M−H)⁻ Exact mass: 500.0. ¹H NMR (400 MHz, METHANOL-d₄) δ ppm 1.80-1.91 (m, 2H), 2.09-2.19 (m, 2H), 3.62-3.72 (m, 2H), 3.76-3.83 (m, 2H), 3.86 (s, 3H), 7.51 (s, 1H), 7.63 (dd, J=5.7, 2.0 Hz, 1H), 7.88 (d, J=1.8 Hz, 1H), 8.26 (d, J=5.7 Hz, 1H)

Compound 181: 3-cyano-N-(6-cyano-5-fluoro-2-pyridyl)-1-methyl-4-[[(1R)-2,2,2-trifluoro-1-methyl-ethyl]sulfamoyl]pyrrole-2-carboxamide

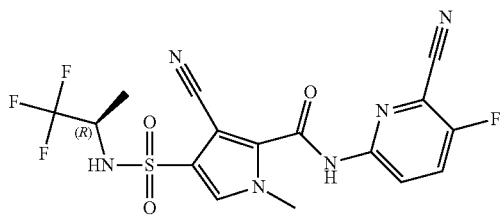

Compound 76 (100 mg, 0.2 mmol), zinc cyanide (23.1 mg, 0.2 mmol) and 1,1'-bis(diphenylphosphino)ferrocenedichloro palladium(II) (14.45 mg, 0.02 mmol) were dispensed in DMF (4 mL) and heated in the microwave for 20 minutes at 160° C. The reaction mixture was filtered and the mixture was purified via prep. HPLC (Stationary phase: RP XBridge Prep C18 OBD-10 μm, 30×150 mm, Mobile phase: 0.25% NH₄HCO₃ solution in water, MeOH), resulting in compound 181 (11 mg). Method B: Rt: 0.99 min. m/z: 443.0 (M−H)⁻ Exact mass: 444.1. DSC: From 30 to 300° C. at 10° C./min, peak 197.2° C. ¹H NMR (400 MHz, DMSO-d₆) δ ppm 1.21 (d, J=7.0 Hz, 3H), 3.85 (s, 3H), 3.97-4.09 (m, 1H), 7.81 (s, 1H), 8.14-8.22 (m, 1H), 8.45 (dd, J=9.5, 4.0 Hz, 1H), 8.71-8.82 (m, 1H), 11.96 (br. s., 1H).

Compound 182: 3-chloro-N-[2-(1,1-difluoroethyl)-4-pyridyl]-1-methyl-4-[[(1R)-2,2,2-trifluoro-1-methyl-ethyl]sulfamoyl]pyrrole-2-carboxamide

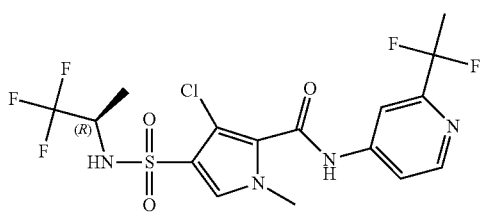

Compound 16 (50 mg, 0.12 mmol), sodium 1,1 difluoroethanesulfinate (37.02 mg, 0.24 mmol), TFA (9.31 μL, 0.12 mmol) and tert-butyl hydroperoxide (83.4 μL, 0.94 g/mL, 0.61 mmol) were dispensed in CH₂Cl₂ (1 mL) and water (0.4 mL) and vigorously stirred. DMSO (1 mL) was added and stirring was continued overnight. More sodium 1,1 difluoroethanesulfinate (37.02 mg, 0.24 mmol) and tert-butyl hydroperoxide (83.4 μL, 0.94 g/mL, 0.61 mmol) were added and stirring was continued over weekend. More sodium 1,1 difluoroethanesulfinate (37.02 mg, 0.24 mmol) and tert-butyl hydroperoxide (83.35 μL, 0.94 g/mL, 0.61 mmol) were added and stirring was continued overnight. The volatiles were removed under reduced pressure and the residue was purified via preparative HPLC (Stationary phase: RP XBridge Prep C18 OBD-10 μm, 30×150 mm, Mobile phase: 0.25% NH₄HCO₃ solution in water, CH₃CN) yielding compound 182 (7 mg). Method B: Rt: 0.98 min. m/z: 473.0 (M−H)⁻ Exact mass: 474.1. ¹H NMR (400 MHz, CHLOROFORM-d) δ ppm 1.40 (d, J=6.8 Hz, 3H), 2.03 (t, J=18.7 Hz, 3H), 3.92-3.99 (m, 1H), 4.01 (s, 3H), 5.01 (d, J=8.4 Hz, 1H), 7.37 (s, 1H), 7.72 (dd, J=5.5, 2.0 Hz, 1H), 7.79 (d, J=1.8 Hz, 1H), 8.56 (s, 1H), 8.59 (d, J=5.5 Hz, 1H).

Compound 183: 3-chloro-N-(4-cyano-2-pyridyl)-1-methyl-4-[[(1R)-2,2,2-trifluoro-1-methyl-ethyl]sulfamoyl]pyrrole-2-carboxamide

Compound 183 (20 mg) was prepared similarly as described for compound 7, using 2-amino-4-cyanopyridine instead of 2-amino-5-fluoro-6-methylpyridine. Method B: Rt: 0.94 min. m/z: 434.0 (M−H)⁻ Exact mass: 435.0. ¹H NMR (400 MHz, DMSO-d₆) δ ppm 1.19 (d, J=6.8 Hz, 3H), 3.80 (s, 3H), 3.90-4.01 (m, 1H), 7.64 (dd, J=5.1, 1.3 Hz, 1H), 7.70 (s, 1H), 8.40 (s, 1H), 8.48 (d, J=8.8 Hz, 1H), 8.62-8.65 (m, 1H), 11.09 (s, 1H).

Compound 184: 3-chloro-1-methyl-4-[[(1R)-2,2,2-trifluoro-1-methyl-ethyl]sulfamoyl]-N-(3,5,6-trifluoro-2-pyridyl)pyrrole-2-carboxamide

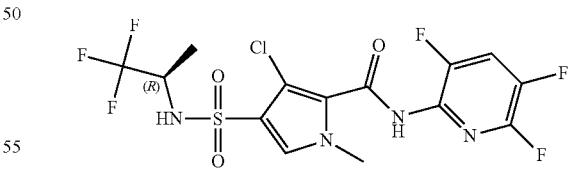

Compound 184 (65 mg) was prepared similarly as described for compound 43, using 2-amino-3,5,6-trifluoropyridine instead of 4-amino-2,3,6-trifluoropyridine. Method B: Rt: 0.94 min. m/z: 463.0 (M−H)⁻ Exact mass: 464.0. DSC: From 30 to 300° C. at 10° C./min, peak 184.8° C. ¹H NMR (400 MHz, DMSO-d₆) δ ppm 1.18 (d, J=7.0 Hz, 3H), 3.76 (s, 3H), 3.88-4.02 (m, 1H), 7.69 (s, 1H), 8.36-8.55 (m, 2H), 10.87 (br. s., 1H).

Compound 185: 3-chloro-N-(3-chloro-2,6-difluoro-4-pyridyl)-1-methyl-4-[[(1R)-2,2,2-trifluoro-1-methyl-ethyl]sulfamoyl]pyrrole-2-carboxamide

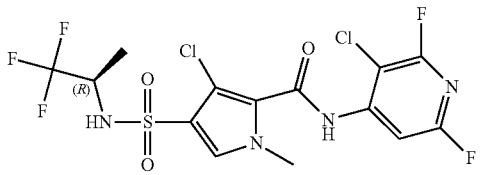

Compound 185 (169 mg) was prepared similarly as described for compound 43, using 4-amino-3-chloro-2,6-difluoropyridine instead of 4-amino-2,3,6-trifluoropyridine. Method B: Rt: 1.16 min. m/z: 479.0 (M–H)⁻ Exact mass: 480.0. DSC: From 30 to 300° C. at 10° C./min, peak 225.5° C. ¹H NMR (400 MHz, DMSO-d₆) δ ppm 1.19 (d, J=7.0 Hz, 3H), 3.88 (s, 3H), 3.93-4.06 (m, 1H), 7.82 (s, 1H), 7.96 (s, 1H), 8.60 (d, J=8.8 Hz, 1H), 10.18 (s, 1H).

Compound 186: 3-chloro-N-(3,5-dichloro-2,6-difluoro-4-pyridyl)-1-methyl-4-[[(1R)-2,2,2-trifluoro-1-methyl-ethyl]sulfamoyl]pyrrole-2-carboxamide

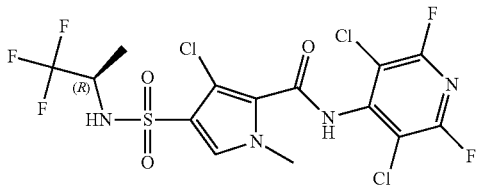

Compound 186 (mg) was prepared similarly as described for compound 43, using 4-amino-3,5-dichloro-2,6-difluoropyridine instead of 4-amino-2,3,6-trifluoropyridine. Method B: Rt: 1.02 min. m/z: 512.9 (M–H)⁻ Exact mass: 513.9. DSC: From 30 to 300° C. at 10° C./min, peak 183.5° C. ¹H NMR (400 MHz, DMSO-d₆) δ ppm 1.19 (d, J=7.0 Hz, 3H), 3.79 (s, 3H), 3.93-4.04 (m, 1H), 7.73 (s, 1H), 8.52 (d, J=8.8 Hz, 1H), 11.05 (s, 1H).

Compound 187: 3-chloro-N-(3-chloro-2,5,6-trifluoro-4-pyridyl)-1-methyl-4-[[(1R)-2,2,2-trifluoro-1-methyl-ethyl]sulfamoyl]pyrrole-2-carboxamide

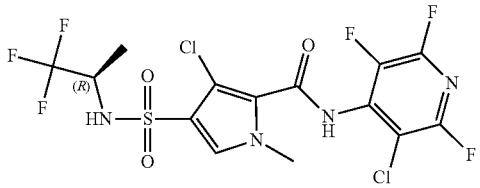

Compound 187 (100 mg) was prepared similarly as described for compound 43, using 4-amino-3-chloro-2,5,6-trifluoropyridine instead of 4-amino-2,3,6-trifluoropyridine. Method B: Rt: 1.03 min. m/z: 496.9 (M–H)⁻ Exact mass: 498.0. DSC: From 30 to 300° C. at 10° C./min, peak 162.8° C. ¹H NMR (400 MHz, DMSO-d₆) δ ppm 1.19 (d, J=6.8 Hz, 3H), 3.78 (s, 3H), 3.92-4.05 (m, 1H), 7.74 (s, 1H), 8.53 (d, J=8.8 Hz, 1H), 11.07 (s, 1H).

Compound 188: N-(2-cyano-4-pyridyl)-3-fluoro-1-methyl-4-[(2,2,2-trifluoro-1,1-dimethyl-ethyl)sulfamoyl]pyrrole-2-carboxamide

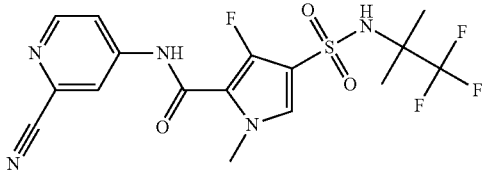 [SMILES: Cn1cc(S(=O)(=O)NC(C)(C)C(F)(F)F)c(F)c1C(=O)Nc1ccnc(C#N)c1]

Ethyl 4-chlorosulfonyl-3-fluoro-1-methyl-pyrrole-2-carboxylate (1200 mg, 4.45 mmol) was dissolved in dry pyridine (21 mL, 0.98 g/mL, 260.17 mmol). 1,1,1-trifluoro-2-methylpropan-2-amine (1131.2 mg, 8.9 mmol) was added and the mixture was stirred at room temperature for 3 hours. The mixture was concentrated in vacuo. The residue was purified by silica gel column chromatography using gradient elution from heptane to EtOAc (100:0 to 0:100) yielding ethyl 3-fluoro-1-methyl-4-[(2,2,2-trifluoro-1,1-dimethyl-ethyl)sulfamoyl]pyrrole-2-carboxylate (1.15 g) as a beige powder which was used as such in the next step. Ethyl 3-fluoro-1-methyl-4-[(2,2,2-trifluoro-1,1-dimethyl-ethyl)sulfamoyl]pyrrole-2-carboxylate (0.15 g, 0.42 mmol) and 4-aminopyridine-2-carbonitrile (54.55 mg, 0.46 mmol) were dissolved in THF (4.1 mL) in a tube. The tube was flushed with nitrogen, capped with a septum and stirred at room temperature. To this was added lithium bis(trimethylsilyl)amide (1.04 mL, 1 M, 1.04 mmol) at once using a syringe. The obtained solution was stirred for 3 hours. Then ammonium chloride (aq./sat./10 mL) was added and the layers where separated. Then it was extracted once using ethyl acetate (10 mL). The combined extracts were concentrated in vacuo and purified by silica gel column chromatography using gradient elution from heptane to EtOAc. (100:0 to 0:100). The obtained fractions were concentrated in vacuo and repurified by Prep HPLC (RP SunFire Prep C18 OBD-10 μm, 30×150 mm), mobile phase (0.25% NH₄HCO₃ solution in water, MeOH). The desired fractions were concentrated under reduced pressure and co-evaporated twice with methanol (2×20 mL) and dried in a vacuum oven at 55° C. for 18 hours yielding compound 188 (45 mg) as a white powder. Method B: Rt: 0.94 min. m/z: 432.1 (M–H)⁻ Exact mass: 433.1. ¹H NMR (400 MHz, DMSO-d₆) δ ppm 1.39 (s, 6H), 3.83 (s, 3H), 7.58 (d, J=4.4 Hz, 1H), 7.91 (dd, J=5.6, 1.9 Hz, 1H), 8.21 (d, J=1.8 Hz, 1H), 8.47 (br. s., 1H), 8.63 (d, J=5.7 Hz, 1H), 10.67 (br. s., 1H)

Compound 189: N-(2,6-difluoro-4-pyridyl)-3-fluoro-1-methyl-4-[(2,2,2-trifluoro-1,1-dimethyl-ethyl)sulfamoyl]pyrrole-2-carboxamide

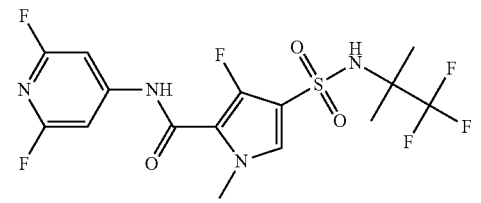 [SMILES: Cn1cc(S(=O)(=O)NC(C)(C)C(F)(F)F)c(F)c1C(=O)Nc1cc(F)nc(F)c1]

Compound 189 (86 mg) was prepared similarly as described for compound 188, using 4-amino-2,6-difluoropyridine instead of 4-aminopyridine-2-carbonitrile. Method B: Rt: 1.06 min. m/z: 443.0 (M−H)⁻ Exact mass: 444.1. $^1$H NMR (400 MHz, DMSO-$d_6$) δ ppm 1.39 (s, 6H), 3.82 (s, 3H), 7.34 (s, 2H), 7.58 (d, J=4.4 Hz, 1H), 8.47 (br. s., 1H), 10.84 (br. s., 1H).

Compound 190: N-[2-(difluoromethyl)-4-pyridyl]-3-fluoro-1-methyl-4-[(2,2,2-trifluoro-1,1-dimethyl-ethyl)sulfamoyl]pyrrole-2-carboxamide

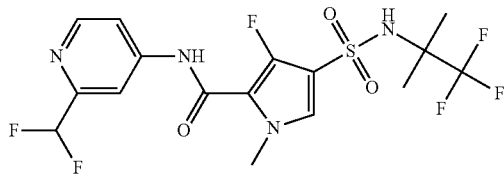 [SMILES: Cn1cc(S(=O)(=O)NC(C)(C)C(F)(F)F)c(F)c1C(=O)Nc1ccnc(C(F)F)c1]

Compound 190 (42 mg) was prepared similarly as described for compound 188, using 2-(difluoromethyl)pyridin-4-amine instead of 4-aminopyridine-2-carbonitrile. Method B: Rt: 0.96 min. m/z: 457.0 (M−H)⁻ Exact mass: 458.1. $^1$H NMR (400 MHz, DMSO-$d_6$) δ ppm 1.39 (s, 6H), 3.77-3.88 (m, 3H), 6.92 (t, J=55.0 Hz, 1H), 7.55 (d, J=4.4 Hz, 1H), 7.72-7.84 (m, 1H), 8.03 (d, J=1.5 Hz, 1H), 8.45 (br. s., 1H), 8.57 (d, J=5.7 Hz, 1H), 10.60 (br. s., 1H).

Compound 191: N-(2-bromo-4-pyridyl)-3-fluoro-1-methyl-4-[(2,2,2-trifluoro-1,1-dimethyl-ethyl)sulfamoyl]pyrrole-2-carboxamide

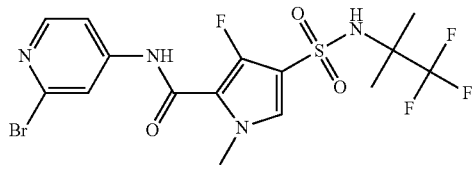 [SMILES: Cn1cc(S(=O)(=O)NC(C)(C)C(F)(F)F)c(F)c1C(=O)Nc1ccnc(Br)c1]

Compound 191 (89 mg) was prepared similarly as described for compound 188, using 4-amino-2-bromopyridine instead of 4-aminopyridine-2-carbonitrile. Method B: Rt: 1.00 min. m/z: 485.0 (M−H)⁻ Exact mass: 486.0. $^1$H NMR (400 MHz, DMSO-$d_6$) δ ppm 1.39 (s, 6H), 3.81 (s, 3H), 7.55 (d, J=4.4 Hz, 1H), 7.64 (dd, J=5.7, 1.8 Hz, 1H), 7.97 (d, J=1.8 Hz, 1H), 8.27 (d, J=5.7 Hz, 1H), 8.45 (br. s., 1H), 10.52 (br. s., 1H).

Compound 192: N-(2-cyano-4-pyridyl)-3-fluoro-1-methyl-4-[[1-(trifluoromethyl)cyclopropyl]sulfamoyl]pyrrole-2-carboxamide

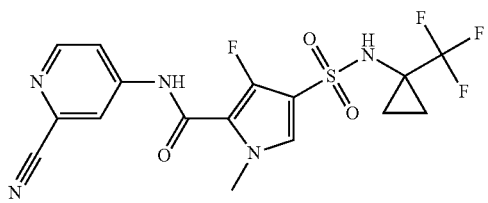 [SMILES: Cn1cc(S(=O)(=O)NC2(C(F)(F)F)CC2)c(F)c1C(=O)Nc1ccnc(C#N)c1]

Ethyl 4-chlorosulfonyl-3-fluoro-1-methyl-pyrrole-2-carboxylate (1500 mg, 5.56 mmol) was dissolved in dry pyridine (26.25 mL, 325.2 mmol). 1-(trifluoromethyl)cyclopropan-1-amine (1392 mg, 11.1 mmol) was added and the mixture was stirred at 70° C. for 6 hours. The mixture was concentrated in vacuo. The obtained residue was purified by silica gel column chromatography using gradient elution from heptane to EtOAc (100:0 to 0:100) yielding ethyl 3-fluoro-1-methyl-4-[[1-(trifluoromethyl)cyclopropyl]sulfamoyl]pyrrole-2-carboxylate (1.21 g) as a beige powder. Ethyl 3-fluoro-1-methyl-4-[[1-(trifluoromethyl)cyclopropyl]sulfamoyl]pyrrole-2-carboxylate (0.15 g, 0.31 mmol) and 4-aminopyridine-2-carbonitrile (40.05 mg, 0.34 mmol) were dissolved in THF (3 mL) in a tube. The tube was flushed with nitrogen, capped with a septum and stirred at room temperature. To this was added lithium bis(trimethyl-silyl)amide (0.76 mL, 1 M, 0.76 mmol) at once using a syringe. The obtained solution was stirred for 3 hours. Then ammonium chloride (aq./sat./10 mL) was added and the layers where separated. Then it was extracted once using ethyl acetate (10 mL). The combined extracts were concentrated in vacuo and purified by silica gel column chromatography using gradient elution from heptane to EtOAc. (100:0 to 0:100). The obtained fractions were concentrated in vacuo and repurified by Prep HPLC on (RP SunFire Prep C18 OBD-10 μm, 30×150 mm). Mobile phase (0.25% NH₄HCO₃ solution in water, MeOH). The desired fractions were concentrated under reduced pressure and co-evaporated twice with methanol (2×20 mL) and dried in a vacuum oven at 55° C. for 18 hours resulting in compound 192 (51 mg) as a white powder. Method B: Rt: 0.90 min. m/z: 430.1 (M−H)⁻ Exact mass: 431.1. $^1$H NMR (400 MHz, DMSO-$d_6$) δ ppm 1.14-1.30 (m, 4H), 3.75-3.89 (m, 3H), 7.57 (d, J=4.6 Hz, 1H), 7.90 (dd, J=5.6, 2.1 Hz, 1H), 8.21 (d, J=2.0 Hz, 1H), 8.63 (d, J=5.7 Hz, 1H), 9.15 (br. s., 1H), 10.67 (br. s., 1H).

Compound 193: N-(2,6-difluoro-4-pyridyl)-3-fluoro-1-methyl-4-[[1-(trifluoromethyl)cyclopropyl]sulfamoyl]pyrrole-2-carboxamide

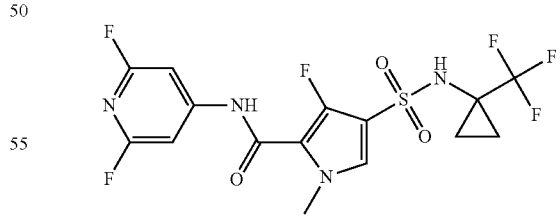

Compound 193 (87 mg) was prepared similarly as described for compound 192, using 4-amino-2,6-difluoropyridine instead of 4-aminopyridine-2-carbonitrile. Method B: Rt: 1.03 min. m/z: 441.0 (M−H)⁻ Exact mass: 442.1. $^1$H NMR (400 MHz, DMSO-$d_6$) δ ppm 1.20 (br. s., 4H), 3.81 (s, 3H), 7.33 (s, 2H), 7.58 (d, J=4.6 Hz, 1H), 9.16 (br. s., 1H), 10.85 (br. s., 1H).

Compound 194: N-(2-bromo-4-pyridyl)-3-fluoro-1-methyl-4-[[1-(trifluoromethyl)cyclopropyl]sulfamoyl]pyrrole-2-carboxamide

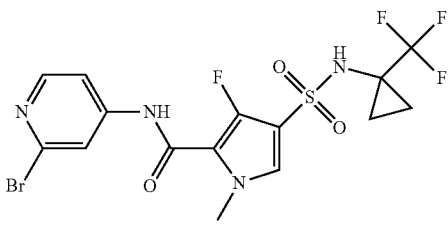 [SMILES: Cn1cc(S(=O)(=O)NC2(C(F)(F)F)CC2)c(F)c1C(=O)Nc1ccnc(Br)c1]

Compound 194 (80 mg) was prepared similarly as described for compound 192, using 4-amino-2-bromopyridine instead of 4-aminopyridine-2-carbonitrile. Method B: Rt: 0.97 min. m/z: 484.9 (M−H)⁻ Exact mass: 486.0. $^1$H NMR (400 MHz, DMSO-d$_6$) δ ppm 1.05-1.30 (m, 4H), 3.72-3.88 (m, 3H), 7.55 (d, J=4.4 Hz, 1H), 7.64 (dd, J=5.6, 1.7 Hz, 1H), 7.96 (d, J=1.5 Hz, 1H), 8.27 (d, J=5.5 Hz, 1H), 9.13 (br. s., 1H), 10.53 (br. s., 1H).

Compound 195: N-[2-(difluoromethyl)-3-fluoro-4-pyridyl]-3-fluoro-1-methyl-4-[[1-(trifluoromethyl)cyclopropyl]sulfamoyl]pyrrole-2-carboxamide

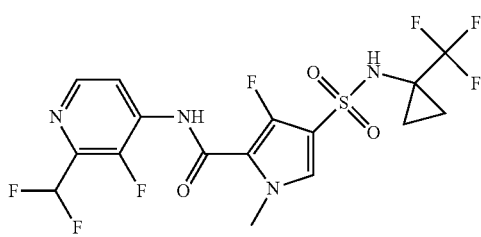 [SMILES: Cn1cc(S(=O)(=O)NC2(C(F)(F)F)CC2)c(F)c1C(=O)Nc1ccnc(C(F)F)c1F]

Compound 195 (53 mg) was prepared similarly as described for compound 192, using 2-(difluoromethyl)-3-fluoro-pyridin-4-amine hydrochloride instead of 4-aminopyridine-2-carbonitrile. Method B: Rt: 0.97 min. m/z: 473.0 (M−H)⁻ Exact mass: 474.1. $^1$H NMR (400 MHz, DMSO-d$_6$) δ ppm 1.15-1.28 (m, 4H), 3.84 (s, 3H), 7.15 (t, J=53.3 Hz, 1H), 7.57 (d, J=4.4 Hz, 1H), 8.20 (t, J=5.5 Hz, 1H), 8.44 (d, J=5.5 Hz, 1H), 9.12 (br. s., 1H), 10.22 (br. s., 1H)

Compound 196: N-[2-(difluoromethyl)-4-pyridyl]-3-fluoro-1-methyl-4-[[1-(trifluoromethyl)cyclopropyl]sulfamoyl]pyrrole-2-carboxamide

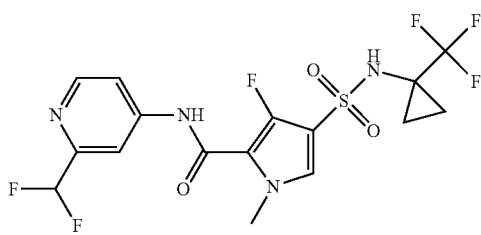 [SMILES: Cn1cc(S(=O)(=O)NC2(C(F)(F)F)CC2)c(F)c1C(=O)Nc1ccnc(C(F)F)c1]

Compound 196 (89 mg) was prepared similarly as described for compound 192, using 2-(difluoromethyl)pyridin-4-amine instead of 4-aminopyridine-2-carbonitrile. Method B: Rt: 0.92 min. m/z: 455.0 (M−H)⁻ Exact mass: 456.1. $^1$H NMR (400 MHz, DMSO-d$_6$) δ ppm 1.15-1.25 (m, 4H), 3.82 (s, 3H), 6.92 (t, J=54.8 Hz, 1H), 7.55 (d, J=4.4 Hz, 1H), 7.75-7.80 (m, 1H), 8.03 (d, J=1.8 Hz, 1H), 8.57 (d, J=5.7 Hz, 1H), 9.13 (br. s., 1H), 10.61 (br. s., 1H).

Compound 197: N-(2-cyano-3-fluoro-4-pyridyl)-4-[(3,3-difluoro-1-methyl-cyclobutyl)sulfamoyl]-3-fluoro-1-methyl-pyrrole-2-carboxamide

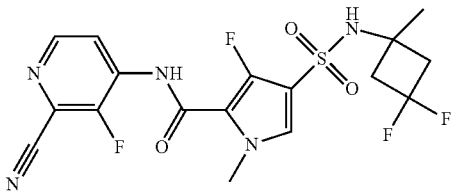 [SMILES: Cn1cc(S(=O)(=O)NC2(C)CC(F)(F)C2)c(F)c1C(=O)Nc1ccnc(C#N)c1F]

A mixture of compound 131 (200 mg, 0.4 mmol) and zinc cyanide (32.93 mg, 0.28 mmol) in DMF (5 mL) was purged with nitrogen for 5 minutes. Then 1,1'-bis(diphenylphosphino)ferrocenedichloro palladium(II) (29.4 mg, 0.04 mmol) was added. The vial was flushed with nitrogen, capped and stirred under MW-irradiation at 160° C. for 30 minutes. The mixture was injected directly on a silica plug and purified by silica gel column chromatography using gradient elution from heptane to EtOAc. (100:0 to 0:100). The desired fraction were concentrated in vacuo and the obtained crude was further purified via Prep SFC (Stationary phase: Chiralpak Diacel AD 20×250 mm, Mobile phase: CO$_2$, EtOH with 0.4% iPrNH$_2$), resulting in compound 197 (84 mg). Method D: Rt: 1.83 min. m/z: 444.1 (M−H)⁻ Exact mass: 445.1. $^1$H NMR (400 MHz, DMSO-d$_6$) δ ppm 1.42 (s, 3H), 2.53-2.62 (m, 2H), 2.79-2.97 (m, 2H), 3.84 (s, 3H), 7.61 (d, J=4.8 Hz, 1H), 8.27 (s, 1H), 8.33 (t, J=5.9 Hz, 1H), 8.51 (d, J=5.3 Hz, 1H), 10.41 (s, 1H).

Compound 198: N-(2-chloro-4-pyridyl)-3-fluoro-1-methyl-4-[[(3-(trifluoromethyl)oxetan-3-yl]sulfamoyl]pyrrole-2-carboxamide

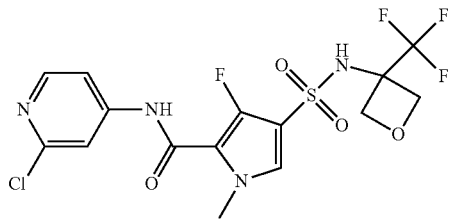 [SMILES: Cn1cc(S(=O)(=O)NC2(C(F)(F)F)COC2)c(F)c1C(=O)Nc1ccnc(Cl)c1]

Ethyl 4-chlorosulfonyl-3-fluoro-1-methyl-pyrrole-2-carboxylate (750 mg, 2.78 mmol) was dissolved in dry pyridine (15 mL, 185.84 mmol). 3-(trifluoromethyl)-3-oxetanamine hydrochloride (740.7 mg, 4.17 mmol) was added and the mixture was stirred at 70° C. for 5 hours. The mixture was concentrated in vacuo and co-evaporated using toluene (2×50 mL). The obtained residue was purified by silica gel column chromatography using gradient elution from heptane to EtOAc. (100:0 to 0:100) yielding of ethyl 3-fluoro-1-methyl-4-[[(3-(trifluoromethyl)oxetan-3-yl]sulfamoyl]pyrrole-2-carboxylate (780 mg) as a beige powder. Ethyl 3-fluoro-1-methyl-4-[[(3-(trifluoromethyl)oxetan-3-yl]sulfamoyl]pyrrole-2-carboxylate (102 mg, 0.27 mmol) and 4-amino-2-chloropyridine (39.3 mg, 0.3 mmol) were dissolved in THF (3 mL) in a tube. The tube was flushed with nitrogen, capped with a septum and stirred at room temperature. To this was added lithium bis(trimethylsilyl)amide in THF (0.68 mL, 1 M, 0.68 mmol) at once using a syringe. The obtained solution was stirred for 3 hours. Then ammonium chloride (aq./sat./10 mL) was added and the layers where separated. Then it was extracted once using ethyl acetate (10 mL). The combined extracts were concentrated in vacuo and purified by silica gel column chromatography using gradient elution from heptane to EtOAc. (100:0 to 0:100). The obtained fractions were concentrated in vacuo and repurified by Prep HPLC on (RP SunFire Prep C18 OBD-10 μm, 30×150 mm). Mobile phase (0.25% NH$_4$HCO$_3$ solution in water, MeOH). The desired fractions were concentrated under reduced pressure, co-evaporated twice with methanol (2×20 mL) and dried in a vacuum oven at 55° C. for 18 hours resulting in compound 198 (83 mg) as a white powder. $^1$H NMR (400 MHz, DMSO-d$_6$) δ ppm 3.83 (s, 3H), 4.66 (d, J=7.9 Hz, 2H), 4.84 (d, J=7.7 Hz, 2H), 7.57-7.70 (m, 2H), 7.82 (d, J=1.5 Hz, 1H), 8.31 (d, J=5.7 Hz, 1H), 9.28 (br. s., 1H), 10.64 (s, 1H). Method B: Rt: 0.86 min. m/z: 455.0 (M–H)$^-$ Exact mass: 456.0.

Compound 199: N-(2,6-difluoro-4-pyridyl)-3-fluoro-1,5-dimethyl-4-[[(1R)-2,2,2-trifluoro-1-methyl-ethyl]sulfamoyl]pyrrole-2-carboxamide

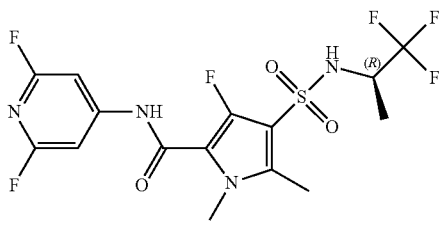

Compound 199 (101 mg) was prepared similarly as described for compound 200, using 4-amino-2,6-difluoropyridine instead of 4-amino-2-chloropyridine. Method B: Rt: 1.05 min. m/z: 443.0 (M–H)$^-$ Exact mass: 444.1. DSC: From 30 to 300° C. at 10° C./min, peak 196.6° C. $^1$H NMR (400 MHz, DMSO-d$_6$) δ ppm 1.16 (d, J=7.0 Hz, 3H), 2.44 (s, 3H), 3.70 (s, 3H), 3.92 (br. s., 1H), 7.33 (s, 2H), 8.60 (br. s., 1H), 10.84 (br. s., 1H).

Compound 200: N-(2-chloro-4-pyridyl)-3-fluoro-1,5-dimethyl-4-[[(1R)-2,2,2-trifluoro-1-methyl-ethyl]sulfamoyl]pyrrole-2-carboxamide

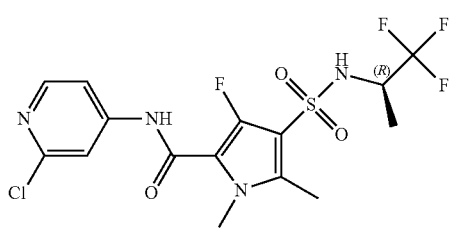

Ethyl 3-fluoro-1-methyl-4-[[(1R)-2,2,2-trifluoro-1-methyl-ethyl]sulfamoyl]pyrrole-2-carboxylate (2500 mg, 7.22 mmol) was added to a solution of Br$_2$ (1731 mg, 10.8 mmol) in acetic acid (50 mL) and brought to a gentle reflux. The reaction mixture was heated for 2 hours, allowed to cool to room temperature and stirred overnight at room temperature. The reaction mixture was concentrated and the residue was dissolved in EtOAc (50 mL) washed with NaHCO$_3$ (aq., sat.), dried over magnesium sulphate, filtered and concentrated to yield ethyl 5-bromo-3-fluoro-1-methyl-4-[[(1R)-2,2,2-trifluoro-1-methyl-ethyl]sulfamoyl]pyrrole-2-carboxylate as a light yellow powder which was used as such in the next step. The obtained ethyl 5-bromo-3-fluoro-1-methyl-4-[[(1R)-2,2,2-trifluoro-1-methyl-ethyl]sulfamoyl]pyrrole-2-carboxylate, tetramethyltin (2718 mg, 14.4 mmol) in DMF (20 mL) was flushed with nitrogen during 5 minutes. Tetrakis(triphenylphosphine)palladium(0) (834.2 mg, 0.72 mmol) was added and the reaction mixture was heated at 140° C. during 30 minutes in a microwave. The volatiles were removed under reduced pressure and the residue was purified by silica gel column chromatography using a gradient from 10 till 100% EtOAc in heptane, resulting in ethyl 3-fluoro-1,5-dimethyl-4-[[(1R)-2,2,2-trifluoro-1-methyl-ethyl]sulfamoyl]pyrrole-2-carboxylate (2.44 g) as an off-white powder. ethyl 3-fluoro-1,5-dimethyl-4-[[(1R)-2,2,2-trifluoro-1-methyl-ethyl]sulfamoyl]pyrrole-2-carboxylate (250 mg, 0.69 mmol) and 4-amino-2-chloropyridine (0.76 mmol) were dissolved in THF (5 mL). Lithium bis(trimethylsilyl)amide (1M in THF) (2.08 mL, 1 M, 2.08 mmol) was added and the reaction mixture was stirred overnight at room temperature. The reaction mixture was quenched with NH$_4$Cl (aq., sat., 10 mL). The organic layer was removed and the aqueous layer extracted with CH$_2$Cl$_2$ (2×5 mL). The combined organic layers were evaporated to dryness and the residue purified on silica using a heptane to EtOAc gradient. Compound 200 (107 mg) was crystallized from a MeOH:water 1:1 mixture, resulting in a white powder. Method B: Rt: 0.97 min. m/z: 441.0 (M–H)$^-$ Exact mass: 442.0. DSC: From 30 to 300° C. at 10° C./min, peak 229.3° C. $^1$H NMR (400 MHz, DMSO-d$_6$) δ ppm 1.16 (d, J=7.0 Hz, 3H), 2.44 (s, 3H), 3.70 (s, 3H), 3.92 (br. s., 1H), 7.60 (dd, J=5.6, 1.9 Hz, 1H), 7.82 (d, J=1.5 Hz, 1H), 8.29 (d, J=5.5 Hz, 1H), 8.58 (br. s., 1H), 10.56 (s, 1H).

Compound 201: N-[2-(difluoromethyl)-3-fluoro-4-pyridyl]-3-fluoro-1-methyl-4-[(2,2,2-trifluoro-1,1-dimethyl-ethyl)sulfamoyl]pyrrole-2-carboxamide

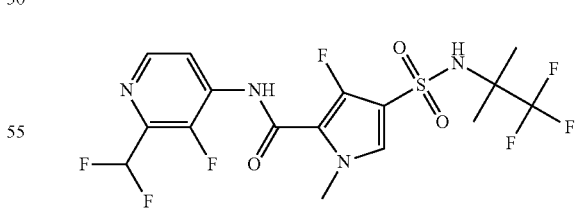

Compound 201 (91 mg) was prepared similarly as described for compound 188, using 2-(difluoromethyl)-3-fluoro-pyridin-4-amine hydrochloride instead of 4-amino-pyridine-2-carbonitrile. Method B: Rt: 1.03 min. m/z: 475.0 (M–H)$^-$ Exact mass: 476.1. $^1$H NMR (400 MHz, DMSO-d$_6$) δ ppm 1.40 (s, 6H), 3.85 (s, 3H), 7.15 (t, J=53.0 Hz, 1H), 7.58 (d, J=4.6 Hz, 1H), 8.22 (t, J=5.6 Hz, 1H), 8.36-8.54 (m, 2H), 10.19 (br. s., 1H).

Compound 202: N-[2-(difluoromethyl)-3-fluoro-4-pyridyl]-3-fluoro-1-methyl-4-[[(1R)-2,2,2-trifluoro-1-methyl-ethyl]sulfamoyl]pyrrole-2-carboxamide

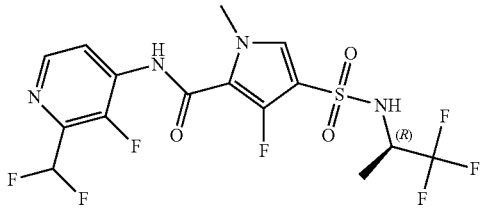

Compound 202 (118 mg) was prepared similarly as described for compound 152, using 2-(difluoromethyl)-3-fluoro-pyridin-4-amine (77.24 mg, 0.48 mmol) instead of 2-fluoro-6-methyl-pyridin-4-amine. $^1$H NMR (400 MHz, DMSO-$d_6$) δ ppm 1.19 (d, J=7.0 Hz, 3H), 3.85 (s, 3H), 3.91-4.07 (m, 1H), 7.15 (t, J=52.6 Hz, 1H), 7.62 (d, J=4.6 Hz, 1H), 8.21 (t, J=5.6 Hz, 1H), 8.45 (d, J=5.3 Hz, 1H), 8.65 (br. s., 1H), 10.23 (br. s., 1H). Method B: Rt: 0.99 min. m/z: 461.0 (M−H)⁻ Exact mass: 462.06

Compound 203: N-(2-bromo-3-fluoro-4-pyridyl)-3-fluoro-1-methyl-4-[[1-(trifluoromethyl)cyclopropyl]sulfamoyl]pyrrole-2-carboxamide

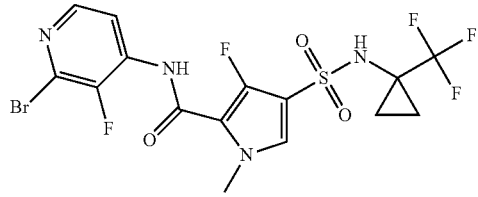 [SMILES: Cn1cc(S(=O)(=O)NC2(C(F)(F)F)CC2)c(F)c1C(=O)Nc1ccnc(Br)c1F]

Compound 203 (43 mg) was prepared similarly as described for compound 192, using 2-bromo-3-fluoro-pyridin-4-amine instead of 4-aminopyridine-2-carbonitrile. Method B: Rt: 1.04 min. m/z: 500.9 (M−H)⁻ Exact mass: 502.0. $^1$H NMR (400 MHz, DMSO-$d_6$) δ ppm 1.10-1.30 (m, 4H), 3.83 (s, 3H), 7.56 (d, J=4.6 Hz, 1H), 8.03 (t, J=5.4 Hz, 1H), 8.18 (d, J=5.3 Hz, 1H), 9.14 (br. s, 1H), 10.20 (br. s., 1H).

Compound 204: N-[2-(difluoromethyl)-3-fluoro-4-pyridyl]-4-[[(1R)-2,2-difluoro-1-methyl-propyl]sulfamoyl]-3-fluoro-1-methyl-pyrrole-2-carboxamide

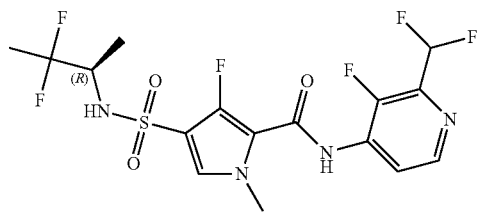

Compound 204 (130 mg) was prepared similarly as described for compound 157, using 2-(difluoromethyl)-3-fluoro-pyridin-4-amine (85.2 mg, 0.53 mmol) instead of 2-bromo-6-methylpyridin-4-amine. Instead of a crystallization out of i-PrOH an extra purification by Prep HPLC was done on (RP SunFire Prep C18 OBD-10 μm, 30×150 mm). Mobile phase (0.25% NH$_4$HCO$_3$ solution in water, MeOH). The desired fractions were concentrated under reduced pressure and co-evaporated twice with methanol (2×20 mL) and dried in a vacuum oven at 55° C. for 18 hours resulting in compound 204 (130 mg) as a white powder. $^1$H NMR (400 MHz, DMSO-$d_6$) δ ppm 1.08 (d, J=7.0 Hz, 3H), 1.58 (t, J=19.1 Hz, 3H), 3.55 (dq, J=14.6, 7.3 Hz, 1H), 3.84 (s, 3H), 7.15 (t, J=53.3 Hz, 1H), 7.59 (d, J=4.6 Hz, 1H), 8.13-8.29 (m, 2H), 8.45 (d, J=5.3 Hz, 1H), 10.20 (s, 1H). Method B: Rt: 0.99 min. m/z: 457.0 (M−H)⁻ Exact mass: 458.08.

Compound 205: N-(2-bromo-4-pyridyl)-3-fluoro-1,5-dimethyl-[[(1R)-2,2,2-trifluoro-1-methyl-ethyl]sulfamoyl]pyrrole-2-carboxamide

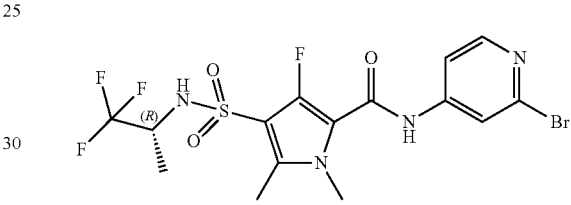

Compound 205 (60 mg) was prepared similarly as described for compound 200, using 4-amino-2-bromopyridine instead of 4-amino-2-chloropyridine. Method B: Rt: 1.01 min. m/z: 486.9 (M−H)⁻ Exact mass: 488.0. DSC: From 30 to 300° C. at 10° C./min, peak at 222.7° C. $^1$H NMR (400 MHz, DMSO-$d_6$) δ ppm 1.16 (d, J=6.8 Hz, 3H), 2.44 (s, 3H), 3.70 (s, 3H), 3.84-4.02 (m, 1H), 7.63 (dd, J=5.7, 1.8 Hz, 1H), 7.97 (d, J=1.5 Hz, 1H), 8.27 (d, J=5.7 Hz, 1H), 8.58 (d, J=7.9 Hz, 1H), 10.54 (s, 1H).

Compound 206: N-[2-(difluoromethyl)-4-pyridyl]-3-fluoro-1,5-dimethyl-4-[[(1R)-2,2,2-trifluoro-1-methyl-ethyl]sulfamoyl]pyrrole-2-carboxamide

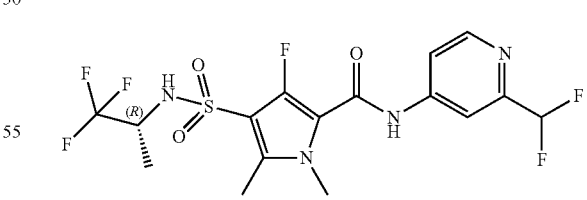

Compound 206 (101 mg) was prepared similarly as described for compound 200, using 2-(difluoromethyl)pyridin-4-amine instead of 4-amino-2-chloropyridine. Method B: Rt: 0.97 min. m/z: 457.0 (M−H)⁻ Exact mass: 458.1. $^1$H NMR (400 MHz, DMSO-$d_6$) δ ppm 1.16 (d, J=7.0 Hz, 3H), 2.44 (s, 3H), 3.71 (s, 3H), 3.85-3.99 (m, 1H), 6.92 (t, J=55.0 Hz, 1H), 7.73-7.81 (m, 1H), 8.03 (d, J=1.8 Hz, 1H), 8.51-8.59 (m, 2H), 10.60 (s, 1H).

Compound 207: N-[2-(difluoromethyl)-3-fluoro-4-pyridyl]-3-fluoro-1,5-dimethyl-4-[[(1R)-2,2,2-trifluoro-1-methyl-ethyl]sulfamoyl]pyrrole-2-carboxamide

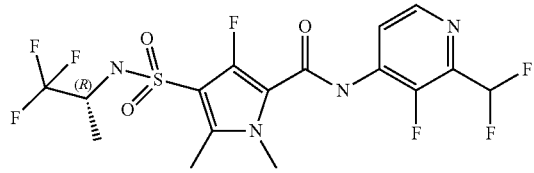

Compound 207 (54 mg) was prepared similarly as described for compound 200, using 2-(difluoromethyl)-3-fluoro-pyridin-4-amine instead of 4-amino-2-chloropyridine. Method B: Rt: 1.02 min. m/z: 475.0 (M−H)⁻ Exact mass: 476.1. DSC: From 30 to 300° C. at 10° C./min, peak 201.9° C. ¹H NMR (400 MHz, DMSO-d₆) δ ppm 1.17 (d, J=6.8 Hz, 3H), 2.45 (s, 3H), 3.74 (s, 3H), 3.88-3.98 (m, 1H), 7.15 (t, J=53.1 Hz, 1H), 8.22 (t, J=5.6 Hz, 1H), 8.44 (d, J=5.3 Hz, 1H), 8.59 (d, J=7.7 Hz, 1H), 10.21 (br. s., 1H).

Compound 208: N-[2-(difluoromethyl)-3-fluoro-4-pyridyl]-3-fluoro-1-methyl-4-[[3-(trifluoromethyl)oxetan-3-yl]sulfamoyl]pyrrole-2-carboxamide

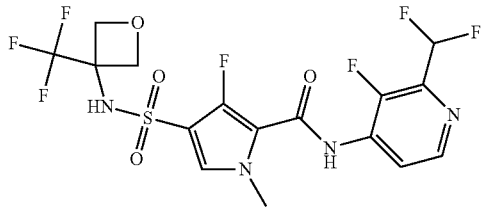

Compound 208 (70 mg) was prepared similarly as described for compound 198, using 2-(difluoromethyl)-3-fluoro-pyridin-4-amine (61.9 mg, 0.38 mmol) instead of 4-amino-2-chloropyridine. ¹H NMR (400 MHz, DMSO-d₆) δ ppm 3.86 (s, 3H), 4.66 (d, J=8.1 Hz, 2H), 4.84 (d, J=7.7 Hz, 2H), 7.13 (t, J=52.4 Hz, 1H), 7.67 (d, J=4.6 Hz, 1H), 8.21 (t, J=5.6 Hz, 1H), 8.46 (d, J=5.3 Hz, 1H), 9.29 (br. s., 1H), 10.30 (br. s., 1H) Method B: Rt: 0.91 min. m/z: 489.0 (M−H)⁻ Exact mass: 490.05.

Compound 209: N-(2-bromo-4-pyridyl)-3-fluoro-1-methyl-4-[[3-(trifluoromethyl)oxetan-3-yl]sulfamoyl]pyrrole-2-carboxamide

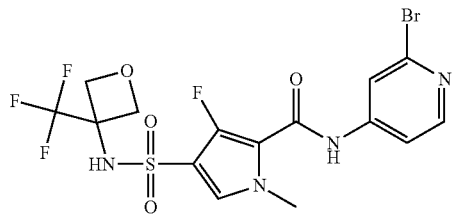 [SMILES: Cn1cc(S(=O)(=O)NC2(C(F)(F)F)COC2)c(F)c1C(=O)Nc1ccnc(Br)c1]

Compound 209 (70 mg) was prepared similarly as described for compound 198, using 4-amino-2-bromopyridine instead of 4-amino-2-chloropyridine. ¹H NMR (400 MHz, DMSO-d₆) δ ppm 3.83 (s, 3H), 4.66 (d, J=8.1 Hz, 2H), 4.84 (d, J=7.7 Hz, 2H), 7.58-7.70 (m, 2H), 7.97 (d, J=1.8 Hz, 1H), 8.28 (d, J=5.7 Hz, 1H), 9.27 (br. s., 1H), 10.61 (s, 1H) Method B: Rt: 0.9 min. m/z: 498.9 (M−H)⁻ Exact mass: 499.98.

Compound 210: N-[2-(difluoromethyl)-4-pyridyl]-3-fluoro-1-methyl-4-[[(3-(trifluoromethyl)oxetan-3-yl]sulfamoyl]pyrrole-2-carboxamide

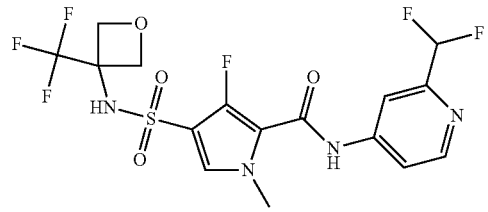 [SMILES: Cn1cc(S(=O)(=O)NC2(C(F)(F)F)COC2)c(F)c1C(=O)Nc1ccnc(C(F)F)c1]

Compound 210 (77 mg) was prepared similarly as described for compound 198, using 2-(difluoromethyl)pyridin-4-amine (55.1 mg, 0.38 mmol) instead of 4-amino-2-chloropyridine. ¹H NMR (400 MHz, DMSO-d₆) δ ppm 3.84 (s, 3H), 4.66 (d, J=8.1 Hz, 2H), 4.84 (d, J=7.7 Hz, 2H), 6.93 (t, J=55.0 Hz, 1H), 7.64 (d, J=4.4 Hz, 1H), 7.78 (m, J=5.5 Hz, 1H), 8.04 (d, J=1.8 Hz, 1H), 8.57 (d, J=5.5 Hz, 1H), 9.27 (br. s., 1H), 10.68 (s, 1H) Method B: Rt: 0.86 min. m/z: 471.0 (M−H)⁻ Exact mass: 472.06.

Compound 211: N-(2,6-difluoro-4-pyridyl)-3-fluoro-1-methyl-4-[[(3-(trifluoromethyl)oxetan-3-yl]sulfamoyl]pyrrole-2-carboxamide

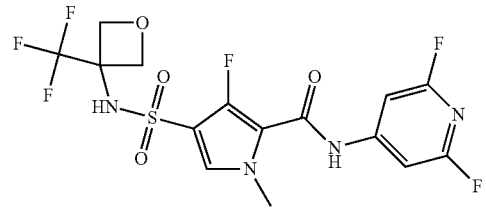 [SMILES: Cn1cc(S(=O)(=O)NC2(C(F)(F)F)COC2)c(F)c1C(=O)Nc1cc(F)nc(F)c1]

Compound 211 (40 mg) was prepared similarly as described for compound 198, using 4-amino-2,6-difluoropyridine instead of 4-amino-2-chloropyridine.

¹H NMR (400 MHz, DMSO-d₆) δ ppm 3.84 (s, 3H), 4.66 (d, J=8.1 Hz, 2H), 4.83 (d, J=7.7 Hz, 2H), 7.34 (s, 2H), 7.67 (d, J=4.2 Hz, 1H), 9.29 (br. s., 1H), 10.92 (s, 1H) Method B: Rt: 0.97 min. m/z: 457.0 (M−H)− Exact mass: 458.05.

Compound 212: N-(2-chloro-3-fluoro-4-pyridyl)-3-fluoro-1-methyl-4-[[3-(trifluoromethyl)oxetan-3-yl]sulfamoyl]pyrrole-2-carboxamide

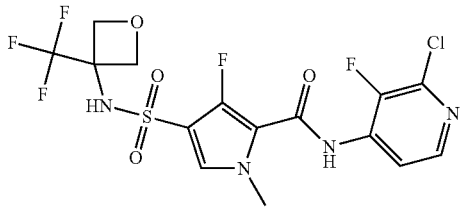 [SMILES: Cn1cc(S(=O)(=O)NC2(C(F)(F)F)COC2)c(F)c1C(=O)Nc1ccnc(Cl)c1F]

Compound 212 (43 mg) was prepared similarly as described for compound 198, using 2-chloro-3-fluoropyridin-4-amine instead of 4-amino-2-chloropyridine. $^1$H NMR (400 MHz, DMSO-$d_6$) δ ppm 3.85 (s, 3H), 4.66 (d, J=8.1 Hz, 2H), 4.84 (d, J=7.7 Hz, 2H), 7.67 (d, J=4.6 Hz, 1H), 8.03 (t, J=5.4 Hz, 1H), 8.21 (d, J=5.3 Hz, 1H), 9.29 (br. s., 1H), 10.31 (br. s., 1H) Method B: Rt: 0.95 min. m/z: 473.0 (M–H)– Exact mass: 474.02.

Compound 213: N-(2-chloro-6-methyl-4-pyridyl)-3-fluoro-1-methyl-4-[[(1R)-2,2,2-trifluoro-1-methyl-ethyl]sulfamoyl]pyrrole-2-carboxamide

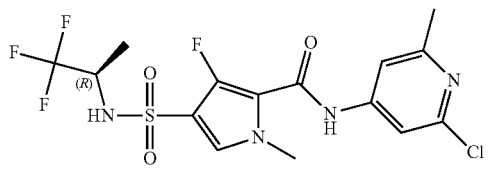

Compound 213 (212 mg) was prepared similarly as described for compound 152, using 2-chloro-6-methyl-pyridin-4-amine (142 mg, 0.79 mmol) instead of 2-fluoro-6-methyl-pyridin-4-amine. $^1$H NMR (400 MHz, DMSO-$d_6$) δ ppm 1.18 (d, J=6.8 Hz, 3H), 2.42 (s, 3H), 3.73-3.87 (m, 3H), 3.98 (dt, J=14.3, 7.2 Hz, 1H), 7.48 (d, J=1.1 Hz, 1H), 7.59 (d, J=4.4 Hz, 1H), 7.62 (d, J=1.1 Hz, 1H), 8.63 (br. s., 1H), 10.48 (br. s., 1H) Method B: Rt: 1.00 min. m/z: 441.0 (M–H)– Exact mass: 442.05.

Synthesis of 2-chloro-6-fluoro-pyridin-4-amine

A mixture of 2,6-dichloroisonicotinic acid (7 g, 36.46 mmol) and 2,4-dimethoxybenzylamine (5 g, 182.29 mmol) in a sealed tube was heated at 150° for 30 minutes under microwave irradiation. The reaction mixture was cooled and purified by prep-HPLC (Column: Phenomenex Synergi Max-RP 250*50 mm*10 um; Condition: 0.225% HCOOH-ACN FlowRate (mL/min): 80). The product fractions were concentrated resulting in 2-chloro-6-[(2,4-dimethoxyphenyl)methylamino]pyridine-4-carboxylic acid as a light yellow solid (6.5 g). NMR (400 MHz, DMSO-$d_6$) δ=7.56 (t, J=5.6 Hz, 1H), 7.13 (d, J=8.0 Hz, 1H), 6.98 (s., 1H), 6.79 (s, 1H), 6.56 (d, J=2.0 Hz, 1H), 6.47 (dd, J=2.0, 8.0 Hz, 1H), 4.32 (d, J=5.6 Hz, 2H), 3.80 (s, 3H), 3.73 (s, 3H).

Trimethylsilyl)diazomethane (8.7 mL, 17.5 mmol) was added dropwise to a solution of 2-chloro-6-[(2,4-dimethoxyphenyl)methylamino]pyridine-4-carboxylic acid (4.7 g, 14.56 mmol) in methanol (5 mL) and dichloromethane (15 mL) at 0° C. and stirred 25 minutes at 25° C. The solution was concentrated resulting in methyl 2-chloro-6-[(2,4-dimethoxyphenyl)methylamino]pyridine-4-carboxylate (5.0 g) as a yellow solid which was used as such. TFA (5 mL) was added to a solution of methyl 2-chloro-6-[(2,4-dimethoxyphenyl)methylamino]pyridine-4-carboxylate (5.0 g, 14.9 mmol) in dichloromethane (20 mL) and stirred 30 minutes at 25° C. The reaction mixture was concentrated. The resulting solid was triturated 30 minutes in methyl tert-butyl ether (40 mL). The solids were filtered off and washed with methyl tert-butyl ether (10 mL) resulting in methyl 2-amino-6-chloro-pyridine-4-carboxylate (3.0 g) as a light yellow solid. Sodium hydroxide (3.0 g, 75.0 mmol) was added to a solution of methyl 2-amino-6-chloro-pyridine-4-carboxylate (2.8 g, 15 mmol) in water (10 mL) and THF (40 mL) at 0° C. and stirred 3 hours at 25° C. The reaction mixture was cooled to 0° C. and acidified with HCl (7 mL). The brown solid was filtered off, washed with water (30 mL) and THF (10 mL) and was lyophilized, resulting in 2-amino-6-chloro-pyridine-4-carboxylic acid (2.2 g). $^1$H NMR (400 MHz, DMSO-$d_6$) δ=6.87 (s, 1H), 6.80 (s, 1H), 6.71 (br. s., 2H). 2-amino-6-chloro-pyridine-4-carboxylic acid (1.2 g, 6.95 mmol) was dissolved in toluene (10 mL). Then triethylamine (2.97 g, 8.35 mmol), benzyl alcohol (3.01 g, 27.82 mmol) and diphenylphosphoryl azide (2.97 g, 8.35 mmol) were added and heated at 110° C. during 16 hours. The reaction mixture was cooled. EtOAc (100 mL) was added and washed with NaHCO$_3$ (sat.aq. 60 mL). The mixture was filtered and the solids washed with EtOAc (30 mL) the organic layer was separated from the filtrate. The water layer was extracted with EtOAc (3×30 mL) The organic layers were combined and washed with brine (70 mL), dried over Na$_2$SO$_4$, filtered and concentrated under reduce pressure resulting in a brown oil. The oil was purified by column chromatography (SiO$_2$, Petroleum ether/Ethyl acetate=0 to 50% resulting in benzyl N-(2-amino-6-chloro-4-pyridyl)carbamate as a colorless oil. Sodium nitrite (894 mg, 12.96 mmol) was added to a solution of benzyl N-(2-amino-6-chloro-4-pyridyl)carbamate (360 mg, 1.30 mmol) in pyridine hydrofluoride (1 mL) at 0° C. and stirred 2 hours at 25° C. NaHCO$_3$ (100 mL sat.aq.) was added. The mixture was extracted with EtOAc (3×30 mL). The combined organic layers were washed with brine (70 mL), dried over Na$_2$SO$_4$, filtered, and concentrated in vacuo. The obtained residue was purified by column chromatography (SiO$_2$, Ethyl acetate/Petroleum ether=0 to 30%, TLC pentane:EtOAc=3:1, Rf=0.8) resulting in benzyl N-(2-chloro-6-fluoro-4-pyridyl)carbamate (200 mg) as a colorless oil. Platinumdioxide (10 mg) was added under nitrogen to a solution of benzyl N-(2-chloro-6-fluoro-4-pyridyl)carbamate in methanol (20 mL) and the mixture was stirred under hydrogen atmosphere for 16 hours at 25° C. The mixture was filtered and the filtrate was concentrated under reduced pressure. The residue was purified by prep-HPLC (Column: Phenomenex Gemini 150*25 mm*10 um. Condition: 0.05% ammonia-ACN). The obtained solid was dried resulting in 2-chloro-6-fluoro-pyridin-4-amine (33 mg) as a white solid. $^1$H NMR (400 MHz, DMSO-$d_6$) δ=6.83 (br. s., 2H), 6.46 (t, J=1.6 Hz, 1H), 6.06 (d, J=1.6 Hz, 1H).

Compound 215: N-(2-chloro-6-fluoro-4-pyridyl)-3-fluoro-1-methyl-4-[[(1R)-2,2,2-trifluoro-1-methylethyl]sulfamoyl]pyrrole-2-carboxamide

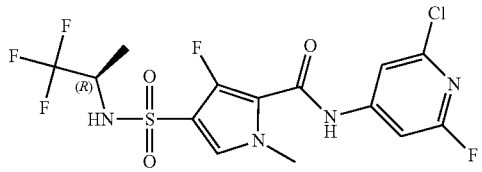

Ethyl 3-fluoro-1-methyl-4-[[(1R)-2,2,2-trifluoro-1-methyl-ethyl]sulfamoyl]pyrrole-2-carboxylate (78 mg, 0.23 mmol) and 2-chloro-6-fluoro-pyridin-4-amine (33 mg, 0.23 mmol) were dissolved in THF (5 mL). Lithium bis(trimethylsilyl)amide (0.68 mL, 1 M, 0.68 mmol) was added and the reaction mixture was stirred at room temperature for 90 minutes. More lithium bis(trimethylsilyl)amide (0.68 mL, 1 M, 0.68 mmol) was added and the reaction mixture was stirred at room temperature for 30 minutes. The reaction mixture was quenched with sat. NH$_4$Cl (1 mL) and the organic layer was separated. The aqueous layer was extracted with CH$_2$Cl$_2$ (2×3 mL) and the combined organic layers were evaporated to dryness. The residue was dissolved in DMF (0.5 mL) and purified using silica gel column chromatography using ethyl acetate in heptane from 0 to 100% to afford a white solid which was purified via Preparative HPLC (Stationary phase: RP XBridge Prep C18 OBD-10 µm, 30×150 mm, Mobile phase: 0.25% NH$_4$HCO$_3$ solution in water, CH$_3$CN) to afford compound 215 (42 mg). Method B: Rt: 1.19 min. m/z: 445.0 (M−H)$^-$ Exact mass: 446.02. $^1$H NMR (400 MHz, DMSO-d$_6$) δ ppm 1.18 (d, J=7.0 Hz, 3H), 3.82 (s, 3H), 3.91-4.06 (m, 1H), 7.43 (d, J=1.5 Hz, 1H), 7.62 (d, J=4.6 Hz, 1H), 7.69 (d, J=0.9 Hz, 1H), 8.69 (br. s., 1H), 10.76 (br. s., 1H).

Synthesis of 2-bromo-6-fluoro-pyridin-4-amine 2,6-difluoropyridin-4-amine (250 mg, 1.92 mmol) in acetic anhydride (20 mL, 212 mmol) was stirred at 100° C. for 3 h. After cooling to 20° C., water (30 mL) was added and stirred for another 30 min. The aqueous phase was basified with aqueous NaHCO$_3$ to pH=10 and extracted with CH$_2$Cl$_2$ (3×20 mL). The organic layer was separated, dried over Na$_2$SO$_4$, filtered and concentrated to dryness. The residue was purified by column chromatography on silica (eluent: petroleum ether/ethyl acetate from 100/0 to 30/70) The product fractions were concentrated resulting in a yellow solid (240 mg, 1.36 mmol). To a solution of N-(2,6-difluoropyridin-4-yl)acetamide (180 mg, 1.05 mmol) in AcOH (4 mL) was added HBr/AcOH (35%, 6.5 g, 16.1 mmol) in a sealed tube which was stirred at 120° C. under microwave irradiation for 1 h. The reaction mixture was concentrated to dryness and was further purified by preparative high performance liquid chromatography over Phenomenex Gemini 150*25 mm*10 um (eluent: HCOOH-ACN/H$_2$O from 3% to 33%, v/v, flow rate: 30 ml/min). The pure fractions were collected and the volatiles were removed under vacuum. The aqueous layer was lyophilized to dryness resulting in 2-bromo-6-fluoro-pyridin-4-amine (9.9 mg). $^1$H NMR (400 MHz, CHLOROFORM-d) δ=6.62 (dd, J=1.0, 1.8 Hz, 1H), 6.05 (d, J=2.0 Hz, 1H), 4.52 (br. s., 2H).

Compound 216: N-(2-bromo-6-fluoro-4-pyridyl)-3-fluoro-1-methyl-4-[[(1R)-2,2,2-trifluoro-1-methylethyl]sulfamoyl]pyrrole-2-carboxamide

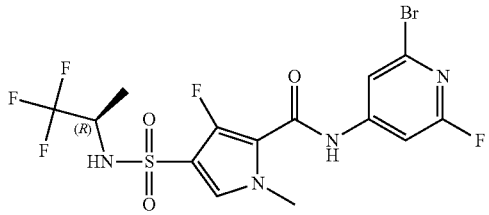

Compound 216 (9 mg) was prepared similarly as described for compound 215, starting from ethyl 3-fluoro-1-methyl-4-[[(1R)-2,2,2-tri fluoro-1-methyl-ethyl]sulfamoyl]pyrrole-2-carboxylate (16 mg), using 2-bromo-6-fluoro-pyridin-4-amine (9 mg) instead of 2-chloro-6-fluoro-pyridin-4-amine. Method B: Rt: 1.20 min. m/z: 488.9 (M−H)$^-$ Exact mass: 489.97. $^1$H NMR (400 MHz, DMSO-d$_6$) δ ppm 1.18 (d, J=6.8 Hz, 3H), 3.82 (s, 3H), 3.92-4.02 (m, 1H), 7.41-7.47 (m, 1H), 7.56-7.63 (m, 1H), 7.80-7.85 (m, 1H), 8.65 (br. s, 1H), 10.75 (br. s, 1H).

Compound 217: N-(2-chloro-4-pyridyl)-3-fluoro-1-methyl-4-[[1-(2,2,2-trifluoroethyl)-4-piperidyl]sulfamoyl]pyrrole-2-carboxamide

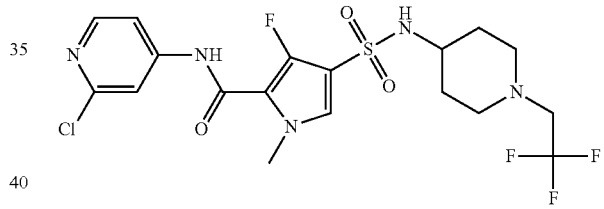

Ethyl 4-chlorosulfonyl-3-fluoro-1-methyl-pyrrole-2-carboxylate (1 g, 3.71 mmol), molecular sieves (4 Å) and 1-(2,2,2-trifluoroethyl)piperidin-4-amine (1.35 g, 7.42 mmol) were dissolved in CH$_3$CN (19 mL) and NaHCO$_3$ (935 mg, 11.1 mmol) was added at room temperature. The solution was then heated to 80° C. for 1 hour. The solution was filtered off, concentrated in vacuo, extracted with EtOAc and washed with water. The EtOAc layer was filtered and the filtrate concentrated in vacuo resulting in ethyl 3-fluoro-1-methyl-4-[[1-(2,2,2-trifluoroethyl)-4-piperidyl]sulfamoyl]pyrrole-2-carboxylate (1.47 g) as a light yellow solid. To ethyl 3-fluoro-1-methyl-4-[[1-(2,2,2-trifluoroethyl)-4-piperidyl]sulfamoyl]pyrrole-2-carboxylate (393 mg, 0.946 mmol) and 2-chloropyridin-4-amine (158 mg, 1.23 mmol) in dry THF (17 mL) under nitrogen, LiHMDS (1M in hexane) (3.78 mL, 1 M, 3.78 mmol) was added dropwise at 0° C. After 16 hours, NH$_4$Cl was added and the solution diluted with EtOAc (200 mL). The combined organics were dried with MgSO$_4$, filtered off and concentrated in vacuo. The crude was purified by silica gel chromatography using gradient elution from 100/0 to 50/50 Heptane/EtOAc followed by precipitation from diisopropylether and finally crystallisation from MeOH/water, resulting in compound 217 (300 mg) as a solid. DSC: From 30 to 300° C. at 10° C./min, peak 191.8° C. $^1$H NMR (400 MHz, DMSO-$d_6$) δ ppm 1.40-1.51 (m, 2H) 1.63-1.71 (m, 2H) 2.28-2.36 (m, 2H) 2.79-2.85 (m, 2H) 2.99-3.16 (m, 3H) 3.80 (s, 3H) 7.51 (d, J=4.8 Hz, 1H) 7.60 (dd, J=5.7, 2.0 Hz, 1H) 7.76 (d, J=7.5 Hz, 1H) 7.81 (d, J=1.5 Hz, 1H) 8.29 (d, J=6.8 Hz, 1H) 10.53 (s, 1H). Method B: Rt: 1.06 min. m/z: 496.0 (M−H)⁻ Exact mass: 497.09.

Biological Examples—Anti-HBV Activity of Compounds of Formula (IA)

The anti-HBV activity was measured using a stable transfected cell line, HepG2.2.15. This cell line was described to secrete relatively consistent high levels of HBV virion particles, which have been shown to cause both acute and chronic infection and disease in chimpanzees. For the antiviral, assay cells were treated twice for three days with serially diluted compound in 96-well plates in duplicate. After 6 days of treatment the antiviral activity was determined by quantification of purified HBV DNA from secreted virions using realtime PCR and an HBV specific primer set and probe.

The anti HBV activity was also measured using the HepG2.117 cell line, a stable, inducibly HBV producing cell line, which replicates HBV in the absence of doxicycline (Tet-off system). For the antiviral assay, HBV replication was induced, followed by a treatment with serially diluted compound in 96-well plates in duplicate. After 3 days of treatment, the antiviral activity was determined by quantification of intracellular HBV DNA using realtime PCR and an HBV specific primer set and probe.

Cytotoxicity of the compounds was tested using HepG2 cells, incubated for 4 days in the presence of compounds. The viability of the cells was assessed using a Resazurin assay. Results are displayed in Table 1.

Alternatively, cytotoxicity was determined via an ATP-assay: The ATPlite kit from Perkin Elmer was used to assess compound cytotoxicity on the HepG2 cell line by determination of the ATP (adenosine triphosphate) levels. ATP is a marker for functional integrity and cell viability, because it is present in all metabolically active cells and any form of cell injury will result in a rapid decline in cellular ATP concentration. After compound incubation, 1 volume of ATPlite solution was added to the cells and the luminescence signal was measured. Results are displayed in table 2.

TABLE 1 anti HBV activity and cytotoxicity

| Co. No. | HepG2 2.15 $EC_{50}$ (µM) | HepG2 117 $EC_{50}$ (µM) | HepG2 4 days $CC_{50}$ (µM) |
|---|---|---|---|
| 1 | 0.86 | 0.65 | >25 |
| 2 | >1 | 10.4 | >25 |
| 3 | >1 | 0.75 | >25 |
| 4 | >1 | 2.34 | >25 |
| 5 | 0.92 | 3.11 | >25 |
| 6 | 0.59 | 0.65 | >25 |
| 7 | 0.09 | 0.25 | >25 |
| 8 | 0.09 | 0.17 | >25 |
| 9 | 0.02 | 0.04 | >25 |
| 10 | 0.07 | 0.16 | >25 |
| 11 | 0.02 | 0.06 | >25 |
| 12 | 0.01 | 0.02 | >25 |
| 13 | 0.11 | 0.18 | >25 |
| 14 | 0.06 | 0.12 | >25 |
| 15 | >1 | >1 | >25 |
| 16 | 0.40 | 0.28 | >25 |
| 17 | 0.75 | 0.53 | >25 |
| 18 | 0.03 | 0.03 | >25 |
| 19 | 0.16 | 0.10 | >25 |
| 20 | 0.03 | 0.02 | >25 |
| 21 | 0.04 | 0.03 | >25 |
| 22 | 0.44 | 0.72 | >25 |
| 23 | 0.01 | 0.01 | >25 |
| 24 | 0.04 | 0.04 | >25 |
| 25 | 0.19 | >1 | >25 |
| 26 | 0.11 | >1 | >25 |
| 27 | | 0.10 | >25 |
| 28 | 0.36 | 0.70 | >25 |
| 29 | 0.04 | 0.06 | >25 |
| 30 | <0.1 | 0.01 | >25 |
| 31 | 0.03 | 0.04 | >25 |
| 32 | 0.02 | 0.02 | >25 |
| 33 | 0.008 | 0.01 | >25 |
| 34 | 0.05 | 0.10 | >25 |
| 35 | 0.005 | 0.01 | >25 |
| 36 | | 0.15 | >25 |
| 37 | 0.15 | 0.20 | >25 |
| 38 | 0.04 | 0.05 | >25 |
| 39 | 0.09 | 0.09 | >25 |
| 40 | 0.02 | 0.02 | >25 |
| 41 | 0.07 | 0.10 | >25 |
| 42 | 0.05 | 0.08 | >25 |
| 43 | | 0.08 | >25 |
| 44 | | 0.64 | >25 |
| 45 | 0.05 | 0.04 | >25 |
| 46 | 0.01 | 0.02 | >25 |
| 47 | 0.06 | 0.04 | >25 |
| 48 | 0.06 | 0.04 | >25 |
| 49 | 0.11 | 0.11 | >25 |
| 50 | | 0.20 | >25 |
| 51 | | 0.60 | >25 |
| 52 | | 0.08 | >25 |
| 53 | | 0.04 | >25 |
| 54 | | 0.02 | >25 |
| 55 | | 0.07 | >25 |
| 56 | | 0.05 | >25 |
| 57 | | 0.06 | >25 |
| 58 | | 0.14 | >25 |
| 59 | | 0.07 | >25 |
| 60 | 0.24 | 0.04 | >25 |
| 61 | 0.01 | 0.02 | >25 |
| 62 | | 0.19 | >25 |
| 63 | 0.01 | 0.03 | >25 |
| 64 | 0.02 | 0.03 | 23 |
| 65 | 0.02 | 0.03 | >25 |
| 66 | | 0.09 | >25 |
| 67 | | 0.03 | >25 |
| 68 | | 0.05 | >25 |
| 69 | | 0.03 | >25 |
| 70 | | 0.15 | >25 |
| 71 | | 0.02 | >25 |
| 72 | | 0.10 | >25 |
| 73 | | 0.09 | 21.6 |
| 74 | 0.02 | 0.02 | >25 |
| 75 | | 0.06 | >25 |
| 76 | | 0.05 | >25 |
| 77 | | 0.30 | >25 |
| 78 | | 0.26 | >25 |
| 79 | | 0.15 | >25 |
| 80 | 0.01 | 0.02 | >25 |
| 81 | 0.01 | 0.008 | 24.3 |
| 82 | 0.07 | 0.10 | >25 |
| 83 | | 0.01 | >25 |
| 84 | | 0.11 | >25 |
| 85 | 0.02 | 0.04 | 24 |
| 86 | | 0.04 | 21.6 |
| 87 | 0.02 | 0.03 | >25 |
| 88 | 0.007 | 0.01 | >25 |
| 89 | | 0.36 | >25 |
| 90 | | 0.45 | >25 |
| 91 | | 0.20 | >25 |
| 92 | | 0.44 | >25 |

TABLE 1-continued anti HBV activity and cytotoxicity

| Co. No. | HepG2 2.15 EC$_{50}$ (μM) | HepG2 117 EC$_{50}$ (μM) | HepG2 4 days CC$_{50}$ (μM) |
|---|---|---|---|
| 93 |  | 0.33 | >25 |
| 94 |  | 0.03 | >25 |
| 95 | 0.06 | 0.04 | 21.6 |
| 96 | 0.04 | 0.04 | >25 |
| 97 | 0.02 | 0.02 | >25 |
| 98 | 0.04 | 0.03 | >25 |
| 99 | 0.01 | 0.02 | >25 |
| 100 |  | 0.08 | >25 |
| 101 |  | 0.43 | >25 |
| 102 |  | 0.18 | >25 |
| 103 |  | 0.14 | >25 |
| 104 | <0.1 | 0.01 | >25 |
| 105 | <0.1 | 0.02 | >25 |
| 106 |  | 0.02 | >25 |
| 107 |  | 0.02 | >25 |
| 108 |  | 0.02 | >25 |
| 109 |  | 0.01 | >25 |
| 110 |  | 0.02 | >25 |
| 111 |  | 0.03 | >25 |
| 112 |  | 0.02 | >25 |
| 113 |  | 0.01 | >25 |
| 114 |  | 0.01 | >25 |
| 115 |  | 0.006 | >25 |
| 116 | 0.21 | 0.02 | >25 |
| 117 |  | 0.01 | >25 |
| 118 | 0.1 | 0.01 | >25 |
| 119 |  | 0.005 | >25 |
| 120 |  | 0.005 | >25 |
| 121 |  | 0.04 | >25 |
| 122 |  | 0.01 | >25 |
| 123 |  | 0.01 | >25 |
| 124 | <0.1 | 0.01 | >25 |
| 125 | <0.1 | 0.008 | >25 |
| 126 | 0.02 | 0.02 | >25 |
| 127 |  | 0.05 | >25 |
| 127a |  | 0.03 | >25 |
| 127b |  | 0.16 | >25 |
| 128 |  | 0.04 | >25 |
| 129 | 0.81 | 0.40 | >25 |
| 130 |  | 0.06 | >25 |
| 131 |  | 0.02 | >25 |
| 132 |  | 0.01 | >25 |
| 133 |  | 0.05 | >25 |
| 134 |  | 0.01 | >25 |
| 135 |  | 0.18 | 13 |
| 136 |  | 0.02 |  |
| 137 | <0.1 | 0.02 | >25 |
| 138 |  | 0.09 | >25 |
| 139 |  | 0.02 | >25 |
| 140 |  | 0.20 | >25 |
| 141 |  | 0.04 | >25 |
| 142 |  | 0.02 | >25 |
| 143 | 0.18 | 0.02 | >25 |
| 144 |  | 0.30 | >25 |
| 145 |  | 0.08 |  |
| 146 |  | 0.03 | >25 |
| 147 |  | 0.02 | >25 |
| 148 |  | 0.02 | >25 |
| 149 |  | 0.06 | >25 |
| 150 |  | 0.09 | >25 |
| 151 |  | 0.03 | >25 |
| 152 | <0.1 | 0.01 | >25 |
| 153 |  | 0.02 | >25 |
| 154 |  | 0.08 | >25 |
| 155 |  | 0.02 | >25 |
| 156 |  | 0.14 | >25 |
| 157 |  | 0.09 | >25 |
| 158 |  | 0.05 | >25 |
| 159 | <0.1 | 0.009 | >25 |
| 160 |  | 0.01 | >25 |
| 161 |  | 0.01 | >25 |
| 162 |  | 0.02 |  |
| 163 |  | 0.02 | >25 |
| 164 |  | 0.04 | >25 |
| 165 |  | 0.003 | >25 |
| 166 |  | 0.003 | >25 |
| 167 |  | 0.005 | >25 |
| 168 |  | 0.006 | >25 |
| 169 |  | 0.03 | >25 |
| 170 |  | 0.04 | >25 |
| 171 |  | 0.10 | >25 |
| 172 |  | 0.01 | >25 |
| 173 |  | 0.02 | >25 |
| 174 |  | 0.11 |  |
| 174a |  | 0.20 |  |
| 174b |  | 0.04 |  |
| 175 | 0.12 | 0.02 |  |
| 176 | <0.1 | 0.003 |  |
| 177 | 0.26 | 0.10 |  |
| 178 | 0.24 | 0.05 |  |
| 179 | 0.21 | 0.07 |  |
| 180 |  | 0.63 | >25 |
| 181 |  | 1.0 | >25 |
| 182 |  | 1.3 | >25 |
| 183 |  | 1.4 | >25 |
| 184 |  | 1.2 | >25 |
| 185 |  | 0.74 | >25 |
| 186 |  | 10.5 | >25 |
| 187 |  | 0.71 | >25 |
| 188 |  | 0.10 |  |
| 189 |  | 0.06 |  |
| 190 |  | 0.05 |  |
| 191 |  | 0.06 |  |
| 192 |  | 0.02 |  |
| 193 |  | 0.009 |  |
| 194 |  | 0.02 |  |
| 195 |  | 0.02 |  |
| 196 |  | 0.02 |  |
| 197 |  | 0.01 |  |
| 198 |  | 0.09 |  |
| 199 | <0.1 | 0.006 |  |
| 200 | 0.11 | 0.02 |  |
| 201 |  | 0.03 |  |
| 202 |  | 0.008 |  |
| 203 |  | 0.008 |  |
| 204 |  | 0.01 |  |
| 205 |  | 0.02 |  |
| 206 |  | 0.02 |  |
| 207 |  | 0.01 |  |
| 208 |  | 0.04 |  |
| 209 |  | 0.09 |  |
| 210 |  | 0.07 |  |
| 211 |  | 0.05 |  |
| 212 |  | 0.06 |  |
| 213 |  | 0.05 |  |
| 214 |  | 0.08 |  |
| 215 |  | 0.006 |  |
| 216 |  | 0.01 |  |
| 217 |  | 0.46 |  |

TABLE 2 results of ATP based toxicity assay

| Co. No. | HepG2 4 days ATPlite CC$_{50}$ (μM) |
|---|---|
| 7 | >25 |
| 9 | >25 |
| 12 | >25 |
| 18 | >25 |
| 20 | >25 |

TABLE 2-continued results of ATP based toxicity assay

| Co. No. | HepG2 4 days ATPlite CC$_{50}$ (μM) |
|---|---|
| 23 | >25 |
| 24 | >25 |
| 32 | >25 |
| 40 | >25 |
| 46 | >25 |
| 53 | >25 |
| 61 | >25 |
| 63 | >25 |
| 74 | >25 |
| 80 | >25 |
| 81 | >25 |
| 83 | >25 |
| 88 | >25 |
| 95 | >25 |
| 97 | >25 |
| 98 | >25 |
| 99 | >25 |
| 100 | >25 |
| 104 | >25 |
| 105 | 23.3 |
| 106 | >25 |
| 108 | >25 |
| 113 | 23.7 |
| 115 | >25 |
| 127a | >25 |
| 127b | >25 |
| 132 | >25 |
| 134 | >25 |
| 136 | 9.5 |
| 139 | >25 |
| 145 | >25 |
| 146 | >25 |
| 152 | >25 |
| 154 | >25 |
| 158 | >25 |
| 159 | >25 |
| 160 | >25 |
| 162 | >25 |
| 172 | >25 |
| 174 | >25 |
| 174a | >25 |
| 174b | >25 |
| 175 | >25 |
| 176 | >25 |
| 177 | >25 |
| 178 | >25 |
| 179 | >25 |
| 185 | >25 |
| 188 | >25 |
| 189 | >25 |
| 190 | >25 |
| 191 | >25 |
| 192 | >25 |
| 193 | >25 |
| 194 | >25 |
| 195 | >25 |
| 196 | >25 |
| 197 | >25 |
| 198 | >25 |
| 199 | >25 |
| 200 | >25 |
| 201 | >25 |
| 202 | >25 |
| 203 | >25 |
| 204 | >25 |
| 205 | >25 |
| 206 | >25 |
| 207 | >25 |
| 208 | >25 |
| 209 | >25 |
| 210 | >25 |
| 211 | >25 |
| 212 | >25 |
| 213 | >25 |
| 214 | >25 |
| 215 | >25 |
| 216 | >25 |
| 217 | >25 |

The invention claimed is:

1. A compound of Formula (A)

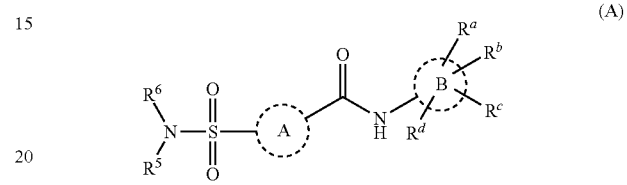

or a stereoisomer or tautomeric form thereof, wherein:

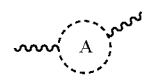

is

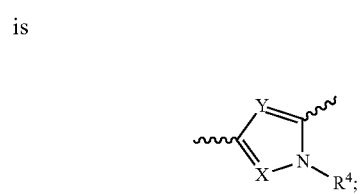

is a 6 membered heteroaryl containing one nitrogen atom;
X is CR$^7$;
Y is CR$^8$;
R$^a$, R$^b$, R$^c$ and R$^d$ are independently selected from the group consisting of hydrogen, fluoro, bromo, chloro, —CHF$_2$, —CF$_2$-methyl, —CH$_2$F, —CF$_3$, —OCF$_3$, —CN, C$_3$-C$_4$cycloalkyl and —C$_1$-C$_4$alkyl;
R$^4$ is hydrogen, —C$_1$-C$_3$alkyl or C$_3$-C$_4$cycloalkyl;
R$^5$ is hydrogen;
R$^6$ is selected from the group consisting of C$_2$-C$_6$alkyl, and a 3-7 membered saturated ring optionally containing one or more heteroatoms each independently selected from the group consisting of O, S and N, wherein said 3-7 membered saturated ring and said C$_2$-C$_6$alkyl are optionally substituted with one or more substituents each independently selected from the group consisting of hydrogen, —OH, fluoro, oxo, and C$_1$-C$_4$alkyl wherein said C$_1$-C$_4$alkyl is optionally substituted with one or more substituents selected from the group consisting of fluoro and —OH; and
R$^7$ and R$^8$ are each independently selected from the group consisting of hydrogen, methyl, —CN, fluoro, bromo and chloro;
or a pharmaceutically acceptable salt or a solvate thereof.

2. A compound according to claim 1 with Formula (ID)

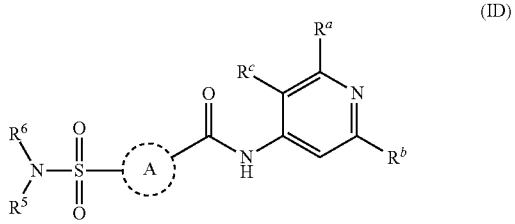
(ID)

or a stereoisomer or tautomeric form thereof, wherein:

is

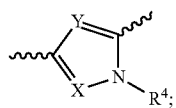

X is CR$^7$;
Y is CR$^8$;
R$^a$ is selected from the group consisting of fluoro, bromo, chloro, —CHF$_2$, —CF$_2$-methyl, —CH$_2$F, —CF$_3$, —OCF$_3$, —CN, C$_3$-C$_4$cycloalkyl and —C$_1$-C$_4$alkyl;
R$^b$ and R$^c$ are each independently hydrogen or fluoro;
R$^4$ is hydrogen, —C$_1$-C$_3$alkyl or C$_3$-C$_4$cycloalkyl;
R$^5$ is hydrogen;
R$^6$ is selected from the group consisting of C$_2$-C$_6$alkyl, a 3-7 membered saturated ring optionally containing one or more heteroatoms each independently selected from the group consisting of O, S and N, such 3-7 membered saturated ring or C$_2$-C$_6$alkyl optionally being substituted with one or more substituents each independently selected from the group consisting of hydrogen, —OH, fluoro, oxo, and C$_1$-C$_4$alkyl optionally substituted with one or more fluoro and/or —OH; and
R$^7$ and R$^8$ are each independently hydrogen, methyl, —CN, fluoro or chloro;
or a pharmaceutically acceptable salt or a solvate thereof.

3. A compound according to claim 1 wherein R$^4$ is methyl.

4. A compound according to claim 1 wherein R$^6$ contains a 3-7 membered saturated ring optionally containing one oxygen.

5. A compound according to claim 1 wherein R$^6$ is a 4 membered saturated ring containing one oxygen, and wherein said 4 membered saturated ring is optionally substituted with one or more C$_1$-C$_4$alkyl.

6. A compound according to claim 1 wherein R$^6$ is a branched C$_3$-C$_6$alkyl optionally substituted with one or more fluoro, or wherein R$^6$ is a C$_3$-C$_6$cycloalkyl wherein said C$_3$-C$_6$cycloalkyl is substituted with one or more fluoro or substituted with C$_1$-C$_4$ substituted with one or more fluoro.

7. A compound according to claim 6 wherein R$^6$ is a branched C$_3$-C$_6$alkyl substituted with one or more fluoro.

8. A compound according to claim 1 wherein R$^8$ is fluoro or chloro.

9. A compound according to claim 1 wherein R$^b$ and R$^c$ are each hydrogen.

10. A method of treating an HBV infection comprising administering a therapeutically effective amount of at least one compound according to claim 1.

11. A pharmaceutical composition comprising a compound according to claim 1, and a pharmaceutically acceptable carrier.

12. A product containing (a) a compound according to claim 1, and (b) at least one HBV inhibitor, as a combined preparation for simultaneous, separate or sequential use in the treatment of HBV infections.

13. A compound according to claim 1, wherein
R$^4$ is methyl;
R$^6$ is a branched C$_3$-C$_6$alkyl optionally substituted with one or more fluoro, or R$^6$ is a C$_3$-C$_6$cycloalkyl optionally substituted with one or more fluoro or substituted with C$_1$-C$_4$ optionally substituted with one or more fluoro;
R$^8$ is fluoro or chloro; and
R$^a$, R$^b$, R$^c$ and R$^d$ are each independently selected from the group consisting of hydrogen, fluoro, bromo, chloro, —CHF$_2$, —CF$_2$-methyl, —CH$_2$F, —CF$_3$, —OCF$_3$, —CN, C$_3$-C$_4$cycloalkyl and —C$_1$-C$_4$alkyl.

14. A compound according to claim 2, wherein R$^4$ is methyl.

15. A compound according to claim 2, wherein R$^6$ contains a 3-7 membered saturated ring optionally containing one oxygen.

16. A compound according to claim 2, wherein R$^8$ is fluoro or chloro.

17. A compound according to claim 1 selected from the group consisting of:
N-(2-cyanopyridin-4-yl)-1-methyl-4-[(3-methyloxetan-3-yl)sulfamoyl]-1H-pyrrole-2-carboxamide;
1-methyl-4-[(3-methyloxetan-3-yl)sulfamoyl]-N-[5-(trifluoromethyl)pyridin-3-yl]-1H-pyrrole-2-carboxamide;
N-(6-fluoro-5-methylpyridin-3-yl)-1-methyl-4-[(3-methyloxetan-3-yl)sulfamoyl]-1H-pyrrole-2-carboxamide;
1-methyl-4-[(3-methyloxetan-3-yl)sulfamoyl]-N-[4-(trifluoromethyl)pyridin-2-yl]-1H-pyrrole-2-carboxamide;
1-methyl-4-[(3-methyloxetan-3-yl)sulfamoyl]-N-[6-(trifluoromethyl)pyridin-2-yl]-1H-pyrrole-2-carboxamide;
4-(tert-butylsulfamoyl)-3-chloro-N-(2-cyanopyridin-4-yl)-1-methyl-1H-pyrrole-2-carboxamide;
3-chloro-N-(5-fluoro-6-methylpyridin-2-yl)-1-methyl-4-{[(1R)-2,2,2-trifluoro-1-methylethyl]sulfamoyl}-1H-pyrrole-2-carboxamide;
3-chloro-1-methyl-N-(2-methylpyridin-4-yl)-4-{[(1R)-2,2,2-trifluoro-1-methylethyl]sulfamoyl}-1H-pyrrole-2-carboxamide;
3-chloro-N-(2-cyanopyridin-4-yl)-1-methyl-4-{[(1R)-2,2,2-trifluoro-1-methylethyl]sulfamoyl}-1H-pyrrole-2-carboxamide;
3-chloro-1-methyl-4-{[(1R)-2,2,2-trifluoro-1-methylethyl]sulfamoyl}-N-[2-(trifluoromethyl)pyridin-4-yl]-1H-pyrrole-2-carboxamide;
3-chloro-N-(2-fluoropyridin-4-yl)-1-methyl-4-{[(1R)-2,2,2-trifluoro-1-methylethyl]sulfamoyl}-1H-pyrrole-2-carboxamide;
3-chloro-N-(2-chloropyridin-4-yl)-1-methyl-4-{[(1R)-2,2,2-trifluoro-1-methylethyl]sulfamoyl}-1H-pyrrole-2-carboxamide;

3-chloro-N-(6-fluoro-5-methylpyridin-3-yl)-1-methyl-4-{[(1R)-2,2,2-trifluoro-1-methylethyl]sulfamoyl}-1H-pyrrole-2-carboxamide;

3-chloro-N-(3-fluoro-2-methyl-4-pyridyl)-1-methyl-4-[[(1R)-2,2,2-trifluoro-1-methyl-ethyl]sulfamoyl]pyrrole-2-carboxamide;

3-chloro-1-methyl-N-(2-pyridyl)-4-[[(1R)-2,2,2-trifluoro-1-methyl-ethyl]sulfamoyl]pyrrole-2-carboxamide;

3-chloro-1-methyl-N-(4-pyridyl)-4-[[(1R)-2,2,2-trifluoro-1-methyl-ethyl]sulfamoyl]pyrrole-2-carboxamide;

3-chloro-1-methyl-N-(3-pyridyl)-4-[[(1R)-2,2,2-trifluoro-1-methyl-ethyl]sulfamoyl]pyrrole-2-carboxamide;

N-(2-Cyanopyridin-4-yl)-3-fluoro-1-methyl-4-{[(1R)-2,2,2-trifluoro-1-methylethyl]sulfamoyl}-1H-pyrrole-2-carboxamide;

N-(2-Cyanopyridin-4-yl)-3-fluoro-1-methyl-4-{[(1S)-2,2,2-trifluoro-1-methylethyl]sulfamoyl}-1H-pyrrole-2-carboxamide;

N-(2-chloro-4-pyridyl)-3-fluoro-1-methyl-4-[[(1R)-2,2,2-trifluoro-1-methyl-ethyl]sulfamoyl]pyrrole-2-carboxamide;

3-fluoro-1-methyl-4-[[(1R)-2,2,2-trifluoro-1-methyl-ethyl]sulfamoyl]-N-[2-(trifluoromethyl)-4-pyridyl]pyrrole-2-carboxamide;

3-chloro-N-(6-cyano-2-pyridyl)-1-methyl-4-[[(1R)-2,2,2-trifluoro-1-methyl-ethyl]sulfamoyl]pyrrole-2-carboxamide;

N-(2-bromo-4-pyridyl)-3-fluoro-1-methyl-4-[[(1R)-2,2,2-trifluoro-1-methyl-ethyl]sulfamoyl]pyrrole-2-carboxamide;

3-fluoro-N-(2-fluoro-4-pyridyl)-1-methyl-4-[[(1R)-2,2,2-trifluoro-1-methyl-ethyl]sulfamoyl]pyrrole-2-carboxamide;

N-(6-cyano-2-pyridyl)-3-fluoro-1-methyl-4-[[(1R)-2,2,2-trifluoro-1-methyl-ethyl]sulfamoyl]pyrrole-2-carboxamide;

3-fluoro-1-methyl-4-[[(1R)-2,2,2-trifluoro-1-methyl-ethyl]sulfamoyl]-N-[6-(trifluoromethyl)-2-pyridyl]pyrrole-2-carboxamide;

N-(2-cyano-4-pyridyl)-3-fluoro-4-(isopropylsulfamoyl)-1-methyl-pyrrole-2-carboxamide;

3-fluoro-N-(5-fluoro-2-pyridyl)-1-methyl-4-[[(1R)-2,2,2-trifluoro-1-methyl-ethyl]sulfamoyl]pyrrole-2-carboxamide;

N-(5-bromo-6-fluoro-3-pyridyl)-3-fluoro-1-methyl-4-[[(1R)-2,2,2-trifluoro-1-methyl-ethyl]sulfamoyl]pyrrole-2-carboxamide;

N-(2,6-difluoro-4-pyridyl)-3-fluoro-1-methyl-4-[[(1R)-2,2,2-trifluoro-1-methyl-ethyl]sulfamoyl]pyrrole-2-carboxamide;

N-(2-cyano-4-pyridyl)-3-fluoro-1-methyl-4-[[(1R)-1-(trifluoromethyl)propyl]sulfamoyl]pyrrole-2-carboxamide;

3-chloro-N-(2-cyano-4-pyridyl)-1,5-dimethyl-4-[[(1R)-2,2,2-trifluoro-1-methyl-ethyl]sulfamoyl]pyrrole-2-carboxamide;

3-chloro-N-(2-chloro-3-fluoro-4-pyridyl)-1-methyl-4-[[(1R)-2,2,2-trifluoro-1-methyl-ethyl]sulfamoyl]pyrrole-2-carboxamide;

N-(5-bromo-6-fluoro-3-pyridyl)-3-chloro-1-methyl-4-[[(1R)-2,2,2-trifluoro-1-methyl-ethyl]sulfamoyl]pyrrole-2-carboxamide;

3-chloro-N-(2,6-difluoro-4-pyridyl)-1-methyl-4-[[(1R)-2,2,2-trifluoro-1-methyl-ethyl]sulfamoyl]pyrrole-2-carboxamide;

3-chloro-N-(2-cyano-6-methyl-4-pyridyl)-1-methyl-4-[[(1R)-2,2,2-trifluoro-1-methyl-ethyl]sulfamoyl]pyrrole-2-carboxamide;

3-chloro-N-(2-cyano-4-pyridyl)-1-methyl-4-[[(1S)-1-(trifluoromethyl)propyl]sulfamoyl]pyrrole-2-carboxamide;

3-chloro-N-(2-cyano-4-pyridyl)-1-methyl-4-[[(1R)-1-(trifluoromethyl)propyl]sulfamoyl]pyrrole-2-carboxamide;

3-chloro-N-(2-cyano-4-pyridyl)-1-methyl-4-[[1-(trifluoromethyl)cyclopropyl]sulfamoyl]pyrrole-2-carboxamide;

3-chloro-N-(2-cyano-4-pyridyl)-1-methyl-4-[[1-(trifluoromethyl)cyclobutyl]sulfamoyl]pyrrole-2-carboxamide;

N-(2-cyano-4-pyridyl)-1-methyl-4-[[(1S)-1-(trifluoromethyl)propyl]sulfamoyl]pyrrole-2-carboxamide;

N-(2-cyano-4-pyridyl)-1-methyl-4-[[1-(trifluoromethyl)cyclobutyl]sulfamoyl]pyrrole-2-carboxamide;

3-chloro-1-methyl-4-[[(1R)-2,2,2-trifluoro-1-methyl-ethyl]sulfamoyl]-N-(2,3,6-trifluoro-4-pyridyl)pyrrole-2-carboxamide;

3-chloro-1-methyl-4-[[(1R)-2,2,2-trifluoro-1-methyl-ethyl]sulfamoyl]-N-(2,3,5-trifluoro-4-pyridyl)pyrrole-2-carboxamide;

3-chloro-N-(2-chloro-4-pyridyl)-1-methyl-4-[[1-(trifluoromethyl)cyclopropyl]sulfamoyl]pyrrole-2-carboxamide;

3-chloro-N-(2-chloro-4-pyridyl)-1-methyl-4-[[1-(trifluoromethyl)cyclobutyl]sulfamoyl]pyrrole-2-carboxamide;

N-(2-chloro-4-pyridyl)-1-methyl-4-[[(1S)-1-(trifluoromethyl)propyl]sulfamoyl]pyrrole-2-carboxamide;

N-(2-chloro-4-pyridyl)-1-methyl-4-[[1-(trifluoromethyl)cyclobutyl]sulfamoyl]pyrrole-2-carboxamide;

N-(2-cyano-4-pyridyl)-1-methyl-4[[1-(trifluoromethyl)cyclopropyl]sulfamoyl]pyrrole-2-carboxamide;

3-chloro-N-(6-fluoro-3-pyridyl)-1-methyl-4-[[(1R)-2,2,2-trifluoro-1-methyl-ethyl]sulfamoyl]pyrrole-2-carboxamide;

3-chloro-N-(5-fluoro-2-pyridyl)-1-methyl-4-[[(1R)-2,2,2-trifluoro-1-methyl-ethyl]sulfamoyl]pyrrole-2-carboxamide;

N-(2-chloro-4-pyridyl)-1-methyl-4-[[1-(trifluoromethyl)cyclopropyl]sulfamoyl]pyrrole-2-carboxamide;

N-(2-cyano-4-pyridyl)-4-[(3,3-difluoro-1-methyl-cyclobutyl)sulfamoyl]-3-fluoro-1-methyl-pyrrole-2-carboxamide;

N-(2-chloro-4-pyridyl)-4-[(3,3-difluoro-1-methyl-cyclobutyl)sulfamoyl]-3-fluoro-1-methyl-pyrrole-2-carboxamide;

4-[(3,3-difluoro-1-methyl-cyclobutyl)sulfamoyl]-3-fluoro-1-methyl-N-[2-(trifluoromethyl)-4-pyridyl]pyrrole-2-carboxamide;

3-chloro-N-[3-fluoro-2-(trifluoromethyl)-4-pyridyl]-1-methyl-4-[[(1R)-2,2,2-trifluoro-1-methyl-ethyl]sulfamoyl]pyrrole-2-carboxamide;

3-chloro-N-(5,6-difluoro-3-pyridyl)-1-methyl-4-[[(1R)-2,2,2-trifluoro-1-methyl-ethyl]sulfamoyl]pyrrole-2-carboxamide;

N-(2-cyano-4-pyridyl)-4-[[(1S)-2,2-difluoro-1-methyl-propyl]sulfamoyl]-3-fluoro-1-methyl-pyrrole-2-carboxamide;

N-(2-chloro-4-pyridyl)-4-[[(1S)-2,2-difluoro-1-methyl-propyl]sulfamoyl]-3-fluoro-1-methyl-pyrrole-2-carboxamide;

4-[[(1R)-2,2-difluoro-1-methyl-propyl]sulfamoyl]-3-fluoro-1-methyl-N-[2-(trifluoromethyl)-4-pyridyl]pyrrole-2-carboxamide;

N-(2-chloro-4-pyridyl)-4-[[(1R)-2,2-difluoro-1-methyl-propyl]sulfamoyl]-3-fluoro-1-methyl-pyrrole-2-carboxamide;

4-[[(1S)-2,2-difluoro-1-methyl-propyl]sulfamoyl]-3-fluoro-1-methyl-N-[2-(trifluoromethyl)-4-pyridyl]pyrrole-2-carboxamide;

N-(2-cyano-4-pyridyl)-4-[[(1R)-2,2-difluoro-1-methyl-propyl]sulfamoyl]-3-fluoro-1-methyl-pyrrole-2-carboxamide;

3-chloro-N-(2-cyano-4-pyridyl)-4-[(3,3-difluoro-1-methyl-cyclobutyl)sulfamoyl]-1-methyl-pyrrole-2-carboxamide;

3-chloro-N-(2-chloro-4-pyridyl)-4-[(3,3-difluoro-1-methyl-cyclobutyl)sulfamoyl]-1-methyl-pyrrole-2-carboxamide;

3-chloro-4-[(3,3-difluoro-1-methyl-cyclobutyl)sulfamoyl]-1-methyl-N-[2-(trifluoromethyl)-4-pyridyl]pyrrole-2-carboxamide;

N-(2-chloro-4-pyridyl)-3-fluoro-1-methyl-4-[[(1R)-1-methylpropyl]sulfamoyl]pyrrole-2-carboxamide;

3-fluoro-1-methyl-4-[[(1R)-1-methylpropyl]sulfamoyl]-N-[2-(trifluoromethyl)-4-pyridyl]pyrrole-2-carboxamide;

N-(2-chloro-4-pyridyl)-3-fluoro-1-methyl-4-[[(1R)-1-methylpropyl]sulfamoyl]pyrrole-2-carboxamide;

3-chloro-1-methyl-4-[[(1R)-1-methylpropyl]sulfamoyl]-N-[2-(trifluoromethyl)-4-pyridyl]pyrrole-2-carboxamide;

N-(2-cyano-4-pyridyl)-3-fluoro-1,5-dimethyl-4-[[(1R)-2,2,2-trifluoro-1-methyl-ethyl]sulfamoyl]pyrrole-2-carboxamide;

3-chloro-N-(2-cyano-4-pyridyl)-1-methyl-4-[[(1R)-1-methylpropyl]sulfamoyl]pyrrole-2-carboxamide;

3-chloro-N-(2-chloro-4-pyridyl)-1-methyl-4-[[(1R)-1-methylpropyl]sulfamoyl]pyrrole-2-carboxamide;

3-chloro-N-[2-(difluoromethyl)-4-pyridyl]-1-methyl-4-[[(1R)-2,2,2-trifluoro-1-methyl-ethyl]sulfamoyl]pyrrole-2-carboxamide;

3-chloro-N-(6-chloro-5-fluoro-2-pyridyl)-1-methyl-4-[[(1R)-2,2,2-trifluoro-1-methyl-ethyl]sulfamoyl]pyrrole-2-carboxamide;

N-(6-bromo-5-fluoro-2-pyridyl)-3-chloro-1-methyl-4-[[(1R)-2,2,2-trifluoro-1-methyl-ethyl]sulfamoyl]pyrrole-2-carboxamide;

3-chloro-N-(2,6-difluoro-3-pyridyl)-1-methyl-4-[[(1R)-2,2,2-trifluoro-1-methyl-ethyl]sulfamoyl]pyrrole-2-carboxamide;

3-fluoro-4-(isopropylsulfamoyl)-1-methyl-N-[2-(trifluoromethyl)-4-pyridyl]pyrrole-2-carboxamide;

N-(2-chloro-4-pyridyl)-3-fluoro-4-(isopropylsulfamoyl)-1-methyl-pyrrole-2-carboxamide;

N-[2-(difluoromethyl)-4-pyridyl]-3-fluoro-1-methyl-4-[[(1R)-2,2,2-trifluoro-1-methyl-ethyl]sulfamoyl]pyrrole-2-carboxamide;

N-(2-chloro-3-fluoro-4-pyridyl)-4-[(3,3-difluoro-1-methyl-cyclobutyl)sulfamoyl]-3-fluoro-1-methyl-pyrrole-2-carboxamide;

N-[2-(difluoromethyl)-4-pyridyl]-3-fluoro-4-(isopropylsulfamoyl)-1-methyl-pyrrole-2-carboxamide;

4-[(3,3-difluoro-1-methyl-cyclobutyl)sulfamoyl]-N-[2-(difluoromethyl)-4-pyridyl]-3-fluoro-1-methyl-pyrrole-2-carboxamide;

3-chloro-N-[2-(difluoromethyl)-4-pyridyl]-1-methyl-4-[[(1S)-1-(trifluoromethyl)propyl]sulfamoyl]pyrrole-2-carboxamide;

3-chloro-N-[2-(difluoromethyl)-4-pyridyl]-1-methyl-4-[[(1R)-1-(trifluoromethyl)propyl]sulfamoyl]pyrrole-2-carboxamide;

N-[2-(difluoromethyl)-4-pyridyl]-3-fluoro-1-methyl-4-[[(1R)-1-methylpropyl]sulfamoyl]pyrrole-2-carboxamide;

N-[2-(difluoromethyl)-4-pyridyl]-3-fluoro-1-methyl-4-[[(1R)-1-(trifluoromethyl)propyl]sulfamoyl]pyrrole-2-carboxamide;

4-[[(1R)-2,2-difluoro-1-methyl-propyl]sulfamoyl]-N-[2-(difluoromethyl)-4-pyridyl]-3-fluoro-1-methyl-pyrrole-2-carboxamide;

3-chloro-N-(2-chloro-4-pyridyl)-4-[[(1R)-2-hydroxy-1-methyl-ethyl]sulfamoyl]-1-methyl-pyrrole-2-carboxamide;

(+/−)-3-chloro-N-(2-chloro-4-pyridyl)-4-[(2-hydroxy-1-methyl-propyl)sulfamoyl]-1-methyl-pyrrole-2-carboxamide;

3-chloro-N-(2-chloro-4-pyridyl)-1-methyl-4-[[(3S)-tetrahydrofuran-3-yl]sulfamoyl]pyrrole-2-carboxamide;

3-chloro-N-(2-chloro-4-pyridyl)-4-[[3-(hydroxymethyl)oxetan-3-yl]sulfamoyl]-1-methyl-pyrrole-2-carboxamide;

3-chloro-N-(2-chloro-4-pyridyl)-4-[(3-hydroxycyclobutyl)sulfamoyl]-1-methyl-pyrrole-2-carboxamide;

3-chloro-N-(2-chloro-4-pyridyl)-4-[[(1R)-2,2-difluoro-1-methyl-propyl]sulfamoyl]-1-methyl-pyrrole-2-carboxamide;

3-chloro-4-[[(1R)-2,2-difluoro-1-methyl-propyl]sulfamoyl]-N-(2-fluoro-4-pyridyl)-1-methyl-pyrrole-2-carboxamide;

3-chloro-N-(2-cyano-4-pyridyl)-4-[[(1R)-2,2-difluoro-1-methyl-propyl]sulfamoyl]-1-methyl-pyrrole-2-carboxamide;

3-chloro-4-[[(1R)-2,2-difluoro-1-methyl-propyl]sulfamoyl]-N-[2-(difluoromethyl)-4-pyridyl]-1-methyl-pyrrole-2-carboxamide;

4-[[(1R)-2,2-difluoro-1-methyl-propyl]sulfamoyl]-3-fluoro-N-(2-fluoro-4-pyridyl)-1-methyl-pyrrole-2-carboxamide;

3-chloro-4-[(3,3-difluoro-1-methyl-cyclobutyl)sulfamoyl]-N-[2-(difluoromethyl)-4-pyridyl]-1-methyl-pyrrole-2-carboxamide;

4-[[(1R)-2,2-difluoro-1-methyl-propyl]sulfamoyl]-N-[2-(difluoromethyl)-4-pyridyl]-1-methyl-pyrrole-2-carboxamide;

N-(2-cyano-4-pyridyl)-4-[[(1R)-2,2-difluoro-1-methyl-propyl]sulfamoyl]-1-methyl-pyrrole-2-carboxamide;

4-[[(1R)-2,2-difluoro-1-methyl-propyl]sulfamoyl]-N-(2-fluoro-4-pyridyl)-1-methyl-pyrrole-2-carboxamide;

N-(2-chloro-4-pyridyl)-4-[[(1R)-2,2-difluoro-1-methyl-propyl]sulfamoyl]-1-methyl-pyrrole-2-carboxamide;

3-chloro-4-[[(1R)-2,2-difluoro-1-methyl-propyl]sulfamoyl]-N-(2,6-difluoro-4-pyridyl)-1-methyl-pyrrole-2-carboxamide;

N-(2-bromo-4-pyridyl)-3-chloro-4-[[(1R)-2,2-difluoro-1-methyl-propyl]sulfamoyl]-1-methyl-pyrrole-2-carboxamide;

N-(2-bromo-4-pyridyl)-3-chloro-1-methyl-4-[[(1R)-2,2,2-trifluoro-1-methyl-ethyl]sulfamoyl]pyrrole-2-carboxamide;

3-chloro-N-(2-chloro-3-fluoro-4-pyridyl)-4-[[(1R)-2,2-difluoro-1-methyl-propyl]sulfamoyl]-1-methyl-pyrrole-2-carboxamide;
3-chloro-N-[2-(difluoromethyl)-4-pyridyl]-1-methyl-4-[[1-(trifluoromethyl)cyclobutyl]sulfamoyl]pyrrole-2-carboxamide;
3-chloro-N-(2,6-difluoro-4-pyridyl)-1-methyl-4-[[1-(trifluoromethyl)cyclobutyl]sulfamoyl]pyrrole-2-carboxamide;
N-(2-bromo-4-pyridyl)-3-chloro-1-methyl-4-[[1-(trifluoromethyl)cyclobutyl]sulfamoyl]pyrrole-2-carboxamide;
3-chloro-N-(2-fluoro-4-pyridyl)-1-methyl-4-[[1-(trifluoromethyl)cyclobutyl]sulfamoyl]pyrrole-2-carboxamide;
3-chloro-N-(2-chloro-3-fluoro-4-pyridyl)-1-methyl-4-[[(1R)-1-(trifluoromethyl)propyl]sulfamoyl]pyrrole-2-carboxamide;
N-(2-bromo-4-pyridyl)-3-chloro-4-[(3,3-difluoro-1-methyl-cyclobutyl)sulfamoyl]-1-methyl-pyrrole-2-carboxamide;
3-chloro-N-(2-chloro-3-fluoro-4-pyridyl)-4-[(3,3-difluoro-1-methyl-cyclobutyl)sulfamoyl]-1-methyl-pyrrole-2-carboxamide;
3-chloro-4-[(3,3-difluoro-1-methyl-cyclobutyl)sulfamoyl]-N-(2,6-difluoro-4-pyridyl)-1-methyl-pyrrole-2-carboxamide;
3-chloro-4-[(3,3-difluoro-1-methyl-cyclobutyl)sulfamoyl]-N-(2-fluoro-4-pyridyl)-1-methyl-pyrrole-2-carboxamide;
N-(2-bromo-4-pyridyl)-4-[(3,3-difluoro-1-methyl-cyclobutyl)sulfamoyl]-3-fluoro-1-methyl-pyrrole-2-carboxamide;
N-(2-chloro-3-fluoro-4-pyridyl)-3-fluoro-1-methyl-4-[[(1R)-2,2,2-trifluoro-1-methyl-ethyl]sulfamoyl]pyrrole-2-carboxamide;
N-[2-(difluoromethyl)-4-pyridyl]-3-fluoro-1-methyl-4-[[1-(trifluoromethyl)cyclobutyl]sulfamoyl]pyrrole-2-carboxamide;
N-(2-chloro-3-fluoro-4-pyridyl)-3-fluoro-1-methyl-4-[[1-(trifluoromethyl)cyclobutyl]sulfamoyl]pyrrole-2-carboxamide;
N-(2-chloro-6-cyano-4-pyridyl)-3-fluoro-1-methyl-4-[[1-(trifluoromethyl)cyclobutyl]sulfamoyl]pyrrole-2-carboxamide;
N-(2-chloro-4-pyridyl)-3-fluoro-1-methyl-4-[[1-(trifluoromethyl)cyclobutyl]sulfamoyl]pyrrole-2-carboxamide;
N-(2-cyano-4-pyridyl)-3-fluoro-1-methyl-4-[[1-(trifluoromethyl)cyclobutyl]sulfamoyl]pyrrole-2-carboxamide;
N-(2-bromo-4-pyridyl)-4-[[(1R)-2,2-difluoro-1-methyl-propyl]sulfamoyl]-3-fluoro-1-methyl-pyrrole-2-carboxamide;
N-(2-chloro-3-fluoro-4-pyridyl)-4-[[(1R)-2,2-difluoro-1-methyl-propyl]sulfamoyl]-3-fluoro-1-methyl-pyrrole-2-carboxamide;
N-(2,6-dichloro-4-pyridyl)-3-fluoro-1-methyl-4-[[(1R)-2,2,2-trifluoro-1-methyl-ethyl]sulfamoyl]pyrrole-2-carboxamide;
4-[(2,2-difluorocyclobutyl)sulfamoyl]-N-[2-(difluoromethyl)-4-pyridyl]-3-fluoro-1-methyl-pyrrole-2-carboxamide;
N-[2-(difluoromethyl)-4-pyridyl]-3-fluoro-4-[[1-(fluoromethyl)cyclobutyl]sulfamoyl]-1-methyl-pyrrole-2-carboxamide;
N-[2-(1,1-difluoroethyl)-4-pyridyl]-3-fluoro-1-methyl-4-[[(1R)-2,2,2-trifluoro-1-methyl-ethyl]sulfamoyl]pyrrole-2-carboxamide;
N-(2-chloro-6-methyl-4-pyridyl)-4-[(3, 3-difluoro-1-methyl-cyclobutyl)sulfamoyl]-3-fluoro-1-methyl-pyrrole-2-carboxamide;
N-(2-bromo-3-fluoro-4-pyridyl)-4-[(3,3-difluoro-1-methyl-cyclobutyl)sulfamoyl]-3-fluoro-1-methyl-pyrrole-2-carboxamide;
4-[(3,3-difluoro-1-methyl-cyclobutyl)sulfamoyl]-N-(2,6-difluoro-4-pyridyl)-3-fluoro-1-methyl-pyrrole-2-carboxamide;
4-[(3,3-difluoro-1-methyl-cyclobutyl)sulfamoyl]-3-fluoro-N-(2-fluoro-4-pyridyl)-1-methyl-pyrrole-2-carboxamide;
4-[(3,3-difluoro-1-methyl-cyclobutyl)sulfamoyl]-3-fluoro-N-(2-fluoro-6-methyl-4-pyridyl)-1-methyl-pyrrole-2-carboxamide;
N-(2,6-dibromo-4-pyridyl)-4-[(3,3-difluoro-1-methyl-cyclobutyl)sulfamoyl]-3-fluoro-1-methyl-pyrrole-2-carboxamide;
N-(2,6-dichloro-4-pyridyl)-4-[(3,3-difluoro-1-methyl-cyclobutyl)sulfamoyl]-3-fluoro-1-methyl-pyrrole-2-carboxamide;
3-chloro-N-(2-fluoro-6-methyl-4-pyridyl)-1-methyl-4-[[(1R)-2,2,2-trifluoro-1-methyl-ethyl]sulfamoyl]pyrrole-2-carboxamide;
3-chloro-N-(2,3-difluoro-4-pyridyl)-1-methyl-4-[[(1R)-2,2,2-trifluoro-1-methyl-ethyl]sulfamoyl]pyrrole-2-carboxamide;
N-(2-bromo-3-fluoro-4-pyridyl)-3-chloro-1-methyl-4-[[(1R)-2,2,2-trifluoro-1-methyl-ethyl]sulfamoyl]pyrrole-2-carboxamide;
3-chloro-N-(2,5-difluoro-4-pyridyl)-1-methyl-4-[[(1R)-2,2,2-trifluoro-1-methyl-ethyl]sulfamoyl]pyrrole-2-carboxamide;
3-chloro-N-(2-chloro-6-methyl-4-pyridyl)-1-methyl-4-[[(1R)-2,2,2-trifluoro-1-methyl-ethyl]sulfamoyl]pyrrole-2-carboxamide;
3-chloro-N-[2-(difluoromethyl)-3-fluoro-4-pyridyl]-1-methyl-4-[[(1R)-2,2,2-trifluoro-1-methyl-ethyl]sulfamoyl]pyrrole-2-carboxamide;
3-chloro-N-(2-cyano-3-fluoro-4-pyridyl)-1-methyl-4-[[(1R)-2,2,2-trifluoro-1-methyl-ethyl]sulfamoyl]pyrrole-2-carboxamide;
3-chloro-N-(2,6-dimethyl-4-pyridyl)-1-methyl-4-[[(1R)-2,2,2-trifluoro-1-methyl-ethyl]sulfamoyl]pyrrole-2-carboxamide;
3-chloro-N-[2-(fluoromethyl)-4-pyridyl]-1-methyl-4-[[(1R)-2,2,2-trifluoro-1-methyl-ethyl]sulfamoyl]pyrrole-2-carboxamide;
3-chloro-N-(6-cyano-5-fluoro-2-pyridyl)-1-methyl-4-[[(1R)-2,2,2-trifluoro-1-methyl-ethyl]sulfamoyl]pyrrole-2-carboxamide;
3-chloro-N-[2-(difluoromethyl)-6-methyl-4-pyridyl]-1-methyl-4-[[(1R)-2,2,2-trifluoro-1-methyl-ethyl]sulfamoyl]pyrrole-2-carboxamide;
3-chloro-4-[[(1R)-2,2-difluoro-1-methyl-propyl]sulfamoyl]-N-(2-fluoro-6-methyl-4-pyridyl)-1-methyl-pyrrole-2-carboxamide;
3-chloro-N-[2-(difluoromethyl)-3-fluoro-4-pyridyl]-4-[[(1R)-2,2-difluoro-1-methyl-propyl]sulfamoyl]-1-methyl-pyrrole-2-carboxamide;
N-(2-bromo-3-fluoro-4-pyridyl)-3-chloro-4-[[(1R)-2,2-difluoro-1-methyl-propyl]sulfamoyl]-1-methyl-pyrrole-2-carboxamide;

3-chloro-N-(2-chloro-6-methyl-4-pyridyl)-4-[[(1R)-2,2-difluoro-1-methyl-propyl]sulfamoyl]-1-methyl-pyrrole-2-carboxamide;

3-chloro-4-[[(1R)-2,2-difluoro-1-methyl-propyl]sulfamoyl]-1-methyl-N-[2-(trifluoromethyl)-4-pyridyl]pyrrole-2-carboxamide;

3-chloro-N-(2-cyano-3-fluoro-4-pyridyl)-4-[[(1R)-2,2-difluoro-1-methyl-propyl]sulfamoyl]-1-methyl-pyrrole-2-carboxamide;

3-fluoro-N-(2-fluoro-6-methyl-4-pyridyl)-1-methyl-4-[[(1R)-2,2,2-trifluoro-1-methyl-ethyl]sulfamoyl]pyrrole-2-carboxamide;

N-(2-bromo-3-fluoro-4-pyridyl)-3-fluoro-1-methyl-4-[[(1R)-2,2,2-trifluoro-1-methyl-ethyl]sulfamoyl]pyrrole-2-carboxamide;

N-(2-bromo-6-methyl-4-pyridyl)-3-fluoro-1-methyl-4-[[(1R)-2,2,2-trifluoro-1-methyl-ethyl]sulfamoyl]pyrrole-2-carboxamide;

3-fluoro-N-(5-fluoro-6-methyl-2-pyridyl)-1-methyl-4-[[(1R)-2,2,2-trifluoro-1-methyl-ethyl]sulfamoyl]pyrrole-2-carboxamide;

N-(2-cyano-3-fluoro-4-pyridyl)-3-fluoro-1-methyl-4-[[(1R)-2,2,2-trifluoro-1-methyl-ethyl]sulfamoyl]pyrrole-2-carboxamide;

N-(2-bromo-6-methyl-4-pyridyl)-4-[[(1R)-2,2-difluoro-1-methyl-propyl]sulfamoyl]-3-fluoro-1-methyl-pyrrole-2-carboxamide;

N-(2-chloro-6-methyl-4-pyridyl)-4-[[(1R)-2,2-difluoro-1-methyl-propyl]sulfamoyl]-3-fluoro-1-methyl-pyrrole-2-carboxamide;

4-[[(1R)-2,2-difluoro-1-methyl-propyl]sulfamoyl]-N-(2,6-difluoro-4-pyridyl)-3-fluoro-1-methyl-pyrrole-2-carboxamide;

4-[[(1R)-2,2-difluoro-1-methyl-propyl]sulfamoyl]-3-fluoro-N-(2-fluoro-6-methyl-4-pyridyl)-1-methyl-pyrrole-2-carboxamide;

N-(2-bromo-3-fluoro-4-pyridyl)-4-[[(1R)-2,2-difluoro-1-methyl-propyl]sulfamoyl]-3-fluoro-1-methyl-pyrrole-2-carboxamide;

N-(2-bromo-3-fluoro-4-pyridyl)-3-chloro-4-[(3,3-difluoro-1-methyl-cyclobutyl)sulfamoyl]-1-methyl-pyrrole-2-carboxamide;

3-chloro-N-(2-cyano-3-fluoro-4-pyridyl)-4-[(3,3-difluoro-1-methyl-cyclobutyl)sulfamoyl]-1-methyl-pyrrole-2-carboxamide;

3-chloro-4-[(3,3-difluoro-1-methyl-cyclobutyl)sulfamoyl]-N-(2-fluoro-6-methyl-4-pyridyl)-1-methyl-pyrrole-2-carboxamide;

N-(2-bromo-6-methyl-4-pyridyl)-3-fluoro-1-methyl-4-[[1-(trifluoromethyl)cyclobutyl]sulfamoyl]pyrrole-2-carboxamide;

N-[2-(difluoromethyl)-3-fluoro-4-pyridyl]-3-fluoro-1-methyl-4-[[1-(trifluoromethyl)cyclobutyl]sulfamoyl]pyrrole-2-carboxamide;

N-(2-bromo-3-fluoro-4-pyridyl)-3-fluoro-1-methyl-4-[[1-(trifluoromethyl)cyclobutyl]sulfamoyl]pyrrole-2-carboxamide;

N-(2-cyano-3-fluoro-4-pyridyl)-3-fluoro-1-methyl-4-[[1-(trifluoromethyl)cyclobutyl]sulfamoyl]pyrrole-2-carboxamide;

N-(2,6-difluoro-4-pyridyl)-3-fluoro-1-methyl-4-[[1-(trifluoromethyl)cyclobutyl]sulfamoyl]pyrrole-2-carboxamide;

3-fluoro-N-(2-fluoro-4-pyridyl)-1-methyl-4-[[1-(trifluoromethyl)cyclobutyl]sulfamoyl]pyrrole-2-carboxamide;

N-(2,3-difluoro-4-pyridyl)-3-fluoro-1-methyl-4-[[1-(trifluoromethyl)cyclobutyl]sulfamoyl]pyrrole-2-carboxamide;

N-(2-cyano-6-methyl-4-pyridyl)-3-fluoro-1-methyl-4-[[1-(trifluoromethyl)cyclobutyl]sulfamoyl]pyrrole-2-carboxamide;

3-fluoro-N-(2-fluoro-6-methyl-4-pyridyl)-1-methyl-4-[[1-(trifluoromethyl)cyclobutyl]sulfamoyl]pyrrole-2-carboxamide;

N-[2-(difluoromethyl)-6-methyl-4-pyridyl]-3-fluoro-1-methyl-4-[[1-(trifluoromethyl)cyclobutyl]sulfamoyl]pyrrole-2-carboxamide;

N-(2-chloro-4-pyridyl)-4-[(2,2-difluorocyclobutyl)sulfamoyl]-3-fluoro-1-methyl-pyrrole-2-carboxamide;

N-(2-chloro-4-pyridyl)-3-fluoro-1-methyl-4-[[1-(trifluoromethyl)cyclopropyl]sulfamoyl]pyrrole-2-carboxamide;

N-[2-(difluoromethyl)-6-methyl-4-pyridyl]-4-[[(1R)-2,2-difluoro-1-methyl-propyl]sulfamoyl]-3-fluoro-1-methyl-pyrrole-2-carboxamide;

N-[2-(difluoromethyl)-6-methyl-4-pyridyl]-3-fluoro-1-methyl-4-[[(1R)-2,2,2-trifluoro-1-methyl-ethyl]sulfamoyl]pyrrole-2-carboxamide;

3-chloro-N-(2-chloro-4-pyridyl)-1-methyl-4-[[4-(trifluoromethyl)tetrahydropyran-4-yl]sulfamoyl]pyrrole-2-carboxamide;

3-cyano-N-(6-cyano-5-fluoro-2-pyridyl)-1-methyl-4-[[(1R)-2,2,2-trifluoro-1-methyl-ethyl]sulfamoyl]pyrrole-2-carboxamide;

3-chloro-N-[2-(1,1-difluoroethyl)-4-pyridyl]-1-methyl-4-[[(1R)-2,2,2-trifluoro-1-methyl-ethyl]sulfamoyl]pyrrole-2-carboxamide;

3-chloro-N-(4-cyano-2-pyridyl)-1-methyl-4-[[(1R)-2,2,2-trifluoro-1-methyl-ethyl]sulfamoyl]pyrrole-2-carboxamide;

3-chloro-1-methyl-4-[[(1R)-2,2,2-trifluoro-1-methyl-ethyl]sulfamoyl]-N-(3,5,6-trifluoro-2-pyridyl)pyrrole-2-carboxamide;

3-chloro-N-(3-chloro-2,6-difluoro-4-pyridyl)-1-methyl-4-[[(1R)-2,2,2-trifluoro-1-methyl-ethyl]sulfamoyl]pyrrole-2-carboxamide;

3-chloro-N-(3,5-dichloro-2,6-difluoro-4-pyridyl)-1-methyl-4-[[(1R)-2,2,2-trifluoro-1-methyl-ethyl]sulfamoyl]pyrrole-2-carboxamide;

3-chloro-N-(3-chloro-2,5,6-trifluoro-4-pyridyl)-1-methyl-4-[[(1R)-2,2,2-trifluoro-1-methyl-ethyl]sulfamoyl]pyrrole-2-carboxamide;

N-(2-cyano-4-pyridyl)-3-fluoro-1-methyl-4-[(2,2,2-trifluoro-1,1-dimethyl-ethyl)sulfamoyl]pyrrole-2-carboxamide;

N-(2,6-difluoro-4-pyridyl)-3-fluoro-1-methyl-4-[(2,2,2-trifluoro-1,1-dimethyl-ethyl)sulfamoyl]pyrrole-2-carboxamide;

N-[2-(difluoromethyl)-4-pyridyl]-3-fluoro-1-methyl-4-[(2,2,2-trifluoro-1,1-dimethyl-ethyl)sulfamoyl]pyrrole-2-carboxamide;

N-(2-bromo-4-pyridyl)-3-fluoro-1-methyl-4-[(2,2,2-trifluoro-1,1-dimethyl-ethyl)sulfamoyl]pyrrole-2-carboxamide;

N-(2-cyano-4-pyridyl)-3-fluoro-1-methyl-4-[[1-(trifluoromethyl)cyclopropyl]sulfamoyl]pyrrole-2-carboxamide;

N-(2,6-difluoro-4-pyridyl)-3-fluoro-1-methyl-4-[[1-(trifluoromethyl)cyclopropyl]sulfamoyl]pyrrole-2-carboxamide;

N-(2-bromo-4-pyridyl)-3-fluoro-1-methyl-4-[[1-(trifluoromethyl)cyclopropyl]sulfamoyl]pyrrole-2-carboxamide;

N-[2-(difluoromethyl)-3-fluoro-4-pyridyl]-3-fluoro-1-methyl-4-[[1-(trifluoromethyl)cyclopropyl]sulfamoyl]pyrrole-2-carboxamide;

N-[2-(difluoromethyl)-4-pyridyl]-3-fluoro-1-methyl-4-[[1-(trifluoromethyl)cyclopropyl]sulfamoyl]pyrrole-2-carboxamide;

N-(2-cyano-3-fluoro-4-pyridyl)-4-[(3, 3-difluoro-1-methyl-cyclobutyl)sulfamoyl]-3-fluoro-1-methyl-pyrrole-2-carboxamide;

N-(2-chloro-4-pyridyl)-3-fluoro-1-methyl-4-[[3-(trifluoromethyl)oxetan-3-yl]sulfamoyl]pyrrole-2-carboxamide;

N-(2,6-difluoro-4-pyridyl)-3-fluoro-1,5-dimethyl-4-[[(1R)-2,2,2-trifluoro-1-methyl-ethyl]sulfamoyl]pyrrole-2-carboxamide;

N-(2-chloro-4-pyridyl)-3-fluoro-1,5-dimethyl-4-[[(1R)-2,2,2-trifluoro-1-methyl-ethyl]sulfamoyl]pyrrole-2-carboxamide;

N-[2-(difluoromethyl)-3-fluoro-4-pyridyl]-3-fluoro-1-methyl-4-[(2,2,2-trifluoro-1,1-dimethyl-ethyl)sulfamoyl]pyrrole-2-carboxamide;

N-[2-(difluoromethyl)-3-fluoro-4-pyridyl]-3-fluoro-1-methyl-4-[[(1R)-2,2,2-trifluoro-1-methyl-ethyl]sulfamoyl]pyrrole-2-carboxamide;

N-(2-bromo-3-fluoro-4-pyridyl)-3-fluoro-1-methyl-4-[[1-(trifluoromethyl)cyclopropyl]sulfamoyl]pyrrole-2-carboxamide;

N-[2-(difluoromethyl)-3-fluoro-4-pyridyl]-4-[[(1R)-2,2-difluoro-1-methyl-propyl]sulfamoyl]-3-fluoro-1-methyl-pyrrole-2-carboxamide;

N-(2-bromo-4-pyridyl)-3-fluoro-1,5-dimethyl-4-[[(1R)-2,2,2-trifluoro-1-methyl-ethyl]sulfamoyl]pyrrole-2-carboxamide;

N-[2-(difluoromethyl)-4-pyridyl]-3-fluoro-1,5-dimethyl-4-[[(1R)-2,2,2-trifluoro-1-methyl-ethyl]sulfamoyl]pyrrole-2-carboxamide;

N-[2-(difluoromethyl)-3-fluoro-4-pyridyl]-3-fluoro-1,5-dimethyl-4-[[(1R)-2,2,2-trifluoro-1-methyl-ethyl]sulfamoyl]pyrrole-2-carboxamide;

N-[2-(difluoromethyl)-3-fluoro-4-pyridyl]-3-fluoro-1-methyl-4-[[3-(trifluoromethyl)oxetan-3-yl]sulfamoyl]pyrrole-2-carboxamide;

N-(2-bromo-4-pyridyl)-3-fluoro-1-methyl-4-[[3-(trifluoromethyl)oxetan-3-yl]sulfamoyl]pyrrole-2-carboxamide;

N-[2-(difluoromethyl)-4-pyridyl]-3-fluoro-1-methyl-4-[[3-(trifluoromethyl)oxetan-3-yl]sulfamoyl]pyrrole-2-carboxamide;

N-(2,6-difluoro-4-pyridyl)-3-fluoro-1-methyl-4-[[3-(trifluoromethyl)oxetan-3-yl]sulfamoyl]pyrrole-2-carboxamide;

N-(2-chloro-3-fluoro-4-pyridyl)-3-fluoro-1-methyl-4-[[3-(trifluoromethyl)oxetan-3-yl]sulfamoyl]pyrrole-2-carboxamide;

N-(2-chloro-6-methyl-4-pyridyl)-3-fluoro-1-methyl-4-[[(1R)-2,2,2-trifluoro-1-methyl-ethyl]sulfamoyl]pyrrole-2-carboxamide;

N-(2-chloro-6-fluoro-4-pyridyl)-3-fluoro-1-methyl-4-[[(1R)-2,2,2-trifluoro-1-methyl-ethyl]sulfamoyl]pyrrole-2-carboxamide;

N-(2-bromo-6-fluoro-4-pyridyl)-3-fluoro-1-methyl-4-[[(1R)-2,2,2-trifluoro-1-methyl-ethyl]sulfamoyl]pyrrole-2-carboxamide; and N-(2-chloro-4-pyridyl)-3-fluoro-1-methyl-4-[[1-(2,2,2-trifluoroethyl)-4-piperidyl]sulfamoyl]pyrrole-2-carboxamide; and pharmaceutically acceptable salts thereof.

18. A pharmaceutical composition comprising a compound according to claim 17, and a pharmaceutically acceptable carrier.

19. A method of treating an HBV infection comprising administering a therapeutically effective amount of at least one compound of claim 17.

20. A product containing (a) a compound according to claim 17, and (b) at least one HBV inhibitor, as a combined preparation for simultaneous, separate or sequential use in the treatment of HBV infections.

* * * * *